United States Patent
Rousso et al.

(10) Patent No.: US 8,620,679 B2
(45) Date of Patent: *Dec. 31, 2013

(54) RADIOPHARMACEUTICAL DISPENSING, ADMINISTRATION, AND IMAGING

(75) Inventors: Benny Rousso, Rishon-Le-Zion (IL); Shlomo Ben-Haim, London (GB); Haim Melman, Kfar Saba (IL); Zohr Bronshtine, Talmei Elazar (IL); Yoel Zilberstein, Haifa (IL); Michael Nagler, Tel-Aviv (IL); Dalia Dickman, Misgav (IL); Einav Omer, Kfar Monash (IL)

(73) Assignee: Biosensors International Group, Ltd., Hamilton (BM)

( * ) Notice: Subject to any disclaimer, the term of this patent is extended or adjusted under 35 U.S.C. 154(b) by 998 days.

This patent is subject to a terminal disclaimer.

(21) Appl. No.: 11/932,987

(22) Filed: Oct. 31, 2007

(65) Prior Publication Data
US 2008/0195249 A1    Aug. 14, 2008

Related U.S. Application Data

(63) Continuation of application No. 11/750,057, filed on May 17, 2007, now Pat. No. 8,571,881, which is a continuation-in-part of application No. PCT/IL2006/000562, filed on May 11, 2006, which is a continuation-in-part of application No. PCT/IL2005/001173, filed on Nov. 9, 2005, which is a continuation-in-part of application No. PCT/IL2005/000575, filed on Jun. 1, 2005.

(60) Provisional application No. 60/625,971, filed on Nov. 9, 2004, provisional application No. 60/628,105, filed on Nov. 17, 2004, provisional application No.

(Continued)

(51) Int. Cl.
G06Q 10/00    (2012.01)

(52) U.S. Cl.
USPC .................................... 705/2; 705/3

(58) Field of Classification Search
USPC .............................................. 705/2
See application file for complete search history.

(56) References Cited

U.S. PATENT DOCUMENTS

| 630,611 A | 8/1899 | Knapp et al. |
| 2,776,377 A | 1/1957 | Anger |

(Continued)

FOREIGN PATENT DOCUMENTS

| DE | 1516429 | 12/1969 |
| DE | 19814199 | 10/1999 |

(Continued)

OTHER PUBLICATIONS

An Office Action dated Feb. 17, 2011, which issued during the prosecution of Applicant's U.S. Appl. No. 11/932,872.

(Continued)

*Primary Examiner* — Hiep V Nguyen
(74) *Attorney, Agent, or Firm* — William H. Dippert; Eckert Seamans Cherin & Mellott, LLC

(57) ABSTRACT

Apparatus is provided for use with at least one labeled radiopharmaceutical agent, the apparatus including a container (22) containing the at least one labeled radiopharmaceutical agent, and a portable computer-communcatable data carrier (120, 24) associated with the container (22), the data (120, 24) containing imaging protocol information for use with the at least one labeled radiopharmaceutical agent. Other embodiments are also described.

35 Claims, 25 Drawing Sheets

Related U.S. Application Data

60/630,561, filed on Nov. 26, 2004, provisional application No. 60/632,236, filed on Dec. 2, 2004, provisional application No. 60/632,515, filed on Dec. 3, 2004, provisional application No. 60/635,630, filed on Dec. 14, 2004, provisional application No. 60/636,088, filed on Dec. 16, 2004, provisional application No. 60/640,215, filed on Jan. 3, 2005, provisional application No. 60/648,385, filed on Feb. 1, 2005, provisional application No. 60/648,690, filed on Feb. 2, 2005, provisional application No. 60/675,892, filed on Apr. 29, 2005, provisional application No. 60/691,780, filed on Jun. 20, 2005, provisional application No. 60/700,318, filed on Jul. 19, 2005, provisional application No. 60/700,299, filed on Jul. 19, 2005, provisional application No. 60/700,317, filed on Jul. 19, 2005, provisional application No. 60/700,753, filed on Jul. 20, 2005, provisional application No. 60/700,752, filed on Jul. 20, 2005, provisional application No. 60/702,979, filed on Jul. 28, 2005, provisional application No. 60/720,034, filed on Sep. 26, 2005, provisional application No. 60/720,652, filed on Sep. 27, 2005, provisional application No. 60/720,541, filed on Sep. 27, 2005, provisional application No. 60/750,287, filed on Dec. 13, 2005, provisional application No. 60/750,334, filed on Dec. 15, 2005, provisional application No. 60/750,597, filed on Dec. 15, 2005, provisional application No. 60/800,845, filed on May 17, 2006, provisional application No. 60/800,846, filed on May 17, 2006, provisional application No. 60/816,970, filed on Jun. 28, 2006.

(56) References Cited

U.S. PATENT DOCUMENTS

| | | |
|---|---|---|
| 3,340,866 A | 9/1967 | Noeller |
| 3,446,965 A | 5/1969 | Ogier et al. |
| 3,535,085 A | 10/1970 | Shumate et al. |
| 3,684,887 A | 8/1972 | Hugonin |
| 3,690,309 A | 9/1972 | Pluzhnikov et al. |
| 3,719,183 A | 3/1973 | Schwartz |
| 3,739,279 A | 6/1973 | Hollis |
| 3,971,362 A | 7/1976 | Pope et al. |
| 3,978,337 A | 8/1976 | Nickles et al. |
| 3,988,585 A | 10/1976 | O'Neill et al. |
| 4,000,502 A | 12/1976 | Butler et al. |
| 4,015,592 A | 4/1977 | Bradley-Moore |
| 4,055,765 A | 10/1977 | Gerber et al. |
| 4,061,919 A | 12/1977 | Miller et al. |
| 4,095,107 A | 6/1978 | Genna et al. |
| 4,165,462 A | 8/1979 | Macovski et al. |
| 4,181,856 A | 1/1980 | Bone |
| 4,278,077 A | 7/1981 | Mizumoto |
| 4,289,969 A | 9/1981 | Cooperstein et al. |
| 4,291,708 A | 9/1981 | Frei et al. |
| 4,296,785 A | 10/1981 | Vitello et al. |
| 4,302,675 A | 11/1981 | Wake et al. |
| 4,364,377 A | 12/1982 | Smith |
| 4,383,327 A | 5/1983 | Kruger |
| 4,476,381 A | 10/1984 | Rubin |
| 4,503,331 A | 3/1985 | Kovacs, Jr. et al. |
| 4,521,688 A | 6/1985 | Yin |
| H12 H | 1/1986 | Bennett et al. |
| 4,580,054 A | 4/1986 | Shimoni |
| 4,595,014 A | 6/1986 | Barrett et al. |
| 4,674,107 A | 6/1987 | Urban et al. |
| 4,679,142 A | 7/1987 | Lee |
| 4,689,041 A | 8/1987 | Corday et al. |
| 4,689,621 A | 8/1987 | Kleinberg |
| 4,709,382 A | 11/1987 | Sones |
| 4,710,624 A | 12/1987 | Alvarez et al. |
| 4,731,536 A | 3/1988 | Rische et al. |
| 4,773,430 A | 9/1988 | Porath |
| 4,782,840 A | 11/1988 | Martin, Jr. et al. |
| 4,791,934 A | 12/1988 | Brunnett |
| 4,801,803 A | 1/1989 | Denen et al. |
| 4,828,841 A | 5/1989 | Porter et al. |
| 4,834,112 A | 5/1989 | Machek et al. |
| 4,844,067 A | 7/1989 | Ikada et al. |
| 4,844,076 A | 7/1989 | Lesho et al. |
| 4,853,546 A | 8/1989 | Abe et al. |
| 4,854,324 A | 8/1989 | Hirschman et al. |
| 4,854,330 A | 8/1989 | Evans, III et al. |
| 4,867,962 A | 9/1989 | Abrams |
| 4,893,013 A | 1/1990 | Denen et al. |
| 4,893,322 A | 1/1990 | Hellmick et al. |
| 4,919,146 A | 4/1990 | Rhinehart et al. |
| 4,924,486 A | 5/1990 | Weber et al. |
| 4,928,250 A | 5/1990 | Greenberg et al. |
| 4,929,832 A | 5/1990 | Ledley |
| 4,938,230 A | 7/1990 | Machek et al. |
| 4,951,653 A | 8/1990 | Fry et al. |
| 4,959,547 A | 9/1990 | Carroll et al. |
| 4,970,391 A | 11/1990 | Uber, III |
| 4,995,396 A | 2/1991 | Inaba et al. |
| 5,014,708 A | 5/1991 | Hayashi et al. |
| 5,018,182 A | 5/1991 | Cowan et al. |
| 5,032,729 A | 7/1991 | Charpak |
| 5,033,998 A | 7/1991 | Corday et al. |
| 5,039,863 A | 8/1991 | Matsuno et al. |
| 5,042,056 A | 8/1991 | Hellmick et al. |
| 5,070,878 A | 12/1991 | Denen |
| 5,088,492 A | 2/1992 | Takayama et al. |
| 5,115,137 A | 5/1992 | Andersson-Engels et al. |
| 5,119,818 A | 6/1992 | Carroll et al. |
| 5,132,542 A | 7/1992 | Bassalleck et al. |
| 5,145,163 A | 9/1992 | Cowan et al. |
| 5,151,598 A | 9/1992 | Denen |
| 5,170,055 A | 12/1992 | Carroll et al. |
| 5,170,439 A | 12/1992 | Zeng et al. |
| 5,170,789 A | 12/1992 | Narayan et al. |
| 5,179,983 A | 1/1993 | Cordner, Jr. et al. |
| 5,196,796 A | 3/1993 | Misic et al. |
| 5,207,642 A | 5/1993 | Orkin et al. |
| 5,210,421 A | 5/1993 | Gullberg et al. |
| 5,243,988 A | 9/1993 | Sieben et al. |
| 5,246,005 A | 9/1993 | Carroll et al. |
| 5,249,124 A | 9/1993 | DeVito |
| 5,252,830 A | 10/1993 | Weinberg |
| 5,254,101 A | 10/1993 | Trombley, III |
| 5,258,717 A | 11/1993 | Misic et al. |
| 5,263,077 A | 11/1993 | Cowan et al. |
| 5,279,607 A | 1/1994 | Schentag et al. |
| 5,284,147 A | 2/1994 | Hanaoka et al. |
| 5,299,253 A | 3/1994 | Wessels |
| 5,304,165 A | 4/1994 | Haber et al. |
| 5,307,808 A | 5/1994 | Dumoulin et al. |
| 5,307,814 A | 5/1994 | Kressel et al. |
| 5,309,959 A | 5/1994 | Shaw et al. |
| 5,317,506 A | 5/1994 | Coutre et al. |
| 5,317,619 A | 5/1994 | Hellmick et al. |
| 5,323,006 A | 6/1994 | Thompson et al. |
| 5,329,976 A | 7/1994 | Haber et al. |
| 5,334,141 A | 8/1994 | Carr et al. |
| 5,349,190 A | 9/1994 | Hines et al. |
| 5,355,087 A | 10/1994 | Claiborne et al. |
| 5,365,069 A | 11/1994 | Eisen et al. |
| 5,365,928 A | 11/1994 | Rhinehart et al. |
| 5,367,552 A | 11/1994 | Peschmann |
| 5,377,681 A | 1/1995 | Drane |
| 5,381,791 A | 1/1995 | Qian |
| 5,383,456 A | 1/1995 | Arnold et al. |
| 5,383,858 A | 1/1995 | Reilly et al. |
| 5,386,446 A | 1/1995 | Fujimoto et al. |
| 5,387,409 A | 2/1995 | Nunn et al. |
| 5,391,877 A | 2/1995 | Marks |
| 5,395,366 A | 3/1995 | D'Andrea |
| 5,399,868 A | 3/1995 | Jones et al. |
| 5,404,293 A | 4/1995 | Weng et al. |
| 5,415,181 A | 5/1995 | Hogrefe et al. |
| 5,431,161 A | 7/1995 | Ryals et al. |

(56) References Cited

U.S. PATENT DOCUMENTS

| | | |
|---|---|---|
| 5,435,302 A | 7/1995 | Lenkinski et al. |
| 5,436,458 A | 7/1995 | Tran et al. |
| 5,441,050 A | 8/1995 | Thurston et al. |
| 5,448,073 A | 9/1995 | Jeanguillaume |
| 5,451,232 A | 9/1995 | Rhinehart et al. |
| 5,472,403 A | 12/1995 | Cornacchia et al. |
| 5,475,219 A | 12/1995 | Olson |
| 5,475,232 A | 12/1995 | Powers et al. |
| 5,476,095 A | 12/1995 | Schnall et al. |
| 5,479,969 A | 1/1996 | Hardie et al. |
| 5,481,115 A | 1/1996 | Hsieh et al. |
| 5,484,384 A | 1/1996 | Fearnot |
| 5,489,782 A | 2/1996 | Wernikoff |
| 5,493,595 A | 2/1996 | Schoolman |
| 5,493,805 A | 2/1996 | Penuela et al. |
| 5,494,036 A | 2/1996 | Uber, III et al. |
| 5,501,674 A | 3/1996 | Trombley, III et al. |
| 5,507,412 A | 4/1996 | Ebert et al. |
| 5,517,120 A | 5/1996 | Misic et al. |
| 5,519,221 A | 5/1996 | Weinberg |
| 5,519,222 A | 5/1996 | Besett |
| 5,519,931 A | 5/1996 | Reich |
| 5,520,182 A | 5/1996 | Leighton et al. |
| 5,520,653 A | 5/1996 | Reilly et al. |
| 5,521,506 A | 5/1996 | Misic et al. |
| 5,536,945 A | 7/1996 | Reich |
| 5,545,899 A | 8/1996 | Tran et al. |
| 5,547,470 A | 8/1996 | Johnson et al. |
| 5,559,335 A | 9/1996 | Zeng et al. |
| 5,565,684 A | 10/1996 | Gullberg et al. |
| 5,569,181 A | 10/1996 | Heilman et al. |
| 5,572,132 A | 11/1996 | Pulyer et al. |
| 5,572,999 A | 11/1996 | Funda et al. |
| 5,579,766 A | 12/1996 | Gray |
| 5,580,541 A | 12/1996 | Wells et al. |
| 5,585,637 A | 12/1996 | Bertelsen et al. |
| 5,587,585 A | 12/1996 | Eisen et al. |
| 5,591,143 A | 1/1997 | Trombley, III et al. |
| 5,600,145 A | 2/1997 | Plummer |
| 5,604,531 A | 2/1997 | Iddan et al. |
| 5,610,520 A | 3/1997 | Misic |
| 5,617,858 A | 4/1997 | Taverna et al. |
| 5,629,524 A | 5/1997 | Stettner et al. |
| 5,635,717 A | 6/1997 | Popescu |
| 5,657,759 A | 8/1997 | Essen-Moller |
| 5,672,877 A | 9/1997 | Liebig et al. |
| 5,677,539 A | 10/1997 | Apotovsky et al. |
| 5,682,888 A | 11/1997 | Olson et al. |
| 5,687,542 A | 11/1997 | Lawecki et al. |
| 5,690,691 A | 11/1997 | Chen et al. |
| 5,692,640 A | 12/1997 | Caulfield et al. |
| 5,694,933 A | 12/1997 | Madden et al. |
| 5,695,500 A | 12/1997 | Taylor et al. |
| 5,716,595 A | 2/1998 | Goldenberg |
| 5,727,554 A | 3/1998 | Kalend et al. |
| 5,729,129 A | 3/1998 | Acker |
| 5,732,704 A | 3/1998 | Thurston et al. |
| 5,739,508 A | 4/1998 | Uber, III |
| 5,741,232 A | 4/1998 | Reilly et al. |
| 5,742,060 A | 4/1998 | Ashburn |
| 5,744,805 A | 4/1998 | Raylman et al. |
| 5,757,006 A | 5/1998 | De Vito et al. |
| 5,779,675 A | 7/1998 | Reilly et al. |
| 5,780,855 A | 7/1998 | Pare et al. |
| 5,781,442 A | 7/1998 | Engleson et al. |
| 5,784,432 A | 7/1998 | Kurtz et al. |
| 5,786,597 A | 7/1998 | Lingren et al. |
| 5,795,333 A | 8/1998 | Reilly et al. |
| 5,800,355 A | 9/1998 | Hasegawa |
| 5,803,914 A | 9/1998 | Ryals et al. |
| 5,806,519 A | 9/1998 | Evans, III et al. |
| 5,808,203 A | 9/1998 | Nolan, Jr. et al. |
| 5,810,742 A | 9/1998 | Pearlman |
| 5,811,814 A | 9/1998 | Leone et al. |
| 5,813,985 A | 9/1998 | Carroll |
| 5,814,015 A | 9/1998 | Gargano et al. |
| 5,818,050 A | 10/1998 | Dilmanian et al. |
| 5,821,541 A | 10/1998 | Tumer |
| 5,825,031 A | 10/1998 | Wong et al. |
| 5,827,219 A | 10/1998 | Uber, III et al. |
| 5,828,073 A | 10/1998 | Zhu et al. |
| 5,833,603 A | 11/1998 | Kovacs et al. |
| 5,838,009 A | 11/1998 | Plummer et al. |
| 5,840,026 A | 11/1998 | Uber, III et al. |
| 5,841,141 A | 11/1998 | Gullberg et al. |
| 5,842,977 A | 12/1998 | Lesho et al. |
| 5,843,037 A | 12/1998 | Uber, III |
| 5,846,513 A | 12/1998 | Carroll et al. |
| 5,847,396 A | 12/1998 | Lingren et al. |
| 5,857,463 A | 1/1999 | Thurston et al. |
| 5,871,013 A | 2/1999 | Wainer et al. |
| 5,873,861 A | 2/1999 | Hitchins et al. |
| 5,880,475 A | 3/1999 | Oka et al. |
| 5,882,338 A | 3/1999 | Gray |
| 5,884,457 A | 3/1999 | Ortiz et al. |
| 5,885,216 A | 3/1999 | Evans, III et al. |
| 5,891,030 A | 4/1999 | Johnson et al. |
| 5,893,397 A | 4/1999 | Peterson et al. |
| 5,899,885 A | 5/1999 | Reilly et al. |
| 5,900,533 A | 5/1999 | Chou |
| 5,903,008 A | 5/1999 | Li |
| 5,910,112 A | 6/1999 | Judd et al. |
| 5,911,252 A | 6/1999 | Cassel |
| 5,916,167 A | 6/1999 | Kramer et al. |
| 5,916,197 A | 6/1999 | Reilly et al. |
| 5,920,054 A | 7/1999 | Uber, III |
| 5,927,351 A | 7/1999 | Zhu et al. |
| 5,928,150 A | 7/1999 | Call |
| 5,932,879 A | 8/1999 | Raylman et al. |
| 5,938,639 A | 8/1999 | Reilly et al. |
| 5,939,724 A | 8/1999 | Eisen et al. |
| 5,944,190 A | 8/1999 | Edelen |
| 5,944,694 A | 8/1999 | Hitchins et al. |
| 5,947,935 A | 9/1999 | Rhinehart et al. |
| 5,953,884 A | 9/1999 | Lawecki et al. |
| 5,954,668 A | 9/1999 | Uber, III et al. |
| 5,961,457 A | 10/1999 | Raylman et al. |
| 5,967,983 A | 10/1999 | Ashburn |
| 5,973,598 A | 10/1999 | Beigel |
| 5,974,165 A | 10/1999 | Giger et al. |
| 5,984,860 A | 11/1999 | Shan |
| 5,987,350 A | 11/1999 | Thurston |
| 5,993,378 A | 11/1999 | Lemelson |
| 5,997,502 A | 12/1999 | Reilly et al. |
| 6,002,134 A | 12/1999 | Lingren |
| 6,002,480 A | 12/1999 | Izatt et al. |
| 6,017,330 A | 1/2000 | Hitchins et al. |
| 6,019,745 A | 2/2000 | Gray |
| 6,021,341 A | 2/2000 | Scibilia et al. |
| 6,026,317 A | 2/2000 | Verani |
| 6,032,155 A | 2/2000 | de la Huerga |
| 6,037,595 A | 3/2000 | Lingren |
| 6,040,697 A | 3/2000 | Misic |
| 6,042,565 A | 3/2000 | Hirschman et al. |
| RE36,648 E | 4/2000 | Uber, III et al. |
| 6,046,454 A | 4/2000 | Lingren et al. |
| 6,048,334 A | 4/2000 | Hirschman et al. |
| 6,052,618 A | 4/2000 | Dahlke et al. |
| 6,055,450 A | 4/2000 | Ashburn |
| 6,055,452 A | 4/2000 | Pearlman |
| RE36,693 E | 5/2000 | Reich |
| 6,063,052 A | 5/2000 | Uber et al. |
| D426,891 S | 6/2000 | Beale et al. |
| D426,892 S | 6/2000 | Beale et al. |
| 6,072,177 A | 6/2000 | McCroskey et al. |
| 6,076,009 A | 6/2000 | Raylman et al. |
| 6,080,984 A | 6/2000 | Friesenhahn |
| D428,491 S | 7/2000 | Beale et al. |
| 6,082,366 A | 7/2000 | Andra et al. |
| 6,090,064 A | 7/2000 | Reilly et al. |
| 6,091,070 A | 7/2000 | Lingren et al. |
| 6,096,011 A | 8/2000 | Trombley, III et al. |
| 6,107,102 A | 8/2000 | Ferrari |
| 6,115,635 A | 9/2000 | Bourgeois |

(56) References Cited

U.S. PATENT DOCUMENTS

| | | |
|---|---|---|
| 6,116,461 A | 9/2000 | Broadfield et al. |
| 6,129,670 A | 10/2000 | Burdette et al. |
| 6,132,372 A | 10/2000 | Essen-Moller |
| 6,135,955 A | 10/2000 | Madden et al. |
| 6,135,968 A | 10/2000 | Brounstein |
| 6,137,109 A | 10/2000 | Hayes |
| 6,145,277 A | 11/2000 | Lawecki et al. |
| 6,147,352 A | 11/2000 | Ashburn |
| 6,147,353 A | 11/2000 | Gagnon et al. |
| 6,148,229 A | 11/2000 | Morris, Sr. et al. |
| 6,149,574 A | 11/2000 | Trauthen et al. |
| 6,149,627 A | 11/2000 | Uber, III |
| 6,155,485 A | 12/2000 | Coughlin et al. |
| 6,160,398 A | 12/2000 | Walsh |
| 6,162,198 A | 12/2000 | Coffey et al. |
| 6,172,362 B1 | 1/2001 | Lingren et al. |
| 6,173,201 B1 | 1/2001 | Front |
| 6,184,530 B1 | 2/2001 | Hines et al. |
| 6,189,195 B1 | 2/2001 | Reilly et al. |
| 6,194,715 B1 | 2/2001 | Lingren et al. |
| 6,194,725 B1 | 2/2001 | Colsher et al. |
| 6,194,726 B1 | 2/2001 | Pi et al. |
| 6,197,000 B1 | 3/2001 | Reilly et al. |
| 6,202,923 B1 | 3/2001 | Boyer et al. |
| 6,203,775 B1 | 3/2001 | Torchilin et al. |
| 6,205,347 B1 | 3/2001 | Morgan et al. |
| 6,212,423 B1 | 4/2001 | Krakovitz |
| 6,223,065 B1 | 4/2001 | Misic et al. |
| 6,224,577 B1 | 5/2001 | Dedola et al. |
| 6,226,350 B1 | 5/2001 | Hsieh |
| 6,229,145 B1 | 5/2001 | Weinberg |
| 6,232,605 B1 | 5/2001 | Soluri et al. |
| 6,233,304 B1 | 5/2001 | Hu et al. |
| 6,236,050 B1 | 5/2001 | Tumer |
| 6,236,878 B1 | 5/2001 | Taylor et al. |
| 6,236,880 B1 | 5/2001 | Raylman et al. |
| 6,239,438 B1 | 5/2001 | Schubert |
| 6,240,312 B1 | 5/2001 | Alfano et al. |
| 6,241,708 B1 | 6/2001 | Reilly et al. |
| 6,242,743 B1 | 6/2001 | DeVito |
| 6,242,744 B1 | 6/2001 | Soluri et al. |
| 6,242,745 B1 | 6/2001 | Berlad et al. |
| 6,246,901 B1 | 6/2001 | Benaron |
| 6,252,924 B1 | 6/2001 | Davantes et al. |
| 6,258,576 B1 | 7/2001 | Richards-Kortum et al. |
| 6,259,095 B1 | 7/2001 | Bouton et al. |
| 6,261,562 B1 | 7/2001 | Xu et al. |
| 6,263,229 B1 | 7/2001 | Atalar et al. |
| 6,269,340 B1 | 7/2001 | Ford et al. |
| 6,270,463 B1 | 8/2001 | Morris, Sr. et al. |
| 6,271,524 B1 | 8/2001 | Wainer et al. |
| 6,271,525 B1 | 8/2001 | Majewski et al. |
| 6,280,704 B1 | 8/2001 | Schutt et al. |
| 6,281,505 B1 | 8/2001 | Hines et al. |
| 6,308,097 B1 | 10/2001 | Pearlman |
| 6,310,968 B1 | 10/2001 | Hawkins et al. |
| 6,315,981 B1 | 11/2001 | Unger |
| 6,317,623 B1 | 11/2001 | Griffiths et al. |
| 6,317,648 B1 | 11/2001 | Sleep et al. |
| 6,318,630 B1 | 11/2001 | Coughlin et al. |
| 6,322,535 B1 | 11/2001 | Hitchins et al. |
| 6,323,648 B1 | 11/2001 | Belt et al. |
| 6,324,418 B1 | 11/2001 | Crowley et al. |
| RE37,487 E | 12/2001 | Reilly et al. |
| D452,737 S | 1/2002 | Nolan, Jr. et al. |
| 6,336,913 B1 | 1/2002 | Spohn et al. |
| 6,338,007 B1 | 1/2002 | Broadfield et al. |
| 6,339,652 B1 | 1/2002 | Hawkins et al. |
| 6,339,718 B1 | 1/2002 | Zatezalo et al. |
| 6,344,745 B1 | 2/2002 | Reisker et al. |
| 6,346,706 B1 | 2/2002 | Rogers et al. |
| 6,346,886 B1 | 2/2002 | de la Huerga |
| RE37,602 E | 3/2002 | Uber, III et al. |
| 6,353,227 B1 | 3/2002 | Boxen |
| 6,355,024 B1 | 3/2002 | Small et al. |
| 6,356,081 B1 | 3/2002 | Misic |
| 6,368,331 B1 | 4/2002 | Front et al. |
| 6,371,938 B1 | 4/2002 | Reilly et al. |
| 6,375,624 B1 | 4/2002 | Uber, III et al. |
| 6,377,838 B1 | 4/2002 | Iwanczyk et al. |
| 6,381,349 B1 | 4/2002 | Zeng et al. |
| 6,385,483 B1 | 5/2002 | Uber, III et al. |
| 6,388,244 B1 | 5/2002 | Gagnon |
| 6,388,258 B1 | 5/2002 | Berlad et al. |
| 6,392,235 B1 | 5/2002 | Barrett et al. |
| 6,396,273 B2 | 5/2002 | Misic |
| 6,397,098 B1 | 5/2002 | Uber, III et al. |
| 6,399,951 B1 | 6/2002 | Paulus et al. |
| 6,401,071 B1 | 6/2002 | Hogan |
| 6,402,717 B1 | 6/2002 | Reilly et al. |
| 6,402,718 B1 | 6/2002 | Reilly et al. |
| 6,407,391 B1 | 6/2002 | Mastrippolito et al. |
| 6,408,204 B1 | 6/2002 | Hirschman |
| 6,409,987 B1 | 6/2002 | Cardin et al. |
| 6,415,046 B1 | 7/2002 | Kerut, Sr. |
| 6,420,711 B2 | 7/2002 | Tumer |
| 6,425,174 B1 | 7/2002 | Reich |
| 6,426,917 B1 | 7/2002 | Tabanou et al. |
| 6,429,431 B1 | 8/2002 | Wilk |
| 6,431,175 B1 | 8/2002 | Penner et al. |
| 6,432,089 B1 | 8/2002 | Kakimi et al. |
| 6,438,401 B1 | 8/2002 | Cheng et al. |
| 6,439,444 B1 | 8/2002 | Shields, II |
| 6,440,107 B1 | 8/2002 | Trombley, III et al. |
| 6,442,418 B1 | 8/2002 | Evans, III et al. |
| 6,448,560 B1 | 9/2002 | Tumer |
| 6,453,199 B1 | 9/2002 | Kobozev |
| 6,459,925 B1 | 10/2002 | Nields et al. |
| 6,459,931 B1 | 10/2002 | Hirschman |
| 6,468,261 B1 | 10/2002 | Small et al. |
| 6,469,306 B1 | 10/2002 | Van Dulmen et al. |
| 6,471,674 B1 | 10/2002 | Emig et al. |
| 6,475,192 B1 | 11/2002 | Reilly et al. |
| 6,480,732 B1 | 11/2002 | Tanaka et al. |
| 6,484,051 B1 | 11/2002 | Daniel |
| 6,488,661 B1 | 12/2002 | Spohn et al. |
| 6,490,476 B1 | 12/2002 | Townsend et al. |
| 6,504,157 B2 | 1/2003 | Juhi |
| 6,504,178 B2 | 1/2003 | Carlson et al. |
| 6,504,899 B2 | 1/2003 | Pugachev et al. |
| 6,506,155 B2 | 1/2003 | Sluis et al. |
| 6,510,336 B1 | 1/2003 | Daghighian et al. |
| 6,512,374 B1 | 1/2003 | Misic et al. |
| 6,516,213 B1 | 2/2003 | Nevo |
| 6,519,569 B1 | 2/2003 | White et al. |
| 6,520,930 B2 | 2/2003 | Critchlow et al. |
| 6,522,945 B2 | 2/2003 | Sleep et al. |
| 6,525,320 B1 | 2/2003 | Juni |
| 6,525,321 B2 | 2/2003 | Juni |
| 6,541,763 B2 | 4/2003 | Lingren et al. |
| 6,545,280 B2 | 4/2003 | Weinberg et al. |
| 6,549,646 B1 | 4/2003 | Yeh et al. |
| 6,560,354 B1 | 5/2003 | Maurer et al. |
| 6,562,008 B1 | 5/2003 | Reilly et al. |
| 6,563,942 B2 | 5/2003 | Takeo et al. |
| 6,565,502 B1 | 5/2003 | Bede et al. |
| 6,567,687 B2 | 5/2003 | Front et al. |
| 6,575,930 B1 | 6/2003 | Trombley, III et al. |
| 6,576,918 B1 | 6/2003 | Fu et al. |
| 6,584,348 B2 | 6/2003 | Glukhovsky |
| 6,585,700 B1 | 7/2003 | Trocki et al. |
| 6,587,710 B1 | 7/2003 | Wainer |
| 6,589,158 B2 | 7/2003 | Winkler |
| 6,591,127 B1 | 7/2003 | McKinnon |
| 6,592,520 B1 | 7/2003 | Peszynski et al. |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,620,134 B1 | 9/2003 | Trombley, III et al. |
| 6,627,893 B1 | 9/2003 | Zeng et al. |
| 6,628,983 B1 | 9/2003 | Gagnon |
| 6,628,984 B2 | 9/2003 | Weinberg |
| 6,630,735 B1 | 10/2003 | Carlson et al. |

(56) References Cited

U.S. PATENT DOCUMENTS

| | | |
|---|---|---|
| 6,631,284 B2 | 10/2003 | Nutt et al. |
| 6,632,216 B2 | 10/2003 | Houzego et al. |
| 6,633,658 B1 | 10/2003 | Dabney et al. |
| 6,635,879 B2 | 10/2003 | Jimbo et al. |
| 6,638,752 B2 | 10/2003 | Contag et al. |
| 6,643,537 B1 | 11/2003 | Zatezalo et al. |
| 6,643,538 B1 | 11/2003 | Majewski et al. |
| 6,652,489 B2 | 11/2003 | Trocki et al. |
| 6,657,200 B2 | 12/2003 | Nygard et al. |
| 6,662,036 B2 | 12/2003 | Cosman |
| 6,664,542 B2 | 12/2003 | Ye et al. |
| 6,670,258 B2 | 12/2003 | Carlson et al. |
| 6,671,563 B1 | 12/2003 | Engelson et al. |
| 6,673,033 B1 | 1/2004 | Sciulli et al. |
| 6,674,834 B1 | 1/2004 | Acharya et al. |
| 6,676,634 B1 | 1/2004 | Spohn et al. |
| 6,677,182 B2 | 1/2004 | Carlson et al. |
| 6,677,755 B2 | 1/2004 | Belt et al. |
| 6,680,750 B1 | 1/2004 | Tournier et al. |
| 6,685,678 B2 | 2/2004 | Evans et al. |
| 6,694,172 B1 | 2/2004 | Gagnon et al. |
| 6,697,660 B1 | 2/2004 | Robinson |
| 6,699,219 B2 | 3/2004 | Emig et al. |
| 6,704,592 B1 | 3/2004 | Reynolds et al. |
| 6,713,766 B2 | 3/2004 | Garrard et al. |
| 6,714,012 B2 | 3/2004 | Belt et al. |
| 6,714,013 B2 | 3/2004 | Misic |
| 6,716,195 B2 | 4/2004 | Nolan, Jr. et al. |
| 6,722,499 B2 | 4/2004 | Reich |
| 6,723,988 B1 | 4/2004 | Wainer |
| 6,726,657 B1 | 4/2004 | Dedig et al. |
| 6,728,583 B2 | 4/2004 | Hallett |
| 6,731,971 B2 | 5/2004 | Evans, III et al. |
| 6,731,989 B2 | 5/2004 | Engleson et al. |
| 6,733,477 B2 | 5/2004 | Cowan et al. |
| 6,733,478 B2 | 5/2004 | Reilly et al. |
| 6,734,416 B2 | 5/2004 | Carlson et al. |
| 6,734,430 B2 | 5/2004 | Soluri et al. |
| 6,737,652 B2 | 5/2004 | Lanza et al. |
| 6,737,866 B2 | 5/2004 | Belt et al. |
| 6,740,882 B2 | 5/2004 | Weinberg et al. |
| 6,743,202 B2 | 6/2004 | Hirschman et al. |
| 6,743,205 B2 | 6/2004 | Nolan, Jr. et al. |
| 6,747,454 B2 | 6/2004 | Belt |
| 6,748,259 B1 | 6/2004 | Benaron et al. |
| 6,751,500 B2 | 6/2004 | Hirschman et al. |
| 6,765,981 B2 | 7/2004 | Heumann |
| 6,766,048 B1 | 7/2004 | Launay et al. |
| 6,767,319 B2 * | 7/2004 | Reilly et al. .................. 600/5 |
| 6,771,802 B1 | 8/2004 | Patt et al. |
| 6,774,358 B2 | 8/2004 | Hamill et al. |
| 6,776,977 B2 | 8/2004 | Liu |
| 6,787,777 B1 | 9/2004 | Gagnon et al. |
| 6,788,758 B2 | 9/2004 | De Villiers |
| 6,798,206 B2 | 9/2004 | Misic |
| 6,808,513 B2 | 10/2004 | Reilly et al. |
| 6,813,868 B2 | 11/2004 | Baldwin et al. |
| 6,821,013 B2 | 11/2004 | Reilly et al. |
| 6,822,237 B2 | 11/2004 | Inoue et al. |
| 6,833,705 B2 | 12/2004 | Misic |
| 6,838,672 B2 | 1/2005 | Wagenaar et al. |
| 6,841,782 B1 | 1/2005 | Balan et al. |
| 6,843,357 B2 | 1/2005 | Bybee et al. |
| 6,851,615 B2 | 2/2005 | Jones |
| 6,861,954 B2 | 3/2005 | Levin |
| 6,866,654 B2 | 3/2005 | Callan et al. |
| 6,870,175 B2 | 3/2005 | Dell et al. |
| 6,881,043 B2 | 4/2005 | Barak |
| 6,888,351 B2 | 5/2005 | Belt et al. |
| 6,889,074 B2 | 5/2005 | Uber, III et al. |
| 6,897,658 B2 | 5/2005 | Belt et al. |
| 6,901,283 B2 | 5/2005 | Evans, III et al. |
| 6,906,330 B2 | 6/2005 | Blevis et al. |
| D507,832 S | 7/2005 | Yanniello et al. |
| 6,915,170 B2 | 7/2005 | Engleson et al. |
| 6,915,619 B2 | 7/2005 | Baldwin |
| 6,915,823 B2 | 7/2005 | Osborne et al. |
| 6,917,828 B2 | 7/2005 | Fukuda |
| 6,921,384 B2 | 7/2005 | Reilly et al. |
| 6,928,142 B2 | 8/2005 | Shao et al. |
| 6,935,560 B2 | 8/2005 | Andreasson et al. |
| 6,936,030 B1 | 8/2005 | Pavlik et al. |
| 6,937,750 B2 | 8/2005 | Natanzon et al. |
| 6,939,302 B2 | 9/2005 | Griffiths et al. |
| 6,940,070 B2 | 9/2005 | Turner |
| 6,943,355 B2 | 9/2005 | Shwartz et al. |
| 6,957,522 B2 | 10/2005 | Baldwin et al. |
| 6,958,053 B1 | 10/2005 | Reilly |
| 6,963,770 B2 | 11/2005 | Scarantino et al. |
| 6,970,735 B2 | 11/2005 | Uber, III et al. |
| 6,972,001 B2 | 12/2005 | Emig et al. |
| 6,974,443 B2 | 12/2005 | Reilly et al. |
| 6,976,349 B2 | 12/2005 | Baldwin et al. |
| 6,984,222 B1 | 1/2006 | Hitchins et al. |
| 6,985,870 B2 | 1/2006 | Martucci et al. |
| 6,988,981 B2 | 1/2006 | Hamazaki |
| 6,994,249 B2 | 2/2006 | Peterka et al. |
| 7,009,183 B2 | 3/2006 | Wainer et al. |
| 7,011,814 B2 | 3/2006 | Suddarth et al. |
| 7,012,430 B2 | 3/2006 | Misic |
| 7,017,622 B2 | 3/2006 | Osborne et al. |
| 7,018,363 B2 | 3/2006 | Cowan et al. |
| 7,019,783 B2 | 3/2006 | Kindem et al. |
| 7,025,757 B2 | 4/2006 | Reilly et al. |
| 7,026,623 B2 | 4/2006 | Oaknin et al. |
| 7,043,063 B1 | 5/2006 | Noble et al. |
| 7,102,138 B2 | 9/2006 | Belvis et al. |
| 7,103,204 B1 | 9/2006 | Celler et al. |
| 7,127,026 B2 | 10/2006 | Amemiya et al. |
| 7,142,634 B2 | 11/2006 | Engler et al. |
| 7,145,986 B2 | 12/2006 | Wear et al. |
| 7,147,372 B2 | 12/2006 | Nelson et al. |
| 7,164,130 B2 | 1/2007 | Welsh et al. |
| 7,176,466 B2 | 2/2007 | Rousso et al. |
| 7,187,790 B2 | 3/2007 | Sabol et al. |
| 7,217,953 B2 | 5/2007 | Carlson |
| 7,256,386 B2 | 8/2007 | Carlson et al. |
| 7,327,822 B2 | 2/2008 | Sauer et al. |
| 7,359,535 B2 | 4/2008 | Salla et al. |
| 7,373,197 B2 | 5/2008 | Daighighian et al. |
| 7,394,923 B2 | 7/2008 | Zou et al. |
| 7,444,010 B2 | 10/2008 | De Man |
| 7,468,513 B2 | 12/2008 | Charron et al. |
| 7,470,896 B2 | 12/2008 | Pawlak et al. |
| 7,490,085 B2 | 2/2009 | Walker et al. |
| 7,495,225 B2 | 2/2009 | Hefetz et al. |
| 7,502,499 B2 | 3/2009 | Grady |
| 7,570,732 B2 | 8/2009 | Stanton et al. |
| 7,592,597 B2 | 9/2009 | Hefetz et al. |
| 7,620,444 B2 | 11/2009 | Le et al. |
| 7,627,084 B2 | 12/2009 | Jabri et al. |
| 7,652,259 B2 | 1/2010 | Kimchy et al. |
| 7,671,331 B2 | 3/2010 | Hefetz |
| 7,672,491 B2 | 3/2010 | Krishnan et al. |
| 7,680,240 B2 | 3/2010 | Manjeshwar et al. |
| 7,705,316 B2 | 4/2010 | Rousso et al. |
| 7,734,331 B2 * | 6/2010 | Dhawale et al. .............. 600/431 |
| 7,826,889 B2 | 11/2010 | David et al. |
| 7,831,024 B2 | 11/2010 | Metzler et al. |
| 7,835,927 B2 * | 11/2010 | Schlotterbeck et al. .......... 705/3 |
| 7,872,235 B2 | 1/2011 | Rousso et al. |
| 7,894,650 B2 | 2/2011 | Weng et al. |
| 7,968,851 B2 | 6/2011 | Rousso et al. |
| 8,013,308 B2 | 9/2011 | Guerin et al. |
| 8,055,329 B2 | 11/2011 | Kimchy et al. |
| 8,111,886 B2 | 2/2012 | Rousso et al. |
| 8,158,951 B2 | 4/2012 | Bal et al. |
| 8,204,500 B2 | 6/2012 | Weintraub et al. |
| 8,338,788 B2 | 12/2012 | Zilberstein et al. |
| 2001/0016029 A1 | 8/2001 | Tumer |
| 2001/0020131 A1 | 9/2001 | Kawagishi et al. |
| 2001/0035902 A1 | 11/2001 | Iddan et al. |
| 2001/0049608 A1 | 12/2001 | Hochman |
| 2002/0068864 A1 | 6/2002 | Bishop et al. |

(56) References Cited

U.S. PATENT DOCUMENTS

| | | |
|---|---|---|
| 2002/0072784 A1 | 6/2002 | Sheppard, Jr. et al. |
| 2002/0085748 A1 | 7/2002 | Baumberg |
| 2002/0087101 A1 | 7/2002 | Barrick et al. |
| 2002/0099295 A1 | 7/2002 | Gil et al. |
| 2002/0099310 A1 | 7/2002 | Kimchy et al. |
| 2002/0099334 A1 | 7/2002 | Hanson et al. |
| 2002/0103429 A1 | 8/2002 | DeCharms |
| 2002/0103431 A1 | 8/2002 | Toker et al. |
| 2002/0145114 A1 | 10/2002 | Inoue et al. |
| 2002/0148970 A1 | 10/2002 | Wong et al. |
| 2002/0165491 A1 | 11/2002 | Reilly |
| 2002/0168094 A1 | 11/2002 | Kaushikkar et al. |
| 2002/0168317 A1 | 11/2002 | Daighighian et al. |
| 2002/0172405 A1 | 11/2002 | Schultz |
| 2002/0179843 A1 | 12/2002 | Tanaka et al. |
| 2002/0183645 A1 | 12/2002 | Nachaliel |
| 2002/0188197 A1 | 12/2002 | Bishop et al. |
| 2002/0198738 A1 | 12/2002 | Osborne |
| 2003/0001098 A1 | 1/2003 | Stoddart et al. |
| 2003/0001837 A1 | 1/2003 | Baumberg |
| 2003/0006376 A1 | 1/2003 | Tumer |
| 2003/0013950 A1 | 1/2003 | Rollo et al. |
| 2003/0013966 A1 | 1/2003 | Barnes et al. |
| 2003/0038240 A1 | 2/2003 | Weinberg |
| 2003/0055685 A1 | 3/2003 | Cobb et al. |
| 2003/0063787 A1 | 4/2003 | Natanzon et al. |
| 2003/0071219 A1 | 4/2003 | Motomura et al. |
| 2003/0081716 A1 | 5/2003 | Tumer |
| 2003/0135388 A1 | 7/2003 | Martucci et al. |
| 2003/0136912 A1 | 7/2003 | Juni |
| 2003/0144322 A1 | 7/2003 | Kozikowski et al. |
| 2003/0147887 A1 | 8/2003 | Wang et al. |
| 2003/0158481 A1 | 8/2003 | Stotzka et al. |
| 2003/0183226 A1 | 10/2003 | Brand et al. |
| 2003/0189174 A1 | 10/2003 | Tanaka et al. |
| 2003/0191430 A1 | 10/2003 | D'Andrea et al. |
| 2003/0202629 A1 | 10/2003 | Dunham et al. |
| 2003/0208117 A1 | 11/2003 | Shwartz et al. |
| 2003/0215122 A1 | 11/2003 | Tanaka |
| 2003/0215124 A1 | 11/2003 | Li |
| 2003/0216631 A1 | 11/2003 | Bloch et al. |
| 2003/0219149 A1 | 11/2003 | Vailaya et al. |
| 2004/0003001 A1 | 1/2004 | Shimura |
| 2004/0010397 A1 | 1/2004 | Barbour et al. |
| 2004/0015075 A1 | 1/2004 | Kimchy et al. |
| 2004/0021065 A1 | 2/2004 | Weber |
| 2004/0044282 A1 | 3/2004 | Mixon et al. |
| 2004/0051368 A1 | 3/2004 | Caputo et al. |
| 2004/0054248 A1 | 3/2004 | Kimchy et al. |
| 2004/0054278 A1 | 3/2004 | Kimchy et al. |
| 2004/0065838 A1 | 4/2004 | Tumer |
| 2004/0075058 A1 | 4/2004 | Blevis et al. |
| 2004/0081623 A1 | 4/2004 | Eriksen et al. |
| 2004/0082918 A1 | 4/2004 | Evans et al. |
| 2004/0084340 A1 | 5/2004 | Morelle et al. |
| 2004/0086437 A1 | 5/2004 | Jackson et al. |
| 2004/0101176 A1 | 5/2004 | Mendonca et al. |
| 2004/0101177 A1 | 5/2004 | Zahlmann et al. |
| 2004/0116807 A1 | 6/2004 | Amrami et al. |
| 2004/0120557 A1 | 6/2004 | Sabol |
| 2004/0122311 A1 | 6/2004 | Cosman |
| 2004/0125918 A1 | 7/2004 | Shanmugaval et al. |
| 2004/0138557 A1 | 7/2004 | Le et al. |
| 2004/0143449 A1* | 7/2004 | Behrenbruch et al. ............ 705/1 |
| 2004/0144925 A1 | 7/2004 | Stoddart et al. |
| 2004/0153128 A1 | 8/2004 | Suresh et al. |
| 2004/0156081 A1 | 8/2004 | Bril et al. |
| 2004/0162492 A1 | 8/2004 | Kobayashi |
| 2004/0171924 A1 | 9/2004 | Mire et al. |
| 2004/0183022 A1 | 9/2004 | Weinberg |
| 2004/0184644 A1 | 9/2004 | Leichter et al. |
| 2004/0193453 A1 | 9/2004 | Butterfield et al. |
| 2004/0195512 A1 | 10/2004 | Crosetto |
| 2004/0204646 A1 | 10/2004 | Nagler et al. |
| 2004/0205343 A1 | 10/2004 | Forth et al. |
| 2004/0210126 A1 | 10/2004 | Hajaj et al. |
| 2004/0238743 A1 | 12/2004 | Gravrand et al. |
| 2004/0251419 A1 | 12/2004 | Nelson et al. |
| 2004/0253177 A1 | 12/2004 | Elmaleh et al. |
| 2004/0263865 A1 | 12/2004 | Pawlak et al. |
| 2005/0001170 A1 | 1/2005 | Juni |
| 2005/0006589 A1 | 1/2005 | Joung et al. |
| 2005/0020898 A1 | 1/2005 | Vosniak et al. |
| 2005/0020915 A1 | 1/2005 | Belardinelli et al. |
| 2005/0023474 A1 | 2/2005 | Persyk et al. |
| 2005/0029277 A1 | 2/2005 | Tachibana |
| 2005/0033157 A1 | 2/2005 | Klein et al. |
| 2005/0049487 A1 | 3/2005 | Johnson et al. |
| 2005/0055174 A1 | 3/2005 | David et al. |
| 2005/0056788 A1 | 3/2005 | Juni |
| 2005/0074402 A1 | 4/2005 | Cagnolini et al. |
| 2005/0088306 A1 | 4/2005 | Andreasson |
| 2005/0107698 A1 | 5/2005 | Powers et al. |
| 2005/0107914 A1 | 5/2005 | Engleson et al. |
| 2005/0108044 A1 | 5/2005 | Koster |
| 2005/0113945 A1 | 5/2005 | Engleson et al. |
| 2005/0121505 A1 | 6/2005 | Metz et al. |
| 2005/0131270 A1 | 6/2005 | Weil et al. |
| 2005/0131397 A1 | 6/2005 | Levin |
| 2005/0131579 A1 | 6/2005 | Andreasson |
| 2005/0145797 A1 | 7/2005 | Oaknin et al. |
| 2005/0148869 A1 | 7/2005 | Masuda |
| 2005/0149350 A1 | 7/2005 | Kerr et al. |
| 2005/0156115 A1 | 7/2005 | Kobayashi et al. |
| 2005/0171815 A1 | 8/2005 | Vanderveen |
| 2005/0173643 A1 | 8/2005 | Tumer |
| 2005/0187465 A1 | 8/2005 | Motomura et al. |
| 2005/0198800 A1 | 9/2005 | Reich |
| 2005/0203389 A1 | 9/2005 | Williams |
| 2005/0205792 A1 | 9/2005 | Rousso et al. |
| 2005/0205796 A1 | 9/2005 | Bryman |
| 2005/0211909 A1 | 9/2005 | Smith |
| 2005/0215889 A1 | 9/2005 | Patterson, II |
| 2005/0234424 A1 | 10/2005 | Besing et al. |
| 2005/0240441 A1 | 10/2005 | Suzuki |
| 2005/0247893 A1 | 11/2005 | Fu et al. |
| 2005/0253073 A1 | 11/2005 | Joram et al. |
| 2005/0261936 A1 | 11/2005 | Silverbrook et al. |
| 2005/0261937 A1 | 11/2005 | Silverbrook et al. |
| 2005/0261938 A1 | 11/2005 | Silverbrook et al. |
| 2005/0266074 A1 | 12/2005 | Zilberstein et al. |
| 2005/0277833 A1 | 12/2005 | Williams, Jr. |
| 2005/0277911 A1 | 12/2005 | Stewart et al. |
| 2005/0278066 A1 | 12/2005 | Graves et al. |
| 2005/0288869 A1 | 12/2005 | Kroll et al. |
| 2006/0000983 A1 | 1/2006 | Charron et al. |
| 2006/0033028 A1 | 2/2006 | Juni |
| 2006/0036157 A1 | 2/2006 | Tumer |
| 2006/0072799 A1 | 4/2006 | McLain |
| 2006/0074290 A1 | 4/2006 | Chen et al. |
| 2006/0104519 A1 | 5/2006 | Stoeckel et al. |
| 2006/0109950 A1 | 5/2006 | Arenson et al. |
| 2006/0122503 A1 | 6/2006 | Burbank et al. |
| 2006/0145081 A1 | 7/2006 | Hawman |
| 2006/0160157 A1 | 7/2006 | Zuckerman |
| 2006/0188136 A1 | 8/2006 | Ritt et al. |
| 2006/0214097 A1 | 9/2006 | Wang et al. |
| 2006/0237652 A1 | 10/2006 | Kimchy et al. |
| 2006/0257012 A1 | 11/2006 | Kaufman et al. |
| 2007/0116170 A1 | 5/2007 | De Man et al. |
| 2007/0133852 A1 | 6/2007 | Collins et al. |
| 2007/0156047 A1 | 7/2007 | Nagler et al. |
| 2007/0166227 A1 | 7/2007 | Liu et al. |
| 2007/0189436 A1 | 8/2007 | Goto et al. |
| 2007/0194241 A1 | 8/2007 | Rousso et al. |
| 2007/0265230 A1 | 11/2007 | Rousso et al. |
| 2008/0001090 A1 | 1/2008 | Ben-Haim et al. |
| 2008/0029704 A1 | 2/2008 | Hefetz et al. |
| 2008/0033291 A1 | 2/2008 | Rousso et al. |
| 2008/0036882 A1 | 2/2008 | Uemura et al. |
| 2008/0039721 A1 | 2/2008 | Shai et al. |
| 2008/0042067 A1 | 2/2008 | Rousso et al. |
| 2008/0128626 A1 | 6/2008 | Rousso et al. |
| 2008/0137938 A1 | 6/2008 | Zahniser |

(56) References Cited

U.S. PATENT DOCUMENTS

| | | |
|---|---|---|
| 2008/0230702 A1 | 9/2008 | Rousso et al. |
| 2008/0230705 A1 | 9/2008 | Rousso et al. |
| 2008/0237482 A1 | 10/2008 | Shahar et al. |
| 2008/0260228 A1 | 10/2008 | Dichterman et al. |
| 2008/0260580 A1 | 10/2008 | Helle et al. |
| 2008/0260637 A1 | 10/2008 | Dickman |
| 2008/0277591 A1 | 11/2008 | Shahar et al. |
| 2009/0001273 A1 | 1/2009 | Hawman |
| 2009/0018412 A1 | 1/2009 | Schmitt |
| 2009/0078875 A1 | 3/2009 | Rousso et al. |
| 2009/0112086 A1 | 4/2009 | Melman |
| 2009/0152471 A1 | 6/2009 | Rousso et al. |
| 2009/0190807 A1 | 7/2009 | Rousso et al. |
| 2009/0201291 A1 | 8/2009 | Ziv et al. |
| 2009/0236532 A1 | 9/2009 | Frach et al. |
| 2009/0304582 A1 | 12/2009 | Rousso et al. |
| 2010/0006770 A1 | 1/2010 | Balakin |
| 2010/0021378 A1 | 1/2010 | Rousso et al. |
| 2010/0102242 A1 | 4/2010 | Burr et al. |
| 2010/0121184 A1 | 5/2010 | Dhawale et al. |
| 2010/0140483 A1 | 6/2010 | Rousso et al. |
| 2010/0202664 A1 | 8/2010 | Busch et al. |
| 2010/0245354 A1 | 9/2010 | Rousso et al. |
| 2012/0106820 A1 | 5/2012 | Rousso et al. |
| 2012/0172699 A1 | 7/2012 | Nagler et al. |
| 2012/0248320 A1 | 10/2012 | Wangerin et al. |
| 2012/0326034 A1 | 12/2012 | Sachs et al. |
| 2013/0114792 A1 | 5/2013 | Zilberstein et al. |

FOREIGN PATENT DOCUMENTS

| | | |
|---|---|---|
| DE | 19815362 | 10/1999 |
| EP | 0273257 | 7/1988 |
| EP | 0525954 | 2/1993 |
| EP | 0526970 | 2/1993 |
| EP | 0543626 | 5/1993 |
| EP | 0592093 | 4/1994 |
| EP | 0697193 | 2/1996 |
| EP | 0813692 | 12/1997 |
| EP | 0887661 | 12/1998 |
| EP | 1237013 | 9/2002 |
| GB | 2031142 | 4/1980 |
| JP | 59-141084 | 8/1984 |
| JP | 61-026879 | 2/1986 |
| JP | 01-324568 | 6/1986 |
| JP | 03-121549 | 5/1991 |
| JP | 04-151120 | 5/1992 |
| JP | 06-109848 | 4/1994 |
| JP | 07-059763 | 3/1995 |
| JP | 07-141523 | 6/1995 |
| JP | 08-292268 | 11/1996 |
| JP | 10-260258 | 9/1998 |
| JP | 11-072564 | 3/1999 |
| WO | WO 92/00402 | 1/1992 |
| WO | WO 98/16852 | 4/1998 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/18294 | 4/2000 |
| WO | WO 00/22975 | 4/2000 |
| WO | WO 00/31522 | 6/2000 |
| WO | WO 00/38197 | 6/2000 |
| WO | WO 01/89384 | 11/2001 |
| WO | WO 02/16965 | 2/2002 |
| WO | WO 02/058531 | 8/2002 |
| WO | WO 02/075357 | 9/2002 |
| WO | WO 03/073938 | 9/2003 |
| WO | WO 03/086170 | 10/2003 |
| WO | WO 2004/004787 | 1/2004 |
| WO | WO 2004/032151 | 4/2004 |
| WO | WO 2004/042546 | 5/2004 |
| WO | WO 2004/113951 | 12/2004 |
| WO | WO 2005/002971 | 1/2005 |
| WO | WO 2005/059592 | 6/2005 |
| WO | WO 2005/059840 | 6/2005 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

An Office Action dated Feb. 4, 2011, which issued during the prosecution of Applicant's U.S. Appl. No. 11/750,057.
Final Office Action Dated Oct. 7, 2011 in U.S. Appl. No. 11/750,057.
Final Office Action Dated Oct. 7, 2011 in U.S. Appl. No. 11/932,872.
Non-Final Office Action Dated Dec. 22, 2011 in U.S. Appl. No. 12/514,785.
Non-Final Office Action Dated May 12, 2011 in U.S. Appl. No. 11/747,378.
An Office action dated Nov. 8, 2011, which issued during the prosecution of U.S. Appl. No. 12/309,479.
An Office Action dated Dec. 20, 2011, which issued during the prosecution of U.S. Appl. No. 12/309,479.
An Office Action dated Dec. 22, 2011, which issued during the prosecution of EP Patent Application No. 06756258.7.
Links JM Ann Nucl Med Sci; 13: 107-120, Revised and accepted Jan. 22, 2000.
Berman et al. Nucl. Cardiol. 1994, 12(2), 261-270.
Degrado et al. J. Nucl Cardiol. 2000, 7, 686-700.
David R Gilland et al: "Long Focal Length, Asymmetric Fan Beam Collimation for Transmission Acquisition with a Triple Camera SPECT System crossref idref=fn1 typeref=fnote This work was supported by PHS grants CA33541 and HL52162 and DOE grant DE-FG02-96ER62150./crossref", IEEE Transactions on Nuclear Science. IEEE Service Center, New York, NY, US, vol. 44, No. 3, Jun. 1, 1997 pp. 1191-1196, XP011087666, ISSN: 0018-9499, DOI:10. 1109/23.596986.
Lisha Zhang et al: "Potential of a Compton camera for high performance scintimammography; Compton scintimammography", Physics in Medicine and Biology, Taylor and Francis Ltd. London, GB, vol. 49 No. 4, Feb. 21, 2004, pp. 617-638, XP020024019, ISBN: 0031-9155, DOI:10.1088/0031-9155/49/011.
Ellestad Mervyn H: "Stress testing: principles and practice (Fifth edition)", Jan. 1, 2003, p. 432, XP008143015, ISBN: 0-19-515928-4.
Meyers Art et al: "Age, perfusion test results and dipyridamole reaction", Radiologic Technology, Grune and Stratton, Orlando, FL, US, vol. 73 No. 5, May 1, 2002, pp. 409-414, XP008142909, ISSN: 0033-8397.
Applicant-Initiated Interview Summary Dated Jan. 28, 2013 From the US Patent and Trademark Office Re.: U.S. Appl. No. 11/798,017.
Official Action Dated Feb. 7, 2013 From the US Patent and Trademark Office Re. U.S. Appl. No. 11/980,653.
Advisory Action Before the Filing of an Appeal Brief Dated Feb. 26, 2013 From the US Patent and Trademark Office Re. U.S. Appl. No. 12/514,785.
Notice of Allowance Dated Feb. 21, 2013 From the US Patent and Trademark Office Re. U.S. Appl. No. 11/798,017.
Communication Under Rule 71(3) EPC Dated Feb. 26, 2013 From the European Patent Office Re. Application No. 06756259.5.
Official Action Dated Feb. 22, 2013 From the US Patent and Trademark Office Re.: U.S. Appl. No. 10/616,307.
Advisory Action before the Filing of an Appeal Brief Dated May 21, 2013 From the US Patent and Trademark Office Re. U.S. Appl. No. 11/980,653.

(56) References Cited

OTHER PUBLICATIONS

Applicant-Initiated Interview Summary Dated May 9, 2013 From the US Patent and Trademark Office Re. U.S. Appl. No. 12/448,473.
Notice of Allowance Dated Jun. 14, 2013 From the US Patent and Trademark Office Re. U.S. Appl. No. 10/616,307.
Official Action Dated Jun. 12, 2013 From the US Patent and Trademark Office Re. U.S. Appl. No. 12/087,150.
Bacharach et al. "Attenuation Correction in Cardiac Positron Emission Tomography and Single-Photon Emission Computed Tomography", Journal of Nucelar Cardiology, 2(3): 246-255, 1995.
Uni Magdeburg "Attenuation Map", University of Magdeburg, Germany, Retrieved From the Internet, Archived on Jul. 31, 2002.
Zaidi et al. "Determination of the Attenuation Map in Emission Tomography", Journal of Nuclear Medicine, 44(2): 291-315, 2003.
Advisory Action Before the Filing of an Appeal Brief Dated Jul. 12, 2012 From the US Patent and Trademark Office Re. U.S. Appl. No. 11/667,793.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Appeal Brief Dated Jan. 19, 2010 to Notice of Appeal of Nov. 16, 2009 From the US Patent and Trademark Office Re.: U.S. Appl. No. 10/616,301.
Communication Pursuant to Article 93(3) EPC Dated Mar. 8, 2010 From the European Patent Office Re.: Application No. 06832278.3.
Communication Pursuant to Article 94(3) EPC Dated Mar. 2, 2011 From the European Patent Office Re.: Application No. 06756259.5.
Communication Pursuant to Article 94(3) EPC Dated Mar. 8, 2010 From the European Patent Office Re.: Application No. 06832278.3.
Communication Pursuant to Article 94(3) EPC Dated Jun. 11, 2012 From the European Patent Office Re.: Application No. 06756259.5.
Communication Pursuant to Article 94(3) EPC Dated May 12, 2010 From the European Patent Office Re. Application No. 06809851.6.
Communication Pursuant to Article 94(3) EPC Dated May 12, 2010 From the European Patent Office Re.: Application No. 06809851.6.
Communication Pursuant to Article 94(3) EPC Dated Apr. 16, 2010 From the European Patent Office Re. Application No. 01951883.6.
Communication Pursuant to Article 94(3) EPC Dated Sep. 17, 2012 From the European Patent Office Re. Application No. 06832278.3.
Communication Pursuant to Article 94(3) EPC Dated Nov. 18, 2011 From the European Patent Office Re. Application No. 05803689.8.
Communication Pursuant to Article 94(3) EPC Dated Oct. 21, 2009 From the European Patent Office Re.: Application No. 02716285.8.
Communication Pursuant to Article 94(3) EPC Dated Jul. 22, 2009 From the European Patent Office Re.: Application No. 06809851.6.
Communication Pursuant to Article 94(3) EPC Dated Sep. 23, 2011 From the European Patent Office Re.: Application No. 06832278.3.
Communication Pursuant to Article 94(3) EPC Dated May 29, 2012 From the European Patent Office Re. Application No. 05803689.8.
Communication Pursuant to Article 96(2) EPC Dated Jun. 19, 2006 From the European Patent Office Re.: Application No. 03810570.6.
Communication Pursuant to Article 96(2) EPC Dated Aug. 30, 2007 From the European Patent Office Re.: Application No. 03810570.6.
Communication Pursuant to Rules 70(2) and 70a(2) EPC Dated Apr. 4, 2011 From the European Patent Office Re. Application No. 05803689.8.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
Communication Under Rule 71(3) EPC Dated May 30, 2012 From the European Patent Office Re.: Application No. 02716285.8.
Examination Report Dated Jun. 22, 2011 From the Government of India, Patent Office, Intellectual Property Building Re. Application No. 2963/CHENP/2006.
International Preliminary Report on Patentability Dated Apr. 7, 2009 From the International Bureau of WIPO Re. Application No. PCT/IL2007/000918.
International Preliminary Report on Patentability Dated Jan. 13, 2009 From the International Bureau of WIPO Re. Application No. PCT/IL2006/000834.
International Preliminary Report on Patentability Dated May 14, 2008 From the International Bureau of WIPO Re. Application No. PCT/IL2006/001291.
International Preliminary Report on Patentability Dated May 15, 2007 From the International Bureau of WIPO Re. Application No. PCT/IL2005/001173.
International Preliminary Report on Patentability Dated Apr. 16, 2009 From the International Bureau of WIPO Re.: Application No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Oct. 10, 2006 From the International Searching Authority of the Patent Cooperation Treaty Re.: Application No. PCT/IL06/00059.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Jul. 1, 2008 From the International Searching Authority Re. Application No. PCT/IL2006/000834.
International Search Report Dated Nov. 1, 2007 From the International Searching Authority of the Patent Cooperation Treaty Re.: Application No. PCT/IL06/00840.
International Search Report Dated Jul. 2, 2007 From the International Searching Authority of the Patent Cooperation Treaty Re.: Application No. PCT/IL2006/001291.
International Search Report Dated Jul. 2, 2007 From the International Searching Authority Re. Application No. PCT/IL2006/001291.
International Search Report Dated Aug. 3, 2006 From the International Searching Authority of the Patent Cooperation Treaty Re.: Application No. PCT/IL05/001173.
International Search Report Dated Aug. 3, 2006 From the International Searching Authority Re. Application No. PCT/IL2005/001173.
International Search Report Dated Jul. 11, 2008 From the International Searching Authority of the Patent Cooperation Treaty Re.: Application No. PCT/IL06/01511.
International Search Report Dated May 11, 2006 From the International Searching Authority of the Patent Cooperation Treaty Re.: Application No. PCT/IL05/001215.

(56) References Cited

OTHER PUBLICATIONS

International Search Report Dated Sep. 11, 2002 From the International Searching Authority of the Patent Cooperation Treaty Re.: Application No. PCT/IL01/00638.
International Search Report Dated Sep. 12, 2002 From the International Searching Authority of the Patent Cooperation Treaty Re: Application No. PCT/IL02/00057.
International Search Report Dated Oct. 15, 2008 From the International Searching Authority Re. Application No. PCT/2007/000918.
International Search Report Dated Oct. 15, 2008 From the International Searching Authority Re.: Application No. PCT/IL07/00918.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.
International Search Report Dated May 24, 2007 From the International Searching Authority of the Patent Cooperation Treaty Re.: Application No. PCT/IL05/00575.
International Search Report Dated Mar. 26, 2007 From the International Searching Authority of the Patent Cooperation Treaty Re.: Application No. PCT/IL05/00394.
Interview Summary Dated Mar. 25, 2011 From the US Patent and Trademark Office Re.: U.S. Appl. No. 10/836,223.
Interview Summary Dated May 31, 2011 From the US Patent and Trademark Office Re. U.S. Appl. No. 10/616,301.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Notice of Allowance Dated Feb. 2, 2012 From the US Patent and Trademark Office Re. U.S. Appl. No. 11/628,074.
Notice of Allowance Dated May 5, 2011 From the US Patent and Trademark Office Re.: U.S. Appl. No. 10/240,239.
Notice of Allowance Dated May 6, 2011 From the US Patent and Trademark Office Re. U.S. Appl. No. 11/980,617.
Notice of Allowance Dated Oct. 11, 2011 From the US Patent and Trademark Office Re. U.S. Appl. No. 11/988,926.
Notice of Allowance Dated Nov. 15, 2010 From the US Patent and Trademark Office Re. U.S. Appl. No. 10/616,301.
Notice of Allowance Dated Jul. 16, 2009 From the US Patent and Trademark Office Re.: U.S. Appl. No. 12/084,559.
Notice of Allowance Dated Sep. 16, 2011 From the US Patent and Trademark Office Re.: U.S. Appl. No. 11/607,075.
Notice of Allowance Dated Dec. 17, 2010 From the US Patent and Trademark Office Re. U.S. Appl. No. 11/980,617.
Notice of Allowance Dated Sep. 17, 2009 From the US Patent and Trademark Office Re.: U.S. Appl. No. 10/533,568. Suppl. IDS VIII in 25855.
Notice of Allowance Dated Jul. 22, 2010 From the US Patent and Trademark Office Re.: U.S. Appl. No. 11/794,799.
Notice of Allowance Dated Feb. 23, 2011 From the US Patent and Trademark Office Re.: U.S. Appl. No. 12/728,383.
Notice of Allowance Dated Jun. 23, 2011 From the US Patent and Trademark Office Re.: U.S. Appl. No. 10/616,301.
Notice of Allowance Dated Nov. 23, 2009 From the US Patent and Trademark Office Re.: U.S. Appl. No. 12/084,559.
Notice of Allowance Dated Aug. 25, 2010 From the US Patent and Trademark Office Re. U.S. Appl. No. 11/980,617.
Notice of Allowance Dated Sep. 28, 2012 From the US Patent and Trademark Office Re. U.S. Appl. No. 12/792,856.
Notice of Allowance Dated Jun. 30, 2010 From the United States Patent and Trademark Office Re.: U.S. Appl. No. 09/727,464.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Notice of Non-Compliant Amendment Dated Feb. 14, 2011 From the US Patent and Trademark Office Re.: U.S. Appl. No. 10/616,307.
Notice of Panel Decision From Pre-Appeal Brief Review Dated Feb. 29, 2012 From the US Patent and Trademark Office Re.: U.S. Appl. No. 10/836,223.
Office Action Dated Dec. 2, 2007 From the Israeli Patent Office Re.: Application No. 158442.
Office Action Dated Jan. 2, 2006 From the Israeli Patent Office Re.: Application No. 154323.
Office Action Dated Sep. 4, 2007 From the Israeli Patent Office Re.: Application No. 157007.
Office Action Dated Jul. 17, 2007 From the Israeli Patent Office Re.: Application No. 154323 and Its Translation Into English.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated Mar. 1, 2010 From the US Patent and Trademark Office Re.: U.S. Appl. No. 11/794,799.
Official Action Dated Mar. 1, 2012 From the US Patent and Trademark Office Re.: U.S. Appl. No. 10/616,307.
Official Action Dated Nov. 1, 2010 From the US Patent and Trademark Office Re. U.S. Appl. No. 12/728,383.
Official Action Dated Nov. 1, 2010 From the US Patent and Trademark Office Re.: U.S. Appl. No. 12/728,383.
Official Action Dated Sep. 1, 2009 From the US Patent and Trademark Office Re.: U.S. Appl. No. 11/794,799.
Official Action Dated Aug. 2, 2012 From the US Patent and Trademark Office Re. U.S. Appl. No. 12/087,150.
Official Action Dated Jul. 2, 2004 From the US Patent and Trademark Office Re.: U.S. Appl. No. 09/641,973.
Official Action Dated Mar. 2, 2010 From the US Patent and Trademark Office Re. U.S. Appl. No. 11/980,617.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Sep. 2, 2009 From the US Patent and Trademark Office Re.: U.S. Appl. No. 10/343,792.
Official Action Dated Aug. 3, 2010 From the US Patent and Trademark Office Re.: U.S. Appl. No. 11/980,690.
Official Action Dated May 3, 2007 From the US Patent and Trademark Office Re.: U.S. Appl. No. 10/240,239.
Official Action Dated Sep. 4, 2008 From the US Patent and Trademark Office Re.: U.S. Appl. No. 10/533,568.
Official Action Dated Sep. 5, 2002 From the US Patent and Trademark Office Re.: U.S. Appl. No. 12/084,559.
Official Action Dated Mar. 6, 2012 From the US Patent and Trademark Office Re. U.S. Appl. No. 12/792,856.
Official Action Dated Jan. 7, 2009 From the US Patent and Trademark Office Re.: U.S. Appl. No. 10/616,307.
Official Action Dated Jul. 7, 2009 From the US Patent and Trademark Office Re.: U.S. Appl. No. 10/533,568.
Official Action Dated Oct. 7, 2008 From the US Patent and Trademark Office Re.: U.S. Appl. No. 10/616,301.
Official Action Dated Apr. 8, 2010 From the US Patent and Trademark Office Re.: U.S. Appl. No. 11/980,690.
Official Action Dated Dec. 8, 2009 From the US Patent and Trademark Office Re.: U.S. Appl. No. 11/132,320.
Official Action Dated Dec. 8, 2010 From the US Patent and Trademark Office Re. U.S. Appl. No. 11/980,690.
Official Action Dated Dec. 8, 2010 From the US Patent and Trademark Office Re.: U.S. Appl. No. 09/641,973.
Official Action Dated Dec. 8, 2010 From the US Patent and Trademark Office Re.: U.S. Appl. No. 11/980,690.
Official Action Dated Jan. 8, 2010 From the US Patent and Trademark Office Re.: U.S. Appl. No. 11/656,548.
Official Action Dated Apr. 9, 2010 From the US Patent and Trademark Office Re. U.S. Appl. No. 11/798,017.

(56) References Cited

OTHER PUBLICATIONS

Official Action Dated Apr. 9, 2010 From the US Patent and Trademark Office Re.: U.S. Appl. No. 11/798,017.
Official Action Dated Mar. 9, 2011 From the US Patent and Trademark Office Re.: U.S. Appl. No. 10/616,301.
Official Action Dated Aug. 10, 2007 From the US Patent and Trademark Office Re.: U.S. Appl. No. 10/836,223.
Official Action Dated Nov. 10, 2010 From the US Patent and Trademark Office Re.: U.S. Appl. No. 10/616,307.
Official Action Dated Nov. 10, 2010 From the US Patent and Trademark Office Re.: U.S. Appl. No. 10/836,223.
Official Action Dated Aug. 11, 2009 From the US Patent and Trademark Office Re.: U.S. Appl. No. 09/641,973.
Official Action Dated Jul. 11, 2011 From the US Patent and Trademark Office Re.: U.S. Appl. No. 11/980,683.
Official Action Dated Mar. 11, 2010 From the US Patent and Trademark Office Re.: U.S. Appl. No. 11/607,075.
Official Action Dated Jul. 12, 2007 From the US Patent and Trademark Office Re.: U.S. Appl. No. 10/616,301.
Official Action Dated Jul. 12, 2011 From the US Patent and Trademark Office Re.: U.S. Appl. No. 09/641,973.
Official Action Dated Sep. 12, 2011 From the US Patent and Trademark Office Re. U.S. Appl. No. 12/087,150.
Official Action Dated Aug. 13, 2008 From the US Patent and Trademark Office Re. U.S. Appl. No. 11/769,826.
Official Action Dated Dec. 13, 2007 From the US Patent and Trademark Office Re.: U.S. Appl. No. 10/616,301.
Official Action Dated May 13, 2009 From the US Patent and Trademark Office Re.: U.S. Appl. No. 11/798,017.
Official Action Dated Sep. 13, 2011 From the US Patent and Trademark Office Re. U.S. Appl. No. 11/976,852.
Official Action Dated May 14, 2009 From the US Patent and Trademark Office Re.: U.S. Appl. No. 11/656,548.
Official Action Dated Apr. 15, 2008 From the US Patent and Trademark Office Re.: U.S. Appl. No. 09/641,973.
Official Action Dated Dec. 15, 2006 From the US Patent and Trademark Office Re.: U.S. Appl. No. 10/616,301.
Official Action Dated Dec. 15, 2011 From the US Patent and Trademark Office Re.: U.S. Appl. No. 10/343,792.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Jul. 15, 2009 From the US Patent and Trademark Office Re.: U.S. Appl. No. 10/616,301.
Official Action Dated Mar. 15, 2004 From the US Patent and Trademark Office Re.: U.S. Appl. No. 09/765,316.
Official Action Dated Mar. 15, 2011 From the US Patent and Trademark Office Re.: U.S. Appl. No. 10/343,792.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Apr. 16, 2012 From the US Patent and Trademark Office Re.: U.S. Appl. No. 10/836,223.
Official Action Dated Dec. 16, 2008 From the US Patent and Trademark Office Re.: U.S. Appl. No. 10/343,792.
Official Action Dated Sep. 16, 2009 From the US Patent and Trademark Office Re.: U.S. Appl. No. 09/727,464.
Official Action Dated Jan. 17, 2006 From the United States Patent and Trademark Office Re.: U.S. Appl. No. 11/034,007.
Official Action Dated May 18, 2012 From the US Patent and Trademark Office Re. U.S. Appl. No. 11/989,223.
Official Action Dated May 18, 2012 From the US Patent and Trademark Office Re. U.S. Appl. No. 12/514,785.
Official Action Dated Apr. 19, 2012 From the US Patent and Trademark Office Re. U.S. Appl. No. 11/750,057.
Official Action Dated Jan. 19, 2012 From the US Patent and Trademark Office Re. U.S. Appl. No. 11/667,793.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Official Action Dated Mar. 19, 2010 From the US Patent and Trademark Office Re.: U.S. Appl. No. 10/240,239.
Official Action Dated Apr. 20, 2006 From the United States Patent and Trademark Office Re.: U.S. Appl. No. 10/240,239.
Official Action Dated Apr. 20, 2011 From the US Patent and Trademark Office Re. U.S. Appl. No. 11/798,017.
Official Action Dated Apr. 20, 2011 From the US Patent and Trademark Office Re.: U.S. Appl. No. 11/798,017.
Official Action Dated Dec. 20, 2011 From the US Patent and Trademark Office Re. U.S. Appl. No. 12/309,479.
Official Action Dated Jul. 20, 2009 From the US Patent and Trademark Office Re.: U.S. Appl. No. 11/980,617.
Official Action Dated Jun. 21, 2012 From the US Patent and Trademark Office Re. U.S. Appl. No. 12/309,479.
Official Action Dated Mar. 21, 2008 From the US Patent and Trademark Office Re.: U.S. Appl. No. 10/533,568.
Official Action Dated Sep. 21, 2009 From the US Patent and Trademark Office Re. U.S. Appl. No. 11/798,017.
Official Action Dated Sep. 21, 2009 From the US Patent and Trademark Office Re.: U.S. Appl. No. 11/798,017.
Official Action Dated Apr. 23, 2012 From the US Patent and Trademark Office Re. U.S. Appl. No. 11/932,987.
Official Action Dated Dec. 23, 2008 From the US Patent and Trademark Office Re.: U.S. Appl. No. 09/727,464.
Official Action Dated Feb. 23, 2010 From the US Patent and Trademark Office Re.: U.S. Appl. No. 09/641,973.
Official Action Dated Jan. 23, 2012 From the US Patent and Trademark Office Re. U.S. Appl. No. 12/087,150.
Official Action Dated Jun. 23, 2006 From the United States Patent and Trademark Office Re.: U.S. Appl. No. 09/727,464.
Official Action Dated May 23, 2011 From the US Patent and Trademark Office Re. U.S. Appl. No. 11/667,793.
Official Action Dated May 23, 2011 From the US Patent and Trademark Office Re. U.S. Appl. No. 11/980,690.
Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
Official Action Dated Nov. 23, 2010 From the US Patent and Trademark Office Re.: U.S. Appl. No. 11/656,548.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Nov. 26, 2008 From the US Patent and Trademark Office Re.: U.S. Appl. No. 10/240,239.
Official Action Dated Oct. 26, 2011 From the US Patent and Trademark Office Re.: U.S. Appl. No. 10/836,223.
Official Action Dated Apr. 27, 2011 From the US Patent and Trademark Office Re.: U.S. Appl. No. 10/836,223.
Official Action Dated Jul. 27, 2010 From the US Patent and Trademark Office Re.: U.S. Appl. No. 10/616,307.
Official Action Dated Oct. 27, 2011 From the US Patent and Trademark Office Re.: U.S. Appl. No. 11/656,548.
Official Action Dated Apr. 28, 2010 From the US Patent and Trademark Office Re.: U.S. Appl. No. 10/616,301.
Official Action Dated Aug. 28, 2009 From the US Patent and Trademark Office Re.: U.S. Appl. No. 10/240,239.
Official Action Dated Dec. 28, 2010 From the US Patent and Trademark Office Re.: U.S. Appl. No. 11/607,075.
Official Action Dated Feb. 28, 2012 From the US Patent and Trademark Office Re.: U.S. Appl. No. 09/641,973.
Official Action Dated Jan. 28, 2011 From the US Patent and Trademark Office Re.: U.S. Appl. No. 09/641,973.
Official Action Dated Jun. 28, 2011 From the US Patent and Trademark Office Re. U.S. Appl. No. 11/628,074.
Official Action Dated Apr. 29, 2009 From the US Patent and Trademark Office Re.: U.S. Appl. No. 11/980,690.

(56) References Cited

OTHER PUBLICATIONS

Official Action Dated Jul. 30, 2012 From the US Patent and Trademark Office Re.: U.S. Appl. No. 11/980,683.
Official Action Dated Oct. 30, 2009 From the US Patent and Trademark Office Re.: U.S. Appl. No. 11/980,690.
Official Action Dated Sep. 30, 2008 From the US Patent and Trademark Office Re.: U.S. Appl. No. 10/616,301.
Official Action Dated Sep. 30, 2010 From the US Patent and Trademark Office Re. U.S. Appl. No. 11/798,017.
Official Action Dated Sep. 30, 2010 From the US Patent and Trademark Office Re.: U.S. Appl. No. 11/798,017.
Official Action Dated Aug. 31, 2012 From the US Patent and Trademark Office Re. U.S. Appl. No. 11/980,653.
Official Action Dated Jan. 31, 2011 From the US Patent and Trademark Office Re. U.S. Appl. No. 11/667,793.
Restriction Official Action Dated Mar. 9, 2012 From the US Patent and Trademark Office Re. U.S. Appl. No. 11/976,852.
Restriction Official Action Dated Sep. 12, 2011 From the US Patent and Trademark Office Re. U.S. Appl. No. 11/980,653.
Restriction Official Action Dated Apr. 13, 2012 From the US Patent and Trademark Office Re. U.S. Appl. No. 11/989,223.
Restriction Official Action Dated Nov. 15, 2011 From the US Patent and Trademark Office Re. U.S. Appl. No. 11/980,683.
Restriction Official Action Dated Aug. 16, 2012 From the US Patent and Trademark Office Re. U.S. Appl. No. 12/448,473.
Second International Search Report Dated Jun. 1, 2009 From the International Searching Authority Re.: Application No. PCT/IL07/00918.
Summons to Attend Oral Proceedings Pursuant to Rule 115(1) EPC Dated Jan. 16, 2009 From the European Patent Office Re.: Application No. 03810570.6.
Supplemental Notice of Allowability Dated Oct. 24, 2011 From the US Patent and Trademark Office Re.: U.S. Appl. No. 11/607,075.
Supplemental Response After Interview Dated Aug. 4, 2010 to Official Action of Mar. 2, 2010 From the US Patent and Trademark Office Re.: U.S. Appl. No. 11/980,617.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Supplementary European Search Report and the European Search Opinion Dated Mar. 16, 2011 From the European Patent Office Re. Application No. 05803689.8.
Supplementary European Search Report Dated Dec. 12, 2005 From the European Patent Office Re.: Application No. 03810570.6.
Supplementary Partial European Search Report and the European Search Opinion Dated Dec. 15, 2009 From the European Patent Office Re.: Application No. 06832278.3.
Supplementary Partial European Search Report and the European Search Opinion Dated Oct. 16, 2009 From the European Patent Office Re.: Application No. 06756259.5.
Supplementary Partial European Search Report Dated Sep. 4, 2007 From the European Patent Office Re.: Application No. 0 2716285.8.
Supplementary Partial European Search Report Dated Nov. 11, 2008 From the European Patent Office Re.: Application No. 01951883.6.
Supplementary Partial European Search Report Dated Nov. 20, 2007 From the European Patent Office Re.: Application No. 02716285.8.
Translation of Office Action Dated May 13, 2005 From the Patent Office of the People's Republic of China Re.: Application No. 01817689.5.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Nov. 1, 2007 from the International Searching Authority of the Patent Cooperation Treaty Re.: Application No. PCT/IL06/00840.
Written Opinion Dated Jul. 2, 2007 From the International Searching Authority of the Patent Cooperation Treaty Re.: Application No. PCT/IL2006/001291.
Written Opinion Dated Aug. 3, 2006 From the International Searching Authority of the Patent Cooperation Treaty Re.: Application No. PCT/IL05/001173.
Written Opinion Dated Oct. 10, 2006 From the International Searching Authority of the Patent Cooperation Treaty Re.: Application No. PCT/IL06/00059.
Written Opinion Dated Jul. 11, 2008 from the International Searching Authority of the Patent Cooperation Treaty Re.: Application No. PCT/IL06/01511.
Written Opinion Dated Oct. 15, 2008 From the International Searching Authority Re.: Application No. PCT/IL07/00918.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Bloch et al. "Application of Computerized Tomography to Radiation Therapy and Surgical Planning", Proceedings of the IEEE, 71(3): 351-355, Mar. 1983.
Bowsher et al. "Treatment of Compton Scattering in Maximum-Likelihood, Expectation-Maximization Reconstructions of SPECT Images", Journal of Nuclear Medicine, 32(6): 1285-1291, 1991.
Bracco Diagnostics "Cardiotec®: Kit for the Preparation of Technetium Tc 99m Teboroxime. For Diagnostic Use", Bracco Diagnostics Inc., Product Sheet, 2 P., Jul. 2003.
Bracco Diagnostics "Techneplex®: Kit for the Preparation of Technetium Tc 99m Pentetate Injection. Diagnostic—for Intravenous Use", Bracco Diagnostics™, Product Sheet, 5 P., Jun. 1995.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, col. 2, § 2.
Brown et al. "Method for Segmenting Chest CT Image Data Using an Anatomical Model: Preliminary Results", IEEE Transactions on Medical Imaging, 16(6): 828-839, Dec. 1997.
Chengazi et al. "Imaging Prostate Cancer With Technetium-99m-7E11-05.3 (CYT-351)", Journal of Nuclear Medicine, 38: 675-682, 1997.
Corstens et al. "Nuclear Medicine's Role in Infection and Inflammation", The Lancet, 354: 765-770, 1999.
Day et al. "Localization of Radioiodinated Rat Fibrogen in Transplanted Rat Tumors", Journal of the National Cancer Institute, 23(4): 799-812, 1959.
Del Guerra et al. "An Integrated PET-SPECT Small Animal Imager: Preliminary Results", Nuclear Science Symposium, IEEE Records, 1: 541-544, 1999.
Dewaraja et al. "Accurate Dosimetry in 131I Radionuclide Therapy Using Patient-Specific, 3-Dimensional Methods for SPECT Reconstruction and Basorbed Dose Calculation", The Journal of Nuclear Medicine, 46(5): 840-849, May 2005.
Dittman "Radiolabeled Anti-CD20 Monoclonal Antibodies for the Treatment of B-Cell Lymphoma", Journal of Clinical Oncology, 20(16): 3545-3557, Aug. 15, 2002.
Erbil et al. "Use and Limitations of Serum Total and Lipid-Bound Sialic Acid Concentrations as Markers for Colorectal Cancer", Cancer, 55: 404-409, 1985.

(56) References Cited

OTHER PUBLICATIONS

Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 23442349, Oct. 1, 2002. p. 2344, Section 'Introduction', First §.
Gugnin et al "Radiocapsule for Recording the Ionizing Radiation in the Gastrointestinal Tract", UDC 615.417:616.34-005.1-073.916-71 (All-Union Scientific-Research Institute of medical Instrument Design, Moscow. Translated from Meditsinskaya Tekhnika, 1:21-25, Jan.-Feb. 1972).
Handrick et al. "Evaluation of Binning Strategies for Tissue Classification in Computed Tomography Images", Medical Imaging 2006: Image Processing, Proceedings of the SPIE, 6144: 1476-1486, 2006.
Hassan et al. "A Radiotelemetry Pill for the Measurement of Ionising Radiation Using a Mercuric Iodide Detector", Physics in Medicine and Biology, 23(2): 302-308, 1978.
Hayakawa et al. "A PET-MRI Registration Technique for PET Studies of the Rat Brain", Nuclear Medicine & Biology, 27: 121-125, 2000. p. 121, col. 1.
Herrmann et al. "Mitochondrial Proteome: Altered Cytochtrome C Oxidase Subunit Levels in Prostate Cancer", Proteomics, XP002625778, 3(9): 1801-1810, Sep. 2003.
Hoffman et al. "Intraoperative Probes and Imaging Probes", European Journal of Nuclear Medicine, 26(8): 913-935, 1999.
Huesman et al. "Kinetic Parameter Estimation From SPECT Cone-Beam Projection Measurements", Physics in Medicine and Biology, 43(4): 973-982, 1998.
Jeanguillaume et al. "From the Whole-Body Counting to Imaging: The Computer Aided Collimation Gamma Camera Project (CACAO)", Radiation Projection Dosimetry, 89(3-4): 349-352, 2000. & RSNA 2000 Infosystem, 87th Scientific Assembly and Annual Meeting, Chicago, Illinois, 2000.
Jessup "Tumor Markers—Prognostic and Therapeutic Implications for Colorectal Carcinoma", Surgical Oncology, 7: 139-151, 1998.
Jin et al. "Reconstruction of Cardiac-Gated Dynamic SPECT Images", IEEE International Conference on Image Processing 2005, ICIP 2005, Sep. 11-14, 2005, 3: 1-4, 2005.
Kadrmas et al. "Static Versus Dynamic Teboroxime Myocardial Perfusion SPECT in Canines", IEEE Transactions on Nuclear Science, 47(3): 1112-1117, Jun. 2000.
Kinahan et al. "Attenuation Correction for a Combined 3D PET/CT Scanner", Medical Physics, 25(10): 2046-2053, Oct. 1998.
Kojima et al. "Quantitative Planar Imaging Method for Measurement of Renal Activity by Using a Conjugate-Emission Image and Transmission Data", Medical Physics, 27(3): 608-615, 2000. p. 608.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Lavallee et al. "Building a Hybrid Patient's Model for Augmented Reality in Surgery: A Registration Problem", Computing in Biological Medicine, 25(2): 149-164, 1995.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First col., 2nd §.

Lin et al. "Improved Sensor Pills for Physiological Monitoring", NASA Technical Brief, JPL New Technology Report, NPO-20652, 25(2), 2000.
Mallinckrodt "Kit for the Preparation of Technetium Tc 99m Sestamibi Injection", Mallinckrodt Inc., Product Sheet, 2 P., Sep. 8, 2008.
Mallinckrodt "OctreoScan®: Kit for the Preparation of Indium In-111 Pentetreotide. Diagnostic—for Intravenous Use. Rx Only", Mallinckrodt Inc., Product Sheet, 2 P., Oct. 25, 2006.
Mao et al. "Human Prostatic Carcinoma: an Electron Microscope Study", Cancer Research, XP002625777, 26(5): 955-973, May 1966.
McJilton et al. "Protein Kinase C? Interacts With Bax and Promotes Survival of Human Prostate Cancer Cells", Oncogene, 22; 7958-7968, 2003.
Mettler et al. "Legal Requirements and Radiation Safety", Essentials of Nuclear Medicine Imaging, 2nd Ed., Chap.13: 323-331, 1985.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Mori et al. "Overexpression of Matrix Metalloproteinase-7mRNA in Human Colon Carcinomas", Cancer, 75: 1516-1519, 1995.
Ogawa et al. "Ultra High Resoultion Pinhole SPECT", IEEE Nuclear Science Symposium, 2: 1600-1604, 1998.
Ouyang et al. "Incorporation of Correlated Structural Images in PET Image Reconstruction", IEEE Transactions of Medical Imaging, 13(4): 627-640, Dec. 1994.
Pardridge et al. "Tracer Kinetic Model of Blood-Brain Barrier Transport of Plasma Protein-Bound Ligands", Journal of Clinical Investigation, 74: 745-752, 1984. Suppl. IDS in 27480.
Pellegrini et al. "Design of Compact Pinhole SPECT System Based on Flat Panel PMT", IEEE Nuclear Science Symposium Conference Record, 3: 1828-1832, 2003.
Pharmalucence "Kit for the Preparation of Technetium Tc99m Sulfur Colloid Injection for Subcutaneous, Intraperitoneal, Intravenous, and Oral Use", Pharmalucence Inc., Reference ID: 2977567, Prescribing Information, 10 P., Jul. 2011.
Piperno et al. "Breast Cancer Screening by Impedance Measurements", Frontiers Med. Biol. Engng., 2(2): 11-17, 1990.
Pluim et al. "Image Registration by Maximization of Combined Mutual Information and Gradient Information", IEEE Transactions on Medical Imaging, 19(8): 1-6, 2000.
Qi et al. "Resolution and Noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.
Quartuccia et al. "Computer Assisted Collimation Gama Camera: A New Approach to Imaging Contaminated Tissues", Radiation Projection Dosimetry, 89(3-4): 343-348, 2000.
Rajshekhar "Continuous Impedence Monitoring During CT-Guided Stereotactic Surgery: Relative Value in Cystic and Solid Lesions", British Journal of Neurosurgery, 6: 439-444, 1992.
Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.
Reutter et al. "Kinetic Parameter Estimation From Attenuated SPECT Projection Measurements", IEEE Transactions on Nuclear Science, 45(6): 3007-3013, 1998.
Saltz et al. "Interim Report of Randomized Phase II Trial of Cetuximab/Bevacizumab/Irinotecan (CBI) Versus Cetuximab/Bevacizumab (CB) in Irinotecan-Refractory Colorectal Cancer", Gastrointestinal Cancer Symposium, Hollywood, FL, USA, Jan. 27-29, 2005, American Society of Clinical Oncology, Abstract 169b, 4P., 2005.
Sands et al. "Methods for the Study of the Metabolism of Radiolabeled Monoclonal Antibodies by Liver and Tumor", The Journal of Nuclear Medicine, 28: 390-398, 1987.

(56) References Cited

OTHER PUBLICATIONS

Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.

Storey et al. "Tc-99m Sestamibi Uptake in Metastatic Prostate Carcinoma", Clinical Nuclear Medicine, XP009145398, 25(2): 133-134, Feb. 2000.

Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.

Thorndyke et al. "Reducing Respiratory Motion Artifacts in Positron Emission Tomography Through Retrospective Stacking", Medical Physics, 33(7): 2632-2641, Jul. 2006.

Toennies et al. "Scatter Segmentation in Dynamic SPECT Images Using Principal Component Analysis", Progress in Biomedical Optics and Imaging, 4(23): 507-516, 2003.

Trikha et al. "Monoclonal Antibodies as Therapeutics in Oncology", Current Opinion in Biotechnology, 13: 609-614, 2002.

Volkow et al. "Imaging the Living Human Brain: Magnetic Resonance Imaging and Positron Emission Tomography", Proc. Natl. Acad. Sci. USA, 94: 2787-2788, Apr. 1997.

Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.

Wu et al. "ECG-Gated Pinhole SPECT in Mice With Millimeter Spatial Resolution", IEEE Transactions on Nuclear Science, 47(3): 1218-1221, Jun. 2000.

Xu et al. "Quantitative Expression Profile of Androgen-Regulated Genes in Prostate Cancer Cells and Identification of Prostate-Specific Genes", International Journal of Cancer, 92: 322-328, 2001.

Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.

Zaidi et al. "Magenetic Resonance Imaging-Guided Attenuation and Scatter Corrections in Three-Dimensional Brain Positron Emission Tomography", Medical Physics, 30(5): 937-948, May 2003.

Zaidi et al. "MRI-Guided Attenuation Correction in 3D Brain PET", Neuroimage Human Brain Mapping 2002 Meeting, 16(2): Abstract 504, Jun. 2002.

Zhang et al. "An Innovative High Efficiency and High Resolution Probe for Prostate Imaging", The Journal of Nuclear Medicine, 68: 18, 2000. Abstract.

Communication Pursuant to Article 94(3) EPC Dated Nov. 12, 2012 From the European Patent Office Re. Application No. 06756258.7.

Notice of Allowance Dated Nov. 15, 2012 From the US Patent and Trademark Office Re.: U.S. Appl. No. 11/980,683.

Notice of Allowance Dated Oct. 26, 2012 From the US Patent and Trademark Office Re. U.S. Appl. No. 12/514,785.

Official Action Dated Feb. 16, 2012 From the US Patent and Trademark Office Re. U.S. Appl. No. 11/747,378.

Official Action Dated Nov. 30, 2012 From the US Patent and Trademark Office Re. U.S. Appl. No. 12/514,785.

Supplementary European Search Report and the European Search Opinion Dated Nov. 13, 2012 From the European Patent Office Re. Application No. 06728347.3.

Official Action Dated Dec. 19, 2012 From the US Patent and Trademark Office Re. U.S. Appl. No. 12/448,473.

Notice of Allowance Dated Mar. 14, 2013 From the US Patent and Trademark Office Re.: U.S. Appl. No. 11/798,017.

Studen "Compton Camera With Position-Sensitive Silicon Detectors", Doctoral Thesis, University of Ljubljana, Faculty of Mathematics and Physics, 36 P.

Communication Pursuant to Article 94(3) EPC Dated Oct. 26, 2012 From the European Patent Office Re. Application No. 05803689.8.

Brzymialkiewicz et al. "Evaluation of Fully 3-D Emission Mammotomography With a Compact Cadmium Zinc Telluride Detector", IEEE Transactions on Medical Imaging, 24(7): 868-877, Jul. 2005.

Jan et al. "Preliminary Results From the AROPET", IEEE Nuclear Science Symposium Conference Record, Nov. 4-10, 2001, 3: 1607-1610, 2001.

Ohno ct al. "Selection of Optimum Projection Angles in Three Dimensional Myocardial SPECT", IEEE Nuclear Science Symposium Conference Record 2001, 4: 2166-2169, 2001.

Seret et al. "Intrinsic Unifoitnity Requirements for Pinhole SPECT", Journal of Nuclear Medicine Technology, 34(1): 43-47, Mar. 2006.

Smither "High Resolution Medical Imaging System for 3-D Imaging of Radioactive Sources With 1 mm FWHM Spatial Resolution", Proceedings of the SPIE, Medical Imaging 2003: Physics of Medical Imaging, 5030: 1052-1060, Jun. 9, 2003.

Tornai et al. "A 3D Gantry Single Photon Emission Tomograph With Hemispherical Coverage for Dedicated Breast Imaging", Nuclear Instruments & Methods in Physics Research, Section A, 497: 157-167, 2003.

Notice of Allowance Dated Dec. 26, 2012 From the US Patent and Trademark Office Re.: U.S. Appl. No. 11/980,690.

Official Action Dated Dec. 28, 2012 From the US Patent and Trademark Office Re.: U.S. Appl. No. 10/343,792.

Charland et al. "The Use of Deconvolution and Total Least Squares in Recovering a Radiation Detector Linc Spread Function", Medical Physics, 25(2): 152-160, Feb. 1998. Abstract Only!

Official Action Dated Mar. 11, 2013 From the US Patent and Trademark Office Re. U.S. Appl. No. 13/345,719.

Applicant-Initiated Interview Summary Dated May 1, 2013 From the US Patent and Trademark Office Re. U.S. Appl. No. 10/343,792.

Applicant-Initiated Interview Summary Dated May 1, 2013 From the US Patent and Trademark Office Re. U.S. Appl. No. 11/980,653.

Advisory Action Before the Filing of an Appeal Brief Dated Feb. 26, 2013 From the US Patent and Trademark Office Re. U.S. Appl. No. 11/989,223.

Official Action Dated Nov. 30, 2012 From the US Patent and Trademark Office Re. U.S. Appl. No. 11/989,223.

Cancer Medicine "Radiolabeled Monoclonal Antibodies. Historical Perspective", Cancer Medicine, 5th Ed., Sec.16: Principles of Biotherapeutics, Chap.65: Monoclonal Serotherapy, 2000.

Lange et al. "EM Reconstruction Algorithms for Emission and Transmission Tomography", Journal of Computer Assisted Tomography, 8(2): 306-316, Apr. 1984.

Ohrvall et al. "Intraoperative Gamma Detection Reveals Abdominal EndocrineTumors More Efficiently Than Somatostatin Receptor Scintigraphy", 6th Conference on Radioimmunodetection and Radioimmunotherapy of Cancer, Cancer, 80: 2490-2494, 1997.

Rockmore et al. "A Maximum Likelihood Approach to Emission Image Reconstruction From Projections", IEEE Transactions on Nuclear Science, 23(4): 1428-1432, Aug. 1976.

Shepp et al. "Maximum Likelihood Reconstruction for Emission Tomography", IEEE Transactions on Medical Imaging, MI-1: 113-122, Oct. 1982.

Sitek et al. "Reconstruction of Dynamic Renal Tomographic Data Acquired by Slow Rotation", The Journal of Nuclear Medicine, 42(11): 1704-1712, Nov. 2001.

Solanki "The Usc of Automation in Radiopharmacy", Hospital Pharmacist, 7(4): 94-98, Apr. 2000.

Weldon et al. "Quantification of Inflammatory Bowel Disease Activity Using Technetium-99m HMPAO Labelled Leucocyte Single Photon Emission Computerised Tomography (SPECT)", Gut, 36: 243-250, 1995.

Official Action Dated Oct. 11, 2012 From the US Patent and Trademark Office Re. U.S. Appl. No. 11/976,852.

An Office Action dated Feb. 17, 2011, which issued during the prosecution of Applicant's U.S. Appl. No. 11/932,987.

An Office Action dated Feb. 18, 2011, which issued during the prosecution of Applicant's U.S. Appl. No. 11/932,872.

U.S. Appl. No. 60/625,971.
U.S. Appl. No. 60/628,105.
U.S. Appl. No. 60/630,561.
U.S. Appl. No. 60/632,236.
U.S. Appl. No. 60/632,515.

(56) References Cited

OTHER PUBLICATIONS

U.S. Appl. No. 60/635,630.
Van Den Bossche B et al., "Receptor Imaging in Oncology by Means of Nuclear Medicine: Current Status", Journal of Clinical Oncology 22(17): 3593-3607, 2004 (an abstract).
Yao D et al., "The utility of monoclonal antibodies in the imaging of prostate cancer", Semin Urol Oncol 20(3):211-8, 2002 (an abstract).
U.S. Appl. No. 60/636,088.
U.S. Appl. No. 60/640,215.
Van der Laken CJ et al., "Technetium-99m-labeled chemotactic peptides in acute infection and sterile inflammation", J Nucl Med 38(8):1310-5, 1997 (an abstract).
Babich JW et al., "Localization of radiolabeled chemotactic peptide at focal sites of *Escherichia coli* infection in rabbits: evidence for a receptor-specific mechanism", J Nucl Med 38(8):1316-22 (an abstract).
U.S. Appl. No. 60/648,385.
U.S. Appl. No. 60/648,690.
Rao PS et al., "99mTc-peptide-peptide nucleic acid probes for imaging oncogene mRNAs in tumours", Nuclear Medicine Communications 24(8):857-863, 2003 (an abstract).
Fischman AJ et al., "Infection imaging with technetium-99m-labeled chemotactic peptide analogs", Semin Nucl Med 24(2):154-68, 1994 (an abstract).
U.S. Appl. No. 60/675,892.
U.S. Appl. No. 60/691,780.
Massoud TF et al., "Molecular imaging in living subjects: seeing fundamental biological processes in a new light", Genes & development 17:545-580, 2003.
Gambhir SS, "Molecular imaging of cancer with positron emission tomography", Nature Reviews 2:683-693, 2002.
U.S. Appl. No. 60/700,318.
U.S. Appl. No. 60/700,299.
"Keeping Pace with Targeted Therapies in Lung Cancer" Highlights from the ASCO 2006 Annual Meeting.
U.S. Appl. No. 60/700,317.
U.S. Appl. No. 60/700,753.
U.S. Appl. No. 60/700,752.
U.S. Appl. No. 60/702,979.
U.S. Appl. No. 60/720,034.
U.S. Appl. No. 60/720,652.
U.S. Appl. No. 60/720,541.
U.S. Appl. No. 60/750,287.
U.S. Appl. No. 60/750,334.
U.S. Appl. No. 60/750,597.
U.S. Appl. No. 60/800,845.
U.S. Appl. No. 60/800,846.
U.S. Appl. No. 60/816,970.
PCT Patent Application No. PCT/IL2006/000562.
PCT Patent Application No. PCT/IL2005/001215.
PCT Patent Application No. PCT/IL2005/001173.
PCT Patent Application No. PCT/IL2005/000572.
PCT Patent Application No. PCT/IL2005/000575.
PCT Patent Application No. PCT/IL2006/000059.
PCT Patent Application No. PCT/IL2006/001511.
Official Action Dated Oct. 10, 2012 From the US Patent and Trademark Office Re. U.S. Appl. No. 11/798,017.
Summons to Attend Oral Proceedings Pursuant to Rule 115(1) EPC Dated Nov. 29, 2012 From the European Patent Office Re. Application No. 06756259.5.
Official Action Dated Aug. 5, 2013 From the US Patent and Trademark Office Re. U.S. Appl. No. 12/309,479.
Official Action Dated Aug. 14, 2013 From the US Patent and Trademark Office Re. U.S. Appl. No. 12/448,473.
Berman et al. "D-SPECT: A Novel Camera for High Speed Quantitative Molecular Imaging: Initial Clinical Results", The Journal of Nuclear Medicine, 47(Suppl.1): 131P, 2006.
Berman et al. "Myocardial Perfusion Imaging With Technetium-99m-Sestamibi: Comparative Analysis of Available Imaging Protocols", The Journal of Nuclear Medicine, 35: 681-688, 1994.
Borges-Neto et al. "Perfusion and Function at Rest and Treadmill Exercise Using Technetium-99m-Sestamibi: Comparison of One- and Two-Day Protocols in Normal Volunteers", The Journal of Nuclear Medicine, 31(7): 1128-1132, Jul. 1990.
Kwok et al. "Feasability of Simultaneous Dual-Isotope Myocardial Perfusion Acquisition Using a Lower Dose of Sestamibi", European Journal of Nuclear Medicine, 24(3): 281-285, Mar. 1997.
Patton et al. "D-SPECT: A New Solid State Camera for High Speed Molecular Imaging", The Journal of Nuclear Medicine, 47(Suppl.1): 189P, 2006.
Notice of Allowance Dated Jul. 19, 2013 From the US Patent and Trademark Office Re. U.S. Appl. No. 11/989,223.
Notice of Allowance Dated Jul. 25, 2013 From the US Patent and Trademark Office Re. U.S. Appl. No. 13/345,719.
Official Action Dated Jul. 5, 2013 From the US Patent and Trademark Office Re. U.S. Appl. No. 11/656,548.

\* cited by examiner

FIG. 6A

|  | REST PHASE ||||| STRESS PHASE ||||
|  | INJECTION || WAITING TIME [MIN] | ACQUISITION DURATION [MIN] | STRESS | INJECTION || WAITING TIME [MIN] | GATED ACQUISITION DURATION [MIN] |
|  | RP | DOSE [mCi] |  |  |  | RP | DOSE [mCi] |  |  |
| SINGLE ISOTOPE/ LOW DOSE/FAST IMAGING | TL | <0.3 | 2 | 15 | EXERCISE | TL | <3 | 10-15 | 1.5 |
| DUAL ISOTOPE/ LOW DOSE/FAST IMAGING | TL | <0.3 | 2 | 15 | EXERCISE | Tc-MIBI | 30 | 30-60 | 1.5 |
| GATED REST THALLIUM (STUNNING) | TL | 1.5 | 2 | 5 (GATED) | EXERCISE | Tc-MIBI | 30 | 30-60 | 1.5 |
| THALLIUM STRESS PERFUSION | Tc-MIBI | 3 | 30 | 1.5 | PHARMA | TL | 3 | 0 | 10 (DYNAMIC) |
| SIMULTANEOUS DUAL ISOTOPE STRESS PERFUSION | Tc-MIBI | 3 | 20 |  | EXERCISE/PHARMA | TL | 3 |  | 10 (DYNAMIC) |
| DYNAMIC IMAGING | TL | 0.3 |  |  | PHARMA (ADENOSINE) | TL | 3 |  | 10 (DYNAMIC) |

FIG. 6B

| NO. | PROTOCOL NAME | KEY FEATURES AND PROPERTIES | ADMINISTRATION PARAMETERS | | | DETECTOR PARAMETERS |
|---|---|---|---|---|---|---|
| | | | DOSE (mCi) | INJECTION PROFILE | INJECT TO ACQUISITION TIME | DETECTED PHOTON ENERGY / RESOLUTION |
| A | CARDIAC MAPPING | MIBI-TC, FAST, BEFORE LIVER UPTAKE | 20-40 | BOLUS | 2 MIN, OR ADMIN UNDER THE CAMERA | 140 KeV / 15% |
| B | CARDIAC MAPPING | MIBI-TC AFTER LIVER UPTAKE | 20-40 | BOLUS | 30+ MIN | 140 KeV / 15% |
| C | CARDIAC MAPPING | SIMULTANEOUS FAST DUAL-ISOTOPE TL-201+ LOW DOSE MIBI-TC | TL-201: 3.5-5; MIBI-Tc-99m: 4-8 | 2 BOLUS (BEFORE AND AT PEAK STRESS) | TL INJECTED PREVIOUSLY AT REST, TC UNDER CAMERA OR 2 MIN | Tc-140 KeV, Tl-72 KeV / 15% |
| D | CARDIAC MAPPING | SIMULTANEOUS DUAL-ISOTOPE TL-201+ LOW DOSE MIBI-TC | TL-201: 3.5-5; MIBI-Tc-99m: 4-8 | 2 BOLUS (BEFORE AND AT PEAK STRESS) | SAME AS ONE OF FIRST 2 CARDIAC MAPPING PROTOCOLS | Tc-140 KeV, Tl-72 KeV / 15% |
| E | CARDIAC MAPPING | SIMULTANEOUS DUAL-ISOTOPE FULL TL-201+ FULL DOSE MIBI-TC | TL-201: 3.5-5; MIBI-Tc-99m: 20-40 | 2 BOLUS (BEFORE AND AT PEAK STRESS) | SAME AS ONE OF PROTOCOLS A OR B | Tc-140 KeV, Tl-167 KeV / 10% |
| F | CARDIAC MAPPING - UNDERWEIGHT (BMI<18.5) | MIBI-TC-99M AFTER LIVER UPTAKE | 15-20 | BOLUS | 30+ MIN | 140 KeV / 15% |
| G1 | CARDIAC MAPPING - NORMAL (18.6<BMI<24.9) | MIBI-TC-99M AFTER LIVER UPTAKE | 20-30 | BOLUS | 30+ MIN | 140 KeV / 10% |
| G2 | CARDIAC MAPPING - OVERWEIGHT (25<BMI<29.9) | MIBI-TC-99M AFTER LIVER UPTAKE | 30-35 | BOLUS | 30+ MIN | 140 KeV / 10% |

FIG. 6C

| NO. | SCANNING PARAMETERS ||||||| ANALYSIS PARAMETERS ||
|---|---|---|---|---|---|---|---|---|
| | TOTAL SCAN TIME | COLUMNS DIFFERENCES / UNIFORM SCAN | ANGULAR RANGE | TOTAL # ANGULAR ORIENT-TATIONS | ANGULAR STEP / INTERLACE | DWELL TIME | GATED ANALYSIS OF VOLUMES | ANALYSIS ALGORITHM / PARAMETERS |
| A | 120 SEC | a) 4 X OUTER b) 6 X INNER | a) 40-60 DEG b) 90-120 DEG | 120X10 | a) 0.3-0.5 DEG b) 0.75-1 DEG | 1 SEC | YES, 16-32 FRAMES | INTENSITY IMAGE, EJECTION FRACTION |
| B | 120 SEC | a) 4 X OUTER b) 6 X INNER | a) 40-60 DEG b) 90-120 DEG | 120X10 | a) 0.3-0.5 DEG b) 0.75-1 DEG | 1 SEC | YES, 16-32 FRAMES | INTENSITY IMAGE, EJECTION FRACTION |
| C | 120 SEC | a) 4 X OUTER b) 6 X INNER | a) 40-60 DEG b) 90-120 DEG | 120X10 | a) 0.3-0.5 DEG b) 0.75-1 DEG | 1 SEC | YES, 16-32 FRAMES | INTENSITY IMAGE, EJECTION FRACTION |
| D | 120 SEC | a) 4 X OUTER b) 6 X INNER | a) 40-60 DEG b) 90-120 DEG | 120X10 | a) 0.3-0.5 DEG b) 0.75-1 DEG | 1 SEC | YES, 16-32 FRAMES | INTENSITY IMAGE, EJECTION FRACTION |
| E | UP TO 1200 SEC | a) 4 X OUTER b) 6 X INNER | a) 40-60 DEG b) 90-120 DEG | 240X10 | a) 0.15-0.25 DEG b) 0.375-0.5 DEG | 5 SEC | YES, 16-32 FRAMES | INTENSITY IMAGE, EJECTION FRACTION |
| F | 90 SEC | a) 4 X OUTER b) 6 X INNER | a) 20-35 DEG b) 45-60 DEG | 60X10 | a) .3-.75 DEG b) 0.75-1 DEG | 1 SEC | YES, 16-32 FRAMES | INTENSITY IMAGE, EJECTION FRACTION |
| G1 | 120 SEC | a) 4 X OUTER b) 6 X INNER | a) 30-45 DEG b) 75-90 DEG | 120X10 | a) 0.5-0.75 DEG b) 0.625-1 DEG | 1.5 SEC | YES, 16-32 FRAMES | INTENSITY IMAGE, EJECTION FRACTION |
| G2 | 120 SEC | a) 4 X OUTER b) 6 X INNER | a) 40-60 DEG b) 90-120 DEG | 120X10 | a) 0.3-0.5 DEG b) 0.75-1 DEG | 2 SEC | YES, 16-32 FRAMES | INTENSITY IMAGE, EJECTION FRACTION |

FIG. 6D

| NO. | PROTOCOL NAME | KEY FEATURES AND PROPERTIES | ADMINISTRATION PARAMETERS | | | DETECTOR PARAMETERS |
|---|---|---|---|---|---|---|
| | | | DOSE (mCi) | INJECTION PROFILE | INJECT TO ACQUISITION TIME | DETECTED PHOTON ENERGY / RESOLUTION |
| H | CARDIAC MAPPING - OBESE (BMI>30) | MIBI-TC AFTER LIVER UPTAKE | 35-40 | BOLUS | 30+ MIN | 140 KeV / 6% |
| I | CARDIAC DYNAMIC MAPPING | TEBOROXIME-TC | 20-40 | BOLUS | -1 MIN (IMAGE BEFORE INJECT), OR SIMULTANEOUSLY WITH INJECT | 140 KeV / 15% |
| J | CARDIAC DYNAMIC MAPPING (2-STEP) | TEBOROXIME-TC | 20-40 | (i) INITIAL SMALL BOLUS FOR IDENTIFYING ROI, (ii) FULL BOLUS FOR DYNAMIC STUDY | (i) 5+ MIN (ii) -1 MIN (IMAGE BEFORE INJECT) | 140 KeV / 15% |
| K | TUMOR SCAN (MULTIPLE BODY SEGMENTS - HEAD TO LEGS) | MDP-TC-99M AFTER LIVER UPTAKE | 20-40 | BOLUS | 30+ MIN | 140 KeV / 15% |
| L | TUMOR SCAN (MULTIPLE BODY SEGMENTS - HEAD TO LEGS), FOCUSED SCAN | MDP-TC-99M AFTER LIVER UPTAKE | 20-40 | BOLUS | 30+ MIN | 140 KeV / 15% |
| M | TUMOR SCAN WITH COCKTAIL (MULTIPLE BODY SEGMENTS - HEAD TO LEGS); FOCUSED SCAN | FDG (METABOLISM), MIBI-TC-99M AND TL (PERFUSION) | TL-201: 3.5-5; MIBI-TC-99M: 20-40; 18-F FDG 10-30 | BOLUS | 30+ MIN | Tc-140 KeV, Tl-72 KeV, FDG 511 KeV / 10% |

FIG. 6E

| NO. | SCANNING PARAMETERS ||||||| ANALYSIS PARAMETERS ||
|---|---|---|---|---|---|---|---|---|
| | TOTAL SCAN TIME | COLUMNS DIFFERENCES / UNIFORM SCAN | ANGULAR RANGE | TOTAL # ANGULAR ORIENT-TATIONS | ANGULAR STEP / INTERLACE | DWELL TIME | GATED ANALYSIS OF VOLUMES | ANALYSIS ALGORITHM / PARAMETERS |
| H | 180 SEC | a) 4 X OUTER b) 6 X INNER | a) 40-60 DEG b) 90-120 DEG | 160X10 | a) 0.25-0.375 DEG b) 0.6-0.75 DEG | 1.2 SEC | YES, 8-16 FRAMES | INTENSITY IMAGE, EJECTION FRACTION |
| I | <= 600 SEC | a) 2 X OUTER b) 8 X INNER | a) 40-60 DEG b) 90-120 DEG | 600X10 | a) continuous b) continuous INTERLACED SCAN | 1 SEC | YES, 8 FRAMES | KINETIC PARAMETES, PREDEFINED PATHOLOGICAL VALUES |
| J | (i) 60 SEC FOR IDENTIFYING ROI (ii) 600 SEC DYNAMIC STUDY | a) 2 X OUTER b) 8 X INNER | a) 40-60 DEG b) 90-120 DEG | (i) 60X10 (ii) 600X10 | (i) a) 0.75-1 DEG b) 0.75-0.75-1 DEG (ii) a) continuous b) continuous INTERLACED SCAN | 1 SEC | YES, 8 FRAMES | KINETIC PARAMETES, PREDEFINED PATHOLOGICAL VALUES |
| K | 240 SEC PER BODY SEGMENT | 16 | 40-60 DEG | 120X16 | 0.3-0.5 DEG | 2 SEC | NO | INTENSITY IMAGE, PREDEFINED PATHOLOGICAL VALUES |
| L | (i) 120 SEC PER BODY SEGMENT (ii) 60 SEC PER ROI | 16 | (i) 45-60 DEG (ii) 15-20 DEG | (i) 120X16 (ii) 60x16 | (i) 0.375-0.5 DEG (ii) 0.25-0.3 | 1 SEC | NO | INTENSITY IMAGE, PREDEFINED PATHOLOGICAL VALUES |
| M | (i) 120 SEC PER BODY SEGMENT (ii) 60 SEC PER ROI | 16 | (i) 45-60 DEG (ii) 15-20 DEG | (i) 120X16 (ii) 60x16 | (i) 0.375-0.5 DEG (ii) 0.25-0.4 | 1 SEC | NO | INTENSITY IMAGE, PREDEFINED PATHOLOGICAL VALUES |

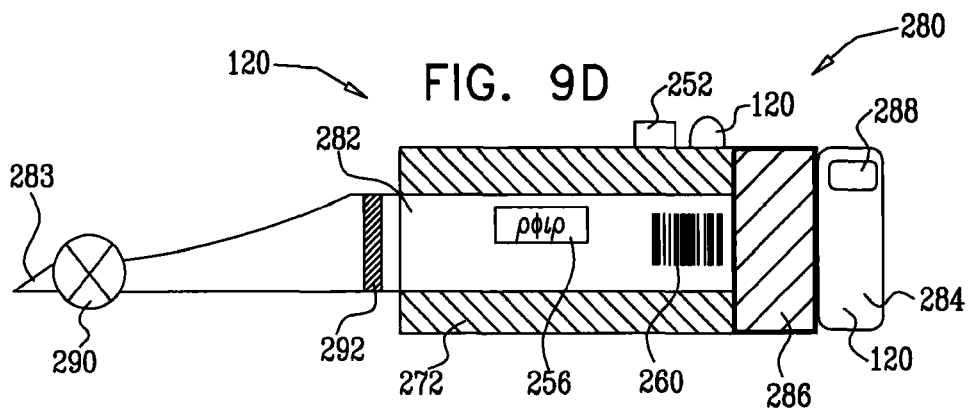
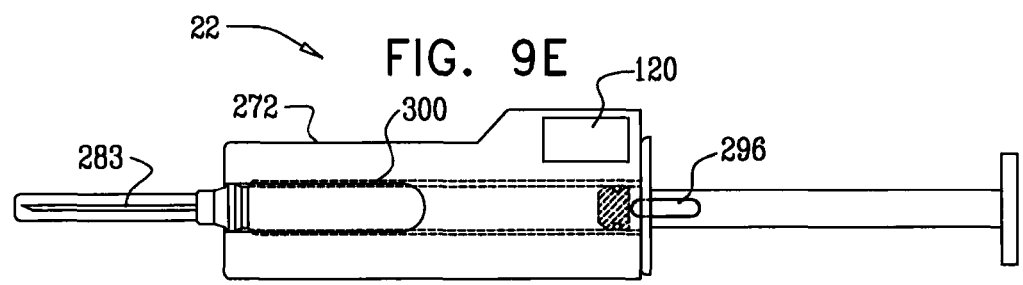
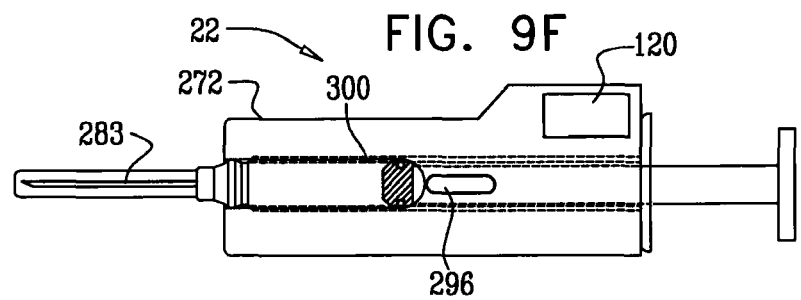
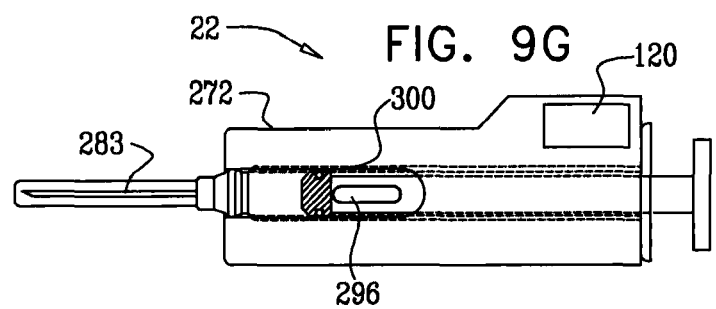
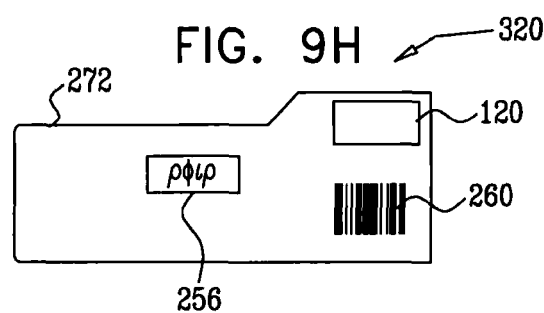

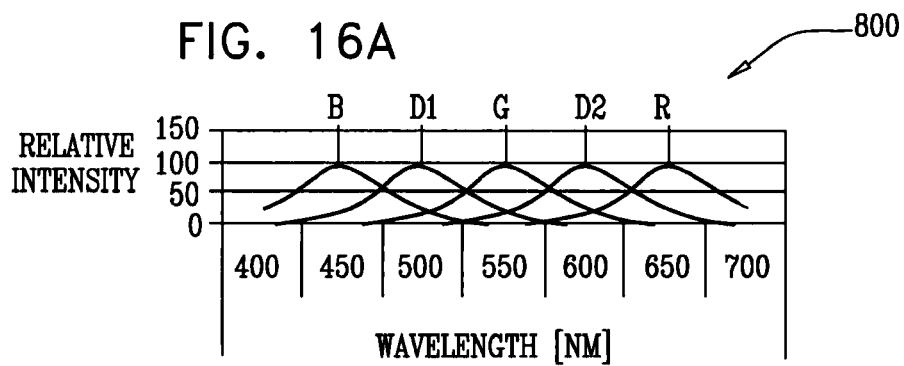
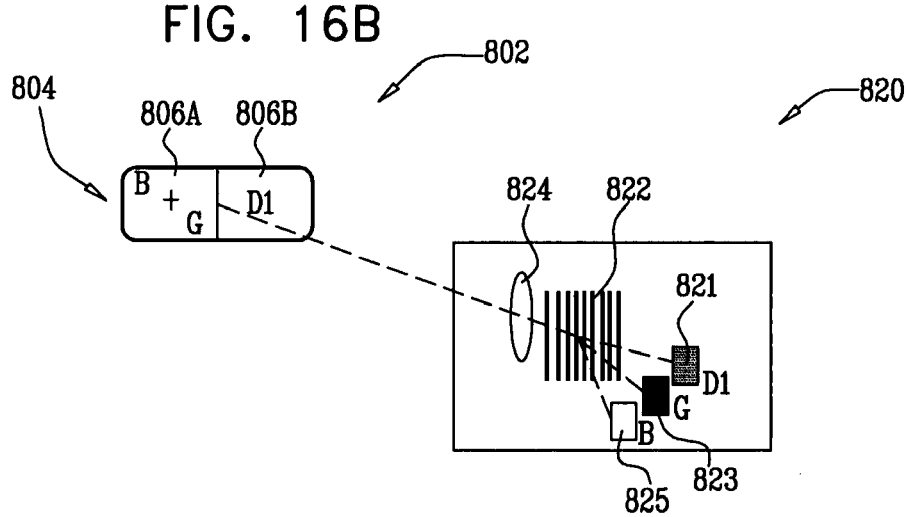

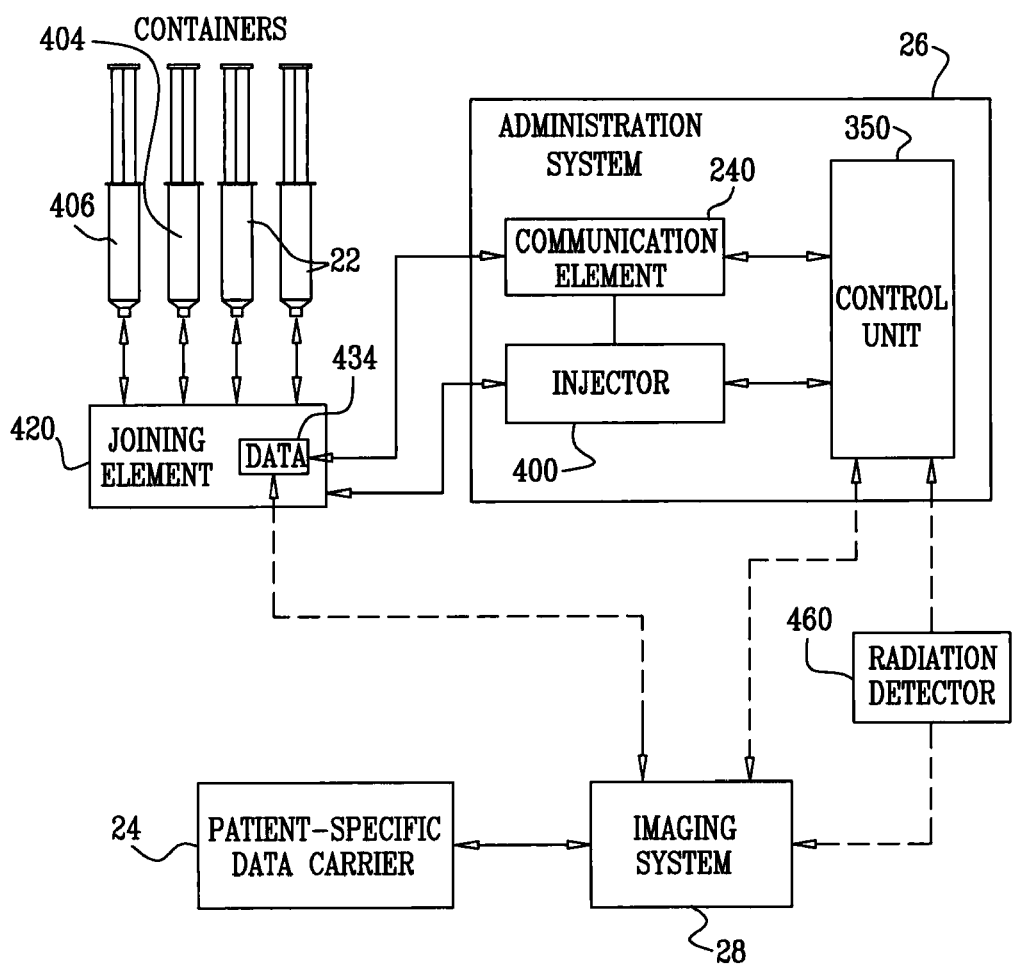

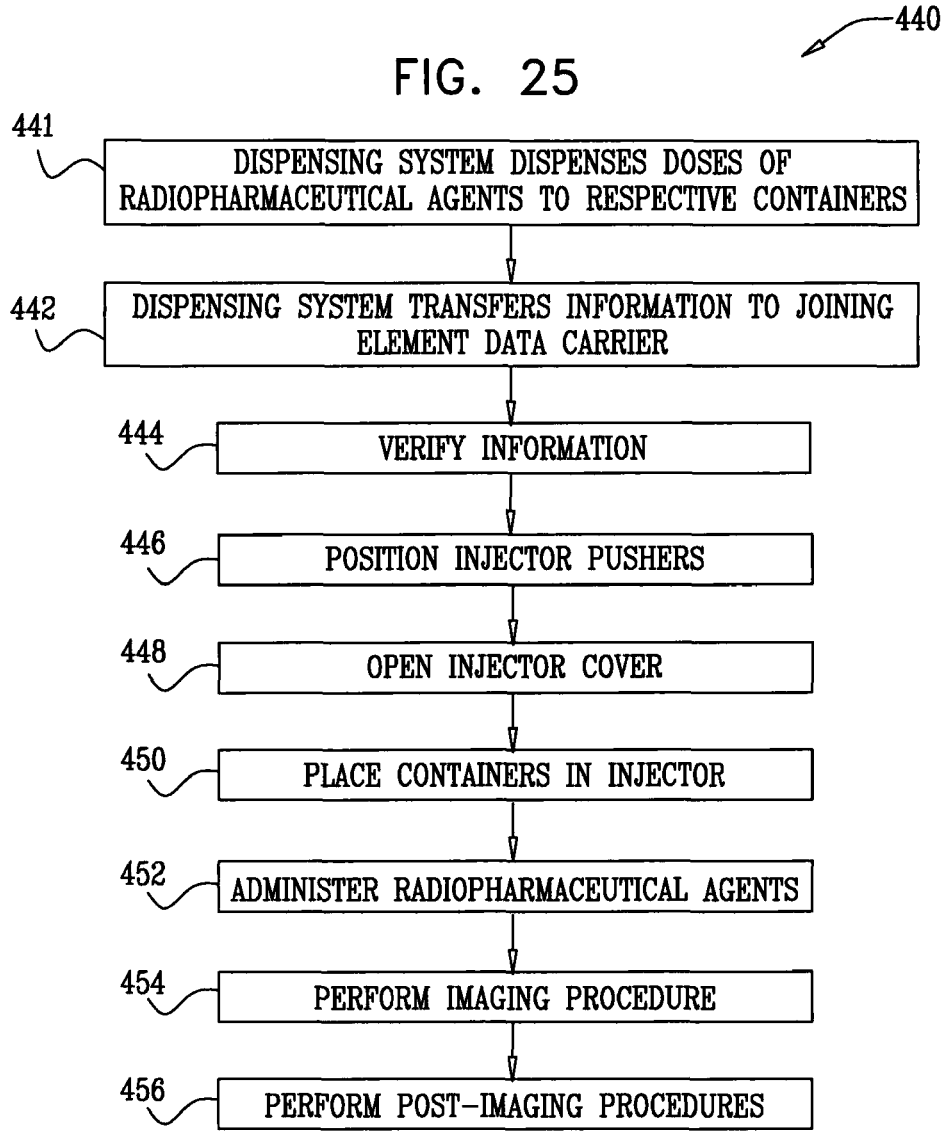

RADIOPHARMACEUTICAL DISPENSING, ADMINISTRATION, AND IMAGING

CROSS-REFERENCES TO RELATED APPLICATIONS

The present patent application is a continuation of U.S. patent application Ser. No. 11/750,057, filed May 17, 2007, entitled, "Radiopharmaceutical dispensing, administration, and imaging," which claims priority from and is a continuation-in-part of International Application PCT/IL2006/000562, filed May 11, 2006, entitled, "Unified management of radiopharmaceutical dispensing, administration, and imaging," which is a continuation-in-part of International Application PCT/IL2005/001173, filed Nov. 9, 2005, which:

(a) claims the benefit of the following U.S. Provisional Patent Applications:
  60/625,971, filed Nov. 9, 2004;
  60/628,105, filed Nov. 17, 2004;
  60/630,561, filed Nov. 26, 2004;
  60/632,236, filed Dec. 2, 2004;
  60/632,515, filed Dec. 3, 2004;
  60/635,630, filed Dec. 14, 2004;
  60/636,088, filed Dec. 16, 2004;
  60/640,215, filed Jan. 3, 2005;
  60/648,385, filed Feb. 1, 2005;
  60/648,690, filed Feb. 2, 2005;
  60/675,892, filed Apr. 29, 2005;
  60/691,780, filed Jun. 20, 2005;
  60/700,318, filed Jul. 19, 2005;
  60/700,299, filed Jul. 19, 2005;
  60/700,317, filed Jul. 19, 2005;
  60/700,753, filed Jul. 20, 2005;
  60/700,752, filed Jul. 20, 2005;
  60/702,979, filed Jul. 28, 2005;
  60/720,034, filed Sep. 26, 2005;
  60/720,652, filed Sep. 27, 2005; and
  60/720,541, filed Sep. 27, 2005, and (b) is a continuation-in-part of International Patent Application PCT/IL2005/000575, filed Jun. 1, 2005.

International Application PCT/IL2006/000562 claims the benefit of the following U.S. Provisional Applications:
  60/750,287, filed Dec. 13, 2005;
  60/750,334, filed Dec. 15, 2005; and
  60/750,597, filed Dec. 15, 2005.

U.S. patent application Ser. No. 11/750,057 claims the benefit of the following U.S. Provisional Patent Applications:
  60/800,845, filed May 17, 2006, entitled, "Radioimaging camera for dynamic studies";
  60/800,846, filed May 17, 2006, entitled, "Radioimaging protocols";
  60/816,970, filed Jun. 28, 2006.

All of the above-mentioned applications are assigned to the assignee of the present application and are incorporated herein by reference.

FIELD OF THE INVENTION

The present invention relates generally to pharmaceutical management and control, and specifically to systems and methods for radiopharmaceutical dispensing, administration, and imaging.

BACKGROUND OF THE INVENTION

US Patent Application Publication 2005/0277833 to Williams, Jr., which is incorporated herein by reference, describes techniques for handling, mixing, dispensing and/or injecting a mixture into an individual during a medical procedure. The mixture contains pharmaceutical agents and/or radiopharmaceutical agents. Also described is a mixing device capable of diluting a radiopharmaceutical agent with, for instance, a diluent, for altering a radiation dose emitted by the radiopharmaceutical agent.

US Patent Application Publication 2005/0203389 to Williams, Jr., which is incorporated herein by reference, describes techniques for an operator to control an injection device and imaging equipment from a common control console. The injection device may be used to administer a contrast medium into a patient so that imaging equipment can acquire internal images of the patient. An injection system is bundled with software and/or hardware that is used to modify an existing imaging control console so that it can be used to operate both the injection device and imaging device. In one embodiment, the common control console can access stored protocols that can contain operational parameters for the injection device, the imaging device, or both.

U.S. Pat. No. 4,679,142 to Lee, which is incorporated herein by reference, describes techniques for dispersing quantities of radioactive material at a user location. Billing is accomplished by monitoring the decay of material and the degree of activity following each user withdrawal.

US Patent Application Publication 2005/0261938 to Silverbrook et al., which is incorporated herein by reference, describes a method for authenticating a pharmaceutical product, the pharmaceutical product being associated with packaging having disposed thereon or therein coded data including a number of coded data portions, each coded data portion being indicative of an identity of the pharmaceutical product and at least part of a digital signature of at least part of the identity. The method includes having a computer system receive indicating data from a sensing device, the sensing device being responsive to sensing of the coded data to generate indicating data at least partially indicative of the identity of the pharmaceutical product and the signature part. The computer system determines the identity at least one determined signature part and uses these to authenticate the pharmaceutical product.

US Patent Application Publication 2005/0261936 to Silverbrook et al., which is incorporated herein by reference, describes a method for allowing a user to interact with a pharmaceutical product, the pharmaceutical product associated with packaging having disposed thereon or therein coded data, at least some of the coded data being indicative of at least an identity. The method includes having a computer system receive indicating data from a sensing device, in response to sensing of the coded data, and determine, using the indicating data, at least one action. The computer system then performs the action associated with the pharmaceutical product, the action including at least one of providing information to a user; updating tracking information relating to the pharmaceutical product; performing a transaction relating to the pharmaceutical product; authenticating the pharmaceutical product; and receiving feedback from the user.

U.S. Pat. Nos. 5,882,338 and 6,019,745 to Gray, which are incorporated herein by reference, describe a medical syringe comprising a cylindrical barrel having therein a plunger which can be axially driven by a plunger rod. The plunger rod passes through an aperture in the center of a finger grip having two finger grip projections at opposite sides thereof. A data carrier means in the form of an electrically or magnetically operable device is mounted near the end of one of the two finger grip projections, with preferably a device mounted near the end of each finger grip projection. The device carries data relating to the medicament contained or to be contained within the syringe, and can be read by a suitably adapted syringe pump when the syringe is mounted thereon to be driven by the syringe pump.

U.S. Pat. No. 6,970,735 to Uber, III et al., which is incorporated herein by reference, describes a system for producing a contrast-enhanced medical image of a patient, including a source of a contrast or enhancement medium, a pressurizing unit in fluid connection with the source of contrast or enhancement medium, an energy source operable to apply energy to a region of the patient, an imaging unit providing a visual display of an internal view of the patient based upon a signal resulting from the energy applied to the region of the patient, and a control unit. In an embodiment, the signal is affected by a condition of the contrast or enhancement medium in the patient. To control an imaging procedure, the control unit adjusts the condition of the contrast or enhancement medium in the patient based upon the signal. A communication interface preferably enables information between an injector subsystem and an imaging subsystem.

U.S. Pat. Nos. 5,781,442, 6,671,563, 6,915,170, and 6,731,989 to Engleson et al., which are incorporated herein by reference, describe a care management system in which the management of the administration of care for patients is automated. Hospital information systems are monitored and the information from those systems is used in verifying the administrations of care to patients. The care management system monitors ongoing administrations for progress and automatically updates records and provides alarms when necessary. The care management system is modular in nature but is fully integrated among its modules. Particular lists of data, such as the termination times of all ongoing infusions, provide hospital staff current information for increased accuracy and efficiency in planning. Features include the automatic provision of infusion parameters to pumps for accurate and efficient configuration of the pump, and providing an alarm when an unscheduled suspension of an infusion exceeds a predetermined length of time. A passive recognition system for identifying patients and care givers is described.

US Patent Application Publication 2003/0055685 to Cobb et al., which is incorporated herein by reference, describes techniques for monitoring administration of a medical product within a delivery device using a medicine data storage device attached to the delivery device, which includes a product identifier identifying the medical product and an intended patient identifier identifying a patient intended to receive the medical product. Before administering the medical product to an individual patient, the product identifier and the intended patient identifier are uploaded into a reader, and a patient identifier is accessed from the reader's memory or uploaded from a patient identification device associated with the individual patient into the reader. The patient identifier is compared with the intended patient identifier to determine whether the individual patient is intended to receive the medical product. Once it is confirmed that the individual patient is intended to receive the medical product, the medical product is administered to the individual patient.

US Patent Application Publication 2005/0131270 to Weil et al., which is incorporated herein by reference, describes a system including a radiation treatment agent to treat tissue in response to received X-ray radiation and an identifier associated with the radiation treatment agent. The identifier may be usable to identify a radiation treatment plan. In some embodiments, a radiation treatment plan associated with a patient is generated, the radiation treatment plan is associated with an identifier and a patient identifier identifying the patient, a radiation treatment agent is prepared for delivery to the patient according to the radiation treatment plan, and the radiation treatment agent is associated with the identifier.

U.S. Pat. No. 6,985,870 to Martucci et al., which is incorporated herein by reference, describes a medication delivery system comprising a medical container holding a prescribed medication to be delivered to a patient, a tag adapted to be worn by the patient, a handheld computing device, and an electronic medication delivery device. Data on the medication is contained in a first label on the medication container. The first label also contains the instruction on how the medication is delivered to the patient, including the appropriate settings for an electronic medication delivery device for delivering the medication to the patient. Patient data is contained in a second label on the tag worn by the patient. The medication data, medication delivery instruction, and patient data are provided in machine readable formats. The handheld computing device reads the medication data and the medication delivery instruction on the medication container and the patient data on the patient tag. The handheld computing device stores the information obtained and performs a matching check to confirm that the medication data matches with the patient data. Upon a confirmed match, it transmits the medication delivery instruction to the electronic medication delivery device, which downloads the instruction, programs the delivery device, and prompts an operator to begin delivering the medication to the patient according to the downloaded instruction.

US Patent Application Publication 2005/0029277 to Tachibana, which is incorporated herein by reference, describes a drug container having an identification tag fixed or detachably provided at a predetermined position of the container, the tag having recorded thereon drug data on a kind and a concentration of a drug, and upper and/or lower limits of a flow rate for continuous infusion, or time and flow rate for one-shot administration.

US Patent Application Publication 2005/0277911 to Stewart et al., which is incorporated herein by reference, describes techniques for programming a medical therapy in a medical device. The medical device has a controller, a memory, a processor, and an input device. The memory is preloaded with at least one of a plurality of patient profiles and condition profiles. The memory is further preloaded with an associated medication therapy for a plurality of the profiles. The input device receives profile data, comprising at least one of a patient profile data and a condition profile data for a specific patient, and the processor processes the received profile data and provides as output one of the preloaded medication therapies based on the processed profile data.

U.S. Pat. No. 6,506,155 to Sluis, which is incorporated herein by reference, describes an ultrasound imaging system including a data entry device that reads storage media that is assigned to each patient on which the system is to be used or the operator of the system to obtain ultrasound images. The storage media, which comprises a barcode, smartcard, or personal digital assistant, contains patient identifying information. The patient or procedure identifying information is used to access a digital requisition that is referenced by the patient identifying information. The digital requisition is stored in a disk drive included in the ultrasound imaging system or in a clinical information system accessed through a communication link included in the ultrasound imaging system. The digital requisition includes information pertaining to an ultrasound examination procedure that is to be performed on the patient, which is used to automatically set up the ultrasound imaging system. The digital requisition may also include the patient's medical history or information about the patient that can be associated with ultrasound images obtained from the patient.

US Patent Application Publication 2005/0121505 to Metz et al., which is incorporated herein by reference, describes patient-centric data acquisition protocol selection systems and methods, and identification tags therefor. A patient-centric data acquisition protocol selection system comprises a programmable identification tag capable of allowing predetermined information about a patient to be stored therein and retrieved therefrom; a medical imaging system capable of communicating with the programmable identification tag; and programming associated with the medical imaging system for selecting an optimal data acquisition protocol. The medical imaging system reads information from the programmable identification tag and then the programming selects an optimal data acquisition protocol based, at least in part, on the predetermined information about the patient that is stored in the programmable identification tag.

PCT Publication WO 04/004787 to Van Naemen et al., which is incorporated herein by reference, describes a method for dispensing individual doses of a radiopharmaceutical solution, which consists of a radioactive parent solution diluted with a diluting solution. Also described is a computer-generated dose dispenser for dispensing individual doses of a radiopharmaceutical solution at a specified speed. The method and device are described as being particularly suitable for use in the field of nuclear medicine, and more in particular for use for PET scan applications.

U.S. Pat. No. 6,032,155 to de la Huerga, which is incorporated herein by reference, describes techniques for administering a prescribed medication to a patient. A medication administration system and apparatus dispense the prescribed medication, verify that the medication is given to a correct patient by an authorized healthcare worker, and track and record the administration of the medication. The system utilizes a workstation connected to a database containing prescribed medication dose information for various patients. A healthcare worker uses the workstation to manually or automatically dispenses the medication the portable container. An information device is secured to the portable container during transport and administration of the medication to the intended patient. The information device prevents access to the medication or warns the healthcare worker of a potential error if the medication is delivered to the wrong patient or administered by an unauthorized healthcare worker. The information device records actual consumption information, and delivers this information back the workstation database or to a hospital or pharmacy database.

U.S. Pat. No. 5,317,506 to Coutre et al., which is incorporated herein by reference, describes an infusion management and pumping system. Infusion prescriptions are generated and monitored by a pharmacy management system. Labels for each infusion to be given to a patient are generated and printed in a barcode format. Each label contains data regarding a prescribed infusion program, including the drug or drugs to be infused, the infusion regimen, the expiration date, and the patient to whom the infusion is to be administered. The management system checks for incompatibilities between drugs that are being prescribed for simultaneous infusion. Each label generated by the management system is attached to the container which holds the infusion solution. The data on the label is transferred to an infusion pumping system by a barcode reader at the infusion pumping system. The pumping system checks that all necessary data has been entered. During operation, the pumping system checks for a variety of alarm conditions and stores any alarms in a ranking according to urgency. The infusion pumping system is responsive to remote or biofeedback instructions to alter the planned infusion program. Central computer records processing receives infusion data and provides infusion, inventory, and use analysis.

U.S. Pat. No. 5,039,863 to Matsuno et al., which is incorporated herein by reference, describes an automatic radioisotope filling apparatus, which is equipped with a radioisotope vial containing a radioisotope solution, a saline vial containing a physiological saline solution, a dilution vial to which a predetermined amount of the radioisotope solution and a predetermined amount of the physiological saline solution are to be transferred to prepare a diluted radioisotope solution, a radiation detector for measuring the radioactive intensity of the diluted radioisotope solution prepared in the dilution vial, and a plurality of label vials containing a drug to be labeled.

US Patent Application Publication 2004/0051368 to Caputo et al., which is incorporated herein by reference, describes a system for delivering medical fluid to a patient. The system includes a medical container including a Radio Frequency Identification (RFID) tag storing data related to the medical fluid therein. A RF reader receives data signals transmitted from the RFID tag that include a desired flow rate for delivering the fluid to the intended patient. A pump coupled to the reader includes a pumping mechanism for pumping the medical fluid from the container, and a pump controller for receiving the data including the desired flow rate from the reader. The pump controller automatically controls the pumping mechanism to pump the medical fluid from the medical container at the desired flow rate based upon the data.

US Patent Application Publication 2005/0171815 to Vanderveen, which is incorporated herein by reference, describes a centralized medication management system for monitoring, managing and controlling medication delivery from a central location. A central computer displays medication orders and ongoing medication administrations for a health care facility. The central computer checks medication delivery against a database of medication administration guidelines, including guidelines for medication interactions with other medications and with patient conditions, and provides an indication of any detected incompatibilities. A clinician at the central location may adjust the medication administration parameters in response to detected incompatibilities and communicate with a caregiver at the point of care to provide decision support. In an embodiment, the central location is a pharmacy at the healthcare facility.

US Patent Application Publication 2005/0240441 to Suzuki, which is incorporated herein by reference, describes a hospital information system. The system enables an RF reader, comprising a personal digital assistant (PDA), to read tag information recorded by RF tags either attached to, or embedded in, various types of a patient wrist bands, injection medicine bottles, patient charts, and medical instrument cases. The PDA transmits a query to a server via a wireless LAN for confirmation from the server. The server collates the query with the content of a medical practice order recorded in its data base, and registers a completion of instructed operation for an instructed item in the database, and replies with a notification if the transmitted readout data from the PDA is correct. If the readout data is incorrect, the PDA is notified and instructed to perform another reading.

US Patent Application Publication 2001/0049608 to Hochman, which is incorporated herein by reference, describes an automated drug administering system such an injection device or infusion pump, which is provided with means for reading information from a container holding the drug. The information is then checked for accuracy before the administration of the drug. Optionally, an ID tag on the patient and/or the health care professional providing the drug may also be scanned and checked. The information thus gathered is sent to another station where it is logged for future use and analyzed.

U.S. Pat. No. 6,743,202 to Hirschman et al., which is incorporated herein by reference, describes apparatus for sharing information on syringe configuration between syringes and injector systems, comprising a storage system to store encoded information on syringe configuration. The encoded information is readable by a detection circuit in an injector. In one embodiment, the storage system is an electronic storage system in which information relevant to the syringe configuration is encoded. A method comprises the step of conveying syringe configuration information to a detector in an injector for use with the syringe.

US Patent Application Publication 2005/0148869 to Masuda, which is incorporated herein by reference, describes a liquid syringe having various kinds of data items recorded in a two-dimensional code format. A liquid injector optically reads the two-dimensional codes, decodes them, and executes a predetermined operations corresponding to the decoded results. Recording, for example, a variable pattern for the liquid of interest in the two-dimensional code format on the liquid syringe makes it possible for the liquid injector to inject the liquid in accordance with the predetermined variable pattern.

U.S. Pat. No. 6,346,886 de la Huerga, which is incorporated herein by reference, describes an electronic identification apparatus having data storage memory on board a removable transceiver device. The transceiver device also includes a processor and a transponder for receiving information pertaining to the object/person to which it is attached and storing the information in memory. The transceiver also transmits stored data to a control computer or the external devices. The transceiver is mounted on a base, such as a wristband, and the apparatus includes an attachment sensor indicating whether the transceiver is attached to the base. If the transceiver has been removed from the base, the processor performs one or more lockdown operations to prevent the stored data from being used in connection with another object or person. The lockdown operations include clearing the contents of the memory, disabling access to the memory, suppressing the display of stored data and activating an alarm.

US Patent Application Publication 2004/0156081 to Bril et al., which is incorporated herein by reference, describes a color-coded signature, for securing documents or encrypting images. The encrypted image comprises an array of printed positions formed using a group of inks each of which has a predetermined spectrum. The positions are selected to form a predetermined image, either real or virtual, when the image is viewed through an optical processor. The optical processor may further use a distorted grating or a distorted lens. The correct image is the spectrum, as distorted by the optical processor. An image formed using inks having the same colors as experienced by the human eye, or even by a standard spectrometer will fail to form the correct predetermined image.

The following patents and patent application publications, all of which are incorporated herein by reference, may be of interest:

US Patent Applications 2005/0131579 and 2005/0088306, and U.S. Pat. No. 6,935,560, all to Andreasson U.S. Pat. No. 6,851,615 to Jones US Patent application 2005/0131397 and U.S. Pat. No. 6,861,954 to Levin U.S. Pat. No. 6,519,569 to White et al.
U.S. Pat. No. 5,692,640 to Caulfield et al.
U.S. Pat. Nos. 6,475,192 and 6,733,478 to Reilly et al.
U.S. Pat. No. 6,958,053 to Reilly
US Patent Application Publications 2005/0261937 and 2005/0261938 to Silverbrook et al.
U.S. Pat. No. 6,994,249 to Peterka et al.
U.S. Pat. No. 6,843,357 to Bybee et al.
U.S. Pat. No. 6,425,174 to Reich
U.S. Pat. No. 6,722,499 to Reich
U.S. Pat. No. 5,536,945 to Reich
U.S. Pat. No. RE36,693 to Reich
U.S. Pat. No. 5,519,931 to Reich
US Patent Application Publication 2005/0198800 to Reich
U.S. Pat. No. 6,576,918 to Fu et al.
US Patent Application Publication 2005/0247893 to Fu et al.
U.S. Pat. No. 5,927,351 to Zhu et al.
U.S. Pat. No. 5,828,073 to Zhu et al.
U.S. Pat. No. 6,162,198 to Coffey et al.
U.S. Pat. Nos. 6,338,007 and 6,116,461 to Broadfield et al.
U.S. Pat. No. 5,944,190 to Edelen
PCT Publication WO 04/032151 to Besing et al.
US Patent Application Publication 2005/0234424 to Besing et al.
U.S. Pat. No. 4,296,785 to Vitello et al.
U.S. Pat. No. 3,446,965 to Ogier et al.
U.S. Pat. No. 6,355,024 to Small et al.
U.S. Pat. No. 6,468,261 to Small et al.
U.S. Pat. No. 5,580,541 to Wells et al.
U.S. Pat. No. 3,535,085 to Shumate
U.S. Pat. No. 4,853,546 to Abe et al.
U.S. Pat. No. 5,329,976 to Haber et al.
U.S. Pat. No. 5,304,165 to Haber et al.
U.S. Pat. No. 5,911,252 to Cassel
U.S. Pat. No. 5,475,232 to Powers et al.
PCT Publication WO 05/002971 to Tochon-Danguy et al.
US Patent Application Publication 2005/0278066 to Graves
U.S. Pat. No. 5,479,969 to Hardie et al.
U.S. Pat. No. 5,309,959 to Shaw et al.
U.S. Pat. No. 6,870,175 to Dell et al.
U.S. Pat. No. 6,767,319 to Reilly et al.
U.S. Pat. No. 6,976,349 to Baldwin et al.
U.S. Pat. No. 6,957,522 to Baldwin et al.
U.S. Pat. No. 6,915,619 to Baldwin
U.S. Pat. No. 6,813,868 to Baldwin et al.
U.S. Pat. No. 5,893,397 to Peterson et al.
U.S. Pat. Nos. 5,885,216, 5,806,519, and 6,901,283 to Evans, III et al.
US Patent Application Publication 2004/0084340 to Morelle et al.
U.S. Pat. No. 6,269,340 to Ford et al.
US Patent Application Publication 2004/0193453 to Butterfield et al.
U.S. Pat. No. 4,476,381 to Rubin
U.S. Pat. Nos. 6,643,537 and 6,339,718 to Zatezalo et al.
US Patent Application Publication 2005/0108044 to Koster
U.S. Pat. No. 6,851,615 to Jones
U.S. Pat. No. 5,840,026 to Uber, III et al.
U.S. Pat. No. 5,920,054 to Uber, III
U.S. Pat. No. 6,685,678 to Evans et al.
US Patent Application Publication 2003/0183226 to Brand et al.
US Patent Application Publications 2005/0107914 and 2005/0113945 to Engleson et al.

US Patent Application Publication 2002/0198738 to Osborne

US Patent Application Publication 2002/0099334 to Hanson et al.

U.S. Pat. Nos. 6,317,648 and 6,522,945 to Sleep et al.

U.S. Pat. Nos. 6,155,485 and 6,318,630 to Coughlin et al.

U.S. Pat. No. 6,202,923 to Boyer et al.

U.S. Pat. No. 6,915,823 to Osborne et al.

US Patent Application Publication 2004/0205343 to Forth et al.

U.S. Pat. No. 5,493,805 to Penuela et al.

U.S. Pat. No. 5,973,598 to Beigel

US Patent Application Publication 2005/0149350 to Kerr et al.

U.S. Pat. No. 5,884,457 to Ortiz et al.

U.S. Pat. No. 5,947,935 to Rhinehart et al.

U.S. Pat. No. 5,207,642 to Orkin et al.

U.S. Pat. No. 5,814,015 to Gargano et al.

U.S. Pat. No. 5,507,412 to Ebert et al.

U.S. Pat. No. 5,547,470 to Johnson et al.

U.S. Pat. No. 5,179,983 to Cordner, Jr. et al.

The following patents and patent application publications, which describe gamma cameras and imaging processing techniques, and which are incorporated herein by reference, may be of interest:

US Patent Application Publication 2005/0205792 to Rousso et al.

PCT Publication WO 05/118659 to Dichterman et al.

PCT Publication WO 05/119025 to Nagler et al.

US Patent Application Publication 2004/0204646 to Nagler et al.

PCT Publication WO 04/042546 to Kimchy et al.

US Patent Application Publication 2004/0054248 to Kimchy et al.

US Patent Application Publication 2004/0015075 to Kimchy et al.

US Patent Application Publication 2004/0054278 to Kimchy et al.

US Patent Application Publication 2005/0266074 to Zilberstein et al.

U.S. Pat. Nos. 5,939,724, 5,587,585, and 5,365,069 to Eisen et al.

U.S. Pat. No. 6,943,355 to Shwartz et al.

U.S. Pat. Nos. 6,242,743 and 5,757,006 to DeVito et al.

U.S. Pat. No. 6,137,109 to Hayes

U.S. Pat. No. 6,388,258 to Berlad et al.

U.S. Pat. No. 6,429,431 to Wilk

U.S. Pat. No. 6,838,672 to Wagenaar et al.

U.S. Pat. Nos. 6,740,882, 6,545,280, 6,229,145, 5,519,221, and 5,252,830 to Weinberg U.S. Pat. No. 6,713,766 to Garrard et al.

U.S. Pat. No. 6,765,981 to Heumann

U.S. Pat. No. 6,664,542 to Ye et al.

U.S. Pat. No. 6,080,984 to Friesenhahn

U.S. Pat. No. 5,818,050 to Dilmanian et al.

U.S. Pat. No. 6,728,583 to Hallett

U.S. Pat. No. 5,481,115 to Hsieh et al.

U.S. Pat. No. 6,723,988 to Wainer

U.S. Pat. No. 6,940,070 to Turner

U.S. Pat. No. 6,635,879 to Jimbo et al.

U.S. Pat. No. 6,353,227 to Boxen

U.S. Pat. No. 6,184,530 to Hines et al.

US Patent Application Publication 2005/0145797 to Oaknin et al.

US Patent Application Publication 2004/0251419 to Nelson et al.

US Patent Application Publication 2003/0001098 to Stoddart et al.

PCT Publication WO 98/16852 to DeVito et al.

PCT Publication WO 05/059840 to Nielsen et al.

SUMMARY OF THE INVENTION

In some embodiments of the present invention, an end-to-end automated system for medical imaging comprises a plurality of integrated elements that are configured to electronically exchange information among one another. The elements include an automated radiopharmaceutical dispensing system, a portable radiopharmaceutical agent container (which, for some applications, is information-bearing), a portable information-bearing joining element, a patient management system, a portable patient-specific data carrier, an automated administration system, and an automated imaging system. The systems perform their respective automated functions at least in part responsively to the exchanged information. The elements typically authenticate one another via the exchanged information, in order to ensure that only authorized elements participate in the system, and that the systems perform only authorized and appropriate functions.

The exchanged information typically includes patient-specific data, radiopharmaceutical agent-specific data, and/or patient- or radiopharmaceutical agent-specific imaging protocol data. Such data enable the systems to customize their respective automated functions for specific patients, radiopharmaceutical agents, indications, and/or imaging procedures. For some applications, the exchanged information includes commercial license information relating to the use of a specific protocol with a specific radiopharmaceutical agent, and one or more of the systems are configured to verify the license information before performing their respective functions.

In some embodiments of the present invention, the information-bearing radiopharmaceutical agent container, the information-bearing joining element, and/or the patient-specific data carrier is configured to contain protocol information for performing an imaging procedure using the labeled radiopharmaceutical agent held by the container. For some applications, the protocol information includes SPECT imaging protocol information, and the imaging system uses the protocol information to perform a SPECT imaging procedure using the labeled radiopharmaceutical agent contained in the container. For some applications, the agent container contains a single dose of the labeled radiopharmaceutical agent, which dose is appropriate for use with the imaging protocol.

In some embodiments of the present invention, the information-bearing radiopharmaceutical agent container, the information-bearing joining element, or the patient-specific data carrier is configured to contain at least one kinetic parameter of the labeled radiopharmaceutical agent contained in the container. The imaging system uses the kinetic parameter to perform a dynamic SPECT imaging procedure.

In some embodiments of the present invention, the information-bearing radiopharmaceutical agent container contains radiopharmaceutical information regarding the labeled radiopharmaceutical agent contained in the container. Alternatively, the information-bearing joining element contains radiopharmaceutical information regarding labeled radiopharmaceutical agents contained in one or more respective containers coupled to the joining element. The portable patient-specific data carrier is configured to contain patient information regarding the patient, and imaging protocol information for use with the labeled radiopharmaceutical agent, such as SPECT imaging protocol information. The imaging system uses the protocol information to perform an imaging procedure, such as a dynamic SPECT imaging procedure. For some applications, the patient-specific data carrier comprises a coupling mechanism configured to be coupled to the patient. For example, the coupling mechanism may comprise a bracelet, a watch, a necklace, or another wearable article.

In some embodiments of the present invention, the information-bearing radiopharmaceutical agent container and/or the information-bearing joining element contains a first identifier value, and the patient-specific data carrier contains a second identifier value. The imaging system is configured to perform an imaging procedure responsively to a detection of a correspondence between the first and second identifier values. For some applications, the first identifier value equals the second identifier value, while for other applications the values do not equal one another, but instead correspond to one another based on information provided by an element of the end-to-end system. For some applications, the first and/or second identifier values are arbitrarily assigned, or pre-loaded into the data carrier by a manufacturer or distributor, while for other applications at least one of the identifier values comprises a patient identifier, or another meaningful value. For some applications, at least one of the information-bearing agent container, the information-bearing joining element, and the patient-specific data carrier performs the detection of the correspondence, while for other applications the imaging system or another element of the end-to-end system performs the detection of the correspondence.

In some embodiments of the present invention, the information-bearing joining element is removably couplable to an injector of the automated administration system. The joining element is configured to be coupled to respective radiopharmaceutical agent containers, such that the containers are in fluid communication with tubing of the joining element. The tubing of the joining element merges the liquid pumped from the containers by the injector, and is removably coupled to an infusion line to the patient. The joining element comprises a data carrier that stores patient-specific information, radiopharmaceutical-related information regarding the radiopharmaceuticals contained in the containers coupled to the joining element, administration protocol information, and/or imaging protocol information. For some applications, at least a portion of such information is read by the administration system and the imaging system. Typically, neither the administration system nor the imaging system write to the data carrier, such that the data carrier does not serve as a communication interface between the imaging system and the administration system.

For some applications, the administration system is programmed with a list of actions the injector is capable of performing, such as actuating each of the syringe pumps at certain rates, and ceasing such actuations. Each of these actions is associated with an identifier code. The imaging system reads administration protocol information from the patient-specific data carrier and/or the data carrier of the joining element. To execute the administration protocol, the imaging system signals the administration system to drive the injector to perform each of the actions specified by the administration protocol, by sending the corresponding identifier code from the imaging system to the administration system at the desired time of the action.

For other applications, the administration system reads administration protocol information from the data carrier of the joining element. The administration protocol includes a plurality of steps associated with actions of the injector, each of which steps has associated therewith a step identifier code. For example, the step identifier codes may simply sequentially number the steps of the administration protocol. To execute the administration protocol, the imaging system signals the administration system to drive the injector to perform each of the actions specified by the administration protocol, by sending the corresponding step identifier code from the imaging system to the administration system at the desired time of the action.

In some embodiments of the present invention, the imaging system comprises a SPECT imaging system configured to utilize the information contained in the labeled radiopharmaceutical agent container, the information-bearing joining element, and/or the patient-specific data carrier to customize at least one function of the system selected from the group consisting of: administration of the labeled radiopharmaceutical agent, acquisition of a SPECT image of the patient to whom the labeled radiopharmaceutical agent is administered, reconstruction of the SPECT image, analysis of the SPECT image, and diagnosis of a condition of the patient based at least in part on the analysis.

The integration of the elements of the end-to-end system, and the exchange of authenticatable information among the elements generally increase patient safety, by ensuring that each patient receives the prescribed labeled radiopharmaceutical agent and dosage, and undergoes the desired imaging protocol. For some applications, one or more elements of the end-to-end system are configured to perform their respective function only upon being triggered by another element of the system. For example, the administration or imaging system may perform its function only upon being triggered by the information-bearing radiopharmaceutical agent container, by the information-bearing joining element, by the patient-specific data carrier, and/or, in the case of the administration system, by the imaging system.

In some embodiments of the present invention, the automated radiopharmaceutical dispensing system comprises an information manager that is configured to receive radiopharmaceutical information regarding a labeled radiopharmaceutical agent and patient information regarding a patient. Responsively to the information, the dispensing system automatically dispenses a dose of the labeled radiopharmaceutical agent to an agent container, and stores the radiopharmaceutical information and at least a portion of the patient information in a data carrier associated with the container, and/or in a data carrier associated with the joining element. For some applications, the radiopharmaceutical information is selected from the group consisting of: imaging protocol information for use with the labeled radiopharmaceutical agent, such as a SPECT imaging protocol; at least one kinetic parameter useful for performing a dynamic SPECT imaging procedure using the at least one labeled radiopharmaceutical agent; and authenticatable information regarding a commercial license for use of a SPECT imaging protocol with the at least one labeled radiopharmaceutical agent.

In some embodiments of the present invention, the dispensing system is configured to receive a mother vial containing a labeled radiopharmaceutical agent in a quantity sufficient for preparation of a plurality of doses of the labeled radiopharmaceutical agent. Associated with the mother vial is a data carrier containing information regarding the labeled radiopharmaceutical agent, such as the formulation, radioactivity information, and protocol information. The information manager of the dispensing system receives at least a portion of the labeled radiopharmaceutical agent information from the data carrier.

In some embodiments of the present invention, use of the end-to-end automated system enables customization of one or more aspects of the imaging process, from dispensing to diagnosis. Customization typically includes one or more of the following:

- The dispensing system customizes the dispensed dose for a specific patient, based on radiopharmaceutical information and patient-specific information. Typically, the dispensing system customizes the dispensed dose (e.g., the radioactivity level thereof) based in part on the scheduled time of the scheduled time of administration of the dose, and/or the scheduled time of the imaging procedure to be performed using the dose.
- The administration system customizes the administered dose for a specific patient, based on radiopharmaceutical information and patient-specific information. For some applications in which the administration system customizes the administered dose, the radiopharmaceutical agent container contains a standard, non-customized dose.
- The imaging system customizes image acquisition, image reconstruction, image analysis, and/or diagnosis, based on radiopharmaceutical information and patient-specific information, such as patient physiology and/or known and/or suspected disease of the patient.

Such customization is typically based at least in part on information provided by the manufacturer or distributor of the radiopharmaceutical agent. Such information may be in the form of lookup tables and/or expert system rules.

As used in the present application, including in the claims, "labeled" means radiolabeled, and "unlabeled" means not radiolabeled.

There is therefore provided, in accordance with an embodiment of the present invention, apparatus for use with at least one labeled radiopharmaceutical agent, the apparatus including:

a container containing the at least one labeled radiopharmaceutical agent; and a portable computer-communicatable data carrier associated with the container, the data carrier containing imaging protocol information for use with the at least one labeled radiopharmaceutical agent.

For some applications, the apparatus includes a device configured to write the imaging protocol information to the data carrier.

For some applications, the data carrier additionally contains administration protocol information useful for administering the at least one labeled radiopharmaceutical agent. For some applications, the administration protocol information and the imaging protocol information specify a protocol using the at least one labeled radiopharmaceutical agent, which protocol has a total duration, including administration and image acquisition, of less than 30 minutes, and includes at least one rest phase and at least one stress phase. For some applications, the total duration is less than 25 minutes, such as less than 20 minutes, or less than 16 minutes.

In an embodiment, the imaging protocol information includes instructions for performing an imaging procedure using the at least one labeled radiopharmaceutical agent. Alternatively or additionally, the imaging protocol information includes an identifier of an imaging protocol. Further alternatively or additionally, the imaging protocol information includes a parameter of the at least one labeled radiopharmaceutical agent. Still further alternatively or additionally, the imaging protocol information includes a parameter useful for configuring at least one aspect of an imaging procedure performed using the at least one labeled radiopharmaceutical agent.

In an embodiment, the container contains a single dose of the radiopharmaceutical agent, which dose is appropriate for use with the imaging protocol information. Alternatively, the container contains a plurality of labeled radiopharmaceutical agents mixed together. For some applications, the container is shaped so as to define a plurality of chambers, each of which contains a respective one of a plurality of labeled radiopharmaceutical agents.

In an embodiment, the data carrier includes a first data carrier, which contains a first identifier value, the apparatus further includes a second computer-communicatable data carrier, which contains a second identifier value, and the apparatus is configured to operate responsively to a detection of a correspondence between the first and second identifier values. For some applications, at least one of the first and second data carriers is configured to perform the detection of the correspondence. Alternatively or additionally, the apparatus includes a correspondence-detection element configured to perform the detection of the correspondence.

In an embodiment, at least one of the first and second data carriers contains an identifier of a patient to whom the labeled radiopharmaceutical agent is to be administered.

For some applications, at least one of the first and second identifier values includes an identifier of a patient to whom the labeled radiopharmaceutical agent is to be administered.

In an embodiment, exactly one of the first and second data carriers includes a coupling mechanism configured to be coupled to a patient to whom the labeled radiopharmaceutical agent is to be administered.

In an embodiment, the apparatus includes an imaging system including imaging functionality, the imaging system configured, responsively to the detection of the correspondence, to drive the imaging functionality to perform an imaging procedure using the at least one labeled radiopharmaceutical agent.

In an embodiment, the apparatus includes a portable joining element, which is configured to be coupled (e.g., removably coupled) to the container, and the data carrier is physically coupled to the joining element. For some applications, the at least one labeled radiopharmaceutical agent includes a plurality of labeled radiopharmaceutical agents, the container includes a plurality of containers containing respective ones of the plurality of labeled radiopharmaceutical agents, and the imaging protocol information contained in the data carrier is for use with the plurality of labeled radiopharmaceutical agents.

In an embodiment, the joining element includes tubing, which is configured to be coupled in fluid communication with the plurality of containers.

For some applications, the data carrier additionally contains administration protocol information useful for administering the at least one labeled radiopharmaceutical agent.

For some applications, the apparatus includes:
an administration system, which includes:
an injector, configured to be coupled to the container; and
an administration control unit; and
an imaging system, which includes:
a communication element, configured to receive, from the data carrier, the administration protocol information, which specifies injector actions of an administration procedure associated with respective action identifier codes; and
an imaging control unit, configured to communicate, responsively to the protocol information, the action identifier codes to the administration system at respective appropriate times, wherein the administration control unit is configured to:
store a list of the injector actions associated with the respective action identifier codes,
receive the action identifier codes communicated by the imaging control unit, and
responsively to the action identifier codes, drive the injector to perform corresponding injector actions, including administering the at least one labeled radiopharmaceutical agent contained in the container.

For some applications, the apparatus includes:
an administration system, which includes:
an injector, configured to be coupled to the container;
a communication element, configured to receive, from the data carrier, the administration protocol information, which specifies a list of steps of an administration protocol associated with respective step identifier codes; and
an administration control unit; and
an imaging system, which includes an imaging control unit, which is configured to communicate the step identifier codes to the administration system at respective appropriate times,
wherein the administration control unit is configured to:
receive the step identifier codes communicated by the imaging control unit, and
responsively to the step identifier codes, drive the injector to perform corresponding injector actions, including administering the at least one labeled radiopharmaceutical agent contained in the container.

In an embodiment, the data carrier is physically coupled to the container. For some applications, the data carrier contains an identifier of a patient to whom the labeled radiopharmaceutical agent is to be administered, and the imaging protocol information includes imaging protocol information selected for the patient. For some applications, the imaging protocol information includes an identifier of an imaging protocol.

For some applications, the imaging protocol information includes imaging protocol information customized for the patient.

In an embodiment, the imaging protocol information includes SPECT imaging protocol information, such as dynamic SPECT imaging protocol information. For some applications, the SPECT imaging protocol information includes at least one kinetic parameter of the at least one labeled radiopharmaceutical agent, the at least one kinetic parameter useful for performing a dynamic SPECT imaging procedure using the at least one labeled radiopharmaceutical agent.

In an embodiment, the apparatus includes an imaging system, which includes a communication element, configured to read the imaging protocol information from the data carrier; and a control unit, including imaging functionality, which is configured to perform an imaging procedure, and to configure the procedure at least in part responsively to the imaging protocol information read from the data carrier by the communication element.

In an embodiment, the imaging system includes a camera, the imaging functionality includes image acquisition functionality, and the image acquisition functionality is configured to perform an image acquisition procedure using the camera, and to configure the procedure at least in part responsively to the imaging protocol information read from the data carrier by the communication element. For some applications, the image acquisition functionality configures a total acquisition time of the image acquisition procedure at least in part responsively to the imaging protocol information. Alternatively or additionally, the camera includes a plurality of detectors, and the image acquisition functionality is configured to configure, at least in part responsively to the imaging protocol information, at least one motion of at least one of the detectors during the image acquisition procedure. For some applications, the control unit is configured to configure, at least in part responsively to the imaging protocol information, a waiting time between administration of the labeled radiopharmaceutical agent and commencement of the image acquisition procedure. For some applications, the image acquisition functionality is configured to perform a gated image acquisition procedure at least in part responsively to the imaging protocol information.

In an embodiment, the imaging functionality includes image reconstruction functionality, and the image reconstruction functionality is configured to perform an image reconstruction procedure, and to configure the procedure at least in part responsively to the imaging protocol information read from the data carrier by the communication element.

In an embodiment, the imaging functionality includes image analysis functionality, and the image analysis functionality is configured to perform an image analysis procedure, and to configure the procedure at least in part responsively to the imaging protocol information read from the data carrier by the communication element.

In an embodiment, the imaging functionality includes diagnosis functionality, and the diagnosis functionality is configured to perform a diagnostic procedure, and to configure the procedure at least in part responsively to the imaging protocol information read from the data carrier by the communication element.

In an embodiment, the imaging procedure includes a three-dimensional dynamic imaging study, and the imaging functionality is configured to perform the three-dimensional dynamic imaging study, and to configure the study at least in part responsively to the imaging protocol information read from the data carrier by the communication element.

In an embodiment, the data carrier is not physically coupled to the container, and the data carrier contains an identifier of a patient to whom the labeled radiopharmaceutical agent is to be administered. For some applications, the data carrier includes a coupling mechanism configured to be coupled to the patient. In an embodiment, the data carrier includes a first data carrier, and the apparatus further includes a second computer-communicatable data carrier physically coupled to the container, the second data carrier containing radiopharmaceutical information regarding the at least one labeled radiopharmaceutical agent.

There is further provided, in accordance with an embodiment of the present invention, apparatus for use with one or more labeled radiopharmaceutical agents, the apparatus including:
one or more containers respectively containing the one or more labeled radiopharmaceutical agents;
a portable joining element, which is configured to be coupled (e.g., removably coupled) to the containers; and
a portable computer-communicatable data carrier physically coupled to the joining element, the data carrier containing imaging protocol information for use with the labeled radiopharmaceutical agents, and administration protocol information for use with the labeled radiopharmaceutical agents.

For some applications, the one or more labeled radiopharmaceutical agents include a plurality of labeled radiopharmaceutical agents, the one or more containers include a plurality of containers containing respective ones of the plurality of labeled radiopharmaceutical agents, and the imaging protocol information and the administration protocol information contained in the data carrier are for use with the plurality of labeled radiopharmaceutical agents.

In an embodiment, the joining element includes tubing, which is configured to be coupled in fluid communication with the plurality of containers.

For some applications, the administration protocol information includes instructions for performing an administration procedure using the one or more labeled radiopharmaceutical agents. Alternatively or additionally, the administration protocol information includes an identifier of an administration protocol.

For some applications, the imaging protocol information includes instructions for performing an imaging procedure using the one or more labeled radiopharmaceutical agents. Alternatively or additionally, the imaging protocol information includes an identifier of an imaging protocol.

There is also provided, in accordance with an embodiment of the present invention, apparatus for use with at least one labeled radiopharmaceutical agent, the apparatus including:

a container containing the at least one labeled radiopharmaceutical agent; and a computer-communicatable data carrier associated with the container, the data carrier containing authenticatable information regarding a commercial license for use of SPECT imaging protocol information with the at least one labeled radiopharmaceutical agent.

In an embodiment, the apparatus includes an imaging system, which includes:

a communication element, configured to read the authenticatable license information from the data carrier;

a control unit, including imaging functionality, the control unit configured to:

authenticate the authenticatable license information, and only upon authentication, drive the imaging functionality to perform an imaging procedure using the SPECT imaging protocol information.

For some applications, the apparatus includes a device configured to write the authenticatable license information to the data carrier.

For some applications, the data carrier is physically coupled to the container.

There is further provided, in accordance with an embodiment of the present invention, apparatus including a portable computer-communicatable data carrier containing authenticatable information regarding a commercial license for use of SPECT imaging protocol information.

For some applications, the data carrier additionally contains patient information regarding a patient upon whom an imaging procedure using the SPECT imaging protocol information is to be performed.

For some applications, the authenticatable license information is encrypted.

In an embodiment, the apparatus includes an imaging system, which includes:

a communication element, configured to read the authenticatable license information from the data carrier, a control unit, including imaging functionality, the control unit configured to:

authenticate the authenticatable license information, and only upon authentication, drive the imaging functionality to perform an imaging procedure using the SPECT imaging protocol information.

For some applications, the apparatus includes a device configured to write the authenticatable license information to the data carrier.

For some applications, the data carrier includes a coupling mechanism configured to be coupled to a patient upon whom an imaging procedure using the SPECT imaging protocol information is to be performed.

There is still further provided, in accordance with an embodiment of the present invention, apparatus including:

a first portable computer-communicatable data carrier containing a first identifier value;

a second portable computer-communicatable data carrier containing a second identifier value; and an imaging system including imaging functionality, the imaging system configured, responsively to a detection of a correspondence between the first and second identifier values, to drive the imaging functionality to perform an imaging procedure on a patient.

For some applications, at least one of the first and second data carriers is configured to perform the detection of the correspondence. Alternatively or additionally, the imaging system includes a correspondence-detection element configured to perform the detection of the correspondence.

For some applications, at least one of the first and second data carriers contains an identifier of a patient to whom the labeled radiopharmaceutical agent is to be administered.

For some applications, at least one of the first and second identifier values includes an identifier of a patient to whom the labeled radiopharmaceutical agent is to be administered.

In an embodiment, one of the first and second data carriers includes a coupling mechanism configured to be coupled to a patient to whom the labeled radiopharmaceutical agent is to be administered.

For some applications, the apparatus includes a device configured to write at least one of the first and second identifier values to the respective first and second data carriers.

In an embodiment, at least one of the first and second data carriers contains radiopharmaceutical information regarding at least one labeled radiopharmaceutical agent, the imaging system includes a communication element, configured to read the radiopharmaceutical information from the at least one of the data carriers, and the imaging system is configured to configure the imaging procedure at least in part responsively to the read radiopharmaceutical information. For some applications, the apparatus includes a container containing the at least one labeled radiopharmaceutical agent. For some applications, one of the first and second data carriers is physically coupled to the container.

In an embodiment, the imaging functionality includes a nuclear camera. For some applications, the nuclear camera includes a SPECT camera.

There is yet further provided, in accordance with an embodiment of the present invention, apparatus for use with first and second portable computer-communicatable data carriers containing first and second identifier values, respectively, the apparatus including an imaging system, which includes:

imaging functionality; and a control unit configured to drive the imaging functionality to perform an imaging procedure on a patient, responsively to a detection of a correspondence between the first and second identifier values.

For some applications, the imaging system includes a correspondence-detection element configured to perform the detection of the correspondence.

There is additionally provided, in accordance with an embodiment of the present invention, apparatus for use with at least one labeled radiopharmaceutical agent for administration to a patient, the apparatus including:

a container containing the at least one labeled radiopharmaceutical agent;

a first computer-communicatable data carrier physically coupled to the container, the first data carrier containing radiopharmaceutical information regarding the at least one labeled radiopharmaceutical agent; and a second portable computer-communicatable data carrier containing patient information regarding the patient, and imaging protocol information for use with the at least one labeled radiopharmaceutical agent.

For some applications, the imaging protocol information includes SPECT imaging protocol information.

For some applications, the patient information includes an identifier of the patient.

For some applications, the second data carrier includes a coupling mechanism configured to be coupled to the patient.

For some applications, the first data carrier contains a first patient identifier, the patient information contained in the second data carrier includes a second patient identifier, and the apparatus includes an administration system, which includes:

a first communication element, configured to read the first patient identifier from the first data carrier;

a second communication element, configure to read the second patient identifier from the second data carrier; and a control unit, configured to compare the first patient identifier to the second patient identifier, and, upon detecting a match, generate an administration signal that triggers administration to the patient of the at least one labeled radiopharmaceutical agent contained in the container.

For some applications, the first data carrier contains a first protocol identifier, the imaging protocol information contained in the second data carrier includes a second protocol identifier, and the apparatus includes an administration system, which includes:

a communication element, configured to read the first and second protocol identifiers from the first and second data carriers, respectively; and a control unit, configured to compare the first protocol identifier to the second protocol identifier, and, upon detecting a match, generate an administration signal that triggers administration to the patient of the at least one labeled radiopharmaceutical agent contained in the container.

For some applications, the first data carrier contains a first protocol identifier, the imaging protocol information contained in the second data carrier includes a second protocol identifier, and the apparatus includes an administration system, which includes:

a first communication element, configured to read the first protocol identifier from the first data carrier;

a second communication element, configured to read the second protocol identifier from the second data carrier; and a control unit, configured to compare the first protocol identifier to the second protocol identifier, and, upon detecting a match, generate an administration signal that triggers administration to the patient of the at least one labeled radiopharmaceutical agent contained in the container.

In an embodiment, the apparatus includes an administration system, which includes:

a communication element; and a control unit, configured to:

generate an administration signal that triggers administration to the patient of the at least one labeled radiopharmaceutical agent contained in the container, and drive the communication element to transmit information regarding the administration to the second data carrier.

For some applications, the apparatus includes a device configured to write the imaging protocol information to the first data carrier. Alternatively or additionally, the apparatus includes a device configured to write the patient information to the second data carrier.

In an embodiment, the imaging protocol information includes imaging protocol information selected for the patient. For some applications, the imaging protocol information includes an identifier of an imaging protocol. For some applications, the imaging protocol information includes imaging protocol information customized for the patient.

In an embodiment, the first data carrier contains a first patient identifier, the patient information contained in the second data carrier includes a second patient identifier, and the apparatus includes an administration system, which includes:

a communication element, configured to read the first and second patient identifiers from the first and second data carriers, respectively; and a control unit, configured to compare the first patient identifier to the second patient identifier, and, upon detecting a match, generate an administration signal that triggers administration to the patient of the at least one labeled radiopharmaceutical agent contained in the container.

For some applications, the administration system includes an automated administration device, configured to administer the at least one labeled radiopharmaceutical agent to the patient upon being triggered by the administration signal.

For some applications, the control unit is configured to generate the administration signal to trigger the administration of the at least one labeled radiopharmaceutical agent by instructing a healthcare worker to administer the at least one labeled radiopharmaceutical agent to the patient.

There is yet additionally provided, in accordance with an embodiment of the present invention, apparatus for use with at least one labeled radiopharmaceutical agent for administration to a patient, the apparatus including:

a container containing the at least one labeled radiopharmaceutical agent;

a computer-communicatable data carrier associated with the container, the data carrier containing data regarding at least one of: the labeled radiopharmaceutical agent and the patient; and a SPECT imaging system including:

a communication element, configured to read the data; and a control unit, configured to utilize the read data to customize at least one function of the system selected from the group consisting of: administration of the labeled radiopharmaceutical agent, acquisition of a SPECT image of the patient to whom the labeled radiopharmaceutical agent is administered, reconstruction of the SPECT image, analysis of the SPECT image, and diagnosis of a condition of the patient based at least in part on the analysis.

For some applications, the data carrier contains the data regarding the labeled radiopharmaceutical agent. Alternatively or additionally, the data carrier contains the data regarding the patient.

For some applications, the control unit is configured to utilize the read data to customize the administration of the labeled radiopharmaceutical agent. Alternatively or additionally, the control unit is configured to utilize the read data to customize the acquisition of a SPECT image of the patient to whom the labeled radiopharmaceutical agent is administered. Further alternatively or additionally, control unit is configured to utilize the read data to customize the reconstruction of the SPECT image. Still further alternatively or additionally, the control unit is configured to utilize the read data to customize the analysis of the SPECT image. Alternatively or additionally, the control unit is configured to utilize the read data to customize the diagnosis of a condition of the patient based at least in part on the analysis.

For some applications, the apparatus includes a device configured to write the data to the data carrier.

There is also provided, in accordance with an embodiment of the present invention, a SPECT imaging system for use with a container containing at least one labeled radiopharmaceutical agent for administration to a patient, and data regarding at least one of: the labeled radiopharmaceutical agent and the patient, the system including:

a communication element, configured to read the data; and a control unit, configured to utilize the read data to customize at least one function of the system selected from the group consisting of: administration of the labeled radiopharmaceutical agent, acquisition of a SPECT image of the patient to whom the labeled radiopharmaceutical agent is administered, reconstruction of the SPECT image, analysis of the SPECT image, and diagnosis of a condition of the patient based at least in part on the analysis.

For some applications, the system includes a device configured to write the data to the container.

There is further provided, in accordance with an embodiment of the present invention, an automated radiopharmaceutical dispensing system for use with a container and a computer-communicatable container data carrier associated with the container, the system including:

a robot, configured to manipulate the container;

a communication element; and a control unit, configured to:

receive radiopharmaceutical information regarding at least one labeled radiopharmaceutical agent, the radiopharmaceutical information selected from the group consisting of: imaging protocol information for use with the at least one labeled radiopharmaceutical agent, and authenticatable information regarding a commercial license for use of an imaging protocol with the at least one labeled radiopharmaceutical agent, receive patient information regarding a patient, drive the robot to automatically dispense a dose of the labeled radiopharmaceutical agent to the container, and drive the communication element to transmit to the container data carrier at least a portion of the radiopharmaceutical information and at least a portion of the patient information.

For some applications, the control unit is configured to receive the radiopharmaceutical information regarding a plurality of labeled radiopharmaceutical agents, and drive the robot to automatically dispense respective doses of the labeled radiopharmaceutical agents to the container.

For some applications, the patient information includes an identifier of an imaging protocol assigned to the patient for performance using the dose, and the control unit is configured to drive the communication element to transmit the imaging protocol identifier to the container data carrier.

For some applications, the control unit is configured to drive the communication element to transmit to the container data carrier at least one of: a time of dispensing of the labeled radiopharmaceutical agent to the container, and information regarding a radioactivity of the dose at the time of dispensing.

In an embodiment, the apparatus includes:

a mother vial that contains the labeled radiopharmaceutical agent prior to dispensing thereof; and a computer-communicatable mother vial data carrier associated with the mother vial, which mother vial data carrier contains the radiopharmaceutical information, and the control unit is configured to receive the radiopharmaceutical information from the mother vial data carrier.

For some applications, the radiopharmaceutical information includes the imaging protocol information. For some applications, the imaging protocol information includes SPECT imaging protocol information, which may include at least one kinetic parameter of the at least one labeled radiopharmaceutical agent.

In an embodiment, the radiopharmaceutical information includes the authenticatable information regarding the commercial license. For some applications, the information regarding the commercial license includes information regarding the commercial license for use of a SPECT imaging protocol with the at least one labeled radiopharmaceutical agent. For some applications, the control unit is configured to authenticate the authenticatable license information, and to drive the robot to automatically dispense the dose only upon authentication.

There is still further provided, in accordance with an embodiment of the present invention, apparatus for use with a container, the apparatus including:

a mother vial having a volume of at least 10 ml, which contains at least 5 ml of a non-diluted labeled radiopharmaceutical agent, and at least 5 ml of saline solution; and an automated radiopharmaceutical dispensing system, configured to contain the mother vial, and to dispense at least one dose from the mother vial to the container.

There is additionally provided, in accordance with an embodiment of the present invention, a method including:

placing at least one labeled radiopharmaceutical agent in a container;

associating a portable computer-communicatable data carrier with the container; and writing, to the data carrier, imaging protocol information for use with the at least one labeled radiopharmaceutical agent.

There is additionally provided, in accordance with an embodiment of the present invention, a method including:

physically coupling a computer-communicatable data carrier to a portable joining element;

placing one or more labeled radiopharmaceutical agents in one or more respective containers;

coupling (e.g., removably coupling) the containers to the joining element; and writing, to the data carrier, imaging protocol information for use with the labeled radiopharmaceutical agents, and administration protocol information for use with the labeled radiopharmaceutical agents.

There is yet additionally provided, in accordance with an embodiment of the present invention, a method including:

placing at least one labeled radiopharmaceutical agent in a container;

associating a computer-communicatable data carrier with the container; and writing, to the data carrier, authenticatable information regarding a commercial license for use of SPECT imaging protocol information with the at least one labeled radiopharmaceutical agent.

There is also provided, in accordance with an embodiment of the present invention, a method including:

providing a portable computer-communicatable data carrier; and writing, to the data carrier, authenticatable information regarding a commercial license for use of SPECT imaging protocol information.

There is further provided, in accordance with an embodiment of the present invention, a method including:

writing first and second identifier values to first and second computer-communicatable data carriers, respectively;

detecting a correspondence between the first and second identifier values; and perform an imaging procedure on a patient responsively to the detecting.

There is still further provided, in accordance with an embodiment of the present invention, a method for use with at least one labeled radiopharmaceutical agent for administration to a patient, the method including:

placing at least one labeled radiopharmaceutical agent in a container;

physically coupling a first computer-communicatable data carrier to the container;

writing, to the first data carrier, radiopharmaceutical information regarding the at least one labeled radiopharmaceutical agent; and writing, to a second portable computer-communicatable data carrier, patient information regarding the patient, and imaging protocol information for use with the at least one labeled radiopharmaceutical agent.

There is additionally provided, in accordance with an embodiment of the present invention, a method including:

placing, in a container, at least one labeled radiopharmaceutical agent for administration to a patient;

associating a computer-communicatable data carrier with the container;

writing data to the data carrier regarding at least one of: the labeled radiopharmaceutical agent and the patient;

reading the data from the data carrier at a SPECT imaging system;

utilizing the read data to customize at least one function of the system selected from the group consisting of: administration of the labeled radiopharmaceutical agent, acquisition of a SPECT image of the patient to whom the labeled radiopharmaceutical agent is administered, reconstruction of the SPECT image, analysis of the SPECT image, and diagnosis of a condition of the patient based at least in part on the analysis.

There is yet additionally provided, in accordance with an embodiment of the present invention, a method for use with a container containing at least one labeled radiopharmaceutical agent for administration to a patient, and data regarding at least one of: the labeled radiopharmaceutical agent and the patient, the method including:

reading the data at a SPECT imaging system; and utilizing the read data to customize at least one function of the system selected from the group consisting of: administration of the labeled radiopharmaceutical agent, acquisition of a SPECT image of the patient to whom the labeled radiopharmaceutical agent is administered, reconstruction of the SPECT image, analysis of the SPECT image, and diagnosis of a condition of the patient based at least in part on the analysis.

There is also provided, in accordance with an embodiment of the present invention, a method for use with a container and a computer-communicatable container data carrier associated with the container, the method including:

receiving, by an automated radiopharmaceutical dispensing system, radiopharmaceutical information regarding at least one labeled radiopharmaceutical agent, the radiopharmaceutical information selected from the group consisting of: imaging protocol information for use with the at least one labeled radiopharmaceutical agent, and authenticatable information regarding a commercial license for use of an imaging protocol with the at least one labeled radiopharmaceutical agent;

receiving, by the dispensing system, patient information regarding a patient;

automatically robotically dispensing, by the dispensing system, a dose of the labeled radiopharmaceutical agent to the container; and transmitting to the container data carrier, by the dispensing system, at least a portion of the radiopharmaceutical information and at least a portion of the patient information.

There is further provided, in accordance with an embodiment of the present invention, a method for automatically dispensing a labeled radiopharmaceutical agent to a container, including:

providing a mother vial having a volume of at least 10 ml;

filling the mother vial with at least 5 ml of a non-diluted labeled radiopharmaceutical agent, and with at least 5 ml of saline solution;

placing the mother vial in an automated radiopharmaceutical dispensing system; and dispensing at least one dose from the mother vial to the container.

There is also provided, in accordance with an embodiment of the present invention, a method for setting a dose of a labeled radiopharmaceutical agent for use for performing an imaging procedure on a patient for studying a physiological characteristic of the patient, the method including:

selecting the radiopharmaceutical agent;

receiving information regarding a medical parameter of the patient not directly related to the physiological characteristic of the patient; and setting the dose at least in part responsively to the received information.

There is further provided, in accordance with an embodiment of the present invention, a substance associated with a time-dependent substance intake program generated by a computer controlled functionality employing a machine readable multi-parameter human physiological profile including at least one of a kinetic and intra-body location dependent parameter and a machine readable multi-parameter substance profile, including at least one kinetic parameter.

There is still further provided, in accordance with an embodiment of the present invention, a computer controlled functionality employing a machine readable multi-parameter human physiological profile including at least one of a kinetic and intra-body location dependent parameter and a machine readable multi-parameter substance profile, including at least one kinetic parameter, for indicating a time-dependent substance intake program.

There is yet further provided, in accordance with an embodiment of the present invention, a substance associated with a time-dependent substance intake program generated by a computer controlled functionality employing a machine readable multi-parameter human physiological profile including at least one of a kinetic and intra-body location dependent parameter and a machine readable multi-parameter substance profile, including at least one kinetic parameter.

There is also provided, in accordance with an embodiment of the present invention, a time-dependent substance intake program generated by a computer controlled functionality employing a machine readable multi-parameter human physiological profile including at least one of a kinetic and intra-body location dependent parameter and a machine readable multi-parameter substance profile, including at least one kinetic parameter.

There is further provided, in accordance with an embodiment of the present invention, a substance formulated in accordance with a time-dependent substance intake program generated by a computer controlled functionality employing a machine readable multi-parameter human physiological profile including at least one of a kinetic and intra-body location dependent parameter and a machine readable multi-parameter substance profile, including at least one kinetic parameter.

There is still further provided, in accordance with an embodiment of the present invention, an apparatus, method, and/or functionality for generation of a machine readable multi-parameter human physiological profile including at least one of a kinetic and intra-body location dependent parameter, including providing a time-dependent substance intake program; a data acquisition system which acquires data from the patient passing through the intake program; and a computerized analysis using a machine readable multi-parameter substance profile, including at least one kinetic parameter.

There is yet further provided, in accordance with an embodiment of the present invention, an apparatus, method, and/or functionality for generation of a human physiological profile, including providing a substance intake program; a data acquisition system which acquires data from the patient passing through the intake program; and a computerized analysis using a substance profile, including at least one kinetic parameter.

There is also provided, in accordance with an embodiment of the present invention, an interactive pharmaceutical-containing, machine-readable information-bearing, customized medicine module suitable for use in computerized customized medicine, said customized medicine module including a computerized customized medicine machine-interfaceable pharmaceutical-containing delivery module and a computerized individualized medicine machine-readable information-containing carrier containing at least data regarding said pharmaceutical which is required for use of said pharmaceutical in computerized customized medicine, said data being useful in computerized customized medicine machine actuation of said pharmaceutical-containing delivery module.

There is additionally provided, in accordance with an embodiment of the present invention, a computerized customized medicine machine including:
  a computerized patient imager;
  a computerized pharmaceutical deliverer employing a pharmaceutical-containing, machine-readable information-bearing, customized medicine module; and
  a customized medicine protocol controller including:
    an interactive patient imager interface including patient information receiving functionality and patient imaging actuation functionality; and
    an interactive pharmaceutical deliverer interface including patient information receiving functionality and patient information-responsive pharmaceutical delivery actuation functionality.

There is also provided, in accordance with an embodiment of the present invention, an interactive pharmaceutical-containing, machine-readable authenticated, authenticated customized medicine module suitable for use in computerized customized medicine, said customized medicine module including a computerized customized medicine machine-interfaceable pharmaceutical-containing module and a computerized individualized medicine machine-readable authentication-containing carrier containing at least authentication data regarding said pharmaceutical which is required for use of said pharmaceutical in computerized customized medicine, said data being useful in said computerized customized medicine machine.

There is further provided, in accordance with an embodiment of the present invention, a computerized customized medicine preparation machine including:
  a computerized patient information manager;
  a computerized customized medicine pharmaceutical information manager;
  a computerized authenticated customized medicine module authenticator; and
  a computerized pharmaceutical-containing, machine-readable information-bearing, customized medicine module generator including:
    a computerized generator protocol manager operative to receive patient information from said patient information manager, to receive authentication of an authenticated customized medicine module from said authenticator, to receive customized medicine pharmaceutical information relating to at least one pharmaceutical contained in said authenticated customized medicine module from said pharmaceutical information manager and to prepare customized medicine information to be included in said customized medicine module; and
    a computerized pharmaceutical-containing, machine-readable information-bearing, customized medicine module preparer operative to associate said customized medicine information prepared by said protocol manager in an authenticatable machine readable form with a quantity of said pharmaceutical contained in said authenticated customized medicine module, thereby providing a pharmaceutical-containing, machine-readable information-bearing, customized medicine module.

There is still further provided, in accordance with an embodiment of the present invention, an interactive pharmaceutical-containing, machine-readable information-bearing, individualized medicine module suitable for use in computerized individualized medicine, said individualized medicine module including a computerized individualized medicine machine actuable pharmaceutical-containing delivery module and a computerized individualized medicine machine-readable information-containing carrier containing at least data regarding said pharmaceutical which is required for use of said pharmaceutical in computerized individualized medicine, said data being useful in computerized individualized medicine machine actuation of said pharmaceutical-containing delivery module.

For some applications, said data is in an encrypted format, readable by said computerized individualized medicine machine upon receipt of a predetermined authentication.

There is also provided, in accordance with an embodiment of the present invention, a computerized individualized medicine machine including:
  a computerized patient imager;
  a computerized pharmaceutical deliverer employing a pharmaceutical-containing, machine-readable information-bearing, individualized medicine module; and
  an individualized medicine protocol controller including:
    an interactive patient imager interface including patient image receiving functionality and patient imaging actuation functionality; and
    an interactive pharmaceutical deliverer interface including patient image receiving functionality and patient image-responsive pharmaceutical delivery actuation functionality.

There is further provided, in accordance with an embodiment of the present invention, use of a high definition, high sensitivity camera for determination of an optimal parameter for a labeled radiopharmaceutical agent, the optimal parameter selected from the group consisting of: optimal dose, optimal mode of administration, optimal mode of acquisition of data with respect to the labeled radiopharmaceutical agent, optimal mode of data processing with respect to the labeled radiopharmaceutical agent, and optimal mode of presentation of information acquired with respect to the labeled radiopharmaceutical agent.

There is still further provided, in accordance with an embodiment of the present invention, a labeled radiopharmaceutical agent that is manufactured or designed or indicated for use with or sold with any one of the above techniques.

The present invention will be more fully understood from the following detailed description of embodiments thereof, taken together with the drawings, in which:

BRIEF DESCRIPTION OF THE DRAWINGS

FIGS. 6A-E are tables showing exemplary preconfigured SPECT protocols and parameters thereof, in accordance with respective embodiments of the present invention;

FIGS. 9A-H are schematic illustrations of respective embodiments of a radiopharmaceutical agent container and data carrier coupled thereto, in accordance with respective embodiments of the present invention;

FIGS. 16A-B are illustrations of color spectra and a color-coded signature, respectively, in accordance with an embodiment of the present invention;

FIG. 24 is a schematic block diagram illustrating a portion of components of the end-to-end automated system of FIG. 1, in accordance with an embodiment of the present invention; and FIG. 25 is a flow chart illustrating a method for using the administration system of FIG. 19 with the joining element of FIG. 21, in accordance with an embodiment of the present invention.

DETAILED DESCRIPTION OF EMBODIMENTS

Figure 1:
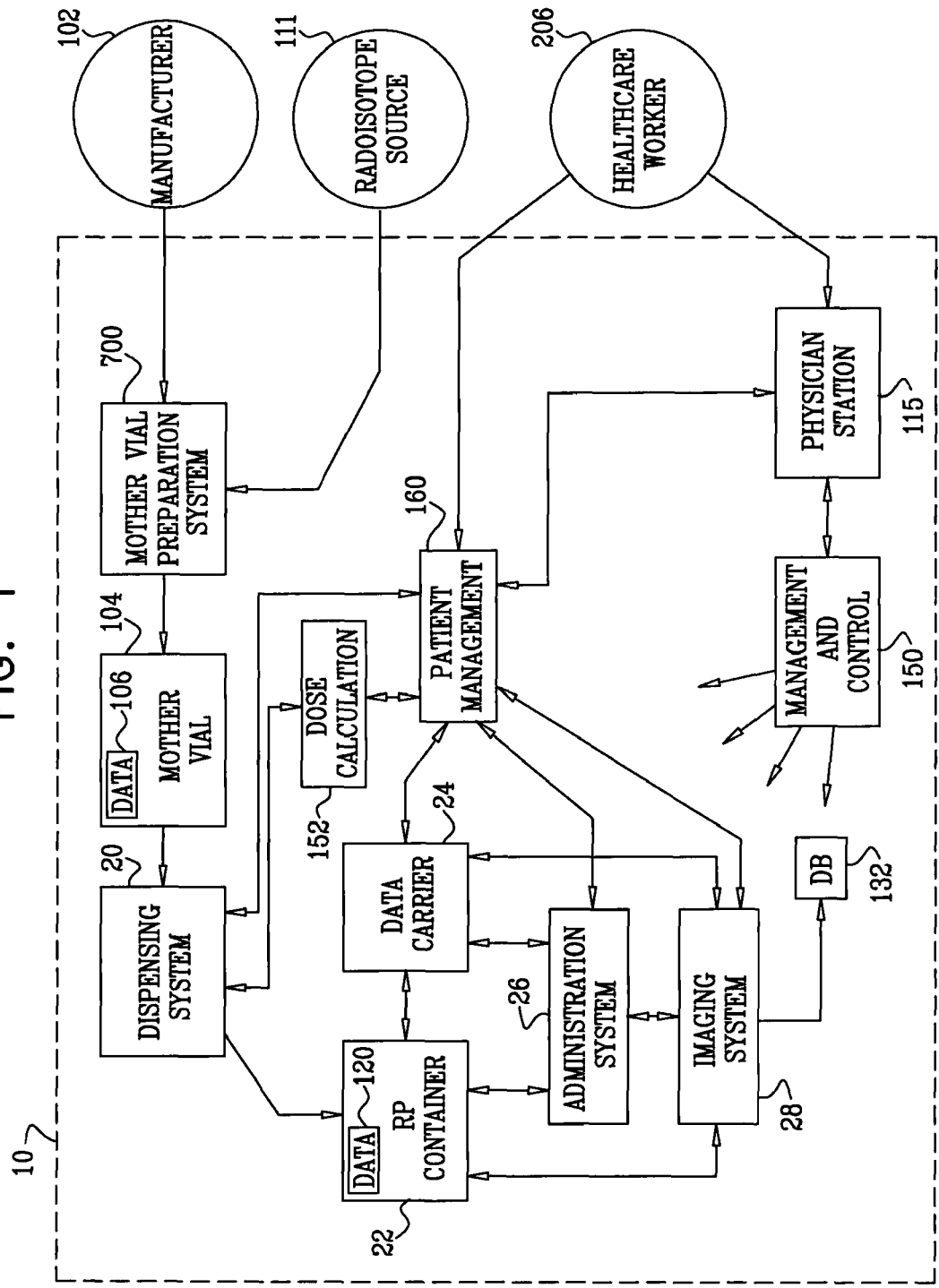
FIG. 1 is a schematic illustration of an end-to-end automated system for medical imaging, in accordance with an embodiment of the present invention.

FIG. 1 is a schematic illustration of an end-to-end automated system 10 for medical imaging, in accordance with an embodiment of the present invention. System 10 comprises a plurality of integrated elements that are configured to electronically exchange information among one another. The elements include an automated radiopharmaceutical dispensing system 20, a portable radiopharmaceutical agent container 22 (which, for some applications, is information-bearing), a portable patient-specific data carrier 24, an automated administration system 26, an automated imaging system 28, and/or an information-bearing joining element described hereinbelow with reference to FIGS. 19-25. The systems perform their respective automated functions at least in part responsively to the exchanged information. The elements typically authenticate one another via the exchanged information, in order to ensure that only authorized elements participate in the system, and that only authorized and appropriate functions are performed. Each of the elements is described in detail hereinbelow.

End-to-End Imaging Method

Figure 2:
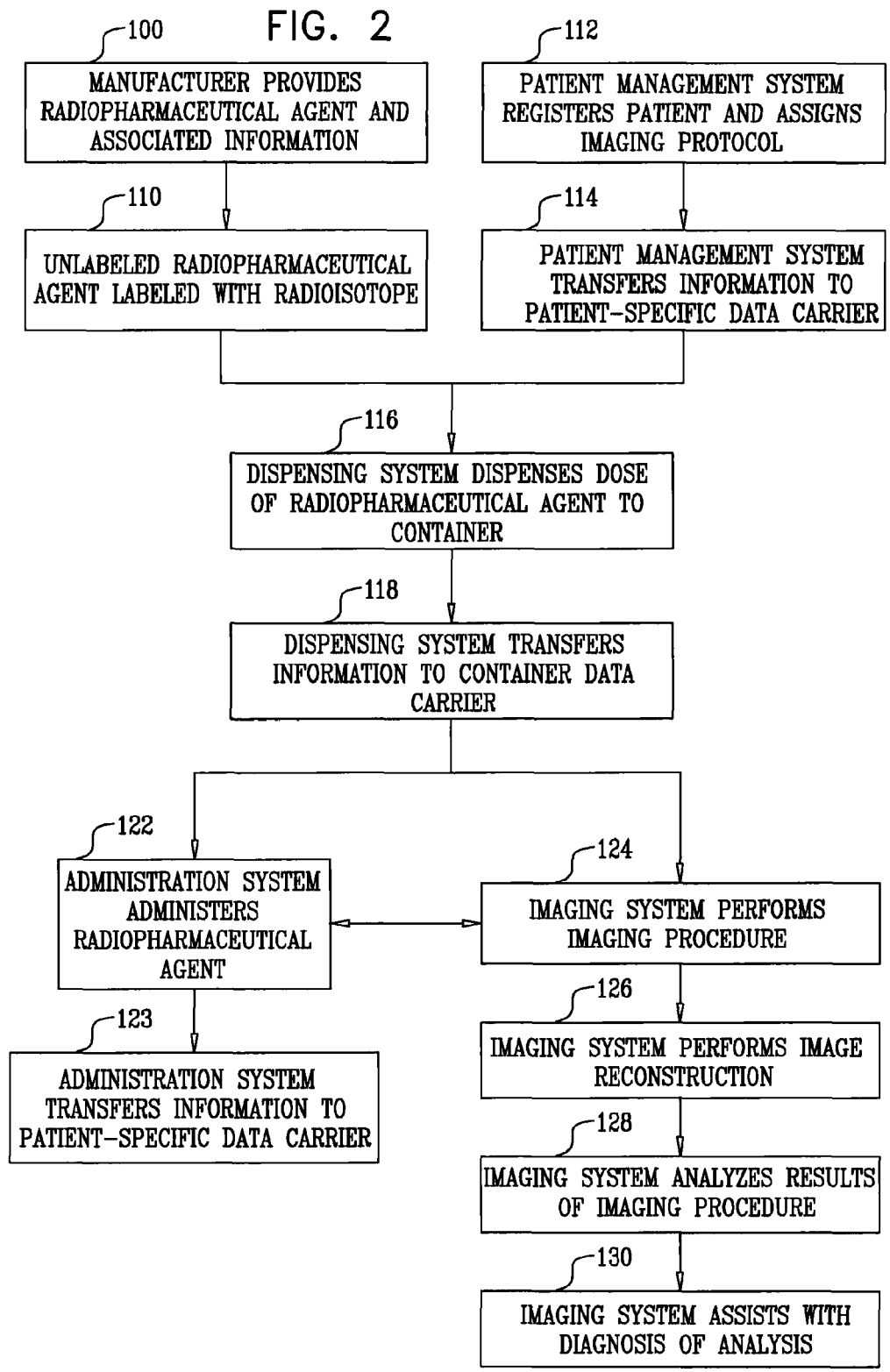
FIG. 2 is a flow chart showing an end-to-end method for medical imaging, in accordance with an embodiment of the present invention.

FIG. 2 is a flow chart showing an end-to-end method for medical imaging, in accordance with an embodiment of the present invention. At a radiopharmaceutical provisioning step 100, a manufacturer 102 (FIG. 1) or distributor provides a mother vial 104 (FIG. 1) containing an unlabeled radiopharmaceutical agent, and information associated with the radiopharmaceutical agent. Such an unlabeled radiopharmaceutical agent typically comprises a pharmaceutical substance, for example an antibody such as Capromab Pendetide marketed by Cytogen Corp. under the name ProstaScint and used in the detection of prostate cancer metastases, or sestamibi used in cardiac perfusion studies and marketed under the name of Cardiolite by Bristol Meyers Squibb Corporation, an ion, or another biological metabolized substance, or a substance which is not metabolized but nevertheless undergoes an interaction with the body. The information is stored in a mother vial data carrier 106 associated with mother vial 104, as described hereinbelow with reference to FIG. 7. For some applications, data carrier 106 is physically coupled to mother vial 104, while for other applications the data carrier is provided as a separate element associated with the mother vial. As described hereinbelow with reference to FIG. 7, the information stored in data carrier 106 typically includes information regarding the radiopharmaceutical agent, such as the formulation, pharmacologic kinetic parameters, radioactivity information, and/or protocol information.

At a labeling step 110, the unlabeled radiopharmaceutical agent is labeled with an appropriate radioisotope, to produce a labeled radiopharmaceutical agent. Such labeling is typically performed using conventional methods, including mixing the agent with a solution containing the radioisotope, heating the mixture, and performing quality testing on the labeled radiopharmaceutical agent. For some applications, step 110 is performed using conventional radiopharmacy labeling techniques, while for other applications system 10 comprises a mother vial preparation system 700, which automatically performs all or a portion of the labeling, as described hereinbelow with reference to FIG. 15. The radioisotopes are provided by a radioisotope supplier 111, such as a conventional radiopharmacy or an automatic elution system 600, described hereinbelow with reference to FIG. 14. Data carrier 106 is typically updated with radioactivity-related information, including the time of labeling, the radioactivity of the radioisotope at the time of labeling, and the volume of the labeled radiopharmaceutical agent, as described hereinbelow with reference to FIG. 7.

For some applications, the only active constituent of the labeled radiopharmaceutical agent is the radioisotope; in other words, the radioisotope is not bound to a biologically active substance. For example, the labeled radiopharmaceutical agent may consist essentially of thallium (as well as pH-balancing constituents, salt ions, and preservatives). As used in the present application, including in the claims, a "labeled radiopharmaceutical agent" means either: (a) an agent comprising a diagnostic radioisotope, such as thallium, or (b) an agent comprising a radioisotope bound to a biologically active substance, such as an antibody, a pharmaceutical compound, an ion, or another biological metabolized substance, or a substance which is not metabolized but nevertheless undergoes an interaction with the body.

At a patient registration and imaging protocol assignment step 112, a healthcare worker 206 uses a patient management system 160 to register a patient into system 10, and to assign appropriate administration and imaging protocols for the patient, as described in detail hereinbelow with reference to FIG. 4. At an information transfer step 114, patient management system 160 assigns a portable patient-specific data carrier 24 to the patient, and transmits information to data carrier 24, including at least a patient identifier (typically, the patient's identification code and/or name), and the assigned administration and imaging protocols. Additional patient data parameters recorded may include physiological data such as girth, height and weight. The patient management system additionally transmits an order for one or more patient-specific doses of the appropriate labeled radiopharmaceutical agent(s) to dispensing system 20 or a conventional radiopharmacy.

At a dose dispensing step 116, dispensing system 20 dispenses the ordered customized dose of the labeled radiopharmaceutical agent from mother vial 104, as described in detail hereinbelow with reference to FIG. 12. Prior to dispensing the dose, dispensing system 20 typically authenticates the mother vial using information stored in mother vial data carrier 106. For some applications, dispensing system 20 verifies the authenticity of a commercial license contained in data carrier 106. Typically, all or a portion of the information used for such verification is encrypted, and dispensing system 20 decrypts the information during the verification procedure. Alternatively or additionally, dispensing system 20 accesses, over a network, information stored at a remote site, and utilizes the information for such verification. The dispensing system dispenses the dose based on patient-specific prescription information, radiopharmaceutical agent-related information stored in data carrier 106, and/or patient-specific information provided by an element of system 10. Such patient-specific information may include, for example, age, weight, Body Mass Index (BMI), body dimensions, metabolic rate, hemodynamic state, kinetic parameters of the labeled radiopharmaceutical agent as determined during previous imaging procedures performed on the patient, and/or information regarding medical devices implanted in the patient (e.g., pacemakers or ICDs). For some applications, dosage information is provided directly or indirectly by patient management system 160 and/or a radiopharmaceutical dose calculation system 152, which are described hereinbelow with reference to FIGS. 4 and 5, respectively.

At an information transfer step 118, dispensing system 20 transfers patient-specific information and radiopharmaceutical-related information to a data carrier 120 physically coupled to container 22, as described hereinbelow with reference to FIGS. 9A-H and 10. "Physically coupled," as used in the present application, including the claims, includes both direct and indirect physical coupling. For example, data carrier 120 may be indirectly physically coupled to container 22 via shielding of container 22, or shielding of a cylinder in which container 22 is stored during transport and handling thereof. The patient-specific information includes the patient's identification code and/or name, and the assigned administration and imaging protocols. The radiopharmaceutical-related information typically includes: (a) all or a portion of the information provided by the manufacturer in data carrier 106, such as described hereinbelow with reference to FIG. 7, e.g., intended use, formulation, pharmacologic kinetic parameters, and protocol information; (b) information regarding the radioactivity and volume of the dose; and (c) time of dispensing, as described in detail hereinbelow with reference to FIG. 8. In addition, the dispensing system typically prints and attaches a conventional information label to container 22, such as in order to comply with regulatory labeling requirements. For applications in which the labeled radiopharmaceutical agent(s) is dispensed using conventional radiopharmacy techniques, dispensing system 20, or another element of system 10, such as dose calculation system 152, typically transfers the radiopharmaceutical-related information to data carrier 120. Alternatively, all or a portion of the information is transferred directly from mother vial data carrier 106 to container data carrier 120.

At an administration step 122, administration system 26 receives radiopharmaceutical agent container 22, and administers the labeled radiopharmaceutical agent contained therein to the appropriate patient. As described hereinbelow with reference to FIGS. 10 and 19-24, for some applications, administration system 26 comprises an automated administration device, which is configured to administer the labeled radiopharmaceutical agent, while for other applications, a healthcare worker manually administers the agent upon receiving a signal to do so from system 26. Prior to administration, system 26 authenticates container 22 and verifies the identity of the patient, using information provided by patient-specific data carrier 24 and container data carrier 120, and, optionally, another element of system 10, such as a physician station 115. Typically, all or a portion of the information used for such verification is encrypted, and administration system 26 decrypts the information during the verification procedure. Alternatively or additionally, administration system 26 accesses, over a network, information stored at a remote site, and utilizes the information for such verification. Administration system 26 verifies that the patient identification codes contained in patient-specific data carrier 24 and container data carrier 120 match one another, and, typically, verifies that the administration and/or imaging protocols contained in the data carriers match one another. Typically, at least a portion of the information stored in data carrier 120 of container 22 is transferred to data carrier 24, either directly, via administration system 26, or via a communication element. For some applications, system 26 generates a signal for a healthcare worker confirming that a proper match has been made between agent container 22 and the patient. The system also typically verifies that the current time is the proper administration time, as per the administration protocol, and that container 22 contains the proper dose, as per the selected protocol. Optionally, system 26 is configured to administer the labeled radiopharmaceutical agent only if such matches are confirmed by the system. For some applications, administration system 26 verifies the authenticity of a commercial license contained in data carrier 120, and performs the administration only upon verification of the authenticity.

For some applications, administration system 26 customizes the administration of the labeled radiopharmaceutical agent using information provided by data carrier 24, data carrier 120, physician station 115, and/or patient management system 160. For example, system 26 may customize a time-dependent administration profile of the labeled radiopharmaceutical agent, such as a rate of administration. Alternatively or additionally, system 26 may administer less than the entire dose of the labeled radiopharmaceutical agent, e.g., based on feedback from imaging system 28 during an imaging procedure.

For some applications, such as dynamic studies, administration system 26 administers the labeled radiopharmaceutical agent during an imaging procedure performed by imaging system 28. For these applications, the administration system is in communication with the imaging system during the administration, in order to assure information regarding time-dependent administration is accurately communicated between the administration system and the imaging system. For some applications, imaging system 28 reads information from patient-specific data carrier 24, and transmits at least a portion of the information to administration system 26, thereby obviating the need for the administration system to directly read such information from the data carrier. For some applications, imaging system 28 triggers the commencement of administration. (It is to be understood that although the imaging system triggers administration of the agent, for some applications the agent is not administered until a healthcare worker provides a final authorization to do so, such as to comply with regulatory safety requirements.) For some applications, the labeled radiopharmaceutical agent(s) is administered in a closed loop with an imaging procedure performed by imaging system 28; administration system 26 modifies one or more parameters of the administration in real time based on feedback received from imaging system 28, and/or based on real-time measurements of physiological parameters of the patient (e.g., systemic blood concentrations) during the imaging procedure. For some protocols, the administration system administers a preliminary bolus injection, and, based on feedback from imaging system 28 and/or on physiological parameters of the patient, configures one or more parameters of a subsequent administration of the same or a different labeled radiopharmaceutical agent.

At an information transfer step 123, before, during and/or after administration of the labeled radiopharmaceutical agent, administration system 26 electronically updates patient-specific data carrier 24 and/or another information-storing element of system 10 with details of the administration, such as:

- an identification code of container 22, an administration device, and/or of joining element 420, described hereinbelow with reference to FIGS. 19-25;
- an identification code of the patient to which the labeled radiopharmaceutical agent was dispensed, which should match the patient code already stored in data carrier 24;
- the administered labeled radiopharmaceutical agent;
- the volume of the labeled radiopharmaceutical agent administered;
- the time of administration;
- the time profile of administration;
- the radioactivity of the labeled radiopharmaceutical agent at the time of administration;
- the radioactivity of the labeled radiopharmaceutical agent when dispensed to container 22;
- the time of measurement of the radioactivity when dispensed to container 22; and/or
- at least a portion of the radiopharmaceutical information provided by data carrier 106 of mother vial 104.

For some applications, at least a portion of such administration details is written to new media provided for this purpose, such as a stamp or sticker for placement on patient-specific data carrier 24, container 22, and/or joining element 420, described hereinbelow with reference to FIGS. 19-25, or another portable data carrier. Alternatively or additionally, at least a portion of such administration details is communicated to another element of system 10, such as via a network, e.g., to imaging system 28.

For some applications, data carrier 120 of container 22 communicates administration information to patient-specific data carrier 24, either directly or via administration system 26. For some applications, system 26 provides similar updates to other elements of system 10, such as patient management system 160, management control component 150, physician station 115, and/or imaging system 28. Alternatively or additionally, a healthcare worker manually updates one or more of the data carrier and/or system elements. Typically, for safety purposes, after administration system 26 has read all necessary information from data carrier 120, administration system 26 permanently disables data carrier 120 of container 22, in order to ensure that the data carrier is not accidentally reused for another patient.

Reference is still made to FIG. 2. After or during administration of the labeled radiopharmaceutical agent, imaging system 28 performs an imaging procedure on the patient, at an imaging step 124. Imaging system 28 is described hereinbelow with reference to FIG. 11. Prior to performing the imaging procedure, system 28 verifies one or more of the following:

- the identity of the patient, using information provided by patient-specific data carrier 24;
- the authenticity of patient-specific data carrier 24, typically using information provided by the data carrier itself, a coded signature 256, as described hereinbelow in the section entitled "Signature," and/or a key 852, as described hereinbelow with reference to FIG. 17;

that patient-specific data carrier 24 has been brought within a certain distance of imaging system 28, e.g., within about 30 cm;

the identity of the manufacturer or distributor of the radiopharmaceutical agent, using information stored in data carrier 120;

that a selected camera of imaging system 28, imaging protocol, and patient identification code, as provided to imaging system 28 by one or more elements of system 10, match those stored in patient-specific data carrier 24;

the authenticity of a commercial license contained in patient-specific data carrier 24. For some applications, system 28 verifies that the license has not been previously used, for example by verifying that a registration code associated with the license has not been previously received by system 28 and/or system 10; and/or that administration system 26 used (or is about to use, for procedures in which administration occurs during imaging) the correct container 22 and associated data carrier 120 for the prescribed imaging procedure, and administered (or is about to administer) the appropriate dose of the labeled radiopharmaceutical agent(s) at time(s) appropriate for performance of the imaging procedure.

Typically, all or a portion of the information used for such verification is encrypted, and imaging system 28 decrypts the information during the verification procedure. Alternatively or additionally, imaging system 28 accesses, over a network, information stored at a remote site, and utilizes the information for such verification.

For some applications, system 28 generates a signal for a healthcare worker confirming that a proper match has been made between the patient and one or more of the components described above. Optionally, system 28 is configured to perform the imaging procedure only if such a match is confirmed by the system.

Typically, system 28 customizes the imaging procedure using information provided by administration system 26, data carrier 24, and/or physician station 115. Such information typically includes information regarding the time of labeled radiopharmaceutical administration, the labeled radiopharmaceutical agent (e.g., radioactive strength, time of preparation, and/or kinetic parameters), patient-specific physiological information, and/or imaging protocol information. Parameters of the imaging procedure that are typically customized include, but are not limited to: total acquisition time; detector motions, such as detector angular and translational motions, detector step size (i.e., the density of the step size, typically expressed in degrees), and detector dwell time at each view; type of study, such as standard, active vision (as described in the above-mentioned International Application PCT/IL2005/001173), or gated; definition of the region of interest (ROI), for example, based on the size of the heart; and/or attenuation correction parameters, which are typically based on physiological parameters such as body mass, BMI, and girth. For some applications, when performing gated studies, the imaging system takes into account the possible effect of medical devices implanted in the patient, such as pacemakers, e.g., coordinates the gating with the timing of the pacemaker.

In an embodiment of the present invention, method 440, described hereinbelow with reference to FIG. 25, is performed instead of steps 118 through 124.

At an image reconstruction step 126, imaging system 28 uses the acquired imaging data for image reconstruction. For some applications, system 28 customizes the image reconstruction procedure using information provided by administration system 26, data carrier 24, and/or physician station 115, such as imaging protocol information.

Imaging system 28 analyzes the reconstructed image, at an analysis step 128. For some applications, system 28 customizes the analysis procedure using information provided by administration system 26, data carrier 24, and/or physician station 115, such as imaging protocol information.

The imaging system, or a separate diagnostic system of system 10, assists with developing a diagnosis based on the analysis, at a diagnosis step 130. Typically, system 28 customizes the diagnostic procedure using information provided by administration system 26, data carrier 24, and/or physician station 115, such as imaging protocol information. For some applications, authentication is performed to verify that the imaging was performed as intended. Reconstruction and analysis are preferably based on lookup tables and expert system rules, for example, as provided by the radiopharmaceutical manufacturer, and may be patient customized, taking into account known patient physiology and/or suspected disease. Alternatively or additionally, the lookup tables and/or expert system diagnostic rules are configured to provide such customization. For some applications, customization and/or diagnostic techniques are performed that are described in the above-mentioned International Application PCT/IL2005/001173.

The diagnosis and/or the results of the imaging procedure are typically transmitted to physician station 115, for use by an attending healthcare worker 206. Alternatively or additionally, the diagnosis and/or the results of the imaging procedure are transmitted to a database 132 (FIG. 1). The accumulated results of a number of such imaging procedures for a large population are analyzed in order to develop, optimize, update, or otherwise re-evaluate imaging protocols, and update appropriate lookup tables and/or expert system rules for the use of the radiopharmaceutical agent. For example, the database may contain quantitative data regarding absolute blood flow measurements from healthy patients and patients with varying level of diseases. For some applications, such data is used to obtain disease-specific tissue signatures by performing quantitative analysis of normal and diseased tissue. Alternatively or additionally, the information in database 132 is used for: (a) comparing the results of an imaging procedure (images, and/or quantitative information and/or analyses) with historical results of the patient, in order to classify disease state and/or (b) comparing the results of an imaging procedure with similar results from a patient population, in order to classify disease state.

Typically, physician station 115 comprises one or more standard personal computers or servers with appropriate memory, communication interfaces and software for carrying out the functions prescribed by relevant embodiments of the present invention. This software may be downloaded to the physician station in electronic form over a network, for example, or it may alternatively be supplied on tangible media, such as CD-ROM.

During or after steps 124 through 128, imaging system 28 updates the data stored in patient-specific data carrier 24 and/or other elements of system 10, such as patient information system 160, and/or physician station 115, to reflect details of the imaging procedure performed. In addition, for some applications, imaging system 28 transfers data to the specific camera used for the procedure, such as patient details, radiopharmaceutical information, and/or administration information, which information is received from data carrier 24, or from other elements of system 10.

The Patient-Specific Data Carrier

Figure 3:
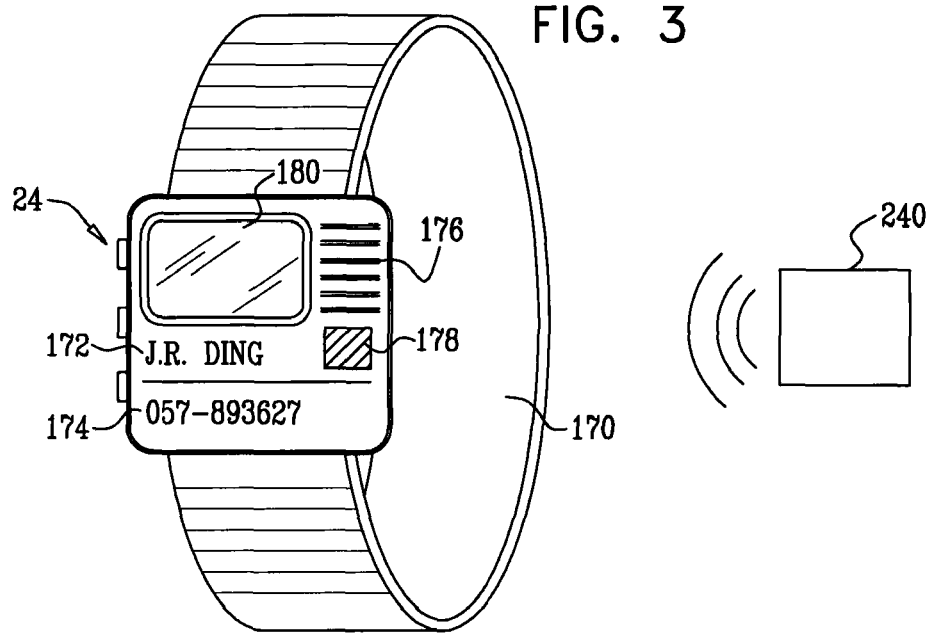
FIG. 3 is a schematic illustration of a patient-specific data carrier, in accordance with an embodiment of the present invention.

Reference is made to FIG. 3, which is a schematic illustration of patient-specific data carrier 24, in accordance with an embodiment of the present invention. Data carrier 24 is configured to be held or worn by the patient, and, for some applications, comprises a coupling mechanism configured to be coupled to the patient, which coupling mechanism, comprises, for example, a bracelet, watch, or necklace (FIG. 3A shows the data carrier integrated into a watch or bracelet 170). Data carrier 24 is computer-communicatable, and typically comprises an RFID tag, smart card, memory card (such as a disk-on-key (e.g., a USB key)), compact disc, minidisk, disposable computer-readable medium, or other electronic memory, as described below. Data carrier 24 is configured to hold information regarding the patient and a selected imaging procedure, as described immediately hereinbelow with reference to FIG. 4.

One or more communication elements 240 are provided for reading data from and transmitting data to data carrier 24, using a proprietary or standard wireless protocol, e.g., Bluetooth, WiFi, W-LAN, or IEEE 802.11. Alternatively, the communication element is brought into physical contact with data carrier 24, and reads and/or writes the information using an electrical contact, or other coupling technique, such as inductive coupling. Respective communication elements 240 are typically in data communication with patient management system 160, physician station 115, dispensing system 20, administration system 26, and/or imaging system 28. For some applications, communication elements 240 comprise one or more coils for transmitting and receiving electromagnetic radiation. Typically, the communication elements are configured to have a short effective transmission range, e.g., no more than between about 20 and 40 cm, such as about 30 cm. Such a short range reduces the likelihood of accidental communication with a data carrier other than the intended data carrier.

For some applications, a portion of the patient information stored in the data carrier is also printed in human- and/or machine-readable form on the data carrier. For example, a name 172 and identification code 174 of the patient, and/or a computer-readable scannable label, such as a barcode 176, two-dimensional bar code, or color-coded code, may be printed on the data carrier.

Data carrier 24 comprises circuitry 178, which comprises memory and logic. For some applications, data carrier 24 is passive, in which case it is configured to receive energy from communication element 240. For other applications, data carrier 24 comprises a power source (not shown). For some applications in which the data carrier comprises a power source, the data carrier comprises a communication element for communicating and/or energizing another electronic apparatus. Alternatively or additionally, the data carrier comprises a communication element configured for wireless communication.

For some applications, data carrier 24 further comprises a user output 180 for outputting information to the patient or healthcare workers. For example, output 180 may comprise a display screen, light, and/or sound generator, which circuitry 178 drives to communicate information, such as when communications have been established with other elements of system 10, e.g., data carrier 120, administration system 26, imaging system 28, and/or patient management system 160. For some applications, circuitry 178 is configured to additionally function as an alarm clock; for example, the circuitry may drive display 180 to alert the patient prior to a scheduled administration or imaging procedure.

Typically, for safety purposes, upon completion of all the imaging procedures associated with a given patient-specific data carrier 24, system 10 permanently disables the data carrier, in order to ensure that the data carrier is not accidentally reused for another patient.

The Patient Management System

Figure 4:
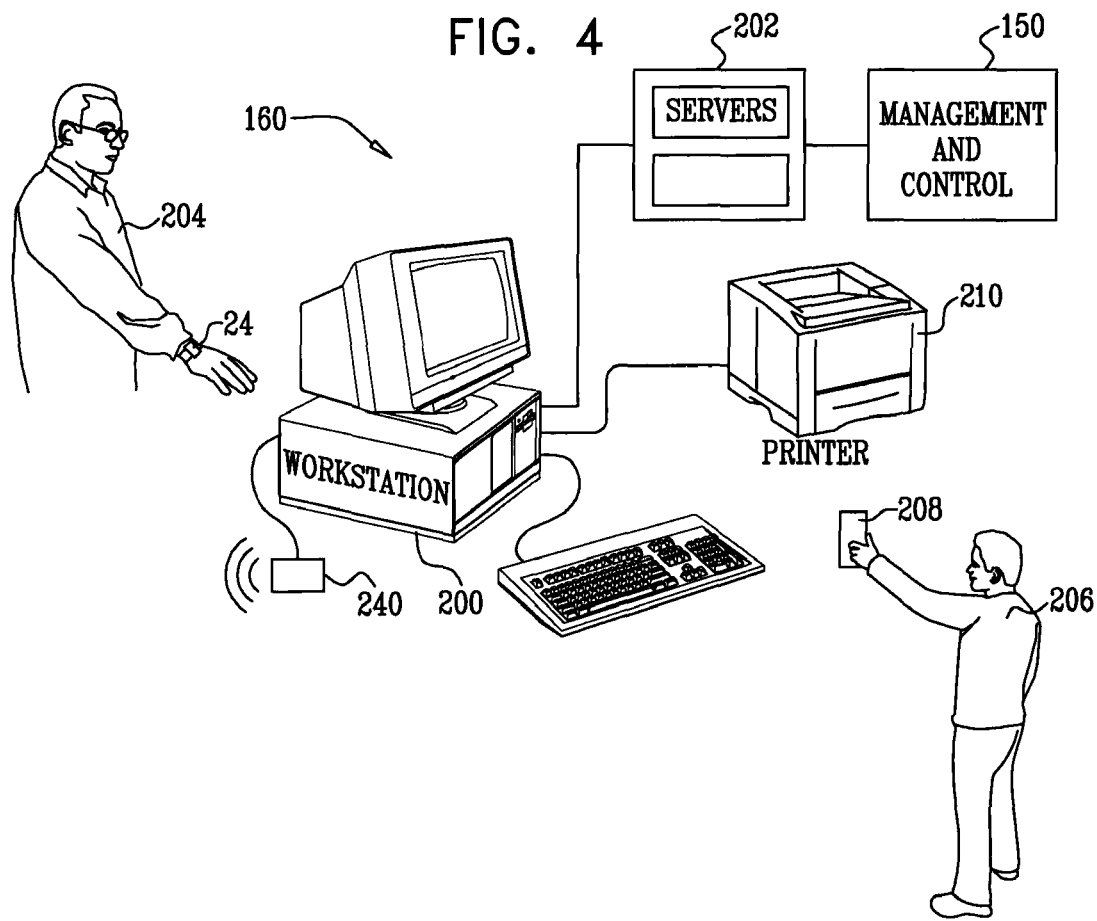
FIG. 4 is a schematic illustration of a patient management system, in accordance with an embodiment of the present invention.

Reference is made to FIG. 4, which is a schematic illustration of patient management system 160, in accordance with an embodiment of the present invention. Patient management system 160 manages patient-related administrative and medical information, and typically comprises at least one workstation 200 in communication with one or more servers 202. Typically, workstation 200 and servers 202 comprise standard personal computers and/or computer servers with appropriate memory, communication interfaces and software for carrying out the functions prescribed by relevant embodiments of the present invention. This software may be downloaded to the workstation and servers in electronic form over a network, for example, or it may alternatively be supplied on tangible media, such as CD-ROM.

System 160 performs the following functions:
- receives and registers new patients into system 10, typically into management and control component 150 thereof;
- assigns patient identification codes;
- assigns, issues, and transfers information to patient-specific data carriers 24;
- receives and tracks patient prescriptions for radiopharmaceuticals, and communicates the prescriptions to other elements of system 10, such as dispensing system 20, administration system 26, and/or management and control component 150; and/or
- suggests and assigns imaging protocols based on the patient's imaging needs and patient-specific information.

During reception of a new patient 204, healthcare worker 206 manually enters patient information into workstation 200. Alternatively or additionally, all or a portion of the patient information is provided electronically by another healthcare system or electronic information source. System 160 typically verifies the healthcare worker's identity and access privileges by interrogating a computer-communicatable identity tag 208 held by the worker, and/or by checking the validity of a password entered into workstation 200 by the healthcare worker.

The patient information provided to system 160 typically includes:
- the patient's general details, such as name, age, gender, address, telephone number, profession, attending and/or treating physician, health insurance plan, and next of kin;
- the patient's medical profile, such as medical condition, medical history, family medical history, BMI, weight, allergies, sensitivity to one or more chemical compounds, metabolic rate, and other physiological conditions;
- medications prescribed to the patient;
- information regarding medical devices implanted in the patient (e.g., pacemakers or ICDs)
- the patient's imaging history; and/or
- information regarding the desired imaging, including reason for imaging, type of imaging, body structure or organ to be imaged, and known or suspected pathology.

In an embodiment of the present invention, upon entry of such patient information into patient management system 160, the system automatically suggests one or more imaging protocols that may be appropriate for the patient's imaging needs and medical condition. When making such suggestion, the system takes into consideration, in addition to the information regarding the desired imaging, such factors as the patient's general details, medical profile, imaging history, and guidelines for medication interactions. The system typically selects the suggested protocol(s) from a database of preconfigured protocols, which is described hereinbelow with reference to FIGS. 6A-E. Healthcare worker 206 selects one of the suggested protocols, or selects another non-suggested protocol directly from the protocol database.

For some applications, the system suggests one or more customizations of the selected protocol, as described hereinbelow with reference to FIGS. 6A-E, which the healthcare worker may accept, decline, or modify, in whole or in part. These suggested customizations are typically based on (a) physiological parameters of the patient, such as age, weight, BMI, metabolic rate, and/or hemodynamic state, and/or kinetic parameters of the radiopharmaceutical agent as determined during previous imaging procedures performed on the patient, (b) a medical profile group to which the patient is assigned, such as high, normal, or low BMI, or high BMI—diabetic, or high BMI—normal metabolic rate, and/or (c) information regarding medical devices implanted in the patient (e.g., pacemakers or ICDs). (For some applications, such profile groups are stored in a database of management and control component 150.) Alternatively or additionally, the healthcare worker may customize the protocol manually.

Upon selection and customization of the protocol, patient management system 160 schedules, typically automatically:
a specific imaging system 28 capable of performing the selected imaging procedure;
a date and time for performing the imaging procedure; and
a date(s) and time(s) for administration of labeled radiopharmaceutical agent(s).

Patient management system 160 transmits the entered and generated patient-specific information, including the selected protocol, to the patient's patient-specific data carrier 24. The transmitted patient-specific information typically includes:
the patient's identification code and name;
an identifier of the selected imaging protocol(s), such as a name and/or an identification code thereof, and/or additional imaging protocol information, such as described hereinbelow with reference to FIGS. 6A-E. For some applications, the protocol(s) are represented by a protocol identifier, while for other applications the protocol information includes steps and/or other details of the protocol(s). For some applications, the imaging protocol includes protocol information regarding image reconstruction, image analysis, and/or diagnosis, which is used at image reconstruction step 126, analysis step 128, and/or diagnosis step 130, respectively, of the method of FIG. 2, described hereinabove. For some applications, the protocol information includes software code for execution by imaging system 28 during image acquisition, image reconstruction, image analysis, and/or diagnosis;
an identifier of the selected administration protocol(s), such as a name and/or an identification code thereof;
the scheduled imaging system 28;
the scheduled imaging date and time;
the scheduled administration date(s) and time(s);
the patient's personal details;
the patient's medical profile; and/or
the patient's imaging history.

The patient management system transmits an order for one or more patient-specific doses of the appropriate labeled radiopharmaceutical agent(s) to dispensing system 20, such as via management and control component 150. Typically, the patient management system additionally transmits at least a portion of the entered and generated patient-specific information to one or more of: (a) management and control component 150, (b) dose calculation system 152, (c) administration system 26, and/or (d) imaging system 28. Typically, a different subset of the information is transmitted to each of these entities.

As described hereinabove with reference to FIG. 3, for some applications, a portion of the patient information stored in data carrier 24 is also printed in human- and/or machine-readable form on the data carrier. For example, a name 172 and identification code 174 of the patient, and/or a barcode 176 may be printed on the data carrier. For such applications, system 160 comprises a printer 210, which is configured to print the information directly on data carrier 24, or to print the information on an adhesive label, which healthcare worker 206 attaches to data carrier 24. For some applications, printer 210 comprises communication element 240, and the printer is configured to both print the information on the data carrier and transmit the information to the data carrier, typically generally at the same time.

In an embodiment of the present invention, system 10 comprises at least one web server, which is configured to accept orders for an imaging procedure over an intranet or the Internet, placed by a physician or other healthcare worker. Such orders can typically be modified up until a deadline, such as midnight before the day of the scheduled imaging procedure.

The Management and Control Component

Reference is again made to FIG. 1. In an embodiment of the present invention, system 10 comprises management and control component 150, which coordinates a portion of the interaction and communication among the elements of system 10. The remainder of the interaction and communication occurs directly between the elements of the system, and/or via other elements of the system. For some applications, component 150 issues a password and/or computer-communicatable identity tags 208 to healthcare workers 206 authorized to interact with one or more elements of system 10. For example, tag 208 may comprise an RFID tag, smart card, memory card (such as a disk-on-key (e.g., a USB key)), compact disc, minidisk, disposable computer-readable medium, or other electronic memory, or a machine-readable code, e.g., a computer-readable scannable label, such as a barcode, two-dimensional bar code, or color-coded code. As appropriate, healthcare workers 206 may be assigned various permission levels, such as permission to view or modify particular system and/or patient data.

Typically, management and control component 150 comprises one or more standard personal computers or servers with appropriate memory, communication interfaces and software for carrying out the functions prescribed by relevant embodiments of the present invention. This software may be downloaded to the management and control component in electronic form over a network, for example, or it may alternatively be supplied on tangible media, such as CD-ROM.

The Dose Calculation System

Figure 5:
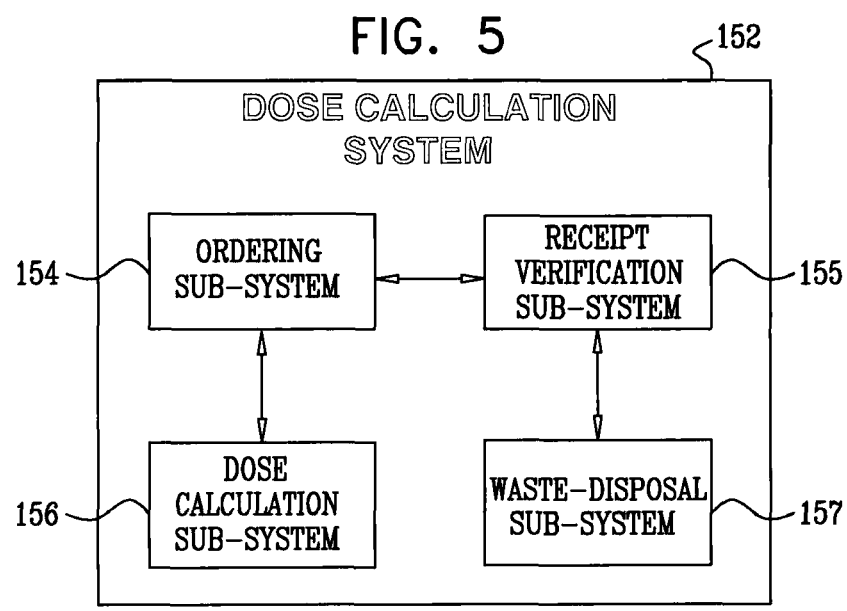
FIG. 5 is a schematic illustration of a radiopharmaceutical dose calculation system, in accordance with an embodiment of the present invention.

Reference is made to FIG. 5, which is a schematic illustration of radiopharmaceutical dose calculation system 152, in accordance with an embodiment of the present invention. The dose calculation system manages and tracks, typically automatically, radiopharmaceutical inventory, ordering, dose dispensing, and disposal. Typically, the dose calculation system comprises one or more standard personal computers or servers with appropriate memory, communication interfaces and software for carrying out the functions prescribed by relevant embodiments of the present invention. This software may be downloaded to the dose calculation system in electronic form over a network, for example, or it may alternatively be supplied on tangible media, such as CD-ROM. The dose calculation system receives information from dispensing system 20 regarding doses drawn from the inventory.

Dose calculation system 152 typically comprises:
- an ordering sub-system 154, which orders radiopharmaceutical products from radiopharmaceutical manufacturers, distributors, and/or radiopharmacies, typically automatically, such as when the dose calculation system identifies that inventories of a given radiopharmaceutical are lower than needed;
- a receipt and verification sub-system 155, which manages the receipt and registration of radiopharmaceutical products. The receipt and verification sub-system checks the received products against orders placed by the ordering sub-system, and typically performs license management. When a received mother vial 104 includes a mother vial data carrier 106, the sub-system reads information contained in the data carrier to verify that the order has been accurately fulfilled, and, typically, verifies the authenticity of the mother vial;
- a dose calculation sub-system 156, which calculates customized doses of labeled radiopharmaceutical agents for patients based on patient-specific information, protocol information, and/or prescription information, and communicates the customized doses to patient management system 160 and/or dispensing system 20; and/or
- a waste-disposal sub-system 157, which tracks radioactive waste disposal by system 10, such as disposal of radioactive materials contained in waste container 512, described hereinbelow with reference to FIG. 12. For some applications, sub-system 157 additionally tracks radioactive waste disposal of materials in the clinical environment not associated with system 10.

Ordering sub-system 154 and waste-disposal sub-system 157 typically operate in accordance with per country requirements for radiopharmaceutical use. A reporting sub-system reports to relevant nuclear regulatory commissions as required, based on information obtained from the other sub-systems.

In an embodiment of the present invention, dose calculation sub-system 156 designs a cocktail of labeled radiopharmaceutical agents or a series of labeled radiopharmaceutical agents to carry out the desired imaging. When designing such a cocktail or series, the sub-system considers constraints imposed by the physical properties of the agents and by the patient history, and other requirements, such as safety and efficacy requirements. The sub-system determines an appropriate dose for the specific patient having particular physiological parameters (e.g., weight, BMI, and age), and determines the times at which multiple agents are to be administered to the patient in order to achieve optimal imaging.

For some applications, sub-system 156 determines that a plurality of labeled radiopharmaceutical agents are to be administered together and thus must be combined in a single preparation, i.e., a cocktail. For other applications, the sub-system determines that a plurality of labeled radiopharmaceutical agents are to be administered separately at different times and thus must be contained in separate containers 22. As appropriate, sub-system 156 takes into consideration differing half-lives of the plurality of labeled radiopharmaceutical agents, in conjunction with the prescribed time of the imaging procedure. For example, a simultaneous imaging protocol is provided for assessing cardiac perfusion using a cocktail comprising Tc-99m sestamibi injected at rest, and thallium-201 injected at stress, wherein the desired activities at imaging time of the Tc-99m sestamibi and the thallium are 6 mCi and 4 mCi, respectively. When calculating the necessary activity of the dispensed dose, sub-system 156 accounts for the respective half-lives of Tc-99m (6 hours) and thallium-201 (64 hours) in view of the planned time interval between the dispensing time and administration time. For example, if dispensing is performed 24 hours before administration, sub-system 156 calculates the activities of the Tc-99m and thallium-201 at the time of dispensing to be 96 mCi and 5.5 mCi, respectively.

Protocol Information

Reference is made to FIG. 6A and FIGS. 6B-E, which are tables showing exemplary preconfigured SPECT protocols and parameters thereof, in accordance with respective embodiments of the present invention. These protocols are appropriate, for example, for use with the SPECT imaging methods and apparatus described hereinbelow with reference to FIG. 11, and/or in the co-assigned patent applications and/or patent application publications incorporated herein by reference hereinabove. For some applications, the techniques described herein utilize additional protocols described in above-mentioned International Application PCT/IL2005/001173, International Application PCT/IL2005/001215, filed Nov. 16, 2005, above-mentioned U.S. Provisional Patent Application 60/628,105, above-mentioned U.S. Provisional Patent Application 60/675,892, or in one or more of the other co-assigned patent applications and/or patent application publications incorporated herein by reference. Alternatively or additionally, the techniques described herein utilize protocols for non-SPECT imaging modalities, such as PET or CT, or other imaging modalities known in the art. The preconfigured protocols are stored in a database, which is typically used by patient management system 160 for suggesting protocols and/or by dose calculation sub-system 156, as described hereinabove with reference to FIGS. 4 and 5, respectively.

For each of the exemplary protocols shown in FIG. 6A, the table indicates general parameters for a rest phase and a stress phase of the protocol. For example, for the "single isotope/low dose/fast imaging" protocol, the table shows that the radiopharmaceutical (RP) for the rest phase of the protocol is less than 0.3 mCi of Thallium, that the waiting time after injection of the radiopharmaceutical is 2 minutes, and that the image acquisition duration is 15 minutes. Parameters for the stress phase are similarly indicated, with the addition of the type of stress (exercise, e.g., treadmill or bicycle, or pharmaceutical, e.g., adenosine). The "thallium stress perfusion" and "simultaneous dual isotope stress perfusion" protocols are optionally dynamic.

Figure 11:
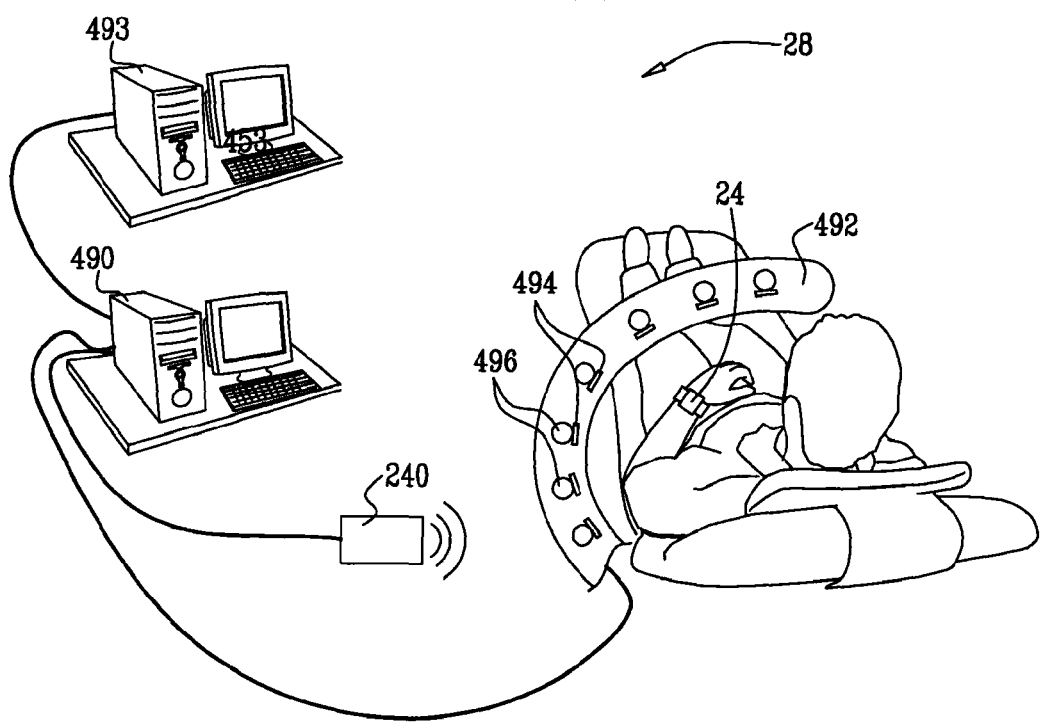
FIG. 11 is a schematic illustration of an imaging system, in accordance with an embodiment of the present invention.

For each of the exemplary protocols shown in FIGS. 6B-E, the table indicates administration parameters, detector parameters, scanning parameters, and analysis parameters for the protocol. For example, for Protocol A of FIGS. 6B-C ("Cardiac mapping"), the table indicates:
- the labeled radiopharmaceutical agent is Tc-99-sestamibi (MIBI);
- the protocol is a fast protocol, with image acquisition completed prior to substantial uptake of the agent by the liver;
- the injection is by a single bolus;
- image acquisition begins either about 2 minutes after injection, or during or immediately administration, for applications in which the administration is performed while the patient is already placed at camera 492 (FIG. 11);

the detected photon energy is 140 KeV with an energy resolution of 15%, i.e., the total range of energy levels detected by the detectors 494 of camera 492 (FIG. 11) is set to be 15% of the emitted energy level of the labeled radiopharmaceutical agent (140 Kev). Typically, this range is not centered around the emitted energy level, but instead is shifted towards lower energy levels;

the total scan time is 120 seconds;

four detectors 494 of camera 492 are assigned as outer (distal) detectors, and six detectors 494 are assigned as inner (proximal) detectors, as described hereinbelow with reference to FIG. 11;

each of the inner detectors has an angular range of between 90 and 120 degrees, and each of the outer detectors has an angular range of between 40 and 60 degrees;

the total number of angular orientations assumed by the detectors in aggregate is 1200, i.e., 10 detectors times 120 orientations each;

each angular step of the inner detectors is one degree, and each angular step of the outer detectors is 0.3 to 0.5 degrees (corresponding to the range of 40 to 60 degrees described above);

the dwell time at each step is one second, for both the inner and outer detectors;

the imaging procedure is gated using 16 to 32 frames;

the analyses to be performed include intensity image and ejection fraction.

For some applications, the protocol information includes additional information not shown in FIGS. 6B-E, such as:

additional scanning parameters, such as whether the detectors perform multiple scans (in all the protocols shown in the table, the detectors typically perform a single scan); and additional analysis parameters, such as:

saturation handling (in the first cardiac mapping protocol shown in the table, no saturation handling is performed, while in the second cardiac mapping protocol shown in the table, the analysis is configured to dismiss saturated pixels);

whether the analysis handles scatter from multiple sources (in the protocols shown in the table, the analysis does not handle scatter from multiple sources);

reconstruction resolution (in all of the protocols shown in the table, the image reconstruction resolution is 2.5 mm in the z-direction, and 5 mm in the x- and y-directions); and parameters that provide the diagnosis system (e.g., expert system) with information regarding how to interpret the results of the imaging study, such as kinetic parameters, predefined pathological values, or patient-specific physiological parameters (e.g., BMI, age, or a group to which the patient is assigned), and/or (particularly for gated studies), information regarding medical devices implanted in the patient (e.g., pacemakers or ICDs).

Reference is made to Protocol E of FIGS. 6B-C. In this cardiac mapping protocol, simultaneous image acquisition is performed using, typically using full conventional doses of both thallium and MIBI-Tc. The detected photon energy of the thallium is 167 KeV, rather than the 72 KeV that is conventionally detected during nuclear imaging procedures. Unlike conventional SPECT cameras, the camera described hereinbelow with reference to FIG. 11 is sufficiently sensitive to detect a clinically-relevant count of the relatively low percentage (8%) of photons emitted at the 167 KeV energy level. (Detection of 72 KeV energy is generally not practical when a conventional dose of MIBI-Tc is used, because the scatter from the 140 KeV energy level of MIBI-Tc masks the 72 KeV photons emitted by the thallium.)

Reference is made to Protocol I of FIGS. 6D-E. In this cardiac dynamic mapping protocol, image acquisition typically begins prior to administration of the radiopharmaceutical agent, such as at one minute prior to administration, as shown in the table. This allows the imaging system to complete one full scan of the region of interest prior to administration of the radiopharmaceutical agent, in order to ensure that the imaging system is able to acquire photons of radiation beginning immediately after the radiopharmaceutical agent is administered.

Typically, a selected preconfigured protocol is customized based on physiological parameters of the specific patient, and/or a medical profile group of the patient, as described hereinabove with reference to FIG. 4. Such customization typically includes customization of the radiopharmaceutical agent, administration parameters, and/or imaging parameters.

For some applications, one or more of the following parameters of the radiopharmaceutical agent are customized:

the dose, or for multiple radiopharmaceutical agents, the respective doses;

the radioactivity;

for cocktails, the ratio of the different radiopharmaceutical agents; and/or the volume of the dose, or for multiple radiopharmaceutical agents, the volumes of the respective doses.

For some applications, one or more of the following parameters of the administration are customized:

the dose administered, or for multiple radiopharmaceutical agents, the respective doses per administration;

the type of administration, e.g., a single bolus, a plurality of boluses (e.g., two boluses), pulsatile administration, or constant drip administration;

the labeled radiopharmaceutical agent for each administration, whether a single agent or a cocktail of agents;

the time of the administration with respect to the time of imaging;

the timings of multiple administrations with respect to each other and with respect to other activities, such as rest or stress (physical or pharmacological);

the administration device, e.g., a syringe, a dual-needle syringe, a pump, or an IV line; and/or the mode of administration, e.g., manual, automatic, or computer driven.

For some applications, one or more of the following parameters of the imaging procedure are customized. For some applications, such parameters are separately specified for individual components of camera 492 of imaging system 28, or groups of components, such as for individual detectors 494 or groups of detectors of camera 492, described hereinbelow with reference to FIG. 11.

total acquisition time, and/or acquisition time for a plurality of phases of acquisition;

detector scanning plan, including detector motions, such as detector angular and translational motions, detector step size (i.e., the density of the step size, typically expressed in degrees), number of detectors utilized for image acquisition, and detector dwell time at each view;

detector sensitivity;

detection energy resolution;

detector calibration plan;

definition of the region of interest (ROI);

gating parameters;

energy bands, i.e., a plurality of non-overlapping energy windows;

collimator positioning, shape, structure, and orientation;
multiple/interlaced scans;
zooming parameters;
uniformity/non-uniformity of scan;
Compton scatter map calculation and correction parameters;
optimal energy window;
optimal energy resolution, i.e., the range of energy level windows for which detection is enabled; and/or
adaptivity of scan pattern to acquired counts, e.g., active vision parameters (as described in the above-mentioned International Application PCT/IL2005/001173).

In an embodiment of the present invention, system 10 uses high definition protocols in conjunction with SPECT imaging techniques to enable personalized functional imaging at higher speeds and resolutions than can be achieved using conventional radiopharmaceutical protocols and imaging technology, using imaging techniques described herein and/or incorporated herein by reference. Alternatively or additionally, the system uses low dose protocols that enable personalized functional imaging at higher resolutions but with substantially lower doses than possible using conventional methods.

In an embodiment of the present invention, system 10 uses a protocol pursuant to which a patient undergoes a rest thallium (Tl-201-thallous chloride) and stress Tc-99-sestamibi (MIBI) study having a total study duration of between about 60 and about 90 minutes, and a total image acquisition duration of between about 0.5 and about 6 minutes, e.g., about four minutes. For example, pursuant to the protocol:
 about 3 mCi of thallium may be administered to the patient as a bolus IV injection,
 the patient may rest for between about 10 and about 15 minutes,
 an image acquisition having a duration of about two minutes may be performed,
 the patient may be physically stressed,
 about 20-30 mCi of Tc-99-sestamibi may be administered as a bolus IV injection, and
 a second image acquisition having a duration of about two minutes may be performed.

Such dual-isotope imaging is generally useful for assessing myocardial perfusion of patients with suspected ischemic syndromes and a variety of other conditions. Alternatively, in an embodiment, the rest phase is performed using an approximately 8 to 10 mCi dose of Tc-99-sestamibi, in which case image acquisition typically commences about 30 minutes after injection of the sestamibi. Further alternatively, in an embodiment, image acquisition for the rest phase is performed about two minutes after injection of the thallium, the stress is pharmacological (e.g., using adenosine), and image acquisition for the stress phase is performed essentially immediately after injection of the sestamibi. Still further alternatively, in an embodiment, the rest phase is performed using Tc-99-sestamibi, and image acquisition commences essentially immediately upon injection of a dose of about 8 to 10 mCi.

In accordance with respective embodiments of the present invention, dual-radiopharmaceutical protocols include the administration and simultaneous imaging of the following combinations of labeled radiopharmaceutical agents. Typically, the labeled radiopharmaceutical agents are administered as a mixture (i.e., a cocktail) before or during a simultaneous imaging procedure; alternatively, the labeled radiopharmaceutical agents are administered separately before or during a simultaneous imaging procedure.

(a) I-123 BMIPP, a fatty acid imaging agent that has been available in Japan for many years, and is currently in Phase III clinical trials in the United States, and (b) a myocardial perfusion agent (e.g., Tc-99m sestamibi, Tc-99m tetrofosmin, or Tl-201-thallous chloride), for simultaneously studying myocardial perfusion and fatty acid metabolism;

(a) Tl-201-thallous chloride and (b) Tc-99m pertechnetate, for differentiating an organ from its anatomical surroundings, such as differentiating parathyroid glands from the thyroid gland;

(a) In-111 DTPA, and (b) Tc-99m-MAG3, for differentiating pathological processes in a given organ, such as performing differential diagnosis of a hypo-perfused kidney, e.g., to study true glomerular filtration rate and tubular secretion simultaneously;

a cocktail of labeled radiopharmaceutical agents, for studying cancer, including simultaneous diagnosis, prediction of therapy response, and monitoring of therapy, such as simultaneously identifying a tumor, and characterizing tumor perfusion and metabolic activity, e.g., in order to provide a disease signature; and the combinations shown in the following table.

TABLE 1

| First radiopharmaceutical | First application | Second radiopharmaceutical | Second application |
|---|---|---|---|
| $^{201}$Tl | Myocardial perfusion | Tc-99m-teboroxime Tc-99m-sestamibi Tc-99m-tetrophosmin | Myocardial perfusion |
| $^{201}$Tl | Myocardial perfusion | Tc-99m-PYP | Infarct Imaging |
| $^{201}$Tl | Myocardial perfusion | Tc-99m-Annexin | Apoptosis |
| $^{201}$Tl | Myocardial perfusion | $^{123}$I-BMIPP | Hypoxia |
| Tc-99m-teboroxime | Myocardial perfusion | $^{111}$In-Annexin | Apoptosis |
| Tc-99m-teboroxime | Myocardial perfusion | $^{123}$I-Fatty acid | Metabolism |
| $^{111}$In-WBC | Infection | Tc-99m-SC | Bone Marrow |
| $^{111}$In-DTPA | Kidney (GFR) | Tc-99m-MAG3 | Kidney (tubular secretion) |
| Tc-99m-RBC | Blood pool | $^{111}$In-Prostascint | Prostate cancer |
| Tc-99m-HMPAO | Cerebral blood flow | $^{123}$I-IBZM | Dopamine D2 receptors |

In an embodiment of the present invention, system 10 uses protocols for studying the kinetics of thallium. For some applications, such protocols provide dynamic information regarding myocardial function, such as blood flow, rate of thallium uptake, thallium accumulation/redistribution, thallium metabolism, and/or thallium and/or metabolite secretion and/or wash-out (active or passive). Kinetic perfusion radiopharmaceutical modeling provides absolute myocardial perfusion measurements, coronary flow reserve, and parametric representation of cellular function.

In accordance with respective embodiments of the present invention, thallium protocols include:
 protocols using a conventional dose of thallium, with a substantially reduced SPECT image acquisition duration, e.g., less than about 6 minutes, such as less than about 2 minutes, e.g., about 0.5 minutes. By way of comparison, conventional thallium SPECT imaging procedures generally have image acquisition durations of between about 10 and about 20 minutes. For some applications, the thallium protocol is customized for a specific patient, as described hereinabove;

protocols using a conventional dose of thallium and a conventional image acquisition duration, with a substantially increased image resolution. For some applications, acquired photon counts are at least 5 times greater than those acquired using conventional SPECT techniques, e.g., at least 10 times greater, resulting in an image with substantially higher resolution; and dynamic protocols for myocardial perfusion studies that provide absolute quantitative measurements. For example, images of the heart may be reconstructed from list mode data, with a temporal resolution of 5-10 seconds. This temporal resolution is typically appropriate for the measurement of the kinetics of uptake and wash-out of thallium from the myocardium, as well as those of an input bolus as it passes through the left ventricle. Such data enables the measurement of absolute myocardial blood flow at rest and during peak stress.

In an embodiment of the present invention, system 10 uses protocols for cardiac stress testing studies, using, for example, Tc99m-sestamibi, Tc-99m tetrofosmin, or thallium. Such protocols differentiate between healthy cardiac tissue and scarred or poorly perfused cardiac tissue. Perfusion defects that appear after exercise or pharmacologic stress suggest either vascular occlusion or myocardial infarction. For some applications, such studies are performed gated to the patient's ECG, in order to study cardiac wall motion. Wall motion studies allow calculation of key cardiac function parameters, such as ejection fraction and estimated cardiac output.

In accordance with respective embodiments of the present invention, cardiac stress testing protocols, which use, for example, Tc99m-sestamibi, Tc-99m tetrofosmin, or thallium, include:

protocols using a conventional dose, with a substantially reduced SPECT image acquisition duration, e.g., less than about 6 minutes, such as less than about 2 minutes, e.g., about 0.5 minutes. By way of comparison, conventional cardiac stress testing SPECT imaging procedures generally have image acquisition durations of between about 10 and about 20 minutes. For some applications, the protocol is customized for a specific patient, as described hereinabove. For some applications, such as when the protocol uses Tc99m-sestamibi, image acquisition is performed immediately following administration of the labeled radiopharmaceutical agent, before the agent reaches the liver, thereby reducing interference by the liver on the resulting images.

protocols using a dose of the labeled radiopharmaceutical agent that is substantially lower than conventional SPECT protocols using the agent. For example, the dose may be between about 50% and about 90% lower than a conventional dose, e.g., about 50% lower than a conventional dose. By using the image acquisition techniques described herein and/or incorporated herein by reference, even at such reduced doses, acquired photon counts are typically at least 5 times greater than those acquired using conventional SPECT techniques at conventional SPECT doses, e.g., at 10 times greater, and image acquisition duration is typically about 50% less than conventional durations, e.g., about 80% less (such as four minutes instead of 20 minutes). Alternatively, the dose may be reduced by about 90%, and the image acquisition duration is approximately the same as conventional image acquisition durations.

In an embodiment of the present invention, system 10 uses Tc-99m teboroxime for performing a SPECT myocardial perfusion study. This radiopharmaceutical is extracted by the myocardium in proportion to myocardial blood flow throughout the entire range of achievable flow rates. When conventional imaging techniques are used, the wash-out rate of Tc-99m teboroxime from cardiac tissue is so rapid that there is inadequate time for imaging, because the radiopharmaceutical rapidly and avidly accumulates in the liver, which emits gamma rays that blind the imaging of the heart. By using the imaging techniques described herein and/or incorporated herein by reference, sufficient photon counts are obtained in an image acquisition period of no more than approximately two minutes, immediately following administration. The use of such a short period enables the completion of image acquisition prior to substantial uptake of the radiopharmaceutical by the liver, thereby enabling the effective clinical use of Tc-99m teboroxime for cardiac imaging.

In an embodiment of the present invention, a dynamic multiple isotope combination protocol is provided for studying different pathological processes of the same organ, such as studying acute myocardial ischemia. In accordance with this protocol, the following labeled radiopharmaceutical agents are administered as bolus IV injections:

(a) an approximately 2 mCi dose of I-123-BMIPP, followed by a wait of about 48 hours;
(b) an approximately 1 mCi dose of Tl-201-thallous chloride; and
(c) either (i) an approximately 10 mCi dose of Tc-99m-sestamibi or (ii) an approximately 10 mCi dose of Tc-99m-teboroxime.

Agents (b) and (c) are administered as a cocktail, or as separate injections at approximately the same time. Simultaneous image acquisition of all three radiopharmaceutical agents is performed during or soon after administration of agents (b) and (c), typically using an up to about 30 minute acquisition time, such as between about 5 and about 15 minutes, which is faster than that of standard imaging protocols. Typically, camera 492 of imaging system 28, described hereinbelow with reference to FIG. 11, performs image acquisition using an energy window of between about 2% and about 10% of the emitted energy levels of the radiopharmaceutical agents. Typically, detectors 494 of camera 492 sweep the region of interest once every approximately 10 to approximately 15 seconds. The I-123-BMIPP identifies the ischemic/infarcted area of the myocardium, while the other radiopharmaceutical agents identify the perfused area of the myocardium. Simultaneous imaging provides more accurate identification of myocardial perfusion pathologies than is generally possible using conventional imaging techniques and protocols.

In an embodiment of the present invention, system 10 uses an ultra-fast protocol pursuant to which a patient undergoes a rest and stress Tc-99-sestamibi (MIBI) study having a total study duration of between about 12 and about 18 minutes, e.g., about 15 minutes, and a total image acquisition duration of between about eight and about 12 minutes, e.g., about ten minutes. For example, pursuant to the protocol:

about 3 mCi of MIBI may be administered to the patient as a bolus IV injection (alternatively, about 8 mCi is administered), followed by saline administration,
the patient may rest for between about zero and about two minutes, e.g., about one minute,
an image acquisition having a duration of between about six and ten minutes may be performed, e.g., about eight minutes, the patient may be physically stressed, such as by adenosine infusion for about three to about four minutes, about 20-45 mCi of MIBI (e.g., about 25-35 mCi, e.g., 30 mCi) may be administered as a bolus IV injection, such as about two minutes after the beginning of the adenosine infusion (i.e., at peak stress), followed by saline administration, and a second image acquisition having a duration of about two minutes may be performed after the conclusion of the adenosine infusion (optionally, after a wait period of approximately two minutes).

Alternatively, the protocol is performed using Tc-99m tetrofosmin instead of MIBI.

Such a protocol typically has a total duration of only about 15 minutes, and is performed in a single sitting under the imaging camera, which is typically enabled by the use of the automated administration and imaging protocol techniques described herein. The use of such a low dose during the rest phase of the protocol obviates the conventional need to wait between rest and stress injections for decay of the rest dose.

For some applications, a kit is provided for performing the protocol, comprising a saline syringe, an adenosine syringe, a thallium syringe, and a MIBI (or tetrofosmin) syringe. The four syringes are optionally coupled to joining element 420, as described hereinbelow with reference to FIGS. 19-25, and information regarding the administration protocol and/or imaging protocol is stored in data carrier 434 and/or patient-specific data carrier 24.

In an embodiment of the present invention, system 10 uses an ultra-fast protocol pursuant to which a patient undergoes a rest thallium and stress Tc-99-sestamibi (MIBI) study having a total study duration of between about 15 and about 19 minutes, e.g., about 17 minutes, and a total image acquisition duration of between about six and about ten minutes, e.g., about eight minutes. For example, pursuant to the protocol:

about 2-5 mCi of thallium (e.g., about 3-4.5 mCi) may be administered to the patient as a bolus IV injection, followed by saline administration, the patient may rest for between about two and about six minutes, e.g., about five minutes, an image acquisition having a duration of between about two and six minutes, e.g., between about three and about four minutes, the patient may be physically stressed, such as by adenosine infusion for about three to about four minutes, about 20-40 mCi of MIBI (e.g., about 25-35 mCi, such as about 30 mCi) may be administered as a bolus IV injection, such as about two minutes after the beginning of the adenosine infusion (i.e., at peak stress), followed by saline administration, and a second image acquisition having a duration of about two to four minutes, e.g., about two minutes, may be performed after the conclusion of the adenosine infusion (optionally, after a wait period of approximately two minutes).

Alternatively, the protocol is performed using Tc-99m tetrofosmin instead of MIBI.

Such a protocol typically has a total duration of only about 20 minutes, and is performed in a single sitting under the imaging camera, which is typically enabled by the use of the automated administration and imaging protocol techniques described herein. The use of different isotopes during the rest and stress phases of the protocol obviates the conventional need to wait between rest and stress injections for decay of the rest dose.

For some applications, a kit is provided for performing the protocol, comprising a saline syringe, an adenosine syringe, a first MIBI (or tetrofosmin) syringe, and a second MIBI (or tetrofosmin) syringe. Alternatively, the kit comprises a single MIBI (or tetrofosmin) syringe, which has a sufficient dose for both the rest and stress phases. The three or four syringes are optionally coupled to joining element 420, as described hereinbelow with reference to FIGS. 19-25, and information regarding the administration protocol and/or imaging protocol is stored in data carrier 434 and/or patient-specific data carrier 24.

In an embodiment of the present invention, system 10 uses a dynamic protocol for blood flow and coronary flow reserve measurements. Pursuant to the protocol a patient undergoes a rest and stress Tc-99m-teboroxime study having a total study duration of between about 12 and about 16 minutes, e.g., about 14 minutes, and a total image acquisition duration of between about eight and about 12 minutes, e.g., about ten minutes. For example, pursuant to the protocol:

about 8-12 mCi of teboroxime may be administered to the patient as a bolus IV injection, followed by a saline flush, beginning substantially simultaneously with the administration, a low-resolution image acquisition having a duration of between about 0.4 and 0.6 minutes, e.g., about 0.5 minutes is performed, using, for example, 5 second frames, beginning substantially immediately upon conclusion of the low-resolution image acquisition procedure, a high-resolution image acquisition having a duration of between about four and about five minutes, e.g. about 4.5 minutes, using, for example, 20 second frames, the patient may be physically stressed, such as by adenosine infusion for about three to about four minutes, about 25-35 mCi of teboroxime may be administered as a bolus IV injection, such as substantially immediately after or about two minutes after the beginning of the adenosine infusion (i.e., at peak stress), followed by a saline flush, beginning upon conclusion of the adenosine administration, a low-resolution image acquisition having a duration of between about 0.4 and 0.6 minutes, e.g., about 0.5 minutes is performed, using, for example, 5 second frames, and beginning substantially immediately upon conclusion of the low-resolution image acquisition procedure, a high-resolution image acquisition having a duration of between about four and about five minutes, e.g. about 4.5 minutes, using, for example, 20 second frames.

Such a protocol typically has a total duration of only about 14 minutes, and is performed in a single sitting under the imaging camera, which is typically enabled by the use of the automated administration and imaging protocol techniques described herein.

The dynamic imaging of teboroxime using the imaging techniques described herein and/or in the co-assigned applications incorporated herein by reference allows the assessment of absolute myocardial perfusion as well as coronary flow reserve, for both rest and stress studies. By sampling the myocardium in five-second intervals during the first pass stage, it is possible to accurately estimate the input function. Once the tracer begins to diffuse into the myocardium, sampling time of the myocardium is increased to thirty-second intervals, and subsequently the dynamic sequences are analyzed using a compartmental analysis approach. This protocol requires exact knowledge of the rate of the injection of the bolus and also requires a flush immediately following the injection of the radiopharmaceutical. The use of the automated administration and imaging protocol techniques described herein enable performance of this protocol. In addition, it is important that the bolus be in a relatively small volume. The use of the kit described immediately hereinbelow ensures such an accurate volume. The flush is used to push the bolus through and to keep it tight as well as to wash out residual radioactivity from the infusion line, so that this activity does not contaminate the next bolus injection.

For some applications, a kit is provided for performing the protocol, comprising a saline syringe, an adenosine syringe, a first teboroxime syringe, and a second teboroxime syringe. Alternatively, the kit comprises a single teboroxime syringe, which has a sufficient dose for both the rest and stress phases. The three or four syringes are optionally coupled to joining element 420, as described hereinbelow with reference to FIGS. 19-25, and information regarding the administration protocol and/or imaging protocol is stored in data carrier 434 and/or patient-specific data carrier 24.

In an embodiment of the present invention, system 10 uses one or more of the protocols described in the above-mentioned U.S. Provisional Application 60/799,688, filed May 11, 2006, entitled, "Imaging protocols."

In some embodiments of the present invention, the protocols described herein (including those shown in FIGS. 6A-E), and in the co-assigned patent applications incorporated herein by reference, are performed using values that vary from those provided in the protocols by +/−20%, e.g., +/−5%, +/−10%, or +/−15%. Furthermore, in some embodiments, the protocols are performed with a range of doses from 50%, 75%, 90%, or 100% of the dosage value given for the respective protocol, up to 10 times the dosage value given for the respective protocol (such as up to 2, 4, 6, or 8 times the given dosage value). For example, a dose shown as 3 mCi for a given protocol may, in some embodiments, have a range of 1.5 mCi to 30 mCi, or from 2.7 mCi to 6 mCi. Similarly, in some embodiments, the protocols are performed with a range of acquisition durations (total scan times) from 50%, 75%, 90%, or 100% of the duration value given for the respective protocol, up to 5 times the duration value given for the respective protocol, such as up to 1.5, 2, 3, or 4 times the given duration value. Other protocol values, such as waiting times, energy windows/resolution, angular range, angular step, and dwell time, may also have a range from 50%, 75%, 90%, or 100% of the value given for the respective protocol, up to 5 times the value given for the respective protocol, such up to 1.5, 2, 3, or 4 times the given value.

In respective embodiments of the present invention, all of the protocols described herein and/or in the co-assigned patent applications incorporated herein by reference are enabled to generate clinically-valuable images. A "clinically-valuable image" is an image of an intra-body region of interest (ROI) containing the labeled radiopharmaceutical agent(s), which image fulfills one or more of the following criteria:

the image is generated according to a protocol, including at the radiopharmaceutical dose specified by the protocol, using a high-definition SPECT camera, for example, camera 492 of imaging system 28, described hereinbelow with reference to FIG. 11, which camera, during the imaging of the ROI, is capable of acquiring at least one of 5000 photons emitted from the ROI during the image acquisition procedure, such as at least one of 4000, 3000, 2500, 2000, 1500, 1200, 1000, 800, 600, 400, 200, 100, or 50 photons emitted from the ROI. In one particular embodiment, the camera is capable of acquiring at least one of 2000 photons emitted from the ROI during the image acquisition procedure;

the image is generated according to a protocol, including at the radiopharmaceutical dose and image acquisition duration specified by the protocol, using a high-definition SPECT camera, for example, camera 492, which, during the imaging of the ROI, is capable of acquiring at least 200,000 photons, such as at least 500,000, 1,000,000, 2,000,000, 3,000,000, 4,000,000, 5,000,000, 8,000,000, or 10,000,000 photons, emitted from a portion of the ROI having a volume of no more than 500 cc, such as a volume of no more than 500 cc, 400 cc, 300 cc, 200 cc, 150 cc, 100 cc, or 50 cc. In one particular embodiment, the camera is capable of acquiring at least 1,000,000 photons emitted from a volume of the ROI having a volume of no more than 200 cc;

the image has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein the labeled radiopharmaceutical agent as distributed within the ROI has a range of emission-intensities R (which is measured as emitted photons/unit time/volume), and wherein at least 50% of the voxels of the reconstructed three-dimensional emission-intensity image of the ROI have inaccuracies of less than 30% of range R, such as less than 25%, 20%, 15%, 10%, 5%, 2%, 1%, or 0.5% of range R. For example, the agent may emit over a range from 0 photons/second/cc to 10^5 photons/second/cc, such that the range R is 10^5 photons/second/cc, and at least 50% of the voxels of the reconstructed three-dimensional intensity image of the ROI have inaccuracies of less than 15% of range R, i.e., less than 1.5×10^4 photons/second/cc. For some applications, the study produce a parametric image related to a physiological process occurring in each voxel. In one particular embodiment, the image has a resolution of at least 5×5×5 mm, and at least 50% of the voxel have inaccuracies of less than 15% of range R;

the image is generated according to a protocol, including at the radiopharmaceutical dose and image acquisition duration specified by the protocol, the image has a resolution of at least 7×7×7 mm, such as at least 6×6×6 mm, 5×5×5 mm, 4×4×4 mm, 4×3×3 mm, or 3×3×3 mm, wherein the labeled radiopharmaceutical agent has a range of intensities R (photons/unit time/volume), and wherein at least 50% of the voxels of the reconstructed three-dimensional intensity image of the ROI have inaccuracies of less than 30% of range R, such as less than 25%, 20%, 15%, 10%, 5%, 2%, 1%, or 0.5% of range R. For some applications, the study produce a parametric image related to a physiological process occurring in each voxel; and/or the image has a resolution of at least 20×20×20 mm, such as at least 15×15×15 mm, 10×10×10 mm, 7×7×7 mm, 5×5×5 mm, 4×4×4 mm, 4×3×3 mm, or 3×3×3 mm, wherein values of parameters of a physiological process modeled by a parametric representation have a range of physiological parameter values R, and wherein at least 50% of the voxels of the reconstructed parametric three-dimensional image have inaccuracies less than 100% of range R, such as less than 70%, 50%, 40%, 30%, 25%, 20%, 15%, 10%, 5%, 2%, 1%, or 0.5% of range R. For example, the physiological process may include blood flow, the values of the parameters of the physiological process may have a range from 0 to 100 cc/minute, such that the range R is 100 cc/minute, and at least 50% of the voxels of the reconstructed parametric three-dimensional image have inaccuracies less than 25% of range R, i.e., less than 25 cc/minute. In one particular embodiment, the image has a resolution of at least 5×5×5 mm, and at least 50% of the voxels have inaccuracies of less than 25% of range R.

The Mother Vial

Figure 7:
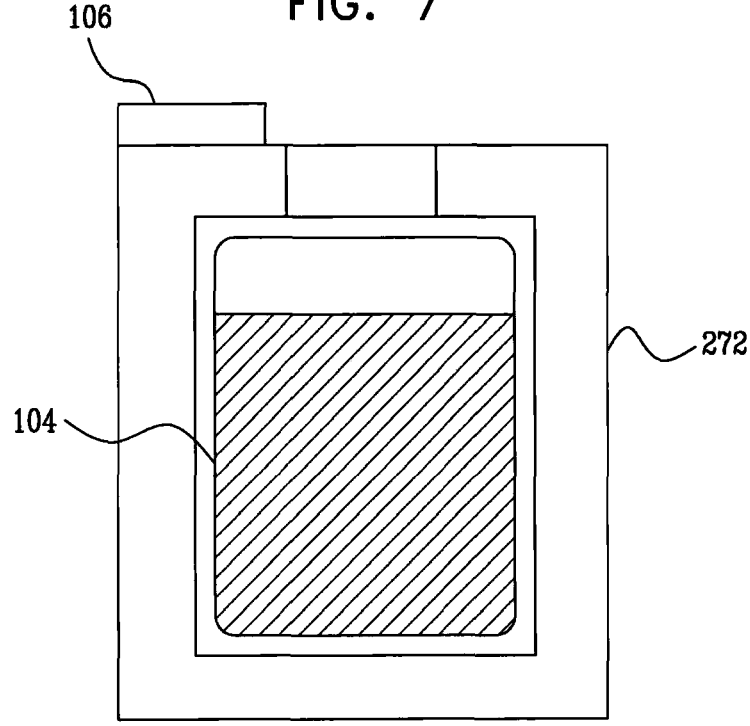
FIG. 7 is a schematic illustration of a mother vial and attached data carrier, in accordance with an embodiment of the present invention.

Reference is made to FIG. 7, which is a schematic illustration of mother vial 104 and attached data carrier 106, in accordance with an embodiment of the present invention. Data carrier 106 is computer-communicatable, and typically comprises an RFID tag, smart card, memory card (such as a disk-on-key (e.g., a USB key)), compact disc, minidisk, disposable computer-readable medium, or other electronic memory, or a machine-readable code, e.g., a computer-readable scannable label, such as a barcode, two-dimensional bar code, or color-coded code. Mother vial 104 is shown contained within shielding 272, to which data carrier 106 is attached. Alternatively, the data carrier is attached directly to the mother vial, or otherwise associated with the mother vial, such as by being stored in proximity to the mother vial, e.g., in a tray that also contains the mother vial.

Data carrier 106 typically contains at least some of the following information:
  a coded signature 256, for authenticating mother vial 104;
  radiopharmaceutical information, a portion of which is typically supplied by the manufacturer, and a portion of which is typically generated by dispensing system 20 in conjunction with dispensing the radiopharmaceutical agent(s). For some applications, a portion of the information is generated by mother vial preparation system 700, described hereinbelow with reference to FIG. 15, in conjunction with preparing the radiopharmaceutical. The information includes, for example:
    the name of and/or information regarding the manufacturer;
    the indicated use(s) (e.g., "Formulation for Cardiac Dynamic Studies");
    the pre-labeled composition;
    the time of preparation of the labeled radiopharmaceutical agent(s);
    the radioactivity at the time of preparation;
    the total solution volume;
    the pre-labeled-composition expiration date;
    the appropriate labeling isotope(s);
    the decay scheme(s) of the appropriate labeling isotope(s);
    the radiopharmaceutical biodistribution as a function of time;
    the radiopharmaceutical clearance rate;
    the percent clearance by the liver;
    the percent clearance by the kidneys;
    the breakdown rate;
    the liver uptake as a function of time; and/or
    radiopharmaceutical kinetic parameters, such as described hereinbelow, which parameters may be stored in one or more lookup tables;
  administration protocol information, such as described hereinbelow;
  image acquisition protocol information, such as described hereinbelow;
  image reconstruction protocol information, such as described hereinbelow;
  image analysis protocol information, such as described hereinbelow;
  expert system protocol information, such as described hereinbelow;
  radiolabeling information, which, for some applications, is generated by mother vial preparation system 700, described hereinbelow with reference to FIG. 15. Such information includes, for example:
    the labeling radioisotope(s), e.g., Tc-99m;
    time of labeling;
    activity of the radioisotope(s) per volume at the time of labeling;
    total solution volume in the mother vial; and/or
    ratio of radioisotopes (e.g., Tc-99m to Tc-99) at the time of labeling.

If the labeled radiopharmaceutical agent stored in the mother vial is radiolabeled by mother vial preparation system 700, as described hereinbelow with reference to FIG. 15, the labeling information is provided by the mother vial preparation system. Otherwise, the labeling information is provided by the pharmacist and/or conventional labeling system that radiolabels the unlabeled radiopharmaceutical agent.

The radiopharmaceutical kinetic parameters are used by imaging system 28 for performing dynamic imaging studies, for example as described in the above-mentioned International Patent Application PCT/IL2005/001173, and/or in the above-mentioned U.S. Provisional Application 60/799,688, filed May 11, 2006, entitled, "Imaging protocols". For some applications, respective sets of these parameters are provided for:
  different patient populations, such as a healthy population and populations which suffer from various pathologies;
  different organs and/or tissue types, for example, brain tissue, cardiac tissue, liver tissue, and tumor tissue;
  different pathologies;
  different patient physiologies;
  different organs, according to the physiology of the specific patient;
  different patient groups, as expected according to the physiology of the specific patient;
  different pathologies, as expected according to the physiology of the specific patient;
  different organs, as measured for the specific patient;
  different patient groups, as measured for the specific patient; and/or
  different pathologies, as measured for the specific patient.

Such kinetic parameters may include, for example:
  volume of blood in a voxel;
  density of blood in a tissue within a voxel;
  labeled radiopharmaceutical agent concentration in the blood within a voxel;
  labeled radiopharmaceutical agent concentration in a tissue within a voxel;
  total labeled radiopharmaceutical agent concentration in a voxel;
  labeled radiopharmaceutical agent concentration in the systemic blood circulation;
  linearity with blood flow;
  receptor binding for molecular radiotracers;
  labeled radiopharmaceutical accumulation/redistribution in tissue;
  labeled radiopharmaceutical metabolic rate;
  diffusion coefficient from the blood to the tissue (i.e., rate of wash-out, passive or active);
  diffusion coefficient from the tissue to the blood (i.e., rate of uptake, passive or active); and/or
  accumulation rate in a tissue within a voxel.

The administration protocol information is used by administration system 26 to set parameters of administration of the labeled radiopharmaceutical agent(s) contained in container 22. This protocol information may include, for example:
  the dose administered, or for multiple radiopharmaceutical agents, the respective doses per administration;

the type of administration, e.g., a single bolus, a plurality of boluses (e.g., two boluses), pulsatile administration, or constant drip administration;

the labeled radiopharmaceutical agent for each administration, whether a single agent or a cocktail of agents;

the time of the administration with respect to the time of imaging;

the timings of multiple administrations with respect to each other and with respect to other activities, such as rest or stress (physical or pharmacological);

the administration device, e.g., a syringe, a dual-needle syringe, a pump, or an IV line;

the mode of administration, e.g., manual, automatic, or computer driven; and/or an algorithm for customizing the administration based on physiological parameters of the specific patient.

The image acquisition protocol information is used by imaging system 28 to set parameters of the image acquisition process. For some applications, such parameters are separately specified for individual components of camera 492 of imaging system 28, or groups of components, such as for individual detectors 494 or groups of detectors. Such acquisition protocol information may include, for example:

the name(s) and/or identification code(s) of one or more protocols for which the radiopharmaceutical agent contained in mother vial 104 is suitable;

total acquisition time, and/or acquisition time for a plurality of phases of acquisition;

detector scanning plan, including detector motions, such as detector angular and translational motions, detector step size (typically expressed in degrees), and detector dwell time at each view;

detector sensitivity;

detector energy resolution;

detector calibration plan;

definition of the region of interest (ROI);

gating parameters;

energy bands, i.e., a plurality of non-overlapping energy windows;

collimator positioning, shape, structure, and orientation;

multiple/interlaced scans;

zooming parameters;

uniformity/non-uniformity of scan;

Compton scatter map calculation and correction parameters;

optimal energy window;

optimal energy resolution, i.e., the range of energy window levels detected; and/or adaptivity of scan pattern to acquired counts, e.g., active vision parameters (as described in the above-mentioned International Application PCT/IL2005/001173).

For some applications, the optimal energy window is set at least in part responsively to the BMI of the patient. For example, the width of the energy window (i.e., the energy resolution) may be inversely related to the BMI, because the tissue of patients with higher BMIs tends to create more scatter. To compensate for narrower energy windows, a longer acquisition time and/or a higher dose of radiopharmaceutical agent is typically used. For some applications, the protocol information includes a look-up table of BMIs and associated energy windows. For some applications, the energy window is non-symmetrical around a peak of the energy curve.

The image reconstruction protocol information is used by imaging system 28 to set parameters of the image reconstruction process. Such parameters may include, for example:

calibration parameters;

timing of acquisition;

reconstruction parameters and algorithms;

priors, i.e., mathematical constants signifying pre-imaging phase knowledge about system behavior;

multi-resolution reconstruction parameters;

non-uniform reconstruction grid;

filters;

noise modeling and handling;

mode selection;

information derived during image acquisition and/or gating;

protocols for handling interfering organs;

protocols describing the precise procedure to be followed in radiopharmaceutical administration, time management, patient activity status, imaging process, and other parameters that can affect imaging results;

optimization parameters per dose and/or cocktail of doses; and/or attenuation correction parameters, which are typically based on physiological parameters such as body mass, BMI, and girth.

For some applications, imaging system 28 uses one or more of these parameters to perform the image reconstruction process using techniques described in one or more of the co-assigned patent applications incorporated herein by reference.

The image analysis protocol information includes analysis algorithms and/or parameters of the image analysis process, which are used by imaging system 28 for performing diagnostic analysis of the reconstructed image. For some applications, such analysis includes tracer kinetics analysis. Such parameters may include, for example:

information for selection of a model of tracer kinetics;

information for selection of one or more time scales for tracer kinetics;

tracer parameters;

information for analysis of multiple time points;

information for analysis regarding the clinical meaning of radiation distribution within the patient's body for the purpose of making a clinical diagnosis regarding the patient's health state;

information for identifying the signatures of multiple labeled radiopharmaceutical agents; and/or optimization parameters per dose and/or cocktail of doses.

The expert system protocol information, such as expert system rules, is used by imaging system 28 to set parameters of the expert system used for assisting with diagnosis. For some applications, the expert system is implemented using techniques described in the above-mentioned International Application PCT/IL2005/001173, or in one or more of the other co-assigned patent applications incorporated by reference. Such parameters may include, for example:

classification of the patient into a patient population;

multi-parameter vectors of radiopharmaceutical kinetic parameters for different patient populations, such as a healthy population and populations which suffer from various pathologies, and for different tissue types, for example, brain tissue, cardiac tissue, liver tissue, or tumor tissue;

patient history;

multi-dimensional thresholds for defining healthy-disease state;

disease signature classifications per pathology and/or organ (typically per patient population); and/or optimization parameters per dose and/or cocktail of doses.

The Portable Information-Bearing Radiopharmaceutical Agent Container

Figure 8:
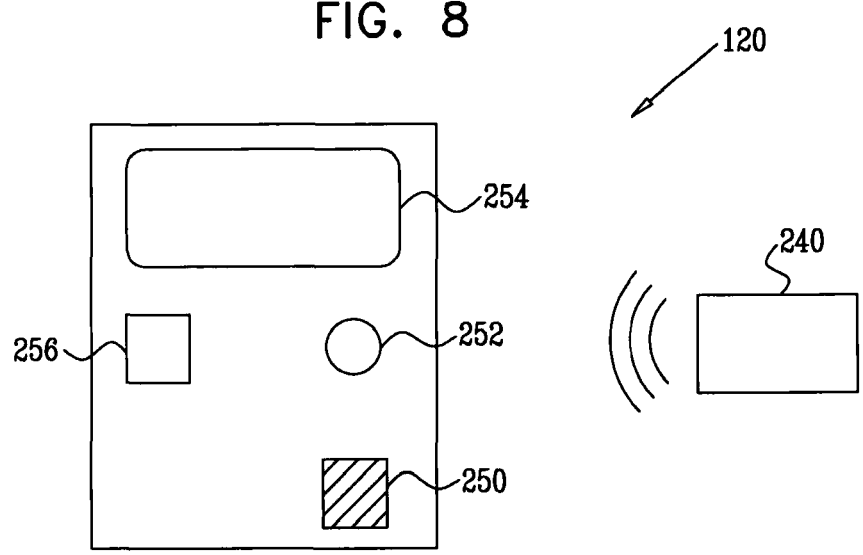
FIG. 8 is a schematic illustration of a data carrier coupled to a radiopharmaceutical agent container, in accordance with an embodiment of the present invention.

FIG. 8 is a schematic illustration of data carrier 120, in accordance with an embodiment of the present invention. As mentioned above, data carrier 120 is physically coupled to radiopharmaceutical agent container 22. Data carrier 120 is computer-communicatable, and typically comprises an RFID tag, smart card, memory card (such as a disk-on-key (e.g., a USB key)), compact disc, minidisk, disposable computer-readable medium, or other electronic memory, or a machine-readable code, e.g., a computer-readable scannable label, such as a barcode, two-dimensional bar code, or color-coded code. One or more communication elements 240 are provided for reading data from and transmitting data to data carrier 24. Respective communication elements 240 are typically in data communication with dispensing system 20 and administration system 26. For some applications, communication elements 240 comprise one or more coils for transmitting and receiving electromagnetic radiation. Typically, the communication elements are configured to have a short effective transmission range, e.g., no more than between about 20 and 40 cm, such as about 30 cm. Such a short range reduces the likelihood of accidental communication with a data carrier other than the intended data carrier.

Data carrier 120 comprises circuitry 250, which comprises memory and logic. For some applications, data carrier 120 is passive, in which case it is configured to receive energy from communication element 240. For other applications, data carrier 120 comprises a power source (not shown). For some applications in which the data carrier comprises a power source, the data carrier comprises a communication element for communicating and/or energizing another electronic apparatus. Alternatively or additionally, the data carrier comprises a communication element 252 configured for wireless communication. For some applications, data carrier 24 further comprises a user output 254 for outputting information to the patient or healthcare workers. For example, output 254 may comprise a display screen, light, and/or sound generator, which the circuitry drives to communicate information, such as when communications have been established with other elements of system 10, e.g., data carrier 120, administration system 26, or imaging system 28. For some applications, data carrier 120 further comprises coded signature 256, which is typically encrypted, color-coded, or both encrypted and color-coded, as described hereinbelow in the section entitled "Signature,"

The information contained in data carrier 120 typically includes some or all of the following:

an administration-device identification code;

an identifier, such as an identification code and/or name, of the patient for which the specific attached radiopharmaceutical agent container 22 is intended;

the formulation of the labeled radiopharmaceutical agent(s) contained in attached container 22;

the time of dispensing of the labeled radiopharmaceutical agent(s) to container 22;

activity of the labeled radiopharmaceutical agent(s), at the time of dispensing of the labeled radiopharmaceutical agent(s) to container 22;

the assigned protocol(s) for use with the labeled radiopharmaceutical agent(s) contained in attached container 22;

the intended time(s) and date(s) of administration of the labeled radiopharmaceutical agent(s) contained in container 22;

the intended activity(ies) of the labeled radiopharmaceutical agent(s) at the time of administration thereof;

the intended time profile of administration (single bolus, slow-drip administration, or any other form of administration);

the identification code of mother vial 104 from which the labeled radiopharmaceutical agent(s) contained in container 22 were dispensed; and/or at least a portion of the radiopharmaceutical information stored in data carrier 106 of mother vial 104, as described hereinabove with reference to FIG. 7. This information is typically electronically transferred from data carrier 106 during dispensing of the labeled radiopharmaceutical agent(s) to container 22, as described hereinabove with reference to step 118 of FIG. 2 and hereinbelow with reference to FIG. 12.

As mentioned above, for some applications, all or a portion of the information contained in patient-specific data carrier 24 is alternatively or additionally stored in data carrier 120. Such information is described hereinabove with reference to FIG. 7. For some applications, a portion of the information stored in the data carrier is also printed in human- and/or machine-readable form on the data carrier and/or on the container, for example as a barcode 260, as shown below in FIGS. 9A-H.

In an embodiment of the present invention, radiopharmaceutical agent container 22 comprises all or a portion of a drug administration device, such as a syringe or an inhalation device, packaging for an oral dosage form, or radiopharmaceutical packaging.

Reference is made to FIGS. 9A-H, which are schematic illustrations of respective embodiments of radiopharmaceutical agent container 22 and data carrier 120, in accordance with respective embodiments of the present invention. In all of these embodiments, data carrier 120 is physically coupled to agent container 22.

Figure 9A:
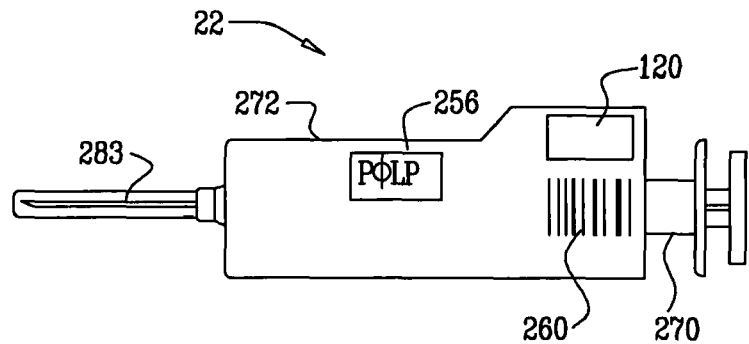

FIG. 9A is a schematic illustration of radiopharmaceutical agent container 22 comprising a manual syringe 270, in accordance with an embodiment of the present invention. Syringe 270 is protected by shielding 272, to which data carrier 120 is coupled. Alternatively, the data carrier is coupled directly to an exposed portion of the syringe, such as the end of the plunger of the syringe, as shown in the figure.

Figure 9B:
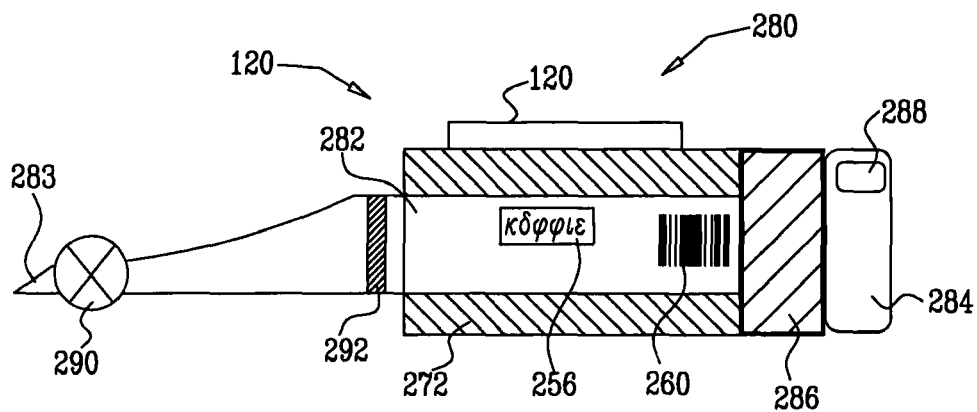

FIG. 9B is a schematic illustration of radiopharmaceutical agent container 22 comprising an automatic administration device 280, in accordance with an embodiment of the present invention. Device 280 comprises a chamber 282 for containing the labeled radiopharmaceutical agent(s), a needle 283, a controller 284, a drive 286, and a power source 288. For some applications, controller 284 is preprogrammed with administration instructions, while for other applications, the controller is coupled to administration system 26 and receives an administration signal therefrom prior to administration, or in real time during administration. Administration device 280 typically includes an interlock 290 to prevent administration without verification, for example, of the patient's identity. For some applications, device 180 comprises a flow meter 292, which measures the volume of labeled radiopharmaceutical agent administered. Controller 284 uses this flow information for regulating parameters of the administration, such as rate of administration and total amount of agent administered. Shielding 272 protects medical personnel from the radioactivity of the labeled radiopharmaceutical agent.

Figure 9C:
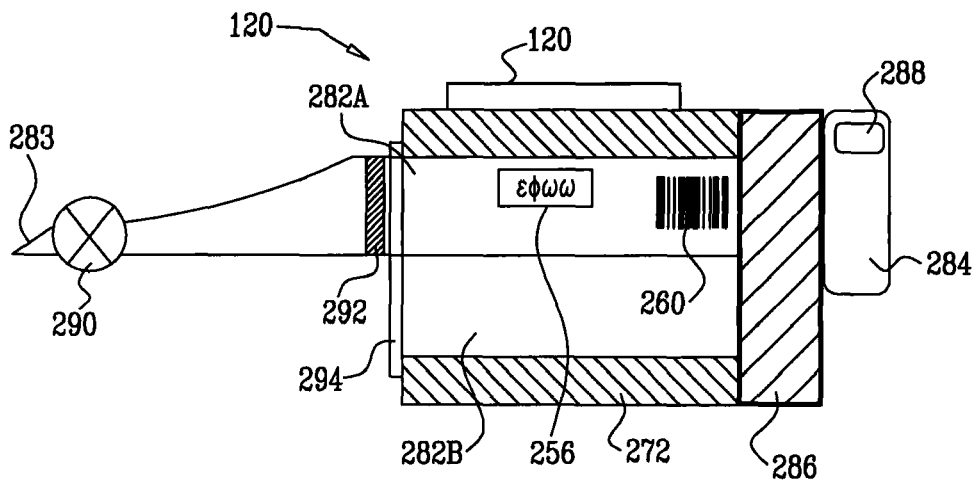

FIG. 9C is a schematic illustration of a multi-chamber embodiment of radiopharmaceutical agent container 22, in accordance with an embodiment of the present invention. In this embodiment, container 22 comprises a plurality of chambers in fluid isolation from one another, each of which chambers contains a labeled radiopharmaceutical agent. In the embodiment shown in FIG. 9C, the container comprises two such chambers, a first chamber 282A and a second chamber 282B. Alternatively, the container comprises more than two chambers (configuration not shown). For some multi-chamber applications, container 22 comprises automatic administration device 280, as shown in FIG. 9C, while for other multi-chamber applications, container 22 comprises a plurality of manual syringes 270, as described hereinabove with reference to FIG. 9A (multi-chamber configuration not shown). For some applications, a separate needle 283 is provided for each injection, while for other applications, container 22 is configured to utilize a single needle 283 for the plurality of injections. For example, needle 283 may be configured to slide along a needle mount 294, so as to service the plurality of chambers.

FIG. 9D is a schematic illustration of another configuration of radiopharmaceutical agent container 22, in accordance with an embodiment of the present invention. In this embodiment, container 22 comprises automatic administration device 280, as described hereinabove with reference to FIG. 9B, and controller 284 is configured to perform all or a portion of the functions of data carrier 120. For some applications, one or more of the elements of data carrier 120 are provided separately from the controller. For example, communication element 252 or user output 254 may be provided separately from the controller.

FIGS. 9E-G are schematic illustrations of another configuration of radiopharmaceutical agent container 22 comprising manual syringe 270, in accordance with an embodiment of the present invention. In this embodiment, syringe 270 comprises a transmitter 296 fixed with respect to a plunger 298 of the syringe, and shielding 272 is configured so as to modulate effective transmission by transmitter 296. For example, shielding 272 may be shaped so as to define a longitudinal slot 300 along a portion of the shielding. This modulation serves to send, from syringe 270 to administration system 26 and/or imaging system 28, a signal indicative of a time of administration of the labeled radiopharmaceutical agent(s) contained in container 22. The techniques of this embodiment are typically useful when registration of the time of administration with imaging system 28 is important, such as for dynamic studies.

FIGS. 9E-G respectively illustrate three steps for administration using these techniques. FIG. 9E shows a first step, during which transmitter 296 is exposed, and therefore effectively transmits a signal. FIG. 9F shows a second step, during which transmitter 296 is shielded by shield 272. FIG. 9G shows a third step, in which transmitter 296 is again exposed. This sequence of exposing, shielding, and again exposing the transmitter serves to signal that administration has occurred. The receiver of the signal (administration system 26 and/or imaging system 28) records the time that this signal is detected. For some applications, other techniques are used to automatically transmit an indication of when the labeled radiopharmaceutical agent(s) are administered. For example, a transmitter may be mounted on shield 272, and may send a signal when electrical contact is established between electrodes (not shown) on plunger 298 and shield 272 at the end of complete motion of the plunger into syringe 270.

FIG. 9H is a schematic illustration of a syringe adaptor 320, in accordance with an embodiment of the present invention. Adaptor 320 comprises shielding 272 and data carrier 120 coupled thereto. The adaptor is configured to placed on a standard administration device, such as a standard syringe. In an embodiment of the present invention, an adaptor similar to adaptor 320 is provided for use with other components of an end-to-end imaging system, such as Tc-99m vials, mother vials, dispensing tools, and dilution containers. Alternatively or additionally, data carrier 120 is configured to be couplable to such other components.

In an embodiment of the present invention, data carrier 120 is configured to be couplable to a standard administration device, such as a syringe. For example, the data carrier may be couplable to the barrel, plunger, or conventional shielding of a conventional syringe, or another syringe known in the art.

The Administration System

Figure 10:
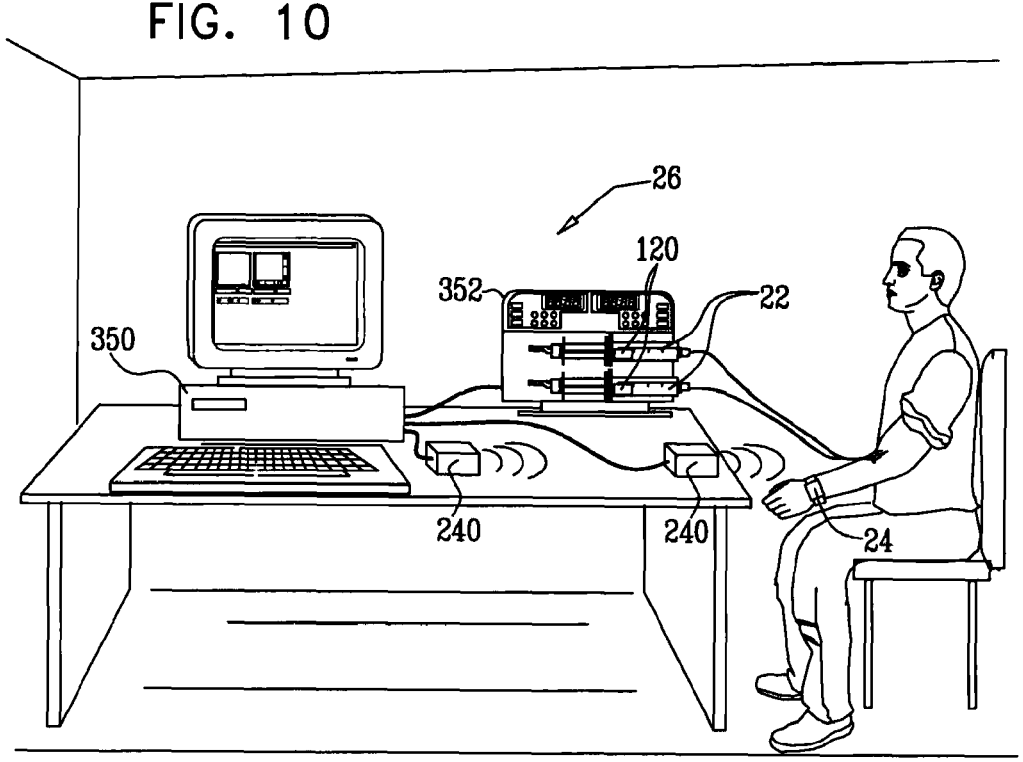
FIG. 10 is a schematic illustration of an administration system, in accordance with an embodiment of the present invention.

Reference is made to FIG. 10, which is a schematic illustration of administration system 26, in accordance with an embodiment of the present invention. Administration system 26 comprises a control unit 350, at least one communication element 240, and, for some applications, an automated administration device 352. Typically, control unit 350 comprises a standard personal computer or server with appropriate memory, communication interfaces and software for carrying out the functions prescribed by relevant embodiments of the present invention. This software may be downloaded to the control unit in electronic form over a network, for example, or it may alternatively be supplied on tangible media, such as CD-ROM. For some applications, administration system 26 comprises a single communication element 240 that communicates with both patient-specific data carrier 24 and data carrier 120 of container 22, while for other applications the administration system comprises separate communication elements 240 for communicating with data carriers 120 and 24 respectively. For example, a communication element for communicating with data carrier 120 may be integrated into or coupled to automated administration device 352.

Upon authenticating container 22, verifying the identity of the patient, and performing additional verifications, as described hereinabove with reference to step 122 of FIG. 2, control unit 350 generates an administration signal that triggers administration to the patient of the labeled radiopharmaceutical agent(s) stored in container 22. For applications in which administration system 26 comprises automated administration device 352, container 22 is operatively coupled to device 352, and the signal drives administration device 352 to administer the labeled radiopharmaceutical agent(s) stored therein to the patient. Automated administration device 352 is configured to perform intravenous (IV) injection, intramuscular (IM) injection, subcutaneous injection, transdermal application, oral administration, nasal administration, inhalation, transcervical application, transrectal administration, or another type of administration known in the art. (It is to be understood that although the administration signal triggers administration of the agent, for some applications automated administration device 352 does not administer the agent until a healthcare worker provides a final authorization to do so, such as to comply with regulatory safety requirements.) For applications in which administration system 26 does not comprise automated administration device 352, the administration signal triggers administration of the agent by instructing a healthcare worker to manually administer the agent to the patient.

For some applications, based on administration protocol information received from data carrier 120 of radiopharmaceutical agent container 22 and/or patient-specific data carrier 24, control unit 350 customizes the administration of the labeled radiopharmaceutical agent(s) contained in agent container 22. Such administration protocol information typically includes all or a portion of the administration protocol information described hereinabove with reference to FIG. 7. For some applications, administration system 26 administers a plurality of labeled radiopharmaceutical agents, either sequentially or premixed together within a single agent container 22 (i.e., as a cocktail).

For some applications, administration system 26 administers the labeled radiopharmaceutical agent(s) responsively at least in part to acquisition of a signal associated with the agent(s). For example, acquisition of the signal may comprise detection of photons emitted from the agent(s), in order to determine a radioactivity level.

For some applications, administration system 26 and/or imaging system 28 monitors uptake and/or clearance of the labeled radiopharmaceutical agent(s) by (a) measuring physiological parameters, e.g., from samples of blood, saliva, or secretions, e.g., urine, breath, feces, or sweat, or (b) by performing an imaging procedure using imaging system 28. For some applications, these measurements are used to estimate pharmacokinetics of the radiopharmaceutical agent(s) in organs, and/or to predict optimal imaging timing (the optimal time to perform the imaging, and/or the optimal timing parameters of the imaging procedure). For some applications, based on these estimates, an expected level of uptake of the radiopharmaceuticals in a target organ is determined, enabling diagnosis of pathologies based on absolute uptake levels in the target organ.

Figure 19:
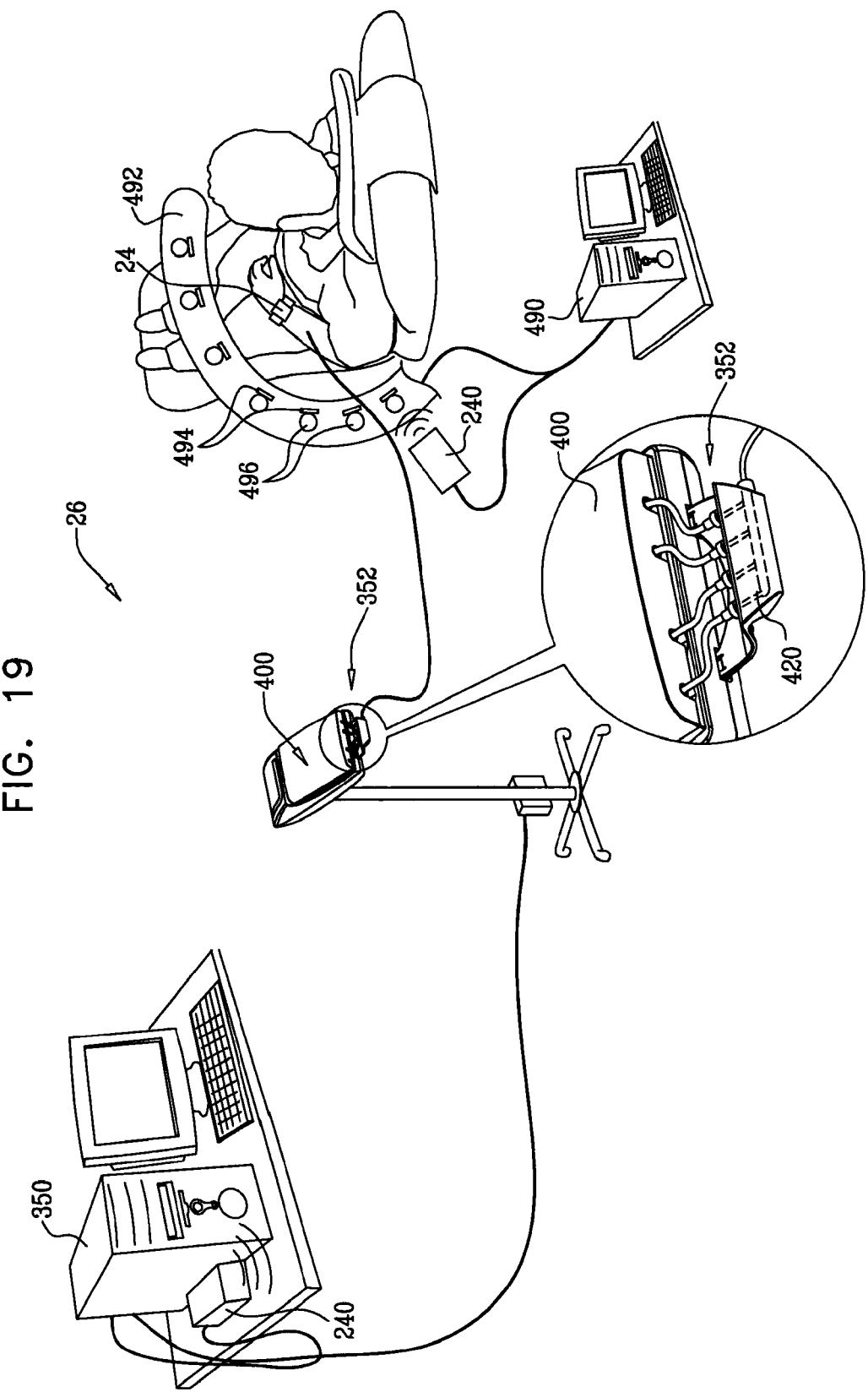
FIG. 19 is a schematic illustration of another configuration of the administration system of FIG. 10, in accordance with an embodiment of the present invention.

Reference is made to FIG. 19, which is a schematic illustration of another configuration of administration system 26, in accordance with an embodiment of the present invention. In this configuration, automated administration device 352 comprises an injector 400, which is configured to perform IV injection. Alternatively or additionally, injector 400 is configured to perform intra-arterial injection, or comprises an inhaler for delivering the contents of one or more of container 401 by inhalation.

Figure 20:
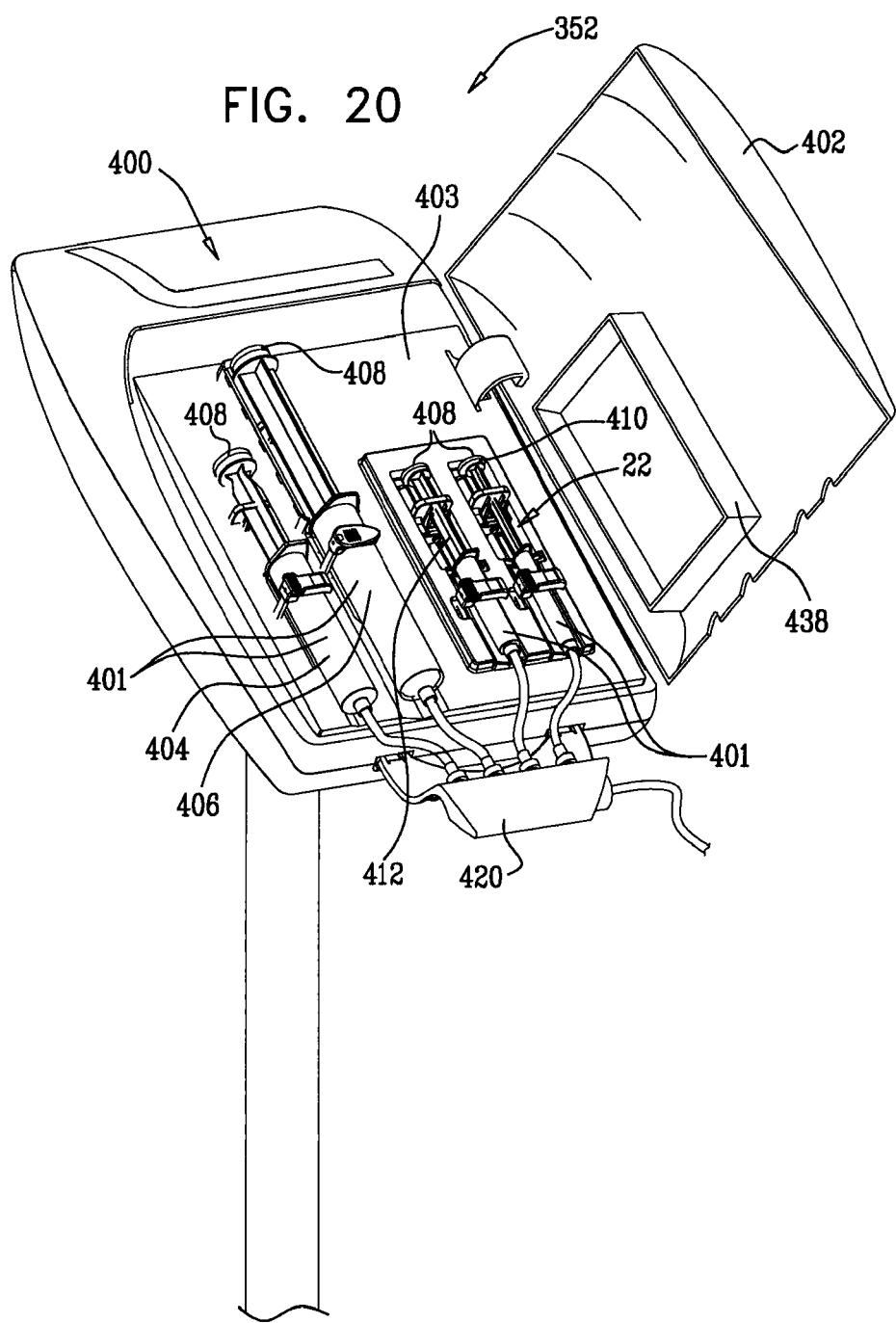
FIG. 20 is a schematic illustration of an injector of the administration system of FIG. 19, in accordance with an embodiment of the present invention.

FIG. 20 is a schematic illustration of injector 400 with a cover 402 thereof in an open position, in accordance with an embodiment of the present invention. Injector 400 is shaped so as define an enclosure 403 that is configured to hold a plurality of containers 401, which typically comprise syringes. Typically, one or more of containers 401 comprise radiopharmaceutical agent containers 22, described hereinabove with reference to FIG. 1, for example. In addition, for some applications, one or more of containers 401 comprise a saline container 404 and/or a non-radioactive pharmaceutical container 406, which contains, for example, a stress pharmaceutical (e.g., adenosine). For some applications, enclosure 403 is configured to hold containers, e.g., syringes, of differing sizes (e.g., saline container 404 may be larger than radiopharmaceutical agent containers 22), while for other applications, the enclosure is configured to hold containers of the same size.

Injector 400 comprises one or more syringe pumps, typically one per container 401, which are integrated into the injector, and configured to individually actuate dispensing of the liquid contents of the container. For example, the pumps may comprise T34 and/or T34L syringe pumps (e.g., three T34 pumps and one T34L pump), such as are commercially available, e.g., from Caesarea Medical Electronics Ltd. (Caesarea, Israel). Respective pushers 408 of the pumps extend into an interior of enclosure 403, and engage respective heads 410 of respective plungers 412 of the syringes. Each of containers 401 is connected to a joining element 420, which is removably couplable to injector 400, as described hereinbelow with reference to FIG. 22.

Figure 21:
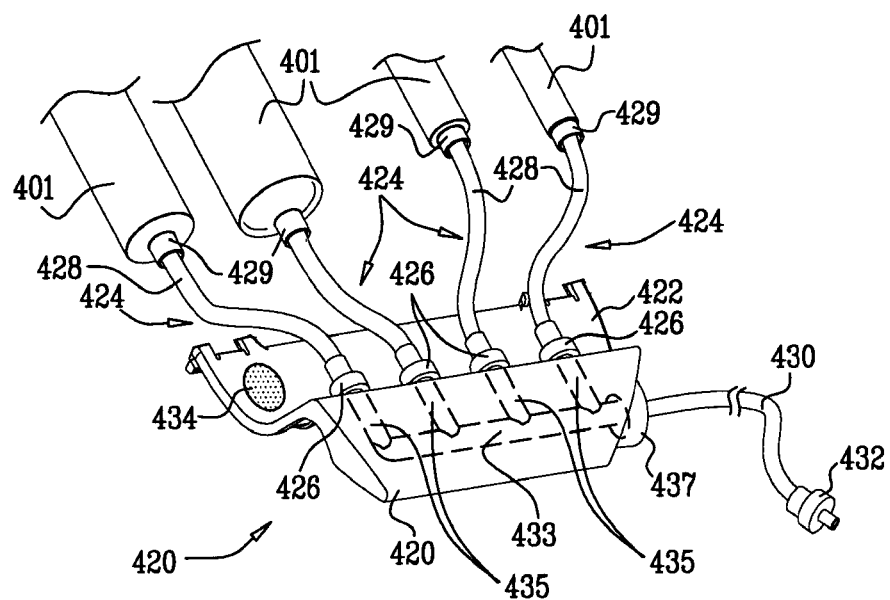
FIG. 21 is a schematic illustration of a joining element, in accordance with an embodiment of the present invention.

FIG. 21 is a schematic illustration of joining element 420, in accordance with an embodiment of the present invention. Joining element 420 comprises a support structure 422, and one or more coupling elements 424, each of which typically comprises one or more valves 426 (which optionally comprise luer locks and/or one-way valves), tubes 428, and/or connectors 429. Coupling elements 424 are configured to be coupled to respective containers 401, such that the containers are in fluid communication with tubing of joining element 420. The tubing of joining element 420 merges the liquid pumped from containers 401, and is removably coupled to an infusion line 430, which comprises a connector 432 to an IV line to the patient. For some applications, at least a portion of the tubing of joining element 420 is shaped so as to define a manifold, i.e., the tubing includes a primary tube 433 in fluid communication with a plurality of lateral tubes 435. Primary tube 433 is in fluid communication with infusion line 430, via a connector 437, and lateral tubes 435 are in fluid communication with respective valves 426 of coupling elements 424. Typically, joining element 420 comprises between two and ten coupling elements 424, such as three, four, or five coupling elements 424. Alternatively, the joining element comprises exactly one or more than ten coupling elements 424. For some applications, if the number of containers 401 needed for a particular administration protocol is less than the number of coupling elements 424, the extra coupling elements, although still provided, are simply not used for the protocol. For other applications, a joining element having the precise number of coupling elements 424 needed for a given protocol is provided.

Joining element 420 comprises a data carrier 434, which is physically coupled thereto, as defined hereinabove with reference to FIG. 2. Data carrier 434 is computer-communicatable, and typically comprises an RFID tag, smart card, memory card (such as a disk-on-key (e.g., a USB key)), compact disc, minidisk, disposable computer-readable medium, or other electronic memory, or a machine-readable code, e.g., a computer-readable scannable label, such as a barcode, two-dimensional bar code, or color-coded code. Data carrier 434 typically stores patient-specific information and/or radiopharmaceutical-related information regarding the radiopharmaceuticals contained in radiopharmaceutical agent containers 22, as described in detail hereinbelow with reference to FIG. 24. Typically, data carriers 120 are not provided for containers 22.

Figure 22:
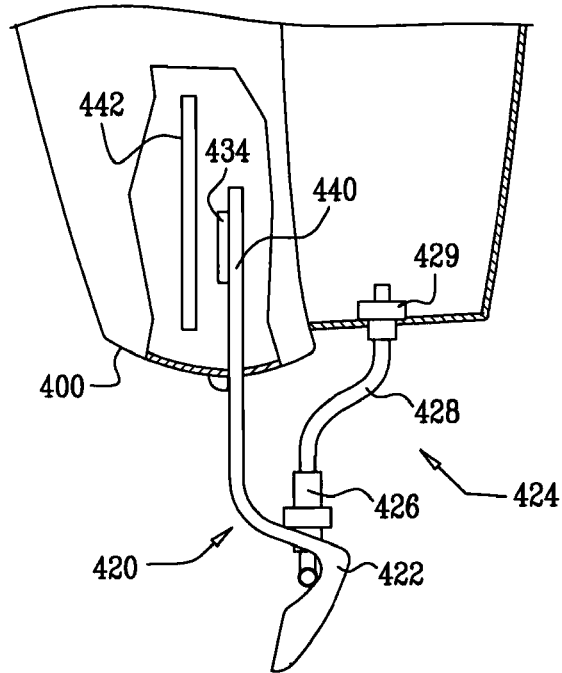
FIG. 22 is a schematic side-view illustration of the coupling of the joining element of FIG. 21 with the injector of FIG. 20, in accordance with an embodiment of the present invention.

FIG. 22 is a schematic side-view illustration of the coupling of joining element 420 with injector 400, in accordance with an embodiment of the present invention. Injector 400 is shaped to define a slot into which a portion 440 of joining element 420 is placed, such that data carrier 434 is brought into a vicinity of a communication element 442 of injector 400. Communication element 442 reads data from and, optionally, transmits data to data carrier 434, using a proprietary or standard wireless protocol, e.g., Bluetooth, WiFi, W-LAN, or IEEE 802.11. For some applications, communication element 442 comprises one or more coils for transmitting and receiving electromagnetic radiation. Alternatively, the communication element is brought into physical contact with data carrier 434, and reads and/or writes the information using an electrical contact, or other coupling technique, such as inductive coupling.

Figure 23:
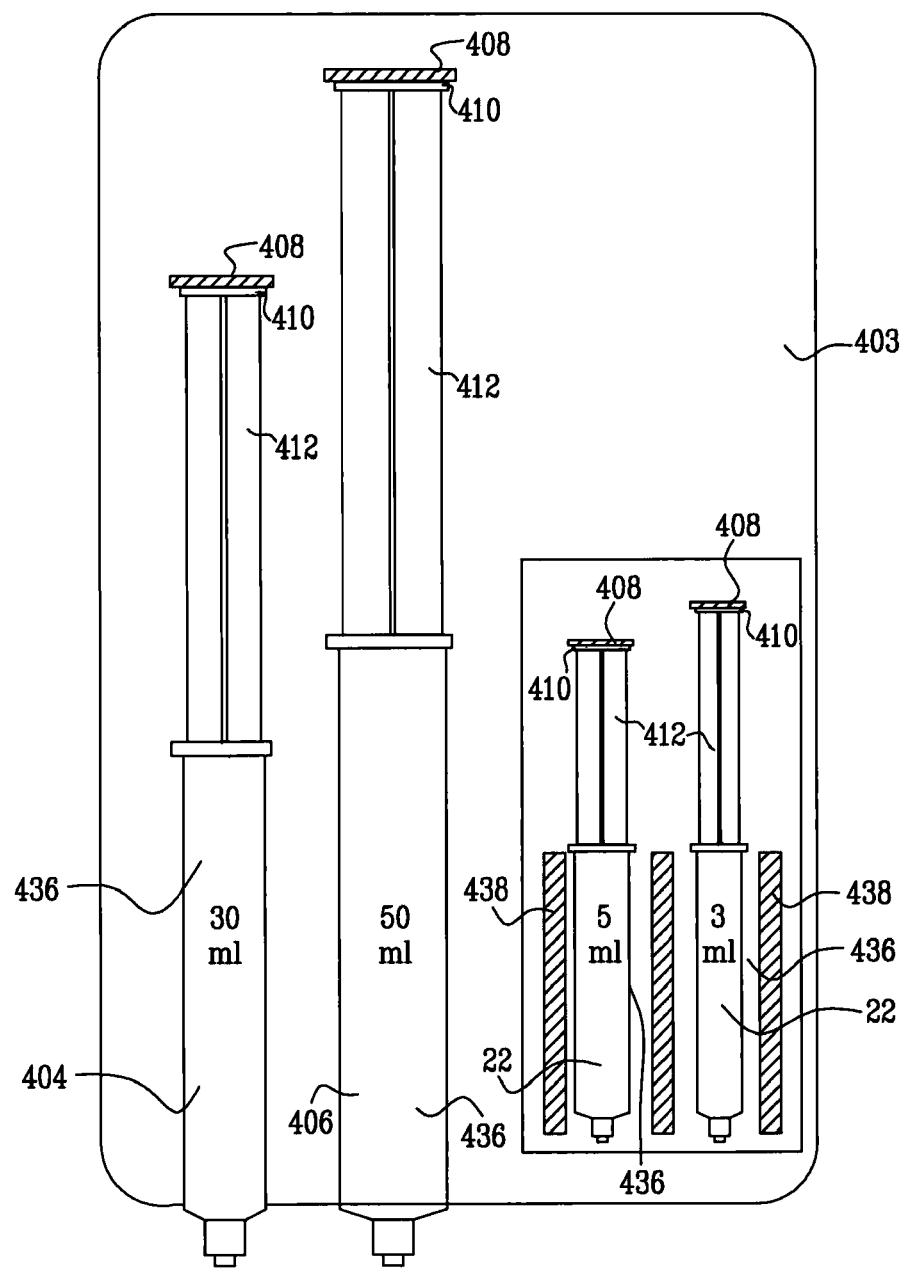
FIG. 23 is a schematic illustration of an interior of an injector enclosure of the injector of FIG. 20 containing four containers, in accordance with an embodiment of the present invention.

FIG. 23 is a schematic illustration of an interior of injector enclosure 403 containing four containers 401, in accordance with an embodiment of the present invention. In this embodiment, containers 401 comprise respective syringes of different sizes. Each of the syringes comprises a head 410, a plunger 412, and a barrel 436. Typically, enclosure 403 comprises radioactive shielding 438 that is configured to shield containers 22 when cover 402 is closed. For some applications, one or more of the containers is delivered from the radiopharmacy with plunger 412 partially depressed, in order to provide a volume of liquid that is less than the maximum volume the container holds, such as shown for container 404 in FIG. 23.

In an embodiment of the present invention, the joining element is shaped so as to define a support structure that is configured to be coupled to containers 401 and physically support the containers. For some applications, the support structure is shaped so as to define a container into which containers 401 are placed. For example, the joining element may be shaped so as to define a cassette. The container typically comprises shielding.

FIG. 24 is a schematic block diagram illustrating a portion of the components of end-to-end automated system 10, in accordance with an embodiment of the present invention. For some applications, data carrier 434 contains all or a portion of the data that data carrier 120 is described as containing hereinabove with reference to FIG. 8, and/or all or a portion of the data that is stored in data carrier 24, as described hereinabove with reference to FIG. 7. For such data that relates to container 22, data carrier 434 typically contains the data for each of containers 22 that is coupled to, or intended to be coupled to, joining element 420. For example, data carrier 434 may contain one or more of the following:

- an identifier, such as an identification code and/or name, of the patient for which the specific associated radiopharmaceutical agent containers 22 are intended;
- information regarding the assigned imaging and/or administration protocol(s) for use with the labeled radiopharmaceutical agent(s) contained in associated containers 22. For some applications, the protocol(s) are represented by a protocol identifier, while for other applications the protocol information includes steps and/or other details of the protocol(s). For some applications, the imaging protocol includes protocol information regarding image reconstruction, image analysis, and/or diagnosis, which is used at image reconstruction step 126, analysis step 128, and/or diagnosis step 130, respectively, of the method of FIG. 2, described hereinabove. For some applications, the protocol information includes software code for execution by imaging system 28 during image acquisition, image reconstruction, image analysis, and/or diagnosis; and
- a commercial license for use of a radioimaging protocol and/or an administration protocol with joining element 420.

In an embodiment of the present invention, administration system 26 and/or imaging system 28, such as described hereinabove with reference to FIG. 10 and/or FIGS. 19-25, comprises a radiation detector 460. For some applications, radiation detector 460 is coupled to or a component of administration system 26, such as of automated administration device 352 or injector 400. Alternatively or additionally, the radiation detector is coupled to imaging system 28. For some applications, whether coupled to the administration system and/or the imaging system, the radiation detector is configured to be coupled to the patient (e.g., a hand or ear of the patient) or in a vicinity of the patient, in order to detect radiation emanating from the patient.

For some applications in which radiation detector 460 is coupled to administration system 26, the administration system uses radiation information detected by the radiation detector to determine which radiopharmaceutical agent(s) have been placed in automated administration device 352 or injector 400 (such as by identifying the detected energy levels if one or more of the radiopharmaceutical agents comprises a unique radioisotope), and, optionally, in which positions in the device. Alternatively or additionally, the administration system used the radiation information to determine a radiation dose of one or more of the radiopharmaceutical agents in respective containers 401, or in tubing of the administration system, such as infusion line 430, tubes 428, and/or connectors 429.

For some applications in which radiation detector 460 is coupled to the imaging system (either directly, or via the administration system or another element of system 10), imaging system 28 uses radiation information detected by the radiation detector, either emanating from the body of the patient, from containers 401, and/or from tubing of the administration system (e.g., infusion line 430) to determine:

- the commencement of, conclusion of, and/or timing of administration of one or more of the radiopharmaceutical agents administered by the administration system;
- a blood concentration of one or more of the radiopharmaceutical agents in the body of the patient, such as a time profile of the blood concentration;
- a radiation level of one or more of the radiopharmaceutical agents; and/or
- an energy level of one or more of the radiopharmaceutical agents.

As described hereinbelow, for some applications such information is used by imaging system 28 to determine administration information without directly receiving the administration information from administration system 26, such as for coordinating aspects of the imaging protocol with the administration protocol, and/or adjusting aspects of the acquisition and/or analysis of images based on actual levels of radiation delivered to the patient (optionally in conjunction with a time profile of the radiation). For example, these measurements may be used to estimate pharmacokinetics of the radiopharmaceutical agent(s) in organs, and/or to predict optimal imaging timing (the optimal time to perform the imaging, and/or the optimal timing parameters of the imaging procedure). For some applications, based on these estimates, an expected level of uptake of the radiopharmaceuticals in a target organ is determined, enabling diagnosis of pathologies based on absolute uptake levels in the target organ.

Reference is made to FIG. 25, which is a flow chart illustrating a method 440 for using administration system 26 with joining element 420, in accordance with an embodiment of the present invention. Method 440 begins at a dose dispensing step 441, at which dispensing system 20 (FIGS. 1 and 12) dispenses customized doses of one or more radiopharmaceutical agents into one or more containers 22, using techniques described at step 116 of the method described hereinabove with reference to FIG. 2. At an information transfer step 442 of method 440, dispensing system 20 transfers patient-specific information and, optionally, radiopharmaceutical-related information to data carrier 434. The patient-specific information includes the patient's identification code and/or name, and, optionally, the assigned administration and/or imaging protocols. The radiopharmaceutical-related information, if provided, typically includes the information described at step 116 of the method described hereinabove with reference to FIG. 2. In addition, the dispensing system typically prints and attaches conventional information labels to containers 22, such as in order to comply with regulatory labeling requirements. For applications in which the labeled radiopharmaceutical agent(s) is dispensed using conventional radiopharmacy techniques, dispensing system 20, or another element of system 10, such as dose calculation system 152, typically transfers the radiopharmaceutical-related information to data carrier 434. Alternatively, all or a portion of the information is transferred directly from mother vial data carrier 106 to container data carrier 434.

At a verification step 444, joining element 420, including data carrier 434 thereof, is brought into a vicinity of communication element 442 of injector 400, typically while cover 402 of injector enclosure 403 is locked closed (see FIG. 19). Administration system 26 verifies the patient, radiopharmaceutical, protocol, and/or license information contained in data carrier 434. Typically, all or a portion of the information used for such verification is encrypted, and administration system 26 decrypts the information during the verification procedure. Alternatively or additionally, administration system 26 accesses, over a network, information stored at a remote site, and utilizes the information for such verification. Optionally, communication element 442 of injector 400, or another communication element of the injector, reads information from patient-specific data carrier 24 and matches the information with information read from data carrier 434.

For some applications, also at verification step 444, joining element 420, including data carrier 434 thereof, is brought into a vicinity of communication element 240 of imaging system 28, which verifies the patient, radiopharmaceutical, protocol, and/or license information contained in data carrier 434. Such verification is performed before, after, or simultaneously with the verification performed by administration system 26. For some applications, all or a portion of the administration protocol is performed before the patient arrives at and is verified by imaging system 28. Imaging system 28 typically also verifies the identity of the patient using information provided by patient-specific data carrier 24, or another element of system 10, such as a physician station 115; this second patient verification is performed after, before, or simultaneously with the verification using data carrier 434.

For some applications, administration system 26 and/or imaging system 28 verifies that the patient identification codes contained in patient-specific data carrier 24 and data carrier 434 match one another, and, typically, verifies that the administration and/or imaging protocols contained in the data carriers match one another. For some applications, at least a portion of the information stored in data carrier 434 is transferred to data carrier 24, either directly, via administration system 26, or via a communication element. For some applications, administration system 26 generates a signal for a healthcare worker confirming that a proper match has been made between agent container 22 and the patient. The system also typically verifies that the current time is the proper administration time, as per the administration protocol, and that container(s) 22 contains the proper dose, as per the selected protocol. Optionally, administration system 26 is configured to administer the labeled radiopharmaceutical agent only if such matches are confirmed by the system. For some applications, administration system 26 verifies the authenticity of a commercial license contained in data carrier 434, and performs the administration only upon verification of the authenticity. For some applications, imaging system 28 alternatively or additionally performs one or more of the verifications described at imaging step 124 of the method of FIG. 2.

Injector 400 positions pushers 408 at respective positions for each of container 22, based on administration protocol information, at a pusher positioning step 446. For some applications, the injector receives the administration protocol information from data carrier 434, while for other applications the injector receives the information from imaging system 28 or another element of system 10.

At an open cover step 448, injector 400 opens cover 402. Cover 402 may be spring-loaded to enable such opening. For some applications, step 448 is performed before step 446.

At a container placement step 450, the imaging technician removes each of containers 22 from the radioactive shielding in which it is stored during transport and handling thereof, and connects the containers to connectors 429 of joining element 420 (FIG. 21). For some applications, the imaging technician determines the respective positions of the containers in enclosure 403 of injector 400 at least in part responsively to the respective positions of pushers 408 and heights of heads 410 with respect to shoulders of the syringes (FIG. 23). Alternatively, containers 22 are connected to joining element 420 in the radiopharmacy, in which case joining element 420 and containers 22 are typically stored together in a radiation-shielded container (not shown) until step 450.

The imaging technician places containers 22 in enclosure 403 of injector 400, and a portion of support structure 422 of joining element 420 into the slot of injector 400 (FIG. 22). Typically, the injector senses that the containers have been placed in enclosure 403, and administration system 26 sends a signal to imaging system 28 notifying the imaging system that that administration system 26 is ready to begin the imaging procedure. Injector 400 typically primes infusion line 430 (FIG. 21) with saline solution from one of containers 401 before connector 432 is connected to the IV line of the patient.

At an administration step 452, administration system 26 administers the one or more labeled radiopharmaceutical agents contained in respective containers 22. Administration system 26 typically customizes the administration of the labeled radiopharmaceutical agent(s) contained in container(s) 22 using information provided by data carrier 24, data carrier 343, imaging system 28, physician station 115, and/or patient management system 160. For example, system 26 may customize a time-dependent administration profile of the labeled radiopharmaceutical agent, such as a rate of administration, and/or an order of administration of multiple radiopharmaceutical agents stored in respective containers 22. Alternatively or additionally, administration system 26 may administer less than the entire dose of the labeled radiopharmaceutical agent, e.g., based on feedback from imaging system 28 during an imaging procedure.

For some applications, administration system 26 administers the radiopharmaceutical agent(s) before the performance of an imaging procedure by imaging system 28, such as immediately before the imaging procedure, several minutes before the imaging procedure, several hours before the imaging procedure, or even one or more days before the imaging procedure. For these applications, administration system 26 and imaging system 28 typically need not communicate with one another. For some applications, the administration system is located in a different location than the imaging system.

For other applications, such as dynamic studies, administration system 26 administers the radiopharmaceutical agent(s) during an imaging procedure performed by imaging system 28. For some of these applications, the administration system is in communication with the imaging system during the administration, in order to assure information regarding time-dependent administration is accurately communicated between the administration system and the imaging system.

For others of these applications, the administration system is not in communication with the imaging system during the administration. Instead, the administration system coordinates performance of the imaging protocol with performance of the administration protocol based on administration information acquired indirectly by the imaging system. According to a first method for performing such indirect coordination, an imaging technician or other healthcare worker approximately simultaneously starts the administration protocol and the imaging procedure, such as by manually pressing separate "start" buttons on the injector and the camera. The administration and imaging protocols are typically preconfigured to coordinate related steps based on an elapsed time from the respective commencements of the protocols, thereby at least approximately coordinating (e.g., synchronizing) their respective steps. Such coordination based on elapsed time obviates the need for communication between the imaging system and the administration system during the administration and imaging procedures.

According to a second method for performing such indirection coordination, imaging system 28 detects the performance of steps of the administration protocol using radiation detector 460, described hereinabove with reference to FIG. 24. For some applications, the imaging system uses the radiation detector to sense radiation emanating from the body of the patient to detect administration of one or more of the radiopharmaceutical agents stored in containers 401, while for other applications, the imaging system uses the radiation detector to sense radiation emanating from an element of injector 400 through which the one or more radiopharmaceutical agents pass during administration, such as infusion line 430, tubes 428, and/or connectors 429. Alternatively or additionally, imaging system 28 detects the performance of the administration protocol using camera 492 (FIG. 11) to detect radiation (e.g., an amount of radiation and/or an energy level of the radiation) emanating from the body of the patient to detect administration of one or more of the radiopharmaceutical agents stored in containers 401.

In an embodiment of the present invention, an element of system 10 other than administration system 26 and imaging system 28 controls and coordinates the execution of the administration protocol by the administration system, and the imaging protocol by the imaging system. In this embodiment, there is typically no need for the administration system and the imaging system to communicate with one another.

For some applications, imaging system 28 reads information from patient-specific data carrier 24, and transmits at least a portion of the information to administration system 26, thereby obviating the need for the administration system to directly read such information from data carrier 434.

In an embodiment of the present invention, administration system 26 is programmed with a list of actions injector 400 is capable of performing, such as actuating each of the syringe pumps at certain rates or volumes, setting whether the administration is drip or bolus, ceasing such actuations, aborting administration, and generating an indication of an alarm condition. Each of these actions is associated with an identifier code. Imaging system 28 reads administration protocol information from patient-specific data carrier 24 and/or data carrier 434, or receives administration protocol information from another element of system 10. For some applications, the administration protocol information includes information regarding the steps and/or other details of the protocol, while for other applications, the information protocol information includes an identifier of the administration protocol, and the imaging system, using the identifier, gets, or is preprogrammed with, information regarding the steps and/or other details of the protocol from another element of system 10. To execute the administration protocol (before, during, and/or after execution of the imaging protocol), imaging system 28 signals administration system 26 to drive injector 400 to perform each of the actions specified by the administration protocol, by sending the corresponding identifier code from the imaging system to the administration system at the desired time of the action. For some applications, separate identifier codes are provided for starting and stopping each action, while for other applications, a single identifier code is provided for each action, and the imaging system sends the desired identifier code together with a start or stop signal. For some applications, administration system 26 sends one or more confirmation signals to imaging system 28 indicating receipt of the identifier code, successful or failed commencement of the action specified by the identifier code, and/or successful or failed completion of the action specified by the identifier code. For some applications, the imaging system is able to query a status of the administration system by sending a request for status signal. It is noted that in this embodiment administration system 26 does not receive and translate administration protocol information into actions of injector 400; such translation is instead performed by imaging system 28. Furthermore, in this embodiment, administration protocol information is typically not transferred from data carrier 434 to administration system 26 and/or injector 400.

In an embodiment of the present invention, administration system 26 controls operation of imaging system 28 using the techniques of the previous paragraph, as appropriately modified to reflect the reverse control.

In an alternative embodiment of the present invention, administration system 26 reads administration protocol information from data carrier 434, or receives the administration protocol information from patient-specific data carrier 24 and/or another element of system 10. For some applications, the administration protocol information includes information regarding the steps and/or other details of the protocol, while for other applications, the information protocol information includes an identifier of the administration protocol, and the administration system, using the identifier, gets, or is preprogrammed with, information regarding the steps and/or other details of the protocol from another element of system 10. The administration protocol includes a plurality of steps associated with actions of injector 400, each of which steps has associated therewith a step identifier code. For example, the step identifier codes may simply sequentially number the steps of the administration protocol. To execute the administration protocol (before, during, and/or after execution of the imaging protocol), imaging system 28 signals administration system 26 to drive injector 400 to perform each of the actions specified by the administration protocol, by sending the corresponding step identifier code from the imaging system to the administration system at the desired time of the action. For some applications, administration system 26 sends one or more confirmation signals to imaging system 28 indicating receipt of the step identifier code, successful or failed commencement of the protocol step specified by the step identifier code, and/or successful or failed completion of the protocol step specified by the step identifier code. It is noted that in this embodiment administration system 26 receives and translates administration protocol information into actions of injector 400; imaging system 28 only specifies when to perform the steps of the administration protocol, without indicating any characteristics of the protocol steps.

In an embodiment of the present invention, administration system 26 controls operation of imaging system 28 using the techniques of the previous paragraph, as appropriately modified to reflect the reverse control.

In an embodiment of the present invention, administration system 26 receives administration protocol information from data carrier 434 or another element of system 10. The administration system performs the administration protocol, without receiving any communication or instructions from imaging system 28. Upon commencing and, optionally, concluding each step of the imaging protocol, the administration system sends a signal to the imaging system indicating such commencement or conclusion. The imaging system typically coordinates performance of the imaging protocol based at least in part on these signals.

In an embodiment of the present invention, administration system 26 receives administration protocol information from data carrier 434 or another element of system 10. The administration system performs the administration protocol, without receiving any communication or instructions from imaging system 28. Upon commencing and, optionally, concluding each step of the administration protocol, the administration system sends a signal to the imaging system indicating such commencement or conclusion. The imaging system typically coordinates performance of the imaging protocol based at least in part on these signals.

In an embodiment of the present invention, imaging system 28 receives imaging protocol information from patient-specific data carrier 24, data carrier 434, or another element of system 10. The imaging system performs the imaging protocol, without receiving any communication or instructions from administration system 26. Upon commencing and, optionally, concluding each step of the imaging protocol, the imaging system sends a signal to the administration system indicating such commencement or conclusion. The administration system typically coordinates performance of the administration protocol based at least in part on these signals.

For some applications, administration system 26 does not begin performance of an administration protocol, and/or perform some or all of the actions thereof, until a healthcare worker provides authorization to do so, such as to comply with regulatory safety requirements.

For some applications, the radiopharmaceutical agent(s) are administered in a closed loop with an imaging procedure performed by imaging system 28; administration system 26 modifies one or more parameters of the administration in real time based on feedback received from imaging system 28, and/or based on real-time measurements of physiological parameters of the patient (e.g., systemic blood concentrations) during the imaging procedure. For some protocols, the administration system administers a preliminary bolus injection, and, based on feedback from imaging system 28 and/or on physiological parameters of the patient, configures one or more parameters of a subsequent administration of the same or a different labeled radiopharmaceutical agent.

Typically, for safety purposes, after administration system 26 has read all necessary information from data carrier 434 of joining element 420, administration system 26 permanently disables data carrier 434, in order to ensure that the data carrier is not accidentally reused for another patient. Also for safety purposes, injector 400 is typically configured to immediately cease pumping if cover 402 is opened during a procedure, and/or if an emergency stop button is pressed by the imaging technician or another healthcare worker. Similarly, injector 400 may comprise a reset button.

For some applications, as a safety feature, if imaging system 28 does not receive, within a certain period after requesting the performance of a protocol step or pumping action, a signal from administration system 26 indicating that the injector has completed the action, or, alternatively or additionally, commenced the step or action, the imaging system determines than an error has occurred, and takes appropriate action. Such action may include terminating the imaging procedure and/or notifying the imaging technician. Alternatively or additionally, the imaging system may take corrective action, such as adjusting one or more parameters of a future step of the imaging protocol and/or administration protocol. Such alternative actions, and one or more error conditions for which they apply, may be provided by the imaging and/or administration protocols, and/or may be determined by the imaging and/or administration systems, optionally at least partially responsive to input from the imaging technician or another healthcare worker.

Reference is still made to FIG. 25. After or during administration of the labeled radiopharmaceutical agent, imaging system 28 performs an imaging procedure on the patient, at an imaging step 454. Imaging system 28 is described hereinbelow with reference to FIG. 11. Typically, imaging system 28 customizes the imaging procedure using information provided by administration system 26, data carrier 24, data carrier 434, and/or physician station 115. Such information typically includes information regarding the time of labeled radiopharmaceutical administration, the labeled radiopharmaceutical agent (e.g., radioactive strength, time of preparation, and/or kinetic parameters), patient-specific physiological information, and/or imaging protocol information. Parameters of the imaging procedure that are typically customized include, but are not limited to: total acquisition time; detector motions, such as detector angular and translational motions, detector step size (i.e., the density of the step size, typically expressed in degrees), and detector dwell time at each view; type of study, such as standard, active vision (as described in the above-mentioned International Application PCT/IL2005/001173), or gated; definition of the region of interest (ROI), for example, based on the size of the heart; and/or attenuation correction parameters, which are typically based on physiological parameters such as body mass, BMI, and girth.

Upon completion of the administration and imaging procedures, method 440 concludes with the performance of image reconstruction step 126, analysis step 128, and diagnosis step 130 of the method of FIG. 2, described hereinabove, at a post-imaging step 456. For some applications, administration system 26 performs information transfer step 123 described hereinabove with reference to FIG. 2. For some applications, the techniques of method 440 of FIG. 25 are combined with at least a portion of the techniques of the method of FIG. 2.

For some applications, administration system 26 comprises a plurality of injectors 400, and/or imaging system 28 is coupled to a plurality of administration systems 26 for execution of an injection protocol for an imaging procedure.

For some applications, respective data carriers 120 are physically coupled to containers 22, and administration system 26 is configured to receive patient-specific and/or protocol information from data carrier 434 of joining element 420 and from data carriers 120.

In an embodiment of the present invention, the administration portions of method 440 of FIG. 25 are performed alone, i.e., without performing the imaging.

The Imaging System

Reference is made to FIG. 11, which is a schematic illustration of imaging system 28, in accordance with an embodiment of the present invention. Imaging system 28 comprises a control unit 490, a communication element 240, a camera 492, and an imaging workstation 493. Typically, control unit 490 and imaging workstation 493 comprise one or more standard personal computers or servers with appropriate memory, communication interfaces and software for carrying out the functions prescribed by relevant embodiments of the present invention. This software may be downloaded to the control unit and imaging workstation in electronic form over a network, for example, or it may alternatively be supplied on tangible media, such as CD-ROM.

Control unit 490 typically comprises: (a) image acquisition functionality, which is configured to drive camera 492 to perform image acquisition of the patient; (b) image reconstruction functionality, which is configured to perform an image reconstruction procedure on the acquired image; (c) image analysis functionality, which is configured to perform an image analysis procedure on the reconstructed image; and (d) diagnosis functionality, which is configured to perform a diagnostic procedure using the results of the image analysis procedure. It will be appreciated that control unit 490 may comprise a plurality of personal computers or servers, each of which performs one or more of these procedures, and that one or more of these computers or servers may be located remotely from camera 492. Imaging workstation 493 displays the reconstructed images and allows the attending healthcare worker to view and manipulate the images.

As mentioned above with reference to steps 124 through 130 of FIG. 2, imaging system 28 typically customizes one or more of these procedures at least in part responsively to imaging protocol information and/or patient-specific information read by communication element 240 from patient-specific data carrier 24.

For some applications, camera 492 comprises a commercially available diagnostic structural or functional camera, such as a SPECT or PET camera, and/or utilizes imaging techniques described in one or more of the patents and patent applications described hereinabove in the section entitled "Background of the Invention." Alternatively, camera 492 utilizes techniques described in the above-mentioned International Application PCT/IL2005/001173, in above-mentioned PCT Publication WO 05/119025, and/or in the other above-mentioned co-assigned patent applications and/or patent application publications.

In an embodiment of the present invention, camera 492 comprises a plurality of detectors 494, each of which is coupled to a respective angular orientator 496. Each of the detectors comprises a plurality of gamma ray sensors, such as a pixelated CZT array, and a collimator. For example, the array may include 16×64 pixels. Control unit 490 drives, typically separately, each of the orientators to orient its respective detector in a plurality of orientations with respect to a region of interest (ROI). Control unit 490 produces a SPECT image from a plurality of radiation acquisitions acquired with the detectors in different relative orientations.

In an embodiment of the present invention, camera 492 is configured to begin an image acquisition procedure by performing a relatively brief, preliminary scan, and, based on the results of this preliminary scan, to determine one or more parameters of the full image acquisition procedure, such as dwell time per orientation of each detector 494. Typically, this determination further takes into account imaging protocol and/or patient-specific information received by imaging system 28 from patient-specific data carrier 24, such as the activity of the labeled radiopharmaceutical agent at the time of administration, the time of administration, the patient's BMI (which may be used to estimate a perfusion percentage), and the pharmacokinetics of the labeled radiopharmaceutical agent.

In an embodiment of the present invention, camera 492 is configured to individually set a total angular range of each of detectors 494 responsively to the detector's orientation with respect to the ROI. For example, at least one detector closer to the ROI (a "proximal detector" or an "inner detector") may have a greater total angular range than at least one detector further from the ROI (a "distal detector" or an "outer detector"). The distal detectors are typically located nearer to the ends of a frame holding the detectors, while the proximal detectors are typically located nearer to center of the frame. The use of narrower angular ranges for some of the detectors generally reduces the photon acquisition time spent by these detectors in orientations aimed outside of the ROI. Alternatively, at least one distal detector has a greater total angular range than at least one proximal detector. In order to reduce the total angular range for a given detector, camera 492 typically drives the associated angular orientator 496 to: (a) increase the dwell time of the detector in at least a portion of its orientations, and/or (b) reduce the angle by which the detector is moved during each orienting of the detector. For some applications, camera 492 sets the angular range of the detectors based on protocol information received by imaging system 28 from patient-specific data carrier 24. For example, the number of distal and proximal detectors, and their respective angular ranges, may be specified by the protocol information, as described hereinabove with reference to FIGS. 6B-E.

In an embodiment of the present invention, camera 492 comprises a plurality of detectors 494, each of which is coupled to a respective angular orientator 496. Each of the detectors comprises a plurality of gamma ray sensors, such as a pixelated CZT array, and a collimator. Control unit 490 drives, typically separately, each of the orientators to orient its respective detector in a plurality of orientations with respect to a region of interest (ROI). Control unit 490 produces a SPECT image from a plurality of radiation acquisitions acquired with the detectors in different relative orientations.

In an embodiment, camera 492 is configured to drive one of orientators 496 to move its respective detector 494 through a plurality of sequential angular positions, e.g., positions 1, 2, 3, . . . , 18, 19, and 20. Typically, a linear relationship relates the sequential positions, such that, for example, positions 1, 2, 3, . . . , 20 represent 1°, 2°, 3°, . . . , 20°, or, 2°, 4°, 6°, . . . , 40°. Alternatively, a non-linear relationship relates the sequential positions. Higher or lower angular resolutions are typically obtainable, as well.

For some applications, camera 492 steps the orientator in a first pass through a subset of the positions spanning most of the range of positions, and in a second pass the camera steps the orientator through a different subset of the positions. At each position, data are acquired by the detector. For example, during the first pass, the camera may drive the orientator to step through positions 1, 5, 9, 13, and 17, and the detector acquires data at each of these positions. During the second pass, the orientator steps through positions 2, 6, 10, 14, and 18. During two subsequent passes, data are acquired at the remainder of the positions. In this manner, a single-direction interlaced scan of the data is acquired by camera 492.

In an embodiment, a back-and-forth interlaced scan is acquired in which data are sampled when the orientator is moving in both directions. For example, during the first pass, the camera may drive the orientator to step through positions 1, 5, 9, 13, and 17. During the second pass, the orientator steps through positions 18, 14, 10, 6, and 2. During the third pass, the orientator steps through positions 3, 7, 11, 15, and 19, while during the fourth pass, the orientator steps through positions 20, 16, 12, 8, and 4. Fifth and higher passes, if desired, typically repeat the motions used in the earlier passes.

For some applications, the positions in a pass are not ordered from lowest-to-highest or highest-to-lowest. For example the positions of a pass may be 1, 15, 11, 19, and 17. Typically, the positions are, however, distributed generally evenly throughout the range of positions, in order to acquire photon counts representative of the entire region of interest.

As appropriate for a given scanning protocol using interlaced scanning, one or more, or even all of orientators 496 are driven to step through their respective positions in an interlaced fashion.

Typically, execution of an interlaced scan as provided by these embodiments of the present invention allows an operator of camera 492, such as an imaging technician or other healthcare worker, to acquire a high-resolution image of the ROI in about 105% to 115% of the amount of time as would be used if orientator 496 were stepped through the positions sequentially. (Typically, each orientation takes between about 50 and about 200 msec, depending upon the angle of the step.) The high-resolution image is completely acquired after the orientator has stepped through each of its positions. In some cases, additional value is attained by interlacing the scanning, however, as this allows the performance of dynamic studies, in which a plurality of images are acquired during a respective plurality of the time periods, i.e., during each complete pass of the orientator. Although each these images is typically of lower resolution than the high-resolution image acquired using photon counts acquired during all of the passes, the images nevertheless have sufficient resolution to produce clinically-meaningful data for each time period of a dynamic study.

For some applications, interlacing the scanning allows an operator to see an initial, lower-resolution scan of the ROI. If, for example, an adjustment of any form is desired, this can often be seen within the first few seconds of a scan. The present scan is terminated, the adjustment made, and a second scan initiated. In the absence of interlacing, it is typically necessary to wait until a scan has completed until an assessment of the scan's results can be made.

For some applications, it is desirable to know whether the patient has moved during a scan. Patient movement is one reason for lower quality images, and when identified it can typically be corrected by suitable instruction and then a second scanning procedure initiated. Interlaced scanning, as provided by these embodiments of the present invention, allows the operator to immediately assess whether there has been patient movement between one pass and a subsequent pass. In an embodiment, the imaging system displays to an operator the scans obtained from the various passes in rapid succession at the same location on a monitor. As appropriate, the imaging system cycles quickly through the scans repeatedly (e.g., pass 1, pass 2, pass 3, pass 4, pass 1, pass 2, pass 3, pass 4 . . . ), e.g., displaying each scan for between about 0.2 and about 2 seconds, allowing an operator to see whether there is jitter between successive scans. If so, patient movement is typically the cause and image acquisition is repeated. For some applications, the scan is acquired in exactly two passes, e.g., the orientator steps through positions 1, 3, 5, . . . , 19 during a first pass, and through positions 2, 4, 6, . . . , 20 during a second pass, or through positions 20, 18, 16, . . . , 2 during the second pass.

Images acquired using these techniques, or other non-interlacing techniques described herein, are generally used to perform one or more of the following image reconstructions: (a) reconstruction of intensity image, (b) reconstruction of intensity over time, followed by fitting a model of the kinetics (which describe for each voxel a parameter set describing its time curve), and followed by presenting a three-dimensional map of the parameters, and/or (c) direct reconstruction of a three-dimensional parametric representation, without performing a reconstruction of an intensity map, typically by plugging an equation of a kinetic model into a reconstruction algorithm, and generating a result directly in terms of the value of the parameters per voxel (the parameters may include, for example, flow, diffusion coefficients, metabolism rate, or bio-clearance rate).

The Radiopharmaceutical Dispensing System

Figure 12:
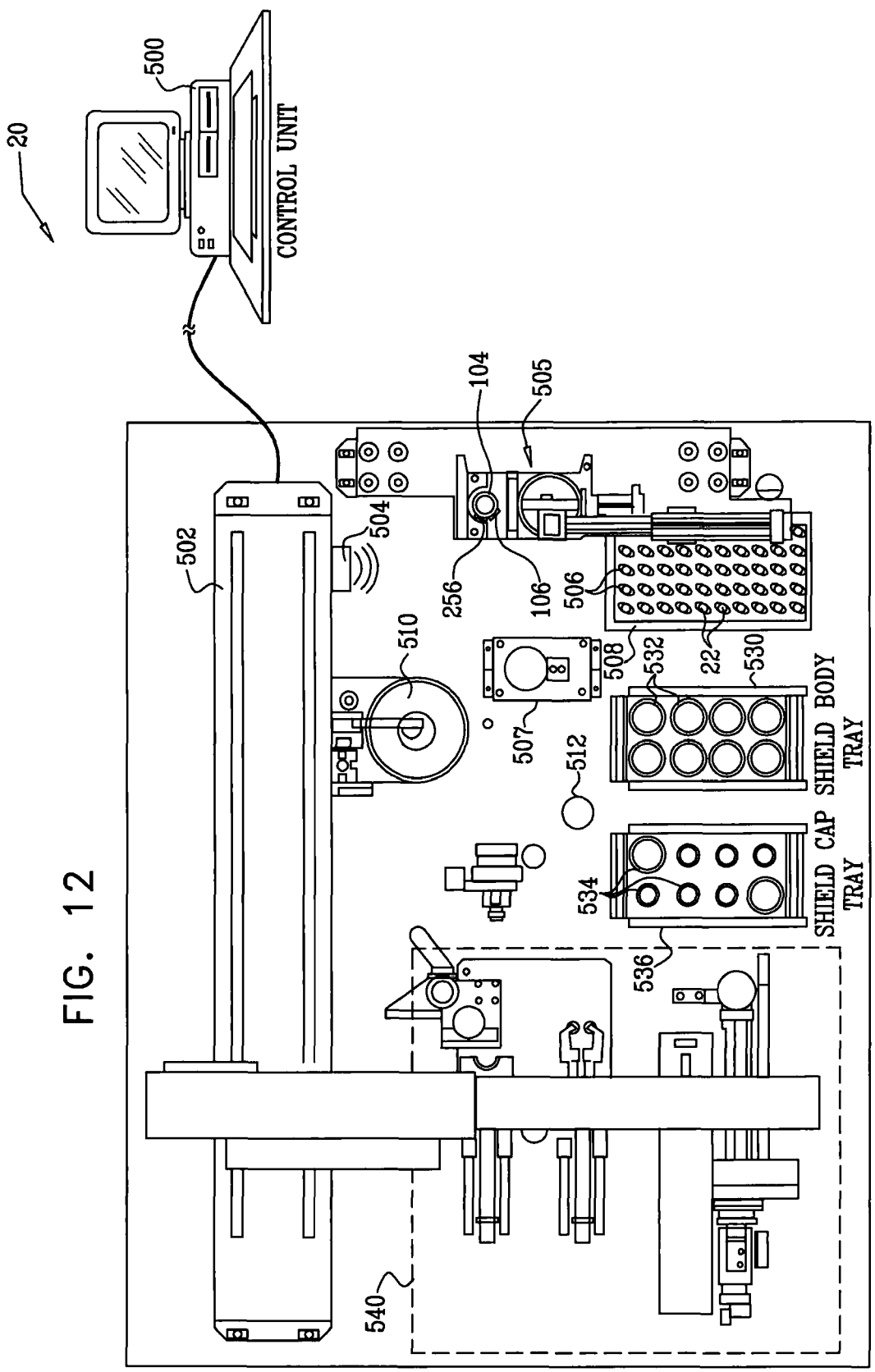
FIG. 12 is a schematic illustration of an automated radiopharmaceutical dispensing system, in accordance with an embodiment of the present invention.

Reference is made to FIG. 12, which is a schematic illustration of automated radiopharmaceutical dispensing system 20, in accordance with an embodiment of the present invention. System 20 comprises a control unit 500, at least one robot 502, and at least one communication element 504, which, for some applications, is coupled to robot 502. Control unit 500 typically comprises a conventional personal computer running a conventional operating system, such as Windows XP, with appropriate memory, communication interfaces and software for carrying out the functions described herein. This software may be downloaded to the control unit in electronic form over a network, for example, or it may alternatively be supplied on tangible media, such as CD-ROM. Control unit 500 is in communication with other elements of system 10, for example via management and control component 150. The control unit notifies appropriate elements of the system upon successful or failed completion of dispensing of a dose.

At least one radiolabeled mother vial 104 is placed in a shielded vials complex 505 of dispensing system 20. Control unit 500 authenticates the mother vial, by actuating communication element 504 to read authentication information stored in data carrier 106, and/or by verifying a coded signature 256 coupled to the mother vial, as described hereinbelow in the section entitled "Signature." Upon successful authentication, control unit 500 actuates communication element 504 to read radiopharmaceutical-related information from data carrier 106 of the mother vial, including the radiopharmaceutical agent type, isotope type, batch, lot, radiochemical purity (RCP), preparation time, and half-life information. Dispensing system 20 assays the radioactivity per unit volume of the labeled radiopharmaceutical agent contained in the mother vial. Robot 502 picks up an empty syringe 506 from a syringe tray 508, draws a predetermined amount of solution from mother vial 104, and brings the syringe to a dose calibrator 510. The syringe used for the assaying is typically discarded into a waste container 512. Typically, robot 502 brings the mother vial to a weighing station 507 for verification that the vial contains the indicated solution volume.

Dispensing system 20 receives a patient-specific dose request for at least one specific labeled radiopharmaceutical agent, having a specific dose, radioactivity, and solution volume. Such a dose is typically calculated by dose calculation sub-system 156 of dose calculation system 152, as described hereinabove with reference to FIG. 5, and/or by patient management system 160, described hereinabove with reference to FIG. 4. Alternatively or additionally, dispensing system 20 is configured to customize, modify, or verify the dose. Further alternatively, dispensing system 20 receives the order from another hospital or radiopharmacy information system, or the order is manually inputted into system 20.

To fill the request, control unit 500 calculates a required volume of the labeled radiopharmaceutical agent and a required volume of saline solution for dilution, if any. To perform this calculation, control unit 500 uses (a) information read from data carrier 106 (such as the half-life of the labeling isotope of the labeled radiopharmaceutical agent), and (b) the assayed radioactivity of the labeled radiopharmaceutical agent. Alternatively, dose calculation sub-system 156 performs all or a portion of this calculation.

For some applications, control unit 500 authenticates mother vial license information read from data carrier 106, in order to verify that a license is available for dispensing the requested dose. Dispensing proceeds only if a license is available and authenticated. The use of such a license generally provides increased quality control of the imaging process, by verifying that only approved manufacturers (or distributors) are able to provide radiopharmaceutical agents for use with system 10. A lack of precision in any aspect of an imaging procedure, which may result from the use of an agent that has not been tested and approved for use with system 10, often causes a deterioration of the resultant image quality and/or ability to make accurate and/or quantitative diagnoses.

Control unit 500 actuates robot 502 to pick up an empty radiopharmaceutical agent container 22 from tray 508. Typically, but not necessarily, container 22 comprises a syringe, such as described hereinabove with reference to FIGS. 9A-H. Container 22 has coupled thereto a data carrier 120. For some applications, syringes 506 and containers 22 are stored in a single tray, as shown in FIG. 12, while for other applications, they are stored in separate trays. Robot 502 typically authenticates container 22, by actuating communication element 504 to read authentication information stored in data carrier 120 and/or verifying coded signature 245 coupled to the container, as described hereinbelow in the section entitled "Signature."

Robot 502 removes the needle cap from container 22, turns the container over, and brings container 22 to the appropriate mother vial 104. The robot actuates the container to draw the calculated volume of labeled radiopharmaceutical agent from the mother vial, typically by inserting the needle of container 22 through a membrane of mother vial 104, and withdrawing a plunger of container 22 until the desired volume of agent has been drawn from the mother vial. The robot typically brings the syringe to dose calibrator 510 for quality control assaying of radioactivity. If necessary, robot 502 brings container 22 to a saline vial 514, and actuates the container to draw the required volume of saline solution into the container. Robot 502 replaces the needle cap on the container, and turns the container over. Alternatively, saline solution is drawn prior to drawing the labeled radiopharmaceutical agent from mother vial 104. For some applications, a needle of the container 22 is changed between drawings.

For dispensing a cocktail of labeled radiopharmaceutical agents, each having a respective dose, robot 502 repeats these steps for a plurality of mother vials 104, typically changing the needle of container 22 between drawings. During dispensing of such a cocktail, robot 502 typically draws first from the mother vial containing the lower or lowest radiation labeled radiopharmaceutical agent, such as to reduce any effect the assaying of the first agent may have on the assaying of the subsequent agent(s).

System 20 typically performs a quality control check on the dispensed radiopharmaceutical solution to confirm that the solution contains the desired dose(s) of the radiopharmaceutical agent(s) and radioactivity level.

Control unit 500 actuates communication element 504 to write radiopharmaceutical information to data carrier 120 of container 22, as described hereinabove with reference to FIG. 8 and step 118 of FIG. 2. For some applications, the data carrier is coupled to the container prior to placement of the container in dispensing system 20, while for other applications, robot 502 couples a data carrier to each container during or after the dispensing process. Similarly, for some applications in which coded signature 256 is provided, the coded signature is attached to container 22 prior to placement of the container in dispensing system 20, while for other applications, robot 502 couples a coded signature to each container during or after the dispensing process.

Robot 502 brings the filled container to a shield body tray 530, and inserts the container into a container shield 532. The robot picks up a shield cap 534 from a shield cap tray 536, and secures it to container shield 532. For some applications, data carrier 120 is coupled to shield 532 or cap 534, rather than directly to container 22. Alternatively, separate data carriers 120 are coupled to the container and the shield or cap.

In an embodiment of the present invention, dispensing system 20 comprises a print area 540, at which dispensing system 20 prints and attaches at least one conventional label to container 22, shield 532, and/or cap 534, in order to comply with regulatory labeling requirements. The dispensing system typically prints yet another conventional label for placement on a basket that holds a plurality of containers 22 for transport within or between healthcare facilities.

After the dispensing of container 22 has been completed, robot 502 brings the container to a completed container tray (tray not shown in the figure).

In an embodiment of the present invention, dispensing system 20 comprises at least one diluted mother vial which has a greater volume than a conventional mother vial. For example, the diluted mother vial may have a volume of at least about 10 ml, e.g., at least about 20 ml, such as 21 ml, while a conventional mother vial may have a volume of less than 10 ml, e.g., less than 7 ml, such as 5.8 ml. The labeled radiopharmaceutical agent solution from a conventionally-sized mother vial 104 is transferred to the diluted mother vial, and the balance of the additional volume of the diluted mother vial is filled with saline solution. The resulting diluted solution is used by dispensing system 20 to fill containers 22 with low-dose labeled radiopharmaceutical agents useful for performing low-dose imaging procedures, such as those described in the above-mentioned International Application IL/2005/001173, in above-mentioned PCT Publication WO 05/119025, or in one or more of the other co-assigned patent applications incorporated herein by reference. Alternatively, the resulting lower-dose solution is used for time-dependent administration protocols, pursuant to which a desired total dose is divided into several sub-doses for sequential administration over time. For mechanical handling and administration reasons, each sub-dose must have a minimum volume, e.g., at least 1 ml.

The information contained in data carrier 106 of conventionally-sized mother vial 104 is transferred to a data carrier 106 of the dilution mother vial, with appropriate adjustments to reflect the diluted dose of the labeled radiopharmaceutical agent.

In an embodiment of the present invention, a method for automatically dispensing a labeled radiopharmaceutical agent comprises providing a mother vial having a volume of at least 10 ml, e.g., at least 20 ml; filling the mother vial with at least 5 ml of a non-diluted labeled radiopharmaceutical agent, and with at least 5 ml of saline solution; placing the mother vial in automated radiopharmaceutical dispensing system 20; and dispensing at least one dose from the mother vial to a container. For some applications, dispensing system 20 further dilutes the dose by dispensing saline solution to the container from a saline solution container.

It is noted that dispensing system 20 is theoretically able to dispense similar low doses to containers 22 by drawing a small volume of labeled radiopharmaceutical agent from a conventionally-sized mother vial, and diluting the agent with saline solution drawn from saline vial 512, as described above. However, the drawing of such a small volume may present mechanical challenges for achieving precise volumes within acceptable variations.

Figures 13A, 13B:
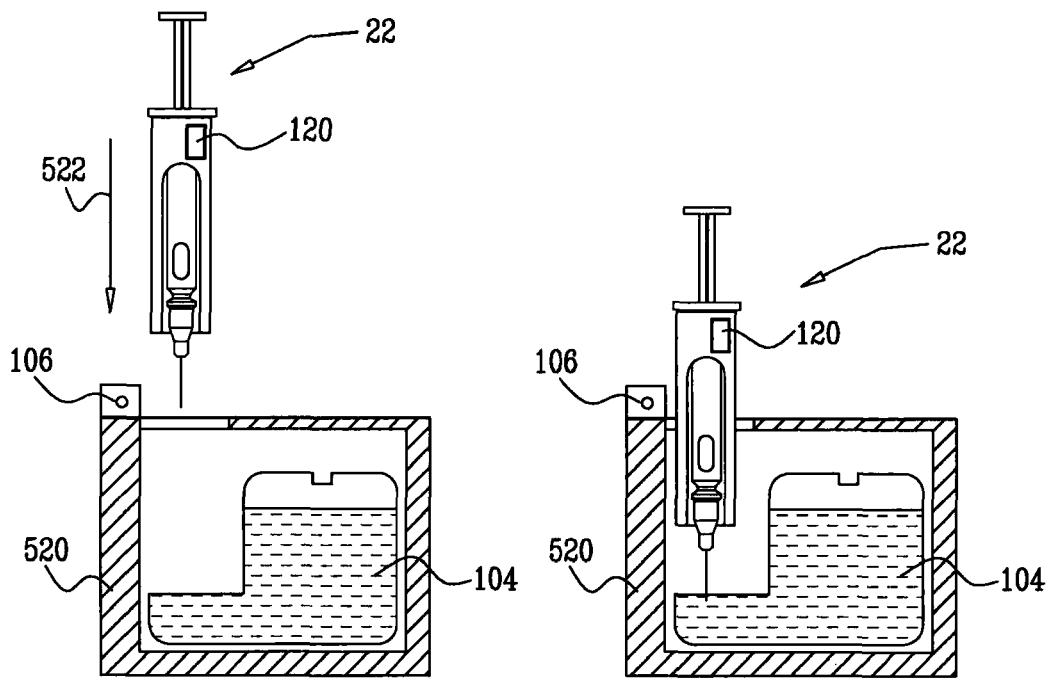
FIGS. 13A-C are schematic illustrations of a system for carrying out a data transfer process, in accordance with an embodiment of the present invention.
Figure 13C:
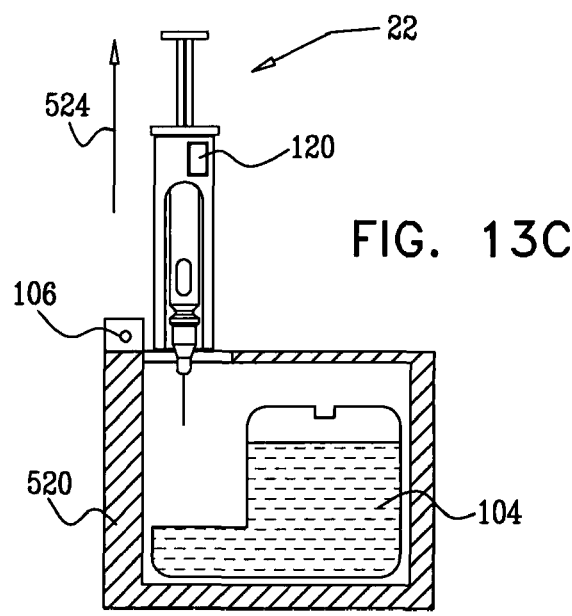

Reference is made to FIGS. 13A-C, which are schematic illustrations of a system for carrying out a data transfer process, in accordance with an embodiment of the present invention. In this embodiment, information is transferred directly from data carrier 106 of mother vial 104 to data carrier 120 of container 22 while container 22 draws the labeled radiopharmaceutical agent from mother vial 104. As shown in FIG. 13A, container 22 is lowered to mother vial 104 (which is contained within shielding 520 of vials complex 505), as indicated by an arrow 522. As shown in FIG. 13B, as container 22 draws labeled radiopharmaceutical solution from mother vial 104, data carrier 120 of the container is positioned in a vicinity of data carrier 106 of the mother vial. Container 22 is raised from mother vial 104, as indicated by an arrow 524 in FIG. 13C. Information transfer takes place during one or more of the steps illustrated in FIGS. 13A-C.

For some applications, information is transferred to data carrier 120 of container 22 during assaying of the contents of the container at dose calibrator 510.

In an embodiment of the present invention, dispensing system 20 is configured to dispense to a plurality of containers 22 for a single patient, or to a plurality of independent chambers within a single container 22 (such as first and second chambers 282A and 282B, described hereinabove with reference to FIG. 9C). For some applications, the plurality of containers are permanently coupled to one another, while for other applications the plurality of containers are removably coupled to one another. Alternatively, the plurality of containers are not coupled to one another, in which case they may be stored in association with one another, e.g., in a single tray.

For some applications, dispensing system 20 utilizes one or more of the dispensing techniques described in the references mentioned hereinabove in the Background of the Invention section, mutatis mutandis.

In an embodiment of the present invention, system 10 does not comprise dispensing system 20. System 10 is instead electronically or manually interfaced with a conventional radiopharmacy. Patient management system 160 places orders with the radiopharmacy for a particular dose of a labeled radiopharmaceutical agent for a particular patient. Upon dispensing of the dose into a conventional container, such as a syringe, data carrier 120 is physically coupled to the container, and information is written to the data carrier, such as the identity of the labeled radiopharmaceutical agent, the time of dispensing, the measured radioactivity level, and/or other information described herein as being contained in the data carrier, such as with reference to FIG. 8. For some applications, system 10 comprises a module for automatically measuring the radioactivity level and recording the information in the data carrier. Optionally, the module is in communication with system 10, such as via management control component 150, and receives additional patient-specific or protocol-related information from system 10, and records the information in data carrier 120. For some applications, the radiopharmacy dispenses the labeled radiopharmaceutical agent to one of the novel radiopharmaceutical agent containers 22 described herein.

The Radioisotope Elution System

Figure 14:
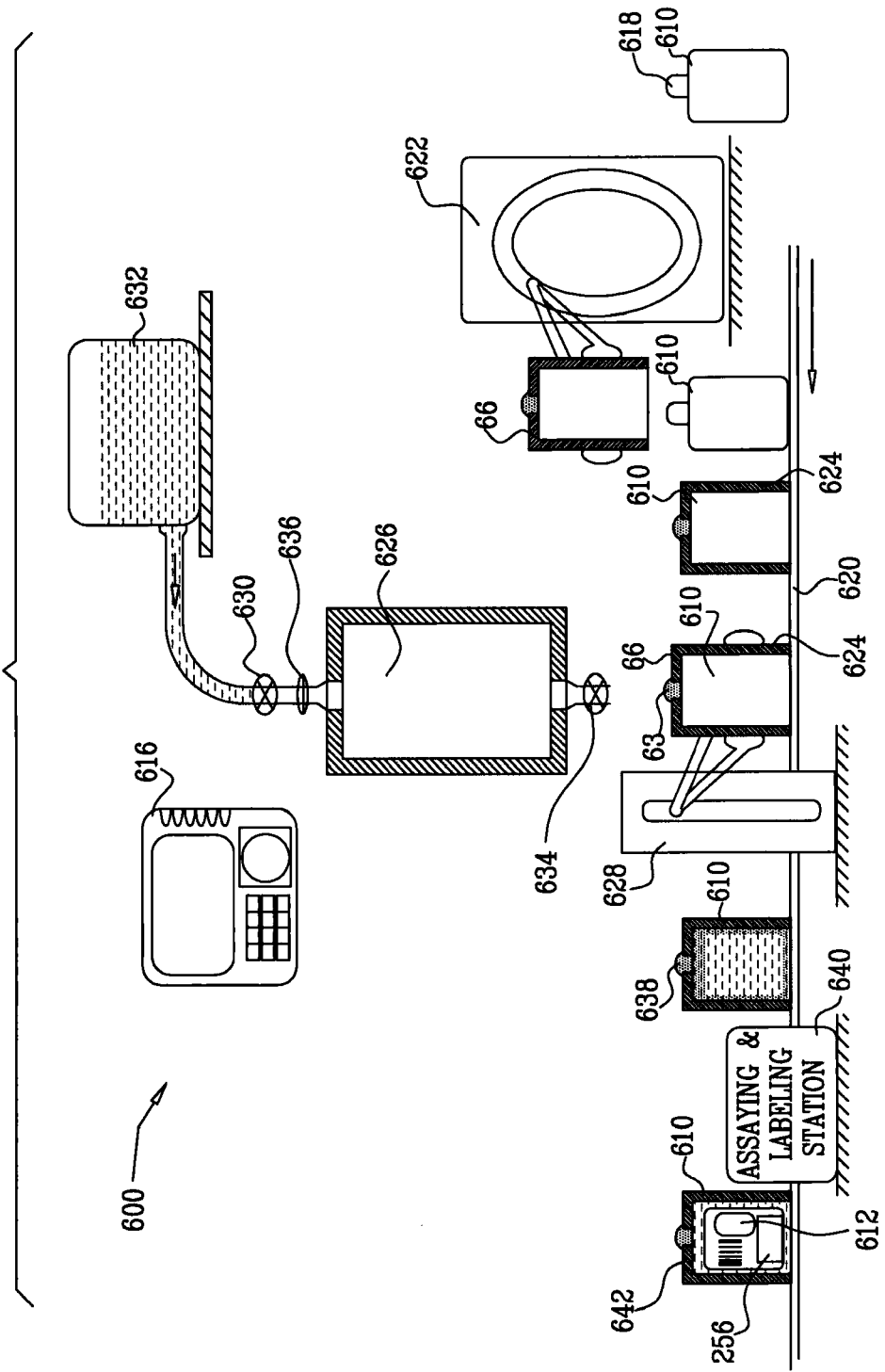
FIG. 14 is a schematic illustration of a radioisotope automatic elution system, in accordance with an embodiment of the present invention.

Reference is made to FIG. 14, which is a schematic illustration of a radioisotope automatic elution system 600, in accordance with an embodiment of the present invention. System 600 automatically elutes a radioisotope, such as technetium Tc-99m, into radioisotope vials 610. The radioisotope is used for radiolabeling the unlabeled radiopharmaceutical agent, as described hereinabove with reference to step 110 of FIG. 2. Vials 610 are coupled to radioisotope data carriers 612 containing information about the radioisotope, such as a vial code, the time of preparation, the activity at the time of preparation, and total solution volume. Labels 612 are computer-communicatable, and typically comprise an RFID tag, smart card, memory card (such as a disk-on-key (e.g., a USB key)), compact disc, minidisk, disposable computer-readable medium, or other electronic memory, or a machine-readable code, e.g., a computer-readable scannable label, such as a barcode, two-dimensional bar code, or color-coded code. For some applications, information contained in data carrier 612 is encrypted for enabling authentication. Alternatively or additionally, data carrier 612 and/or vial 610 comprise coded signature 256, as described hereinabove. The coded signature typically comprises an encrypted signature and/or a color-coded signature, as described hereinbelow in the section entitled "Signature."

The automatic elution process typically begins with a determination by dose calculation system 152 (FIG. 5) of an optimal elution frequency, for example:
- 18 hours, 6 hours, 18 hours, 6 hours, . . . ,;
- 23 hours, 1 hour, 23 hours, 1 hour, . . . ,;
- 18 hours, 1 hour, 5 hours, 18 hours, 1 hour, 5 hours, . . . ,; or
- 18 hours, 6 hours, 23 hours, 1 hour, 18 hours, 6 hours, 23 hours, 1 hour, . . . .

Dose calculation system 152 electronically notifies a control system 616 of elution system 600 of the desired elution frequency. For applications in which the radioisotope comprises Tc-99m, it will be appreciated that the ratio of Tc-99 to Tc-99m, which is determined by the elution frequency, is important for molecular imaging by an antibody, and there is generally an optimal range of the ratio of Tc-99 to Tc-99m, which should be taken into consideration when preparing Tc-99m with an antibody. Typically, control system 616 comprises one or more standard personal computers or servers with appropriate memory, communication interfaces and software for carrying out the functions prescribed by relevant embodiments of the present invention. This software may be downloaded to the control system in electronic form over a network, for example, or it may alternatively be supplied on tangible media, such as CD-ROM.

Sterile, empty vials 610 of predetermined volumes (e.g., 10 ml or 20 ml), and typically comprising caps 618, are placed on a conveyor belt 620. A first robot 622 places a shield 624 on each vial 610. Alternatively, the vials 610 are manually shielded. Conveyor belt 620 moves shielded vial 610 into position under a radioisotope generator 626, such as a TC-99m generator. At a required elution time, a second robot 628 lifts the shielded empty vial 610, and, under sterile conditions, removes cap 618 and engages the shielded empty vial 610 with generator 626.

Upon engagement of vial 610 with generator 626, both a first electronic valve 630 of a saline tank 632 and a second electronic valve 634 of generator 626 open, and vial 610 is filled, while a flow meter 636 monitors the amount of saline flow. After flow of a predetermined volume, control system 616 automatically shuts first electronic valve 630 of saline tank 632 and second electronic valve 634 of generator 626.

Filled, shielded vial 610 is automatically disengaged from generator 626, and is automatically sealed under sterile conditions with a shielded seal 638. Filled, shielded vial 610 is lowered back to conveyor belt 620. The conveyor belt moves filled, shielded vial 610 past an assaying and labeling station 640, which assays and labels the vial with data carrier 612, a barcode 642, and/or coded signature 256. For some applications, coded signature 256 is placed on data carrier 612, while for other applications it is placed on vial 610. For still other applications, separate coded signatures 256 are placed on both vial 610 and data carrier 612, and are used to match the vial with the data carrier. For example, a color-coded signature may be printed on vial 610, either prior to the elution or together with the application of data carrier 612, and an encrypted signature may be stored in the data carrier 612. Alternatively, the encrypted signature may be printed.

It will be appreciated that the elution process is subject to modifications and alterations based on communication and information that is received from system 10. For example, a log book of elution system 600 may specify a Tc-99m vial of 1000 mCi, yet a communication request from dose calculation system 152 may modify the order to be a Tc-99m vial of 200 mCi, based on new requirements, e.g., low-dose administration.

The Mother Vial Preparation System

Figure 15:
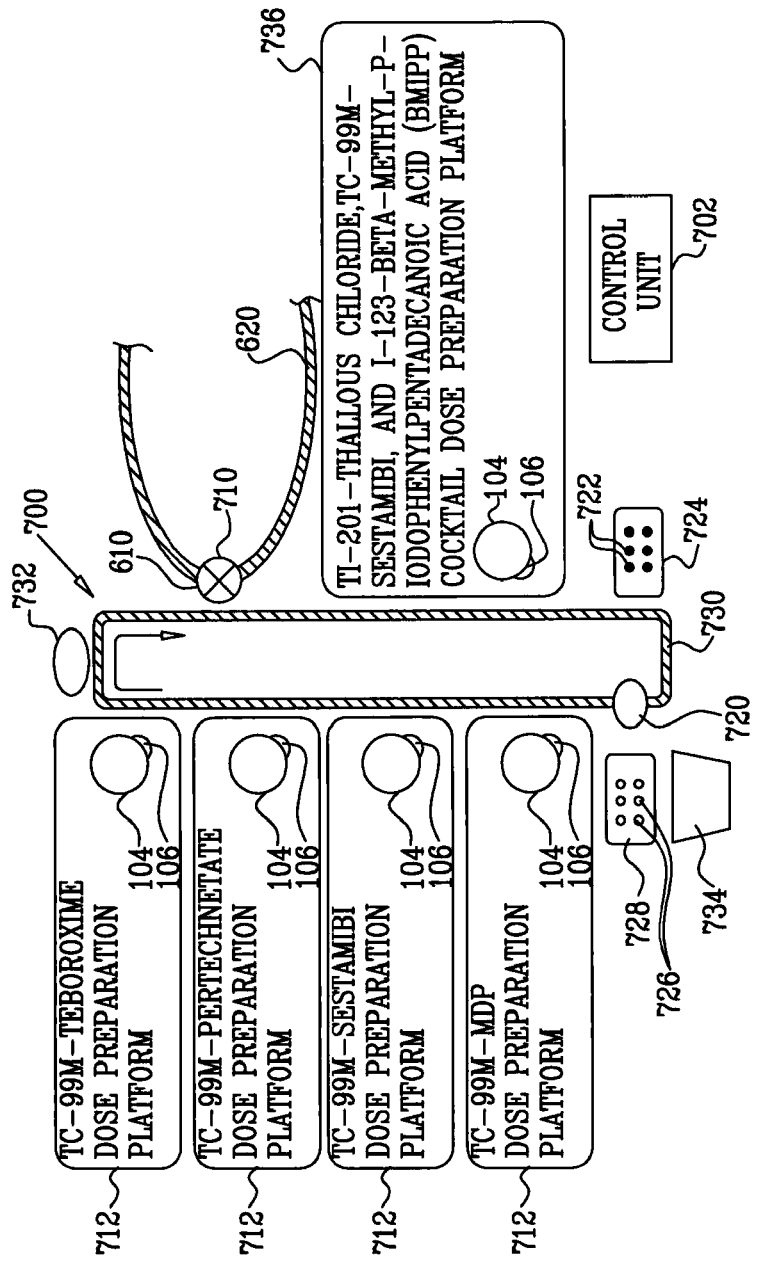
FIG. 15 is a schematic illustration of a mother vial preparation system, in accordance with an embodiment of the present invention.

Reference is made to FIG. 15, which is a schematic illustration of a mother vial preparation system 700, in accordance with an embodiment of the present invention. System 700 automatically labels mother vials 104, containing unlabeled radiopharmaceutical agents, with appropriate radioisotopes. System 700 attaches a data carrier 106 to each mother vial 104, and writes the information to the data carrier that is described hereinabove with reference to FIG. 7. Alternatively, the manufacturer or distributor attaches data carrier 106 to mother vial 104, and writes at least a portion of the information to the carrier.

Prior to beginning the radiolabeling process, a control unit 702 of system 700 authenticates radioisotope vial 610 and mother vial 104, and verifies that radioisotope vial 610 contains the correct radioisotope at the correct radioactivity, and that mother vial 104 contains the correct unlabeled radiopharmaceutical agent. For some applications, such authentication and/or verification is performed by authenticating coded signature 256 of data carrier 612 of radioisotope vial 610. For some applications, such authentication includes authentication of a commercial license associated with the use of mother vial 104. Typically, control unit 702 comprises one or more standard personal computers or servers with appropriate memory, communication interfaces and software for carrying out the functions prescribed by relevant embodiments of the present invention. This software may be downloaded to the control unit in electronic form over a network, for example, or it may alternatively be supplied on tangible media, such as CD-ROM.

Conveyor belt 620 carries shielded radioisotope vial 610 from radioisotope automatic elution system 600 to mother vial preparation system 700. Alternatively, for embodiments in which elution system 600 is not provided, the radioisotope vial is manually placed on conveyor belt 620. The conveyor belt brings vial 610 to a radioisotope filling point 710.

System 700 typically comprises a plurality of dose preparation platforms 712, each of which contains premixed mother vials 104 containing unlabeled radiopharmaceutical agents that require radiolabeling with the radioisotope contained in radioisotope vial 610, e.g., Tc-99m. In the example shown in FIG. 15, preparation platforms 712 comprise a Tc-99m-teboroxime dose preparation platform, a Tc-99m-pertechnetate dose preparation platform, a Tc-99m-sestamibi dose preparation platform, and a Tc-99m-MDP dose preparation platform.

A robot 720 picks up a syringe 722 from a first syringe platform 724, or a micro-syringe 726 from a second syringe platform 728, and travels along a second conveyor belt 730 to filling point 710. It will be appreciated that other types syringes and/or other dispensing tools may also be used. Upon reaching filling point 710, syringe 722 or 726 draws a predetermined amount of radioisotope solution from radioisotope vial 610. The robot typically travels to an assay station 732, which assays the radioisotope solution. Syringe 722 or 726 is then discarded at a discard station 734.

Robot 720 picks up another syringe 722 or 726 from the platform 724 or 728, fills the syringe with a predetermined amount of the radioisotope from vial 610, and travels along second conveyor belt 730 to one of dose preparation platforms 712. At the dose preparation platform, the syringe injects a predetermined amount of radioisotope into mother vial 104 of the dose preparation platform, thereby labeling the unlabeled radiopharmaceutical agent contained in the mother vial.

Robot 720 discards the syringe at discard station 734, picks up a new syringe, draws a predetermined amount of solution from labeled mother vial 104, and assays the solution at assay station 732, in order to determine the radioactivity of the labeled radiopharmaceutical agent contained in mother vial 104. Following the assaying, robot 720 discards the syringe at discard station 734. Typically, system 700 performs one or more quality control procedures on the labeled radiopharmaceutical agent.

System 700 updates data carrier 106 of mother vial 104 with radiolabeling information, such as the time of labeling, and the activity of the radioisotope at the time of labeling, the total solution volume in the mother vial, and the ratio of radioisotopes (e.g., Tc-99m to Tc-99) at the time of labeling, for applications in which the unlabeled radiopharmaceutical agent is labeled with more than one radioisotope.

It is noted that system 700 is configurable to vary a radioactivity of the radioisotope used to label a given radiopharmaceutical agent in order to produce labeled radiopharmaceutical agents of various levels of radioactivity (for example, Tc-99m-teboroxime of 500 mCi and Tc-99m-teboroxime of 50 mCi). For some applications, system 700 comprises at least one cocktail dose preparation platform 736, for labeling a cocktail of radiopharmaceutical agents (for example, Tl-201-thallous chloride, Tc-99m-sestamibi, and I-123-BMIPP).

It will be appreciated that the mother vial preparation process is subject to modifications and alterations based on communication and information that is received from system 10. For example, a log book of system 700 may specify a mother vial of 500 mCi, yet a communication request from dose calculation system 152 may modify the order to be a mother vial of 200 mCi, based on new requirements, e.g., low-dose administration.

The Exercise Room

In an embodiment of the present invention, system 10 comprises at least one exercise room, which comprises one or more pieces of exercise equipment, typically including at least one treadmill. The exercise room, and the equipment therein, is typically in communication with one or more elements of system 10, such as patient-specific data carrier 24, management and control component 150, administration system 26, data carrier 120 of radiopharmaceutical agent container 22, and/or imaging system 28. For example, the exercise room may report the duration, time, and type of exercise to imaging system 28, administration system 26, and/or management control component 150, for synchronizing the exercise with administration and imaging. For some applications, the exercise room receives instructions regarding the duration, time, and/or type of exercise to be performed for a given patient, and schedules an appropriate exercise session in a log book. For some applications, the exercise room sends the patient an SMS-like message notifying the patient of the scheduled session, and/or reminding the patient about a scheduled session. For some applications in which data carrier 24 is integrated into watch or bracelet 170, as described hereinabove with reference to FIG. 3, watch or bracelet 170 is configured to receive and display the SMS-like message to the patient.

Signature

In accordance with an embodiment of the present invention, coded signature 256 comprises a signature encrypted using an encryption algorithm, which is either proprietary or known in the art, e.g., Advanced Encryption Standard (AES), Data Encryption Standard (DES), or Triple DES (3DES). Typically, the encryption algorithm utilizes a symmetric key cipher, as is known in the art.

For some applications, coded signature 256 is stored in one of the data carriers described herein. Alternatively or additionally, the coded signature is printed on the apparatus, e.g., as a computer-readable scannable label, such as a barcode, two-dimensional bar code, or color-coded code.

For some applications, coded signature 256 comprises a color-coded signature which is implemented using techniques described in the above-mentioned U.S. Pat. No. Application Publication 2004/0156081 to Bril et al. Techniques described in the '081 publication include the use of an encrypted image comprising an array of printed positions formed using a group of inks each of which has a predetermined spectrum. The positions are selected to form a predetermined image, either real or virtual, when the image is viewed through an optical processor. The optical processor may further use a distortion, such as a distorted grating or a distorted lens. The correct image is the spectrum, as distorted by the optical processor. An image formed using inks having the same colors as experienced by the human eye, or even by a standard spectrometer, will fail to form the correct predetermined image. Alternatively or additionally, special inks may be used, so that no two ink combinations are exactly alike, and only registered ink combinations provide the correct spectrum. Furthermore, the special inks may be mixtures of 5 or more colors.

FIG. 16A illustrates color spectra 800 of several dyes, for example dyes B, D1, G, D2, and R, each having a well-defined spectral peak, as described in the '081 publication. When dye B and dye G are mixed, the human eye may see a color substantially the same as the color of dye D1. When dye D1 and dye D2 are mixed, the human eye may see a color substantially the same as the color of dye G.

FIG. 16B illustrates a color-coded signature 802, as described in the '081 publication. A color patch 804, which to the human eye may seem a plain orange, for example, may have a first portion 806A, consisting of dye B and dye G, combined to form a hue which is substantially the same as that of dye D1, and a second portion 806B, consisting of dye D1. To the human eye, the color-coded signature 802 appears as a homogeneous patch.

An optical processor 820 comprises an imaging spectrograph, which comprises a grating 822 and, typically, a lens 824. In the example shown in FIG. 16B, the spectrograph produces three structures: a structure 821 formed by diffraction of dye D1 through the grating, a structure 823 formed by diffraction of dye G, and a structure 825 formed by diffraction of dye B. Optical processor 220 thus reveals the authentic spectra of the color-coded signature 802.

For some applications, optical processor 820 comprises two lenses 824 of substantially equal power, one to create a parallel beam at the input to the grating, just before the grating, and one to create an image at the focal point after the grating. Alternatively, a single lens 824, having twice the power of the two lenses, may be placed just before or just after the grating.

For some applications, a more complex color coding is achieved by using a distorted lens or a distorted grating, such that spectral structure 821, 823, and 825 may be reproduced only when an optical processor having the exact distortion is used. It will be appreciated that a single hue may be produced by mixing several dyes, for example, 3, 5, or 10. It will be appreciated that each printing house may be allocated only a specific mix of dyes, so that no two printing houses may have identical dye combinations, and no two printing houses may reproduce the same color-coded signatures 802.

For some applications, color-coded signature 802 is printed directly on an element of system 10, for example, on radiopharmaceutical agent container 22 (FIG. 1), or on radioisotope vial 610 (FIG. 14). Alternatively or additionally, a label, for example, mother vial data carrier 106 or data carrier 120 (FIG. 1) is color-coded, or includes a color-coded patch or pattern, operative as color-coded signature 802.

For some applications, an encrypted signature 256 and a color-coded signature 802 are combined. The resulting color-coded machine-readable signature 256 is authenticated by optical processor 820. For example, an encrypted signature may be provided on a label colored with a coded color. Alternatively or additionally, encrypted signature 256 is printed on a color-coded background, or with color-coded dyes. Alternatively or additionally, coded signature 256 comprises a color-coded barcode. For some applications, the color-coded barcode may appear black or another color to the eye, but reveal a unique spectrum to optical processor 820. For some applications, the color-coded machine-readable signature further comprises a date, to prevent the recycling or re-use of signatures.

Physical Key

Figure 17:
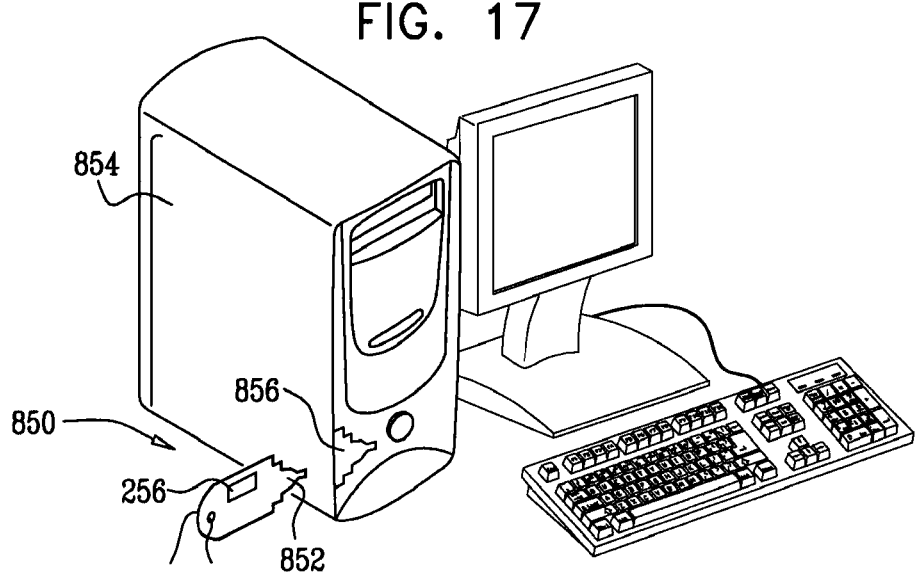
FIG. 17 is a schematic illustration of a computer-readable medium, a portion of which is shaped so as to define a physical key, in accordance with an embodiment of the present invention.

Reference is made to FIG. 17, which is a schematic illustration of a computer-readable medium 850, a portion of which is shaped so as to define a physical key 852, in accordance with an embodiment of the present invention. A communication element 854 is shaped so as to define a dedicated slot 856 having a geometry matching that of key 852. Only keys having the particular geometry of slot 856 can be inserted into the slot. Key 852 thus enables authentication of computer-readable medium 850. Computer-readable medium 850 may comprise, for example, a disk-on-key apparatus or a chip, having, for example, a USB-type connector.

For some applications, patient-specific data carrier 24 comprises computer-readable medium 850, and a communication element of imaging system 28 and/or administration system 26 is shaped so as to define slot 856. Alternatively or additionally, healthcare worker identity tag 208 comprises computer-readable medium 850, and workstation 200, elution system 600, dispensing system 20, administration system 26, and/or imaging system 28 is shaped so as to define slot 856. For some applications, computer-readable medium 850 further comprises coded signature 256, as described hereinabove, while for other applications, key 852 is relied upon in lieu of coded signature 256.

For some applications, authentication, as described herein, is alternatively or additionally based on additional parameters, such as a manufacturer's attribute.

In an embodiment of the present invention, information is transferred from one element of system 10 to another element thereof by physically transferring an electronic information-carrying chip from one element to the other. For example, upon administration of the labeled radiopharmaceutical agent contained in container 22, information may be transferred from data carrier 120 to patient-specific data carrier 24 by physically transferring a memory chip of data carrier 120 to data carrier 24.

Managing Compton Residuals

Figure 18:
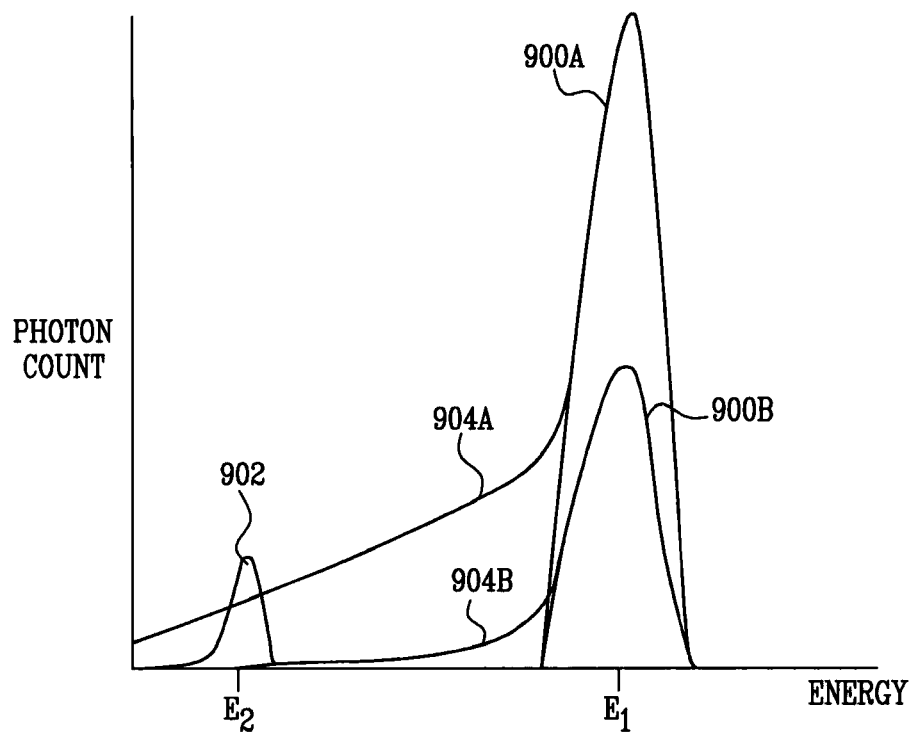
FIG. 18 is a graph showing particle energy vs. photon count at a detector of a camera, in accordance with an embodiment of the present invention.

Reference is made to FIG. 18, which is a graph showing particle energy vs. photon count at a detector 494 of camera 492 of imaging system 28 (FIG. 11), in accordance with an embodiment of the present invention. In this embodiment, dose calculation sub-system 156 of radiopharmaceutical dose calculation system 152, described hereinabove with reference to FIG. 5, takes Compton residuals into consideration when calculating doses of a first and a second labeled radiopharmaceutical agent to be mixed together in a cocktail, or to be separately administered for the same image acquisition procedure. If the first agent were to be provided at a relatively high dose and the second agent were to be provided at a lower dose, the first agent would produce a first peak 900A around a first energy level $E^1$, and the second agent would produce a second peak 902 around a second energy level $E^2$. A Compton residual 904A produced by the first agent at least partially masks second peak 902. For some applications, in order to prevent such masking, dose calculation sub-system 156 reduces the dose of the first agent, thereby producing a first peak 900B and a corresponding Compton residual 904B having lower counts than initial first peak 900A and Compton residual 904A, respectively. Compton residual 904B is sufficiently low so as not to mask second peak 902. By using techniques described hereinabove and/or incorporated herein by reference, camera 492 is sufficiently sensitive to acquire sufficient counts emitted from the lower dose of the second agent. For example, the first and second agents may comprise MIBI-Tc and thallium, respectively, which emit energy at 140 KeV and 72 KeV, respectively.

Alternatively, calculation sub-system 156 determines that the dose of the first labeled radiopharmaceutical agent cannot be reduced sufficiently to prevent such Compton masking. To make such a determination, the sub-system typically takes into consideration constraints applied by the physical properties of the first agent, patient-specific information, and/or camera 492. The sub-system may thus determine that the two agents must be prepared as separate doses for non-simultaneous administration. Alternatively, the sub-system determines that the dose of the second agent is to be increased, so as to prevent the masking. To make such a determination, the sub-system typically takes into consideration constraints applied by the physical properties of the first agent, patient-specific information, camera 492, and/or safety and/or regulatory requirements.

Information-Bearing Radiopharmaceuticals

In an embodiment of the present invention, a portion of the patient, radiopharmaceutical, and/or protocol information described herein is chemically stored together with a labeled radiopharmaceutical agent in a container, such as radiopharmaceutical agent container 22 or mother vial 104. For some applications, such information is chemically stored by providing a chemical indicative of and/or encoding the information, and mixing the chemical with the radiopharmaceutical agent. Alternatively, such information is chemically stored by attaching a chemical marker indicative of the information to the radiopharmaceutical agent or otherwise chemically modifying the radiopharmaceutical agent to store the information. The information-indicative chemical indicator (i.e., chemical or chemical marker) has properties which are machine-readable, for example, using optical, spectral, fluorescence, or isotope emission techniques.

For some applications, the information is stored by setting a level of a parameter of the chemical indicator, such as concentration or radioactivity, which level is indicative of the information. For example, a plurality of concentrations $0, A_1, A_2, A_3, \ldots, A_{max}$ may be defined, each of which represents a respective value. At all of the defined concentrations, the chemical indicator is biologically inert and/or safe in the body, and does not affect the sterility and/or properties of the radiopharmaceutical agent. The plurality of concentrations are sufficiently different from one another so as to be independently measurable and identifiable, such as by measuring a spectral signature of the chemical indicator. For some applications, a plurality of different chemical indicators are used, each of which has defined levels of a parameter representing respective values. The values represented by the plurality of chemical indicators together represent the information.

For some applications, the level of the parameter of the chemical indicator changes over time, e.g., the radioactivity of the chemical indicator declines because of radioactive decay, thereby providing an indication of elapsed time. Such elapsed time may be used, for example, to determine the timing of preparation of the radiopharmaceutical agent and/or subsequent processes, as well as validating whether such timing is within an allowed time window.

For some applications, dispensing system 20 applies the code to the labeled radiopharmaceutical agent and/or container 22 during the dispensing process, and administration system 26 and/or imaging system 28 reads and verifies the stored information. A dedicated reader may be provided for such reading, or a camera of imaging system 28 may be configured to perform such reading.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

International Application PCT/IL2005/001173, filed Nov. 9, 2005;

International Application PCT/IL2005/000572, filed Jun. 1, 2005;

International Application PCT/IL2005/000575, filed Jun. 1, 2005;

International Application PCT/IL2005/001215, filed Nov. 16, 2005, which published as PCT Publication WO 06/054296;

U.S. Provisional Application 60/625,971, filed Nov. 9, 2004;

U.S. Provisional Application 60/628,105, filed Nov. 17, 2004;

U.S. Provisional Application 60/630,561, filed Nov. 26, 2004;

U.S. Provisional Application 60/632,236, filed Dec. 2, 2004;

U.S. Provisional Application 60/632,515, filed Dec. 3, 2004;

U.S. Provisional Application 60/635,630, filed Dec. 14, 2004;

U.S. Provisional Application 60/636,088, filed Dec. 16, 2004;

U.S. Provisional Application 60/640,215, filed Jan. 3, 2005;

U.S. Provisional Application 60/648,385, filed Feb. 1, 2005;

U.S. Provisional Application 60/648,690, filed Feb. 2, 2005;

U.S. Provisional Application 60/675,892, filed Apr. 29, 2005;
U.S. Provisional Application 60/691,780, filed Jun. 20, 2005;
U.S. Provisional Application 60/700,318, filed Jul. 19, 2005;
U.S. Provisional Application 60/700,299, filed Jul. 19, 2005;
U.S. Provisional Application 60/700,317, filed Jul. 19, 2005;
U.S. Provisional Application 60/700,753, filed Jul. 20, 2005;
U.S. Provisional Application 60/700,752, filed Jul. 20, 2005;
U.S. Provisional Application 60/702,979, filed Jul. 28, 2005;
U.S. Provisional Application 60/720,034, filed Sep. 26, 2005;
U.S. Provisional Application 60/720,652, filed Sep. 27, 2005;
U.S. Provisional Application 60/720,541, filed Sep. 27, 2005;
U.S. Provisional Application 60/750,287, filed Dec. 13, 2005;
U.S. Provisional Application 60/750,334, filed Dec. 15, 2005;
U.S. Provisional Application 60/750,597, filed Dec. 15, 2005;
U.S. Provisional Patent Application 60/799,688, filed May 11, 2006;
U.S. Provisional Patent Application 60/800,845, filed May 17, 2006, entitled, "Radioimaging camera for dynamic studies";
U.S. Provisional Patent Application 60/800,846, filed May 17, 2006, entitled, "Radioimaging protocols";
U.S. Provisional Patent Application 60/763,458, filed Jan. 31, 2006;
U.S. Provisional Patent Application 60/741,440, filed Dec. 2, 2005;
U.S. patent application Ser. No. 11/034,007, filed Jan. 13, 2005, which issued as U.S. Pat. No. 7,176,466;
U.S. Provisional patent application Ser. No. 09/641,973, filed Aug. 21, 2000;
U.S. Provisional Patent Application 60/750,294, filed Dec. 13, 2005 (this application has not been assigned to the assignee of the present application; an assignment is in the process of being executed and filed);
U.S. Provisional Patent Application 60/816,970, filed Jun. 28, 2006;
International Patent Application PCT/IL2006/000059, filed Jan. 15, 2006;
International Patent Application PCT/IL2005/000048, filed Jan. 13, 2005;
International Patent Application PCT/IL03/00917, filed Nov. 4, 2003;
Israel Patent Application 172349, filed Nov. 27, 2005; and Israel Patent Application 171346, filed Oct. 10, 2005.
International Patent Application PCT/IL2006/000562, filed May 11, 2006;
U.S. Provisional Patent Application 60/799,688, filed May 11, 2006;
U.S. Provisional Patent Application 60/816,970, filed Jun. 28, 2006;
International Patent Application PCT/IL2006/001511, filed Dec. 28, 2006;
International Patent Application PCT/IL2006/001291, filed Nov. 29, 2006;
International Patent Application PCT/IL2006/000834, filed Jul. 19, 2006;
International Patent Application PCT/IL2006/000840, filed Jul. 19, 2006;
U.S. Provisional Patent Application 60/754,199, filed Dec. 28, 2005;
U.S. patent application Ser. No. 11/607,075, filed Dec. 1, 2006;
U.S. patent application Ser. No. 11/656,548, filed Jan. 13, 2005; and/or
U.S. patent application Ser. No. 10/533,568, filed Nov. 4, 2003.

As used in the present application, including in the claims, a "clinical environment" means any facility or institution in which at least one of radiopharmaceutical preparation, dispensing, and administration occur, including, for example, a radiopharmaceutical manufacturing facility, a pharmacy, a hospital, a doctor's clinic, a day clinic, an out-patient clinic, a laboratory, and a geriatric center.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a container and a computer-communicatable container data carrier physically coupled to the container, the apparatus comprising:
    an imaging system which comprises a camera and an imaging control unit; and
    an automated radiopharmaceutical dispensing system, which comprises:
        a robot, configured to manipulate the container;
        a communication element; and
        a dispensing system control unit, configured to:
            receive imaging protocol information indicative of steps of an imaging procedure, for use with at least one labeled radiopharmaceutical agent,
            receive patient information regarding a patient,
            drive the robot to automatically dispense a dose of the at least one labeled radiopharmaceutical agent to the container, and
            drive the communication element to transmit to the container data carrier (a) the imaging protocol information indicative of the steps of the imaging procedure, for use by the imaging control unit for driving the camera to perform the steps of the imaging procedure, and (b) at least a portion of the patient information,
    wherein the imaging system is configured to receive the imaging protocol information from the container data carrier, and
    wherein the imaging control unit is configured to drive the camera to perform the steps of the imaging procedure responsively to the imaging protocol information received from the container data carrier.

2. The apparatus to claim 1, wherein the imaging control unit is configured to receive the imaging protocol information regarding a plurality of labeled radiopharmaceutical agents, and drive the robot to automatically dispense respective doses of the labeled radiopharmaceutical agents to the container.

3. The apparatus according to claim 1,
wherein the imaging protocol information indicative of the steps of the imaging procedure comprises: an identifier of an imaging protocol assigned to the patient for performance using the dose,
wherein the dispensing system control unit is configured to drive the communication element to transmit the imaging protocol identifier to the container data carrier, and
wherein the imaging control unit is configured to drive the camera to perform the steps of the imaging procedure responsively to the identifier of the imaging protocol received from the container data carrier.

4. The apparatus according to claim 1, wherein the dispensing system control unit is configured to drive the communication element to transmit to the container data carrier at least one of: a time of dispensing of the at least one labeled radiopharmaceutical agent to the container, and information regarding a radioactivity of the dose at the time of dispensing.

5. The apparatus according to claim 1, comprising:
a mother vial that contains the at least one labeled radiopharmaceutical agent prior to dispensing thereof; and
a computer-communicatable mother vial data carrier associated with the mother vial, which mother vial data carrier contains the imaging protocol, information,
wherein the imaging control unit is configured to receive the imaging protocol information from the mother vial data carrier.

6. The apparatus according to claim 5, wherein the mother vial data carrier is physically coupled to the mother vial.

7. The apparatus according to claim 1, wherein the imaging protocol information comprises SPECT imaging protocol information.

8. The apparatus according to claim 1, wherein the dispensing system control unit is configured to further receive the authenticatable information regarding a commercial license for use of the imaging protocol information with the at least one labeled radiopharmaceutical agent.

9. The apparatus according to claim 8, wherein the information regarding the commercial license comprises information regarding the commercial license for use of a SPECT imaging protocol with the at least one labeled radiopharmaceutical agent.

10. The apparatus according to claim 8, wherein the dispensing system control unit is configured to authenticate the authenticatable license information, and to drive the robot to automatically dispense the dose only upon authentication.

11. The apparatus according to claim 1, wherein the system further comprises the container and the computer-communicatable container data carrier physically coupled to the container.

12. The apparatus according to claim 11, wherein the computer-communicatable container data carrier comprises circuitry.

13. The apparatus according to claim 11, wherein the computer-communicatable container data carrier comprises an RFID tag.

14. The apparatus according to claim 11, wherein the computer-communicatable container data carrier comprises a computer-communicable element selected from the group consisting of: a smart card and a disk-on-key.

15. The apparatus according to claim 11, wherein the container comprises shielding.

16. The apparatus according to claim 1,
wherein the imaging protocol information indicative of the steps of the imaging procedure comprises instructions for performing the imaging procedure using the at least one labeled radiopharmaceutical agent, and
wherein the imaging control unit is configured to drive the camera to perform the steps of the imaging procedure by executing the instructions of the imaging protocol information.

17. Apparatus for use with a container and a computer-communicatable container data carrier physically coupled to the container, the apparatus comprising;
an imaging system, which comprises a camera and an imaging control unit; and
an automated radiopharmaceutical dispensing system, which comprises:
a robot, configured to manipulate the container;
a communication element;
a dispensing system control unit, configured to:
receive SPECT imaging protocol information that comprises at least one pharmacologic kinetic parameter of at least one labeled radiopharmaceutical agent, for use with the at least one labeled radiopharmaceutical agent,
receive patient information regarding a patient,
drive the robot to automatically dispense a dose of the at least one labeled radiopharmaceutical agent to the container, and
drive the communication element to transmit to the container data carrier (a) the SPECT the imaging protocol information, for use by the imaging control unit for driving the camera to perform steps of an imaging procedure, and (b) at least a portion of the patient information;
wherein the imaging system is configured to receive the SPECT imaging protocol information from the container data carrier, and
wherein the imaging control unit is configured to drive the camera to perform the imaging procedure responsively to the SPECT imaging protocol information received from the container data carrier.

18. The apparatus according to claim 17, wherein the pharmacologic kinetic parameter is selected from the group of pharmacologic kinetic parameters consisting of: an accumulation/redistribution of the at least one labeled radiopharmaceutical agent in tissue, a metabolic rate of the at least one labeled radiopharmaceutical agent, a diffusion coefficient of the at least one labeled radiopharmaceutical agent from blood to tissue, and a diffusion coefficient of the at least one labeled radiopharmaceutical agent from the tissue to the blood.

19. Apparatus for use with a container, the apparatus comprising:
a mother vial having a volume of at least 10 ml, which contains at least 5 ml of a non-diluted labeled radiopharmaceutical agent, and at least 5 ml of saline solution; and
an automated radiopharmaceutical dispensing system, configured to contain the mother vial, and to dispense at least one dose from the mother vial to the container.

20. The apparatus according to claim 19, wherein the mother vial has a volume of at least 20 ml.

21. A method for use with a container and a computer-communicatable container data carrier physically coupled to the container, the method comprising:
receiving, by an automated radiopharmaceutical dispensing system, imaging protocol information indicative of steps of an imaging procedure, for use with at least one labeled radiopharmaceutical agent;
receiving, by the dispensing system, patient information regarding a patient;
automatically robotically dispensing, by the dispensing system, a dose of the at least one labeled radiopharmaceutical agent to the container;

transmitting to the container data carrier, by the dispensing system, (a) the imaging protocol information indicative of the steps of the imaging procedure to be performed by an imaging system and (b) at least a portion of the patient information;

reading the imaging protocol information from the container data carrier; and performing, by the imaging system, the steps of the imaging procedure responsively to the imaging protocol information read from the container data carrier.

22. The method according to claim 21, wherein receiving the imaging protocol information comprises receiving the imaging protocol information regarding a plurality of labeled radiopharmaceutical agents, and wherein dispensing comprises dispensing respective doses of the labeled radiopharmaceutical agents to the container.

23. The method according to claim 21,
wherein receiving the imaging protocol information indicative of the steps of the imaging procedure comprises receiving an identifier of an imaging protocol assigned to the patient for performance using the dose,
wherein transmitting comprises transmitting the imaging protocol identifier to the container data carrier, and
wherein performing the steps of the imaging procedure comprises performing the steps of the imaging procedure responsively to the identifier of the imaging protocol read from the container data carrier.

24. The method according to claim 21, wherein transmitting comprises transmitting to the container data carrier at least one of: a time of dispensing of the at least one labeled radiopharmaceutical agent to the container, and information regarding a radioactivity of the dose at the time of dispensing.

25. The method according to claim 21, wherein receiving the radiopharmaceutical information comprises:
providing, to the dispensing system, a mother vial that contains the at least one labeled radiopharmaceutical agent prior to dispensing thereof, and a computer-communicatable mother vial data carrier associated with the mother vial, which mother vial data carrier contains the imaging protocol information; and
receiving the imaging protocol information from the mother vial data carrier.

26. The method according to claim 25, wherein providing the mother vial and the mother vial data carrier comprises providing the mother vial data carrier physically coupled to the mother vial.

27. The method according to claim 21, wherein receiving the imaging protocol information comprises receiving SPECT imaging protocol information.

28. The method according to claim 21, further comprising receiving authenticatable information regarding a commercial license for use of the imaging protocol information with the at least one labeled radiopharmaceutical agent.

29. The method according to claim 28, wherein receiving the information regarding the commercial license comprises receiving information regarding the commercial license for use of a SPECT imaging protocol with the at least one labeled radiopharmaceutical agent.

30. The method according to claim 28, wherein dispensing comprises authenticating the authenticatable license information, and dispensing the dose only upon authentication.

31. The method according to claim 21,
wherein receiving the imaging protocol information indicative of the steps of the imaging procedure comprises receiving instructions for performing the imaging procedure using the at least one labeled radiopharmaceutical agent,
wherein transmitting comprises transmitting the instructions to the container data carrier, and
wherein performing the steps of the imaging procedure comprises executing the instructions of the imaging protocol information.

32. A method for use with a container and a computer-communicatable container data carrier physically coupled to the container, the method comprising:
receiving, by an automated radiopharmaceutical dispensing system, SPECT imaging protocol information that includes at least one pharmacologic kinetic parameter of at least one labeled radiopharmaceutical agent, for use with the at least one labeled radiopharmaceutical agent;
receiving, by the dispensing system, patient information regarding a patient;
automatically robotically dispensing, by the dispensing system, a dose of the at least one labeled radiopharmaceutical agent to the container;
transmitting to the container data carrier, by the dispensing system, (a) the SPECT imaging protocol information to be performed by an imaging system and (b) at least a portion of the patient information;
reading the SPECT imaging protocol information from the container data carrier; and
performing, by the imaging system, an imaging procedure responsively to the SPECT imaging protocol information read from the container data carrier.

33. The method according to claim 32, wherein the pharmacologic kinetic parameter is selected from the group of pharmacologic kinetic parameters consisting of: an accumulation/redistribution of the at least one labeled radiopharmaceutical agent in tissue, a metabolic rate of the at least one labeled radiopharmaceutical agent, a diffusion coefficient of the at least one labeled radiopharmaceutical agent from blood to tissue, and a diffusion coefficient of the at least one labeled radiopharmaceutical agent from the tissue to the blood.

34. A method for automatically dispensing a labeled radiopharmaceutical agent to a container, comprising:
providing a mother vial having a volume of at least 10 ml;
filling the mother vial with at least 5 ml of a non-diluted labeled radiopharmaceutical agent, and with at least 5 ml of saline solution;
placing the mother vial in an automated radiopharmaceutical dispensing system; and
dispensing at least one dose from the mother vial to the container.

35. The method according to claim 34, wherein proving the mother vial comprises providing the mother vial having a volume of at least 20 ml.

* * * * *